US006448080B1

(12) United States Patent
Ward et al.

(10) Patent No.: US 6,448,080 B1
(45) Date of Patent: Sep. 10, 2002

(54) ANTISENSE MODULATION OF WRN EXPRESSION

(75) Inventors: Donna T. Ward, Murrieta; Andrew T. Watt, Vista, both of CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/791,211

(22) Filed: Feb. 23, 2001

(51) Int. Cl.[7] .................. C12Q 1/68; C07H 21/04; C12N 15/85
(52) U.S. Cl. .................. 435/375; 435/6; 435/91.1; 435/325; 435/366; 536/23.1; 536/24.31; 536/24.33; 536/24.5
(58) Field of Search .................. 435/6, 325, 366, 435/375, 91.1; 536/23.1, 24.5, 25.3, 24.31, 24.33; 514/44

(56) References Cited

U.S. PATENT DOCUMENTS 5,801,154 A * 9/1998 Baracchini et al. ............ 514/44
5,951,455 A * 9/1999 Cowsert ...................... 495/375
6,090,620 A    7/2000 Fu et al. ...................... 435/325

OTHER PUBLICATIONS

W. Michael Flanagan et al., Cellular penetration and antisense activity by a phenoxazine–substituted heptanucleotide, Research.*
Andrea D. Branch, A good antisense molecule is hard to find, TIBS 23—Feb. 1998, pp. 45–50.*
Brosh et al., Potent inhibition of werner and bloom helicases by DNA minor groove binding drugs, *Nucleic Acids Res.,* 2000, 28:2420–2430.
Chakraverty et al., Defending genome integrity during DNA replication: a proposed role for RecQ family helicases, *BioEssays,* 1999, 21:286–294.
Cogoni et al., Posttranscriptional gene silencing in Neurospora by a RecQ DNA helicase, *Science,* 1999, 286:2342–2344.
Frei et al., RecQ–like helicases: the DNA replication checkpoint connection, *J. Cell Sci.,* 2000, 113:2641–2646.
Goto, Werner's syndrome: from clinics to genetics. [In Process Citation], *Clin. Exp. Rheumatol.,* 2000, 18:760–766.
Karow et al., RecQ family helicases: roles in cancer and aging, *Curr. Opin. Genet. Dev.,* 2000, 10:32–38.
Kawabe et al., Differential regulation of human RecQ family helicases in cell transformation and cell cycle [In Process Citation], *Oncogene,* 2000, 19:4764–4772.
Lebel et al., A deletion within the murine Werner syndrome helicase induces sensitivity to inhibitors of topoisomerase and loss of cellular proliferative capacity, *Proc. Natl. Acad. Sci. U. S. A.,* 1998, 95:13097–13102.
Marciniak et al., Nucleolar localization of the Werner syndrome protein in human cells, *Proc. Natl. Acad. Sci. U. S. A.,* 1998, 95:6887–6892.
Orren et al., Enzymatic and DNA binding properties of purified WRN protein: high affinity binding to single–stranded DNA but not to DNA damage induced by 4NQO, *Nucleic Acids Res.,* 1999, 27:3557–3566.
Oshima, The werner syndrome protein: an update [In Process Citation], *BioEssays,* 2000, 22:894–901.
Shen et al., Werner syndrome protein. I. DNA helicase and dna exonuclease reside on the same polypeptide, *J. Biol. Chem.,* 1998, 273:34139–34144.
Shen et al., The Werner syndrome gene: the molecular basis of RecQ helicase–deficiency diseases, *Trends Genet.,* 2000, 16:213–220.
Wu et al., Genetic recombination: Helicases and topoisomerases link up, *Curr. Biol.,* 1999, 9:R518–520.
Yu et al., Positional cloning of the Werner's syndrome gene, *Science,* 1996, 272:258–262.

* cited by examiner

*Primary Examiner*—John L. LeGuyader
*Assistant Examiner*—M Schmidt
(74) *Attorney, Agent, or Firm*—Licata & Tyrrell P.C.

(57) ABSTRACT

Antisense compounds, compositions and methods are provided for modulating the expression of WRN. The compositions comprise antisense compounds, particularly antisense oligonucleotides, targeted to nucleic acids encoding WRN. Methods of using these compounds for modulation of WRN expression and for treatment of diseases associated with expression of WRN are provided.

27 Claims, No Drawings

ANTISENSE MODULATION OF WRN EXPRESSION

FIELD OF THE INVENTION

The present invention provides compositions and methods for modulating the expression of WRN. In particular, this invention relates to compounds, particularly oligonucleotides, specifically hybridizable with nucleic acids encoding WRN. Such compounds have been shown to modulate the expression of WRN.

BACKGROUND OF THE INVENTION

Genomic integrity is critical to the health and survival of any organisms and cells have evolved multiple pathways for the repair of DNA damage.

One class of enzymes involved in the maintenance of genomic integrity and stability are DNA helicases. These proteins play important roles in DNA replication, repair, recombination and transcription by unwinding duplex genomic strands allowing the repair machinery access to damaged or mispaired DNA. For example, the RecQ family of helicases has been shown to be important players in linking cell cycle checkpoint responses to recombination repair (Chakraverty and Hickson, *BioEssays*, 1999, 21, 286–294; Frei and Gasser, *J. Cell Sci.*, 2000, 113, 2641–2646; Wu et al., *Curr. Biol.*, 1999, 9, R518–520). More recently, these helicases have been implicated in the process of posttranscriptional gene silencing (PTGS) (Cogoni and Macino, *Science*, 1999, 286, 2342–2344). In this process, the helicase is required to separate the double-stranded DNA (dsDNA) before any hybridization and silencing mechanism could be initiated.

The RecQ family consists of five members and can be divided into two distinct groups according to whether they contain an additional carboxy- or amino-terminus group. One class containing the longest members of the family include genes known to be defective in several syndromes including the BLM gene in Bloom's syndrome, the WRN gene in Werner's syndrome and the RECQ4 gene in Rothmund-Thompson syndrome. Mutations in these genes lead to an increase in the incidence of cancer as well as other physiologic abnormalities (Karow et al., *Curr. Opin. Genet. Dev.*, 2000, 10, 32–38; Kawabe et al., *Oncogene*, 2000, 19, 4764–4772).

The second class contains the RECQL gene and the RECQ5 gene which encode little more than the central helicase domain and have not been associated with any human disease.

WRN (also known as RECQL3) was originally identifed by positional cloning as the gene responsible for Werner's syndrome and localized to chromosome 8p12 (Yu et al., *Science*, 1996, 272, 258–262.). Werner's syndrome is a rare autosomal recessive disorder characterized by symptoms similar to premature aging including atherosclerosis, osteoporosis, type II diabetes, cataracts and cancers (Goto, *Clin Exp. Rheumatol.*, 2000, 18, 760–766; Oshima, BioEssays, 2000, 22, 894–901; Shen and Loeb, *Trends Genet.*, 2000, 16, 213–220).

In an effort to better define the role of the WRN gene, Marciniak et al. determined the subcellular localization of the protein using indirect immunofluorescence and a 30 polyclonal antibody. These studies revealed a predominant nuclear localization and no difference in localization was detected in normal compared to transformed human cell lines (Marciniak et al., *Proc. Natl. Acad. Sci. U. S. A.*, 1998, 95, 6887–6892). In addition to having helicase activity, WRN also contains intrinsic exonuclease activity and has been shown to bind single-stranded DNA with higher affinity than double-stranded DNA (Orren et al., Nucleic Acids Res., 1999, 27, 3557–3566; Shen et al., *J. Biol. Chem.*, 1998, 273, 34139–34144).

Disclosed in U.S. Pat. No. 6,090,620 are the nucleic acid molecules encoding the WRN gene as well as WRN gene products, expression vectors, viral vectors and host cells suitable for expressing the WRN gene products (Fu et al., 2000).

Currently, there are no known therapeutic agents which effectively inhibit the synthesis of WRN. There are reports of DNA minor groove-binding drugs which inhibit the helicase activity of WRN (Brosh et al., *Nucleic Acids Res.*, 2000, 28, 2420–2430). WRN-deficient mice display reduced embryonic survival while live-born mice otherwise appear normal during the first year of life (Lebel and Leder, *Proc. Natl. Acad. Sci. U. S. A.*, 1998, 95, 13097–13102).

While mutations and targeted disruptions resulting in altered protein expression in the WRN gene are responsible for Werner's syndrome, the normal function of the WRN gene product and its regulation are still unclear. It is, however, believed to be involved in DNA metabolism and is therefore a potential therapeutic target in conditions involving the production of aberrant DNA products, including the recognition of foreign DNA products as is the case upon viral infection. Consequently, there remains a long felt need for agents capable of effectively inhibiting and/or modulating WRN function.

Antisense technology is emerging as an effective means for reducing the expression of specific gene products and may therefore prove to be uniquely useful in a number of therapeutic, diagnostic, and research applications for the modulation of WRN expression.

The present invention provides compositions and methods for modulating WRN expression.

SUMMARY OF THE INVENTION

The present invention is directed to compounds, particularly antisense oligonucleotides, which are targeted to a nucleic acid encoding WRN, and which modulate the expression of WRN. Pharmaceutical and other compositions comprising the compounds of the invention are also provided. Further provided are methods of modulating the expression of WRN in cells or tissues comprising contacting said cells or tissues with one or more of the antisense compounds or compositions of the invention. Further provided are methods of treating an animal, particularly a human, suspected of having or being prone to a disease or condition associated with expression of WRN by administering a therapeutically or prophylactically effective amount of one or more of the antisense compounds or compositions of the invention.

DETAILED DESCRIPTION OF THE INVENTION

The present invention employs oligomeric compounds, particularly antisense oligonucleotides, for use in modulating the function of nucleic acid molecules encoding WRN, ultimately modulating the amount of WRN produced. This is accomplished by providing antisense compounds which specifically hybridize with one or more nucleic acids encoding WRN. As used herein, the terms "target nucleic acid" and "nucleic acid encoding WRN" encompass DNA encoding WRN, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of WRN. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding WRN. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed MRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding WRN, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an MRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an MRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular MRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense and other compounds of the invention which hybridize to the target and inhibit expression of the target are identified through experimentation, and the sequences of these compounds are hereinbelow identified as preferred embodiments of the invention. The target sites to which these preferred sequences are complementary are hereinbelow referred to as "active sites" and are therefore preferred sites for targeting. Therefore another embodiment of the invention encompasses compounds which hybridize to these active sites.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

For use in kits and diagnostics, the antisense compounds of the present invention, either alone or in combination with other antisense compounds or therapeutics, can be used as tools in differential and/or combinatorial analyses to elucidate expression patterns of a portion or the entire complement of genes expressed within cells and tissues.

Expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.*, 2000, 480, 17–24; Celis, et al., *FEBS Lett.*, 2000, 480, 2–16), SAGE (serial analysis of gene expression) (Madden, et al., *Drug Discov. Today*, 2000, 5, 415–425), READS (restriction enzyme amplification of digested cDNAs) (Prashar and Weissman, *Methods Enzymol.*, 1999, 303, 258–72), TOGA (total gene expression analysis) (Sutcliffe, et al., *Proc. Natl. Acad. Sci. U. S. A.*, 2000, 97, 1976–81), protein arrays and proteomics (Celis, et al., *FEBS Lett.*, 2000, 480, 2–16; Jungblut, et al., *Electrophoresis*, 1999, 20, 2100–10), expressed sequence tag (EST) sequencing (Celis, et al., *FEBS Lett.*, 2000, 480, 2–16; Larsson, et al., *J. Biotechnol.*, 2000, 80, 143–57), subtractive RNA fingerprinting (SuRF) (Fuchs, et al., *Anal. Biochem.*, 2000, 286, 91–98; Larson, et al., Cytometry, 2000, 41, 203–208), subtractive cloning, differential display (DD) (Jurecic and Belmont, *Curr. Opin. Microbiol.*, 2000, 3, 316–21), comparative genomic hybridization (Carulli, et al., *J. Cell Biochem. Suppl.*, 1998, 31, 286–96), FISH (fluorescent in situ hybridization) techniques (Going and Gusterson, *Eur. J. Cancer*, 1999, 35, 1895–904) and mass spectrometry methods (reviewed in (To, *Comb. Chem. High Throughput Screen*, 2000, 3, 235–41).

The specificity and sensitivity of antisense is also harnessed by those of skill in the art for therapeutic uses. Antisense oligonucleotides have been employed as therapeutic moieties in the treatment of disease states in animals and man. Antisense oligonucleotide drugs, including ribozymes, have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 50 nucleobases (i.e. from about 8 to about 50 linked nucleosides). Particularly preferred antisense compounds are antisense oligonucleotides, even more preferably those comprising from about 12 to about 30 nucleobases. Antisense compounds include ribozymes, external guide sequence (EGS) oligonucleotides (oligozymes), and other short catalytic RNAs or catalytic oligonucleotides which hybridize to the target nucleic acid and modulate its expression.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages.

As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and borano-phosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science*, 1991, 254, 1497–1500.

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N ($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$ $CH_3$, O($CH_2$)$_n$O$CH_3$, O($CH_2$)$_n$NH$_2$, O($CH_2$)$_n$$CH_3$, O($CH_2$)$_n$ONH$_2$, and O($CH_2$)$_n$ON[CH($CH_2$)$_n$$CH_3$)]$_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, S$CH_3$, OCN, Cl, Br, CN, $CF_3$, O$CF_3$, SO$CH_3$, SO$_2$$CH_3$, ON$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2$$CH_2$O$CH_3$, also known as 2'-O-(2-methoxyethyl) or 2'-MOE) (Martin et al., *Helv. Chim. Acta*, 1995, 78, 486–504) i.e., an alkoxyalkoxy group. A further preferred modification includes 2'-dimethylaminooxyethoxy, i.e., a O($CH_2$)$_2$ON($CH_3$)$_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_2$)$_2$, also described in examples hereinbelow.

A further prefered modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne (—$CH_2$—)$_n$ group bridging the 2' oxygen atom and the 4' carbon atom wherein n is 1 or 2. LNAs and preparation thereof are described in WO 98/39352 and WO 99/14226.

Other preferred modifications include 2'-methoxy (2'-O—CH$_3$), 2'-aminopropoxy (2'-OCH$_2$CH$_2$CH$_2$NH$_2$), 2'-allyl (2'-CH$_2$—CH=CH$_2$), 2'-O-allyl (2'-O—CH$_2$—CH=CH$_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3'position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858–859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289–302, Crooke, S. T. and Lebleu, B. ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications*, CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Another modification of the oligonucleotides of the invention involves chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., *Proc. Natl. Acad. Sci. USA*, 1989, 86, 6553–6556), cholic acid (Manoharan et al., *Bioorg. Med. Chem. Let.*, 1994, 4, 1053–1060), a thioether, e.g., hexyl-S-tritylthiol (Manoharan et al., *Ann. N.Y. Acad. Sci.*, 1992, 660, 306–309; Manoharan et al., Bioorg. Med. Chem. Let., 1993, 3, 2765–2770), a thiocholesterol (Oberhauser et al., *Nucl. Acids Res.*, 1992, 20, 533–538), an aliphatic chain, e.g., dodecandiol or undecyl residues (Saison-Behmoaras et al., *EMBO J.*, 1991, 10, 1111–1118; Kabanov et al., *FEBS Lett.*, 1990, 259, 327–330; Svinarchuk et al., *Biochimie*, 1993, 75, 49–54), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651–3654; Shea et al., *Nucl. Acids Res.*, 1990, 18, 3777–3783), a polyamine or a polyethylene glycol chain (Manoharan et al., *Nucleosides & Nucleotides*, 1995, 14, 969–973), or adamantane acetic acid (Manoharan et al., *Tetrahedron Lett.*, 1995, 36, 3651–3654), a palmityl moiety (Mishra et al., *Biochim. Biophys. Acta*, 1995, 1264, 229–237), or an octadecylamine or hexylamino-carbonyloxycholesterol moiety (Crooke et al., *J. Pharmacol. Exp. Ther.*, 1996, 277, 923–937. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.*, 1977, 66, 1–19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of WRN is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding WRN, enabling sandwich and other assays to easily be constructed to exploit this fact. Hybridization of the antisense oligonucleotides of the invention with a nucleic acid encoding WRN can be detected by means known in the art. Such means may include conjugation of an enzyme to the oligonucleotide, radiolabelling of the oligonucleotide or any other suitable detection means. Kits using such detection means for detecting the level of WRN in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred topical formulations include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). Oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. patent application Ser. No. 09/315,298 filed on May 20, 1999 which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Prefered bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate, sodium glycodihydrofusidate,. Prefered fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g. sodium). Also prefered are combinations of penetration enhancers, for example, fatty acids/salts in combination with bile acids/salts. A particularly prefered combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally in granular form including sprayed dried particles, or complexed to form micro or nanoparticles. Oligonucleotide complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Particularly preferred complexing agents include chitosan, N-trimethylchitosan, poly-L-lysine, polyhistidine, polyornithine, polyspermines, protamine, polyvinylpyridine, polythiodiethylamino-methylethylene P(TDAE), polyaminostyrene (e.g. p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for oligonucleotides and their preparation are described in detail in U.S. applications Ser. No. 08/886,829 (filed Jul. 1, 1997), Ser. No. 09/108,673 (filed Jul. 1, 1998), Ser. No. 09/256,515 (filed Feb. 23, 1999), Ser. No. 09/082,624 (filed May 21, 1998) and Ser. No. 09/315,298 (filed May 20, 1999) each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

Emulsions

The compositions of the present invention may be prepared and formulated as emulsions. Emulsions are typically heterogenous systems of one liquid dispersed in another in the form of droplets usually exceeding 0.1 μm in diameter. (Idson, in *Pharmaceutical Dosage Forms*, Lieberman, Rieger and Banker (Eds.), 1988, Marcel Dekker, Inc., New York, N.Y., volume 1, p. 199; Rosoff, in *Pharmaceutical Dosage Forms*, Lieberman, Rieger and Banker (Eds.), 1988, Marcel Dekker, Inc., New York, N.Y., Volume 1, p. 245; Block in *Pharmaceutical Dosage Forms*, Lieberman, Rieger and Banker (Eds.), 1988, Marcel Dekker, Inc., New York, N.Y., volume 2, p. 335; Higuchi et al., in *Remington's Pharmaceutical Sciences*, Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in *Pharmaceutical Dosage Forms*, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in *Pharmaceutical Dosage Forms*, Lieberman, Rieger and Banker (Eds.), 1988, Marcel Dekker, Inc., New York, N.Y., volume 1, p. 285; Idson, in *Pharmaceutical Dosage Forms*, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in *Pharmaceutical Dosage Forms*, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms*, Lieberman, Rieger and Banker (Eds.), 1988, Marcel Dekker, Inc., New York, N.Y., volume 1, p. 335; Idson, in *Pharmaceutical Dosage Forms*, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in *Pharmaceutical Dosage Forms*, Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in *Pharmaceutical Dosage Forms*, Lieberman, Rieger and Banker (Eds.), 1988, Marcel Dekker, Inc., New York, N.Y., volume 1, p. 245; Idson, in *Pharmaceutical Dosage Forms*, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile which is a single optically isotropic and thermodynamically stable liquid solution (Rosoff, in *Pharmaceutical Dosage Forms*, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: *Controlled Release of Drugs: Polymers and Aggregate Systems*, Rosoff, M., Ed., 1989, VCH Publishers, New York, pages 185–215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in *Remington's Pharmaceutical Sciences*, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in *Pharmaceutical Dosage Forms*, Lieberman, Rieger and Banker (Eds.), 1988, Marcel Dekker, Inc., New York, N.Y., volume 1, p. 245; Block, in *Pharmaceutical Dosage Forms*, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8–C12) mono, di, and tri-glycerides, polyoxyethylated glyceryl fatty acid esters, fatty alcohols, polyglycolized glycerides, saturated polyglycolized C8–C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research*, 1994, 11, 1385–1390; Ritschel, *Meth. Find. Exp. Clin. Pharmacol.*, 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., *Pharmaceutical Research*, 1994, 11, 1385; Ho et al., *J. Pharm. Sci.*, 1996, 85, 138–143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems*, 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in *Pharmaceutical Dosage Forms*, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.*, 1987, 147, 980–985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release*, 1992, 19, 269–274).

One major type of liposomal composition includes phospholipids other than naturally-derived phosphatidylcholine. Neutral liposome compositions, for example, can be formed from dinyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., *Journal of Drug Targeting*, 1992, 2, 405–410). Further, an additional study tested the efficacy of interferon administered as part of a liposomal formulation to the administration of interferon using an aqueous system, and concluded that the liposomal formulation was superior to aqueous administration (du Plessis et al., *Antiviral Research*, 1992, 18, 259–265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. *S.T.P.Pharma. Sci.*, 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$ or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters*, 1987, 223, 42; Wu et al., *Cancer Research*, 1993, 53, 3765).

Various liposomes comprising one or more glycolipids are known in the art. Papahadjopoulos et al. (*Ann. N.Y. Acad. Sci.*, 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.*, 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (*Bull. Chem. Soc. Jpn.*, 1980, 53, 2778) described liposomes comprising a nonionic detergent, $2C_{12}15G$, that contains a PEG moiety. Illum et al. (*FEBS Lett.*, 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (*FEBS Lett.*, 1990, 268, 235) described experiments demonstrating that liposomes comprising phosphatidylethanolamine (PE) derivatized with PEG or PEG stearate have significant increases in blood circulation half-lives. Blume et al. (*Biochimica et Biophysica Acta*, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1–20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in *Pharmaceutical Dosage Forms*, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in *Pharmaceutical Dosage Forms*, Marcel Dekker, Inc., New York, N.Y., 1988, p. 285).

Penetration Enhancers

In one embodiment, the present invention employs various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., *Critical Reviews in Therapeutic Drug Carrier Systems*, 1991, p.92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., *Critical Reviews in Therapeutic Drug Carrier Systems*, 1991, p.92); and perfluorochemical emulsions, such as FC-43. Takahashi et al., *J. Pharm. Pharmacol.*, 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., *Critical Reviews in Therapeutic Drug Carrier Systems*, 1991, p.92; Muranishi, *Critical Reviews in Therapeutic Drug Carrier Systems*, 1990, 7, 1–33; El Hariri et al., J. Pharm. Pharmacol., 1992, 44, 651–654).

Bile salts: The physiological role of bile includes the facilitation of dispersion and absorption of lipids and fat-soluble vitamins (Brunton, Chapter 38 in: Goodman & Gilman's *The Pharmacological Basis of Therapeutics*, 9th Ed., Hardman et al. Eds., McGraw-Hill, N.Y., 1996, pp. 934–935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., *Critical Reviews in Therapeutic Drug Carrier Systems*, 1991, page 92; Swinyard, Chapter 39 In: *Remington's Pharmaceutical Sciences*, 18th Ed., Gennaro, ed., Mack Publishing Co., Easton, Pa., 1990, pages 782–783; Muranishi, *Critical Reviews in Therapeutic Drug Carrier Systems*, 1990, 7, 1–33; Yamamoto et al., *J. Pharm. Exp. Ther.*, 1992, 263, 25; Yamashita et al., *J. Pharm. Sci.*, 1990, 79, 579–583).

Chelating Agents: Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.*, 1993, 618, 315–339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., *Critical Reviews in Therapeutic Drug Carrier Systems*, 1991, page 92; Muranishi, *Critical Reviews in Therapeutic Drug Carrier Systems*, 1990, 7, 1–33; Buur et al., *J. Control Rel.*, 1990, 14, 43–51).

Non-chelating non-surfactants: As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, *Critical Reviews in Therapeutic Drug Carrier Systems*, 1990, 7, 1–33). This class of penetration enhancers include, for example, unsaturated cyclic ureas, 1-alkyl- and 1-alkenylazacyclo-alkanone derivatives (Lee et al., *Critical Reviews in Therapeutic Drug Carrier Systems*, 1991, page 92); and non-steroidal anti-inflammatory agents such as diclofenac sodium, indomethacin and phenylbutazone (Yamashita et al., *J. Pharm. Pharmacol.*, 1987, 39, 621–626).

Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et al., *Antisense Res. Dev.*, 1995, 5, 115–121; Takakura et al., *Antisense & Nucl. Acid Drug Dev.*, 1996, 6, 177–183).

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, *The Merck Manual of Diagnosis and Therapy*, 15th Ed. 1987, pp. 1206–1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy*, 15th Ed., Berkow et al., eds., 1987, Rahway, N.J., pages 2499–2506 and 46–49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$ s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Nucleoside Phosphoramidites for Oligonucleotide Synthesis Deoxy and 2'-alkoxy Amidites 2'-Deoxy and 2'-methoxy beta-cyanoethyldiisopropyl phosphoramidites were purchased from commercial sources (e.g. Chemgenes, Needham Mass. or Glen Research, Inc. Sterling Va.). Other 2'-O-alkoxy substituted nucleoside amidites are prepared as described in U.S. Pat. No. 5,506, 351, herein incorporated by reference. For oligonucleotides synthesized using 2'-alkoxy amidites, the standard cycle for unmodified oligonucleotides was utilized, except the wait step after pulse delivery of tetrazole and base was increased to 360 seconds.

Oligonucleotides containing 5-methyl-2'-deoxycytidine (5-Me—C) nucleotides were synthesized according to published methods [Sanghvi, et. al., *Nucleic Acids Research*, 1993, 21, 3197–3203] using commercially available phosphoramidites (Glen Research, Sterling Va. or ChemGenes, Needham Mass.).

2'-Fluoro Amidites

2'-Fluorodeoxyadenosine Amidites

2'-fluoro oligonucleotides were synthesized as described previously [Kawasaki, et. al., *J. Med. Chem.*, 1993, 36, 831–841] and U.S. Pat. No. 5,670,633, herein incorporated by reference. Briefly, the protected nucleoside N6-benzoyl-2'-deoxy-2'-fluoroadenosine was synthesized utilizing commercially available 9-beta-D-arabinofuranosyladenine as starting material and by modifying literature procedures whereby the 2'-alpha-fluoro atom is introduced by a $S_N2$-displacement of a 2'-beta-trityl group. Thus N6-benzoyl-9-beta-D-arabinofuranosyladenine was selectively protected in moderate yield as the 3',5'-ditetrahydropyranyl (THP) intermediate. Deprotection of the THP and N6-benzoyl groups was accomplished using standard methodologies and standard methods were used to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate diisobutyrylarabinofuranosylguanosine. Deprotection of the TPDS group was followed by protection of the hydroxyl group with THP to give diisobutyryl di-THP protected arabinofuranosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

2'-Fluorouridine

Synthesis of 2'-deoxy-2'-fluorouridine was accomplished by the modification of a literature procedure in which 2,2'-anhydro-1-beta-D-arabinofuranosyluracil was treated with 70% hydrogen fluoride-pyridine. Standard procedures were used to obtain the 5'-DMT and 5'-DMT-3'phosphoramidites.

2'-Fluorodeoxycytidine

2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3'phosphoramidites.

2'-O-(2-Methoxyethyl) Modified Amidites

2'-O-Methoxyethyl-substituted nucleoside amidites are prepared as follows, or alternatively, as per the methods of Martin, P., *Helvetica Chimica Acta*, 1995, 78, 486–504.

2,2'-Anhydro[1-(beta-D-arabinofuranosyl)-5-methyluridine]

5-Methyluridine (ribosylthymine, commercially available through Yamasa, Choshi, Japan) (72.0 g, 0.279 M), diphenyl-carbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid that was crushed to a light tan powder (57 g, 85% crude yield). The NMR spectrum was consistent with the structure, contaminated with phenol as its sodium salt (ca. 5%). The material was used as is for further reactions (or it can be purified further by column chromatography using a gradient of methanol in ethyl acetate (10–25%) to give a white solid, mp 222–4° C.).

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

2'-O-Nethoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/hexane/acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by TLC by first quenching the TLC sample with the addition of MeOH. Upon completion of the reaction, as judged by TLC, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/hexane(4:1). Pure product fractions were evaporated to yield 96 g (84%). An additional 1.5 g was recovered from later fractions.

3'-O-Acetyl-2'-O-methoxyethyl-5'-O-dimethoxytrityl-5-methyl-4-triazoleuridine A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0–10° C., and the resulting mixture stirred for an additional 2 hours. The first solution was added dropwise, over a 45 minute period, to the latter solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of NaHCO$_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and NH$_4$OH (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with NH$_3$ gas was added and the vessel heated to 100° C. for 2 hours (TLC showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N4-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, TLC showed the reaction to be approximately 95% complete. The solvent was evaporated and the residue azeotroped with MeOH (200 mL). The residue was dissolved in CHCl$_3$ (700 mL) and extracted with saturated NaHCO$_3$ (2×300 mL) and saturated NaCl (2×300 mL), dried over MgSO$_4$ and evaporated to give a residue (96 g). The residue was chromatographed on a 1.5 kg silica column using EtOAc/hexane (1:1) containing 0.5% Et$_3$NH as the eluting solvent. The pure product fractions were evaporated to give 90 g (90%) of the title compound.

N4-Benzoyl-2'-O-methoxyethyl-5'-O-dimethoxytrityl-5-methylcytidine-3'-amidite N4-Benzoyl-2'-O-methoxyethyl-5'-O-dimethoxytrityl-5-methylcytidine (74 g, 0.10 M) was dissolved in CH$_2$Cl$_2$ (1 L). Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (TLC showed the reaction to be 95% complete). The reaction mixture was extracted with saturated NaHCO$_3$ (1×300 mL) and saturated NaCl (3×300 mL). The aqueous washes were back-extracted with CH$_2$Cl$_2$ (300 mL), and the extracts were combined, dried over MgSO$_4$ and concentrated. The residue obtained was chromatographed on a 1.5 kg silica column using EtOAc/hexane (3:1) as the eluting solvent. The pure fractions were combined to give 90.6 g (87%) of the title compound.

2'-O-(Aminooxyethyl) Nucleoside Amidites and 2'-O-(dimethylaminooxyethyl) Nucleoside Amidites

2'-(Dimethylaminooxyethoxy) nucleoside amidites

2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-O$^2$-2'-anhydro-5-methyluridine

O$^2$-2'-anhydro-5-methyluridine (Pro. Bio. Sint., Varese, Italy, 100.0 g, 0.416 mmol), dimethylaminopyridinex (0.66 g, 0.013 eq, 0.0054 mmol) were dissolved in dry pyridine (500 ml) at ambient temperature under an argon atmosphere and with mechanical stirring. Tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-O$^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure<100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-phthalimidoxy)ethyl]-5'-t-butyldiphenylsilyl-5-methyluridine

5'-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over P$_2$O$_5$ under high vacuum for two days at 40° C. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819 g, 86%).

5'-O-tert-butyldiphenylsilyl-2'-O-[(2-formadoximinooxy)ethyl]-5-methyluridine 2'-O-([2-phthalimidoxy)ethyl]-5'-t-butyldiphenylsilyl-5-methyluridine (3.1 g, 4.5 mmol) was dissolved in dry $CH_2Cl_2$ (4.5 mL) and methylhydrazine (300 mL, 4.64 mmol) was added dropwise at −10° C. to 0° C. After 1 h the mixture was filtered, the filtrate was washed with ice cold $CH_2Cl_2$ and the combined organic phase was washed with water, brine and dried over anhydrous $Na_2SO_4$. The solution was concentrated to get 2'-O-(aminooxyethyl) thymidine, which was then dissolved in MeOH (67.5 mL). To this formaldehyde (20% aqueous solution, w/w, 1.1 eq.) was added and the resulting mixture was stirrred for 1 h. Solvent was removed under vacuum; residue chromatographed to get 5'-O-tert-butyldiphenylsilyl-2'-O-[(2-formadoximinooxy) ethyl]-5-methyluridine as white foam (1.95 g, 78%).

5'-O-tert-Butyldiphenylsilyl-2'-O-[N,N-dimethylaminooxyethyl]-5-methyluridine 5'-O-tert-butyldiphenylsilyl-2'-O-[(2-formadoximinooxy) ethyl]-5-methyluridine (1.77 g, 3.12 mmol) was dissolved in a solution of 1 M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 h, the reaction monitored by TLC (5% MeOH in $CH_2Cl_2$). Aqueous $NaHCO_3$ solution (5%, 10 mL) was added and extracted with ethyl acetate (2×20 mL). Ethyl acetate phase was dried over anhydrous $Na_2SO_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% $NaHCO_3$ (25 mL) solution was added and extracted with ethyl acetate (2×25 mL). Ethyl acetate layer was dried over anhydrous $Na_2SO_4$ and evaporated to dryness . The residue obtained was purified by flash column chromatography and eluted with 5% MeOH in $CH_2Cl_2$ to get 5'-O-tert-butyldiphenylsilyl-2'-O-[N,N-dimethylaminooxyethyl]-5-methyluridine as a white foam (14.6 g, 80%).

2'-O-(dimethylaminooxyethyl)-5-methyluridine

Triethylamine trihydrofluoride (3.9 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O-[N,N-dimethylaminooxyethyl]-5-methyluridine (1.40 g, 2.4 mmol) and stirred at room temperature for 24 hrs. Reaction was monitored by TLC (5% MeOH in $CH_2Cl_2$). Solvent was removed under vacuum and the residue placed on a flash column and eluted with 10% MeOH in $CH_2Cl_2$ to get 2'-O-(dimethylaminooxyethyl)-5-methyluridine (766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) was dried over $P_2O_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in $CH_2Cl_2$ (containing a few drops of pyridine) to get 5'-O-DMT-2'-O-(dimethylamino-oxyethyl)-5-methyluridine (1.13 g, 80%).

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over $P_2O_5$ under high vacuum overnight at 40° C. Then the reaction mixture was dissolved in anhydrous acetonitrile (8.4 mL) and 2-cyanoethyl-N,N,$N^1$,$N^1$-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous $NaHCO_3$ (40 mL). Ethyl acetate layer was dried over anhydrous $Na_2SO_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

2'-(Aminooxyethoxy) Nucleoside Amidites

2'-(Aminooxyethoxy) nucleoside amidites [also known in the art as 2'-O-(aminooxyethyl) nucleoside amidites] are prepared as described in the following paragraphs. Adenosine, cytidine and thymidine nucleoside amidites are prepared similarly.

N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite]

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl) diaminopurine riboside along with a minor amount of the 3'-O-isomer. 2'-O-(2-ethylacetyl) diaminopurine riboside may be resolved and converted to 2'-O-(2-ethylacetyl)guanosine by treatment with adenosine deaminase. (McGee, D. P. C., Cook, P. D., Guinosso, C. J., WO 94/02501 A1 940203. ) Standard protection procedures should afford 2'-O-(2-ethylacetyl)-5'-O-(4,4'-dimethoxytrityl)guanosine and 2-N-isobutyryl-6-O-diphenylcarbamoyl-2'-O-(2-ethylacetyl)-5'-O-(4,4'-dimethoxytrityl)guanosine which may be reduced to provide 2-N-isobutyryl-6-O-diphenylcarbamoyl-2'-O-(2-hydroxyethyl)-5'-O-(4,4'-dimethoxytrityl)guanosine. As before the hydroxyl group may be displaced by N-hydroxyphthalimide via a Mitsunobu reaction, and the protected nucleoside may phosphitylated as usual to yield 2-N-isobutyryl-6-O-diphenylcarbamoyl-2'-O-([2-phthalmidoxy]ethyl)-5'-O-(4,4'-dimethoxytrityl)guanosine-3'-[(2-cyanoethyl)-N,N-diisopropylphosphoramidite].

2'-dimethylaminoethoxyethoxy (2'-DMAEOE) Nucleoside Amidites

2'-dimethylaminoethoxyethoxy nucleoside amidites (also known in the art as 2'-O-dimethylaminoethoxyethyl, i.e., 2'-O-CH$_2$-O-CH$_2$-N(CH$_2$)$_2$, or 2'-DMAEOE nucleoside amidites) are prepared as follows. Other nucleoside amidites are prepared similarly.

2'-O-[2(2-N,N-dimethylaminoethoxy)ethyl]-5-methyl Uridine

2[2-(Dimethylamino)ethoxy]ethanol (Aldrich, 6.66 g, 50 mmol) is slowly added to a solution of borane in tetrahydrofuran (1 M, 10 mL, 10 mmol) with stirring in a 100 mL bomb. Hydrogen gas evolves as the solid dissolves. O$^2$-,2'-anhydro-5-methyluridine (1.2 g, 5 mmol), and sodium bicarbonate (2.5 mg) are added and the bomb is sealed, placed in an oil bath and heated to 155° C. for 26 hours. The bomb is cooled to room temperature and opened. The crude solution is concentrated and the residue partitioned between water (200 mL) and hexanes (200 mL). The excess phenol is extracted into the hexane layer. The aqueous layer is extracted with ethyl acetate (3×200 mL) and the combined organic layers are washed once with water, dried over anhydrous sodium sulfate and concentrated. The residue is columned on silica gel using methanol/methylene chloride 1:20 (which has 2% triethylamine) as the eluent. As the column fractions are concentrated a colorless solid forms which is collected to give the title compound as a white solid.

5'-O-dimethoxytrityl-2'-O-[2(2-N,N-dimethylaminoethoxy) ethyl)]-5-methyl Uridine To 0.5 g (1.3 mmol) of 2'-O-[2(2-N,N-dimethylaminoethoxy)ethyl)]-5-methyl uridine in anhydrous pyridine (8 mL), triethylamine (0.36 mL) and dimethoxytrityl chloride (DMT-Cl, 0.87 g, 2 eq.) are added and stirred for 1 hour. The reaction mixture is poured into water (200 mL) and extracted with CH$_2$Cl$_2$ (2×200 mL). The combined CH$_2$Cl$_2$ layers are washed with saturated NaHCO$_3$ solution, followed by saturated NaCl solution and dried over anhydrous sodium sulfate. Evaporation of the solvent followed by silica gel chromatography using MeOH:CH$_2$Cl$_2$:Et$_3$N (20:1, v/v, with 1% triethylamine) gives the title compound.

5'-O-Dimethoxytrityl-2'-O-[2(2-N,N-dimethylaminoethoxy)-ethyl)]-5-methyl uridine-3'-O-(cyanoethyl-N,N-diisopropyl)phosphoramidite Diisopropylaminotetrazolide (0.6 g) and 2-cyanoethoxy-N,N-diisopropyl phosphoramidite (1.1 mL, 2 eq.) are added to a solution of 5'-O-dimethoxytrityl-2'-O-[2(2-N,N-dimethylaminoethoxy)ethyl)]-5-methyluridine (2.17 g, 3 mmol) dissolved in CH$_2$Cl$_2$ (20 mL) under an atmosphere of argon. The reaction mixture is stirred overnight and the solvent evaporated. The resulting residue is purified by silica gel flash column chromatography with ethyl acetate as the eluent to give the title compound.

Example 2

Oligonucleotide Synthesis

Unsubstituted and substituted phosphodiester (P=O) oligonucleotides are synthesized on an automated DNA synthesizer (Applied Biosystems model 380B) using standard phosphoramidite chemistry with oxidation by iodine.

Phosphorothioates (P=S) are synthesized as for the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55° C. (18 h), the oligonucleotides were purified by precipitating twice with 2.5 volumes of ethanol from a 0.5 M NaCl solution.

Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Example 3

Oligonucleoside Synthesis

Methylenemethylimino linked oligonucleosides, also identified as MMI linked oligonucleosides, methylenedimethyl-hydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4

PNA Synthesis

Peptide nucleic acids (PNAs) are prepared in accordance with any of the various procedures referred to in Peptide Nucleic Acids (PNA): Synthesis, Properties and Potential Applications, *Bioorganic & Medicinal Chemistry*, 1996, 4, 5–23. They may also be prepared in accordance with U.S. Pat. Nos. 5,539,082, 5,700,922, and 5,719,262, herein incorporated by reference.

Example 5

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]—[2'-deoxy]—[2'-O-Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 380B, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by increasing the wait step after the delivery of tetrazole and base to 600 s repeated four times for RNA and twice for 2'-O-methyl. The fully protected oligonucleotide is cleaved from the support and the phosphate group is deprotected in 3:1 ammonia/ethanol at room temperature overnight then lyophilized to dryness. Treatment in methanolic ammonia for 24 hrs at room temperature is then done to deprotect all bases and sample was again lyophilized to dryness. The pellet is resuspended in 1M TBAF in THF for 24 hrs at room temperature to deprotect the 2' positions. The reaction is then quenched with 1M TEAA and the sample is then reduced to ½ volume by rotovac before being desalted on a G25 size exclusion column. The oligo recovered is then analyzed spectrophotometrically for yield and for purity by capillary electrophoresis and by mass spectrometry.

[2'-O-(2-Methoxyethyl)]—[2'-deoxy]—[2'-O-(Methoxyethyl)] Chimeric Phosphorothioate Oligonucleotides

[2'-O-(2-methoxyethyl)]—[2'-deoxy]—[-2-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]—[2'-deoxy Phosphorothioate]—[2'-O-(2-Methoxyethyl) Phosphodiester] Chimeric Oligonucleotides

[2'-O-(2-methoxyethyl phosphodiester]—[2'-deoxy phosphorothioate]—[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidization with iodine to generate the phosphodiester internucleotide linkages within the wing portions of the chimeric structures and sulfurization utilizing 3, H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6

Oligonucleotide Isolation

After cleavage from the controlled pore glass column (Applied Biosystems) and deblocking in concentrated ammonium hydroxide at 55° C. for 18 hours, the oligonucleotides or oligonucleosides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}$p nuclear magnetic resonance spectroscopy, and for some studies oligonucleotides were purified by HPLC, as described by Chiang et al., *J. Biol. Chem.* 1991, 266, 18162–18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a standard 96 well format. Phosphodiester internucleotide linkages were afforded by oxidation with aqueous iodine. Phosphorothioate internucleotide linkages were generated by sulfurization utilizing 3, H-1,2 benzodithiole-3-one 1,1 dioxide (Beaucage Reagent) in anhydrous acetonitrile. Standard base-protected beta-cyanoethyldiisopropyl phosphoramidites were purchased from commercial vendors (e.g. PE-Applied Biosystems, Foster City, Calif., or Pharmacia, Piscataway, N.J.). Non-standard nucleosides are synthesized as per known literature or patented methods. They are utilized as base protected betacyanoethyldiisopropyl phosphoramidites.

Oligonucleotides were cleaved from support and deprotected with concentrated NH$_4$OH at elevated temperature (55–60° C.) for 12–16 hours and the released product then dried in vacuo. The dried product was then re-suspended in sterile water to afford a master plate from which all analytical and test plate samples are then diluted utilizing robotic pipettors.

Example 8

Oligonucleotide Analysis—96 Well Plate Format

The concentration of oligonucleotide in each well was assessed by dilution of samples and UV absorption spectroscopy. The full-length integrity of the individual products was evaluated by capillary electrophoresis (CE) in either the 96 well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following 4 cell types are provided for illustrative purposes, but other cell types can be routinely used, provided that the target is expressed in the cell type chosen. This can be readily determined by methods routine in the art, for example Northern blot analysis, Ribonuclease protection assays, or RT-PCR.

T-24 cells:

The human transitional cell bladder carcinoma cell line T-24 was obtained from the American Type Culture Collection (ATCC) (Manassas, Va.). T-24 cells were routinely cultured in complete McCoy's 5A basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 cells:

The human lung carcinoma cell line A549 was obtained from the American Type Culture Collection (ATCC) (Manassas, Va.). A549 cells were routinely cultured in DMEM basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence.

NHDF cells:

Human neonatal dermal fibroblast (NHDF) were obtained from the Clonetics Corporation (Walkersville Md.). NHDFs were routinely maintained in Fibroblast Growth Medium (Clonetics Corporation, Walkersville Md.) supplemented as recommended by the supplier. Cells were maintained for up to 10 passages as recommended by the supplier.

HEK cells:

Human embryonic keratinocytes (HEK) were obtained from the Clonetics Corporation (Walkersville Md.). HEKs were routinely maintained in Keratinocyte Growth Medium (Clonetics Corporation, Walkersville Md.) formulated as recommended by the supplier. Cells were routinely maintained for up to 10 passages as recommended by the supplier.

Treatment With Antisense Compounds:

When cells reached 80% confluency, they were treated with oligonucleotide. For cells grown in 96-well plates, wells were washed once with 200 μL OPTI-MEM™-1 reduced-serum medium (Gibco BRL) and then treated with 130 μL of OPTI-MEM™-1 containing 3.75 μg/mL LIPOFECTIN™ (Gibco BRL) and the desired concentration of oligonucleotide. After 4–7 hours of treatment, the medium was replaced with fresh medium. Cells were harvested 16–24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is ISIS 13920, TCCGTCATCGCTCCTCAGGG, SEQ ID NO: 1, a 2'-O-methoxyethyl gapmer (2'-O-methoxyethyls shown in bold) with a phosphorothioate backbone which is targeted to human H-ras. For mouse or rat cells the positive control oligonucleotide is ISIS 15770, ATGCATTCTGCCCCCAAGGA, SEQ ID NO: 2, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-Ha-ras (for ISIS 13920) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of H-ras or c-raf mRNA is then utilized as the oligonucleotide screening concentration in subsequent experiments for that cell line. If 60% inhibition is not achieved, that particular cell line is deemed as unsuitable for oligonucleotide transfection experiments.

Example 10

Analysis of oligonucleotide inhibition of WRN expression

Antisense modulation of WRN expression can be assayed in a variety of ways known in the art. For example, WRN mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+mRNA. Methods of RNA isolation are taught in, for example, Ausubel, F. M. et al., *Current Protocols in Molecular Biology*, Volume 1, pp. 4.1.1–4.2.9 and 4.5.1–4.5.3, John Wiley & Sons, Inc., 1993. Northern blot analysis is routine in the art and is taught in, for example, Ausubel, F. M. et al., *Current Protocols in Molecular Biology*, Volume 1, pp. 4.2.1–4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Protein levels of WRN can be quantitated in a variety of ways well known in the art, such as immunoprecipitation, Western blot analysis (immunoblotting), ELISA or fluorescence-activated cell sorting (FACS). Antibodies directed to WRN can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., *Current Protocols in Molecular Biology*, Volume 2, pp. 11.12.1–11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1–11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1–10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1–10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1–11.2.22, John Wiley & Sons, Inc., 1991.

Example 11

Poly(A)+mRNA Isolation

Poly(A)+mRNA was isolated according to Miura et al., *Clin. Chem.*, 1996, 42, 1758–1764. Other methods for poly(A)+mRNA isolation are taught in, for example, Ausubel, F. M. et al., *Current Protocols in Molecular Biology*, Volume 1, pp. 4.5.1–4.5.3, John Wiley & Sons, Inc., 1993. Briefly, for cells grown on 96-well plates, growth medium was removed from the cells and each well was washed with 200 μL cold PBS. 60 μL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 μL of lysate was transferred to Oligo d(T) coated 96-well plates (AGCT Inc., Irvine Calif.). Plates were incubated for 60 minutes at room temperature, washed 3 times with 200 μL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 μL of elution buffer (5 mM Tris-HCl pH 7.6), preheated to 70° C. was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Example 12

Total RNA Isolation

Total RNA was isolated using an RNEASY 96™ kit and buffers purchased from Qiagen Inc. (Valencia Calif.) following the manufacturer's recommended procedures. Briefly, for cells grown on 96-well plates, growth medium was removed from the cells and each well was washed with 200 μL cold PBS. 100 μL Buffer RLT was added to each well and the plate vigorously agitated for 20 seconds. 100 μL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. vacuum was applied for 15 seconds. 1 mL of Buffer RW1 was added to each well of the RNEASY 96™ plate and the vacuum gain applied for 15 seconds. 1 mL of Buffer RPE was then added to each well of the RNEASY 96™ plate and the vacuum applied for a period of 15 seconds. The Buffer RPE wash was then repeated and the vacuum was applied for an additional 10 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 60 μL water into each well, incubating 1 minute, and then applying the vacuum for 30 seconds. The elution step was repeated with an additional 60 μL water.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-time Quantitative PCR Analysis of WRN mRNA Levels

Quantitation of WRN mRNA levels was determined by real-time quantitative PCR using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., JOE, FAM, or VIC, obtained from either Operon Technologies Inc., Alameda, Calif. or PE-Applied Biosystems, Foster City, Calif.) is attached to the 5' end of the probe and a quencher dye (e.g., TAMRA, obtained from either Operon Technologies Inc., Alameda, Calif. or PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from PE-Applied Biosystems, Foster City, Calif. RT-PCR reactions were carried out by adding 25 μL PCR cocktail (1×TAQMAN™ buffer A, 5.5 mM MgCl$_2$, 300 μM each of DATP, dCTP and dGTP, 600 μM of dUTP, 100 nM each of forward primer, reverse primer, and probe, 20 Units RNAse inhibitor, 1.25 Units AMPLITAQ GOLD™, and 12.5 Units MuLV reverse transcriptase) to 96 well plates containing 25 μL total RNA solution. The RT reaction was carried out by incubation for 30 minutes at 48° C. Following a 10 minute incubation at 95° C. to activate the AMPLITAQ GOLD™, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent from Molecular Probes. Methods of RNA quantification by RiboGreen™ are taught in Jones, L. J., et al, *Analytical Biochemistry*, 1998, 265, 368–374.

In this assay, 175 μL of RiboGreen™ working reagent (RiboGreen™ reagent diluted 1:2865 in 10 mM Tris-HCl, 1 mM EDTA, pH 7.5) is pipetted into a 96-well plate containing 25μL purified, cellular RNA. The plate is read in a CytoFluor 4000 (PE Applied Biosystems) with excitation at 480 nm and emission at 520 nm. Probes and primers to human WRN were designed to hybridize to a human WRN sequence, using published sequence information (GenBank accession number AF181897, incorporated herein as SEQ ID NO:3). For human WRN the PCR primers were: forward primer: ATCCCAAGCGGTGAAAGCT (SEQ ID NO: 4) reverse primer: GGTTTCGGATAACATCAGCAATAA (SEQ ID NO: 5) and the PCR probe was: FAM-CCCCCTTGATTTGGAGCGAGCA-TAMRA (SEQ ID NO: 6) where FAM (PE-Applied Biosystems, Foster City, Calif.) is the fluorescent reporter dye and TAMRA (PE-Applied Biosystems, Foster City, Calif.) is the quencher dye. For human GAPDH the PCR primers were: forward primer: GAAGGTGAAGGTCGGAGTC (SEQ ID NO: 7) reverse primer: GAAGATGGTGATGGGATTTC (SEQ ID NO: 8) and the PCR probe was: 5' JOE-CAAGCTTCCCGTTCTCAGCCX- TAMRA 3' (SEQ ID NO: 9) where JOE (PE-Applied Biosystems, Foster City, Calif.) is the fluorescent reporter dye and TAMRA (PE-Applied Biosystems, Foster City, Calif.) is the quencher dye.

Example 14

Northern Blot Analysis of WRN mRNA Levels

Eighteen hours after antisense treatment, cell monolayers were washed twice with cold PBS and lysed in 1 mL RNAZOL™ (TEL-TEST "B" Inc., Friendswood, Tex.).

Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then robed using QUICKHYBTM hybridization solution (Stratagene, La Jolla, Calif.) using manufacturer's recommendations for stringent conditions.

To detect human WRN, a human WRN specific probe was prepared by PCR using the forward primer ATC-CCAAGCGGTGAAAGCT (SEQ ID NO: 4) and the reverse primer GGTTTCGGATAACATCAGCAATAA (SEQ ID NO: 5). To normalize for variations in loading and transfer efficiency membranes were stripped and probed for human glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANTTM Software V3.3 (Molecular Dynamics, Sunnyvale, Calif.). Data was normalized to GAPDH levels in untreated controls.

Example 15

Antisense Inhibition of Human WRN Expression by Chimeric Phosphorothioate Oligonucleotides Having 2'-NOE Wings and a Deoxy Gap In accordance with the present invention, a series of oligonucleotides were designed to target different regions of the human WRN gene, using published sequences (GenBank accession number AF181897 characterized as genomic sequence encoding exons 21–35 of the human WRN gene, incorporated herein as SEQ ID NO: 3; GenBank accession number AF181896 characterized as genomic sequence encoding exons 1–20 of the human WRN gene, incorporated herein as SEQ ID NO: 10; GenBank accession number AF091214 encoding the complete cds, incorporated herein as SEQ ID NO: 11; and GenBank accession number AA249288 which extends the 3'UTR region of the human WRN gene, incorporated herein as SEQ ID NO: 12). The oligonucleotides are shown in Table 1. "Target site" indicates the first (5'-most) nucleotide number on the particular target sequence to which the oligonucleotide binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on human WRN mRNA levels by quantitative real-time PCR as described in other examples herein. Data are averages from two experiments. If present, "N.D." indicates "no data".

TABLE 1

Inhibition of human WRN mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 137442 | Intron | 10 | 37091 | tctcacggtttgggactcaa | 91 | 13 |
| 137443 | Intron | 10 | 38448 | agataatagctcttctatat | 50 | 14 |
| 137444 | Intron | 10 | 54755 | tcagtagagcaaagctgctt | 91 | 15 |
| 137445 | Intron | 10 | 55220 | ggtaattacgtggcaaaacc | 24 | 16 |
| 137446 | Intron | 10 | 81922 | caaactttaggttttcaatg | 76 | 17 |
| 137447 | Intron | 10 | 94616 | tcacctaagatctgtagaaa | 69 | 18 |
| 137448 | Intron | 3 | 9993 | gtcagaaaacactttctata | 71 | 19 |
| 137449 | Intron | 3 | 12240 | cacggtttgccaatgaggca | 68 | 20 |
| 137450 | Intron | 3 | 17702 | taaaggaatcatattccctt | 93 | 21 |
| 137451 | Intron | 3 | 18784 | cagaggttcaaagatgttaa | 79 | 22 |
| 137452 | Intron | 3 | 64718 | atgtgtggctgactgctgag | 47 | 23 |
| 137453 | Intron | 3 | 80767 | tgcttcaacaagtaattaca | 0 | 24 |
| 137454 | 5'UTR | 11 | 32 | aaactttattcccgcgctgc | 91 | 25 |
| 137455 | 5'UTR | 11 | 174 | tcttcatgggtaaatacaaa | 70 | 26 |
| 137456 | Start Codon | 11 | 222 | tttcactcatctttgaaatg | 88 | 27 |
| 137457 | Coding | 11 | 318 | gaacacatgcctttcttcct | 60 | 28 |
| 137458 | Coding | 11 | 390 | tagcatcgtaactatacaca | 90 | 29 |
| 137459 | Coding | 11 | 431 | tagactcatgctaatatctt | 80 | 30 |
| 137460 | Coding | 11 | 460 | atgtcaaatcccaccacatc | 91 | 31 |
| 137461 | Coding | 11 | 822 | gaaatttactccaattgcta | 14 | 32 |
| 137462 | Coding | 11 | 844 | agtttctggtcctcagtgag | 67 | 33 |
| 137463 | Coding | 11 | 850 | gcatacagtttctggtcctc | 76 | 34 |
| 137464 | Coding | 11 | 856 | gtggctgcatacagtttctg | 59 | 35 |
| 137465 | Coding | 11 | 862 | gcatcagtggctgcatacag | 63 | 36 |
| 137466 | Coding | 11 | 1249 | gtttcatcttcaacgtgaat | 13 | 37 |
| 137467 | Coding | 11 | 1262 | tgttgggtcccatgtttcat | 75 | 38 |
| 137468 | Coding | 11 | 1282 | tgtttagctaaatgatcaag | 69 | 39 |
| 137469 | Coding | 11 | 1427 | caaaatttggagttcatgtt | 82 | 40 |
| 137470 | Coding | 11 | 1491 | gagataaatgctcagtagat | 26 | 41 |
| 137471 | Coding | 11 | 1496 | attgggagataaatgctcag | 76 | 42 |
| 137472 | Coding | 11 | 1572 | gagataaatgcttaagcatc | 29 | 43 |
| 137473 | Coding | 11 | 1580 | atcattgggagataaatgct | 85 | 44 |
| 137474 | Coding | 11 | 1653 | tttctaaagacttaagcatc | 83 | 45 |
| 137475 | Coding | 11 | 1684 | tgagttggttctaccgtgcc | 84 | 46 |
| 137476 | Coding | 11 | 1847 | gccaaagtacatcttgaggc | 67 | 47 |
| 137477 | Coding | 11 | 1874 | ccactgaactggtttaaaac | 77 | 48 |
| 137478 | Coding | 11 | 1938 | catatccagttgccatgaca | 77 | 49 |
| 137479 | Coding | 11 | 2051 | gttggacatttaagctgta | 0 | 50 |
| 137480 | Coding | 11 | 2153 | tgaacagtattctggagtta | 51 | 51 |
| 137481 | Coding | 11 | 2221 | gcctcatccacagcaatgag | 64 | 52 |
| 137482 | Coding | 11 | 2227 | cagtgagcctcatccacagc | 95 | 53 |
| 137483 | Coding | 11 | 2495 | ccagtgggaacttgttttga | 63 | 54 |
| 137484 | Coding | 11 | 2511 | ttggaccttcaaattcccag | 95 | 55 |
| 137485 | Coding | 11 | 2665 | acacactgaatttcatctct | 56 | 56 |
| 137486 | Coding | 11 | 2670 | ctatgacacactgaatttca | 20 | 57 |
| 137487 | Coding | 11 | 2696 | aatgcccattccaaaagcta | 71 | 58 |
| 137488 | Coding | 11 | 2702 | tttattaatgcccattccaa | 91 | 59 |
| 137489 | Coding | 11 | 2709 | tgtcagctttattaatgccc | 89 | 60 |
| 137490 | Coding | 11 | 2715 | ggcgaatgtcagctttatta | 47 | 61 |
| 137491 | Coding | 11 | 2769 | caatctcctgataatatgat | 88 | 62 |
| 137492 | Coding | 11 | 2852 | aagaaggtgcctatttaagt | 60 | 63 |
| 137493 | Coding | 11 | 2954 | caagatgatttgtctcctac | 72 | 64 |
| 137494 | Coding | 11 | 3016 | cattttcagttcccataat | 77 | 65 |
| 137495 | Coding | 11 | 3024 | tatcacagcattttcagtt | 85 | 66 |
| 137496 | Coding | 11 | 3030 | tgcaattatcacagcatttt | 82 | 67 |
| 137497 | Coding | 11 | 3181 | ttagatcctcggagaaataa | 80 | 68 |
| 137498 | Coding | 11 | 3187 | tgagaattagatcctcggag | 70 | 69 |
| 137499 | Coding | 11 | 3225 | caaataaactgtgcctgcga | 93 | 70 |
| 137500 | Coding | 11 | 3265 | aaagccttccaccaactctc | 92 | 71 |
| 137501 | Coding | 11 | 3455 | agttttcgaactaggcagaa | 59 | 72 |
| 137502 | Coding | 11 | 3531 | ccaagttagacttcttctct | 88 | 76 |
| 137503 | Coding | 11 | 3681 | ataacacaatctgagtctcc | 84 | 74 |
| 137507 | Coding | 11 | 3830 | ttcagaaacaccatcaatcc | 90 | 75 |
| 137505 | Coding | 11 | 3877 | aaatgtttgatgacttccaa | 88 | 76 |
| 137506 | Coding | 11 | 3930 | cttgaggttttgtacttgaa | 80 | 77 |
| 137507 | Coding | 11 | 3999 | atgtgatggccatagactgt | 71 | 78 |
| 137508 | Coding | 11 | 4234 | tcaggaactaacattctgat | 91 | 79 |
| 137509 | Coding | 11 | 4240 | atgttttcaggaactaacat | 77 | 80 |
| 137510 | Coding | 11 | 4274 | gatctcaattgccatgtgga | 74 | 81 |
| 137511 | Stop Codon | 11 | 4519 | ttgccagcttaactaaaaag | 83 | 82 |

TABLE 1-continued

Inhibition of human WRN mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 137512 | 3'UTR | 11 | 4540 | gaaacataattgttctggta | 83 | 83 |
| 137513 | 3'UTR | 11 | 4589 | tccttactcttcagaaataa | 0 | 84 |
| 137514 | 3'UTR | 11 | 4605 | taagccaaaatactactcct | 79 | 85 |
| 137515 | 3'UTR | 11 | 4642 | ttcaataaacagtgaacttt | 88 | 86 |
| 137516 | 3'UTR | 11 | 4980 | acgtatttaagaacttcttc | 86 | 87 |
| 137517 | 3'UTR | 11 | 5156 | aaaaacattgttttattact | 10 | 88 |
| 137518 | 3'UTR | 12 | 261 | gtcacatgtgctacataaga | 72 | 89 |
| 137519 | 3'UTR | 12 | 299 | ttacccaactctgtgtcaca | 90 | 90 |

As shown in Table 1, SEQ ID NOs 13, 14, 15, 17, 18, 19, 20, 21, 22, 23, 25, 26, 27, 28, 29, 30, 31, 33, 34, 35, 36, 38, 39, 40, 42, 44, 45, 46, 47, 48, 49, 51, 52, 53, 54, 55, 56, 58, 59, 60, 61, 62, 63, 64, 65, 66, 67, 68, 69, 70, 71, 72, 73, 74, 75, 76, 77, 78, 79, 80, 81, 82, 83, 85, 86, 87, 89 and 90 demonstrated at least 40% inhibition of human WRN expression in this assay and are therefore preferred. The target sites to which these preferred sequences are complementary are herein referred to as "active sites" and are therefore preferred sites for targeting by compounds of the present invention.

Example 16

Western Blot Analysis of WRN Protein Levels

Western blot analysis (immunoblot analysis) is carried out using standard methods. Cells are harvested 16–20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to WRN is used, with a radiolabelled or fluorescently labeled secondary antibody directed against the primary antibody species. Bands are visualized using a PHOSPHORIMAGER™ (Molecular Dynamics, Sunnyvale Calif.).

What is claimed is:

1. A compound 8 to 50 nucleobases in length targeted to nucleotides 37091 through 37110, nucleotides 38448 through 38467, nucleotides 54755 through 54774, nucleotides 55220 through 55239, nucleotides 81922 through 81941, nucleotides 94616 through 94635 (SEQ ID NO: 10), nucleotides 9993 through 10012, nucleotides 12240 through 12259, nucleotides 17702 through 17721, nucleotides 18784 through 18803, nucleotides 64718 through 64737 or SEQ ID NO: 10, or nucleotides 80767 through 80786 of an intron region (SEQ ID NO: 3), nucleotides 32 through 51 or nucleotides 174 through 193 of a 5'-untranslated region (SEQ ID NO: 11), nucleotides 222 through 241 of a start codon region (SEQ ID NO: 11), nucleotides 318 through 337, nucleotides 390 through 409, nucleotides 431 through 450, nucleotides 460 through 479, nucleotides 822 through 841, nucleotides 844 through 881, nucleotides 1249 through 1301, nucleotides 1427 through 1446, nucleotides 1491 through 1515, nucleotides 1572 through 1599, nucleotides 1653 through 1672, nucleotides 1684 through 1703, nucleotides 1847 through 1866, nucleotides 1874 through 1893, nucleotides 1938 through 1957, nucleotides 2051 through 2070, nucleotides 2153 through 2152, nucleotides 2221 through 2246, nucleotides 2495 through 2530, nucleotides 2665 through 2689, nucleotides 2696 through 2734, nucleotides 2769 through 2788, nucleotides 2852 through 2871, nucleotides 2954 through 2973, nucleotides 3016 through 3049, nucleotides 3181 through 3206, nucleotides 3225 through 3244, nucleotides 3265 through 3284, nucleotides 3455 through 3474, nucleotides 3531 through 3550, nucleotides 3681 through 3700, nucleotides 3830 through 3849, nucleotides 3877 through 3896, nucleotides 3930 through 3949, nucleotides 3999 through 4017, nucleotides 4234 through 4259, nucleotides 4274 through 4293, nucleotides 4519 through 4538, nucleotides 4240 through 4269, or nucleotides 4274 through 4293 of a coding region (SEQ ID NO: 11), nucleotides 4519 through 4538 of a stop codon region SEQ ID NO: 11), or nucleotides 4540 through 4559, nucleotides 4589 through 4624, nucleotides 4642 through 4661, nucleotides 4980 through 4999, nucleotides 5156 through 5175 (SEQ ID NO: 11), nucleotides 261 through 280, or nucleotides 299 through 318 of a 3'-untranslated region (SEQ ID NO: 12) of a nucleic acid molecule encoding human WRN, wherein said compound specifically hybridizes with one of said regions and inhibits the expression of human WRN.

2. The compound of claim 1 which is an antisense oligonucleotide.

3. A compound up to 30 nucleobases in length comprising at least a 8-nucleobase portion of SEQ ID NO: 13, 14, 15, 17, 18, 19, 20, 21, 22, 23, 25, 26, 27, 28, 29, 30, 31, 33, 34, 35, 36, 38, 39, 40, 42, 44, 45, 46, 47, 48, 49, 51, 52, 53, 54, 55, 56, 58, 59, 60, 61, 62, 63, 64, 65, 66, 67, 68, 69, 70, 71, 72, 73, 74, 75, 76, 77, 78, 79, 80, 81, 82, 83, 85, 86, 87, 89 or 90 which inhibits the expression of human WRN.

4. The compound of claim 2 wherein the antisense oligonucleotide comprises at least one modified internucleoside linkage.

5. The compound of claim 4 wherein the modified internucleoside linkage is a phosphorothioate linkage.

6. The compound of claim 2 wherein the antisense oligonucleotide comprises at least one modified sugar moiety.

7. The compound of claim 6 wherein the modified sugar moiety is a 2'-O-methoxyethyl sugar moiety.

8. The compound of claim 2 wherein the antisense oligonucleotide comprises at least one modified nucleobase.

9. The compound of claim 8 wherein the modified nucleobase is a 5-methylcytosine.

10. The compound of claim 2 wherein the antisense oligonucleotide is a chimeric oligonucleotide.

11. A compound 8 to 50 nucleobases in length which specifically hybridizes with at least an 8-nucleobase portion of an active site on a nucleic acid molecule encoding WRN.

12. A composition comprising the compound of claim 1 and a pharmaceutically acceptable carrier or diluent.

13. The composition of claim 12 further comprising a colloidal dispersion system.

14. The composition of claim 12 wherein the compound is an antisense oligonucleotide.

15. A method of inhibiting the expression of human WRN in cells or tissues comprising contacting said cells or tissues in vitro with the compound of claim 1 so that expression of human WRN is inhibited.

16. The compound of claim 3 which is an antisense oligonucleotide.

17. The compound of claim 16 wherein the antisense oligonucleotide comprises at least one modified internucleoside linkage.

18. The compound of claim 17 wherein the modified internucleoside linkage is a phosphorothioate linkage.

19. The compound of claim 16 wherein the antisense oligonucleotide comprises at least one modified sugar moiety.

20. The compound of claim 19 wherein the modified sugar moiety is a 2'-O-methoxyethyl sugar moiety.

21. The compound of claim 16 wherein the antisense oligonucleotide comprises at least one modified nucleobase.

22. The compound of claim 21 wherein the modified nucleobase is a 5-methylcytosine.

23. The compound of claim 16 wherein the antisense oligonucleotide is a chimeric oligonucleotide.

24. A composition comprising the compound of claim 3 and a pharmaceutically acceptable carrier or diluent.

25. The composition of claim 24 further comprising a colloidal dispersion system.

26. The composition of claim 24 wherein the compound is an antisense oligonucleotide.

27. A method of inhibiting the expression of human WRN in human cells or tissues comprising contacting said cells or tissues in vitro with the compound of claim 3 so that expression of human WRN is inhibited.

* * * * *

SEQUENCE LISTING

```
<160> NUMBER OF SEQ ID NOS: 90

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1
tccgtcatcg ctcctcaggg                                              20

<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2
atgcattctg cccccaagga                                              20

<210> SEQ ID NO 3
<211> LENGTH: 87543
<212> TYPE: DNA
<213> ORGANISM: Homo sapiens
<220> FEATURE:
<221> NAME/KEY: unsure
```

-continued

```
<222> LOCATION: 7421
<223> OTHER INFORMATION: unknown
<221> NAME/KEY: unsure
<222> LOCATION: 7427
<223> OTHER INFORMATION: unknown
<221> NAME/KEY: unsure
<222> LOCATION: 11609
<223> OTHER INFORMATION: unknown
<221> NAME/KEY: unsure
<222> LOCATION: 12605
<223> OTHER INFORMATION: unknown
<221> NAME/KEY: unsure
<222> LOCATION: 12742
<223> OTHER INFORMATION: unknown
<221> NAME/KEY: unsure
<222> LOCATION: 29370
<223> OTHER INFORMATION: unknown
<221> NAME/KEY: unsure
<222> LOCATION: 29422
<223> OTHER INFORMATION: unknown
<221> NAME/KEY: unsure
<222> LOCATION: 29979
<223> OTHER INFORMATION: unknown
<221> NAME/KEY: unsure
<222> LOCATION: 29980
<223> OTHER INFORMATION: unknown
<221> NAME/KEY: unsure
<222> LOCATION: 29981
<223> OTHER INFORMATION: unknown
<221> NAME/KEY: unsure
<222> LOCATION: 30136
<223> OTHER INFORMATION: unknown
<221> NAME/KEY: unsure
<222> LOCATION: 30140
<223> OTHER INFORMATION: unknown
<221> NAME/KEY: unsure
<222> LOCATION: 31205
<223> OTHER INFORMATION: unknown
<221> NAME/KEY: unsure
<222> LOCATION: 31206
<223> OTHER INFORMATION: unknown
<221> NAME/KEY: unsure
<222> LOCATION: 31592
<223> OTHER INFORMATION: unknown
<221> NAME/KEY: unsure
<222> LOCATION: 33095
<223> OTHER INFORMATION: unknown
<221> NAME/KEY: unsure
<222> LOCATION: 33160
<223> OTHER INFORMATION: unknown
<221> NAME/KEY: unsure
<222> LOCATION: 34066
<223> OTHER INFORMATION: unknown
<221> NAME/KEY: unsure
<222> LOCATION: 34072
<223> OTHER INFORMATION: unknown
<221> NAME/KEY: unsure
<222> LOCATION: 36816
<223> OTHER INFORMATION: unknown
<221> NAME/KEY: unsure
<222> LOCATION: 39020
<223> OTHER INFORMATION: unknown
<221> NAME/KEY: unsure
<222> LOCATION: 42164
<223> OTHER INFORMATION: unknown
<221> NAME/KEY: unsure
<222> LOCATION: 42459
<223> OTHER INFORMATION: unknown
<221> NAME/KEY: unsure
<222> LOCATION: 46808
<223> OTHER INFORMATION: unknown
<221> NAME/KEY: unsure
<222> LOCATION: 46823
<223> OTHER INFORMATION: unknown
<221> NAME/KEY: unsure
<222> LOCATION: 46826
<223> OTHER INFORMATION: unknown
<221> NAME/KEY: unsure
<222> LOCATION: 47291
```

-continued

```
<223> OTHER INFORMATION: unknown
<221> NAME/KEY: unsure
<222> LOCATION: 52786
<223> OTHER INFORMATION: unknown
<221> NAME/KEY: unsure
<222> LOCATION: 52787
<223> OTHER INFORMATION: unknown
<221> NAME/KEY: unsure
<222> LOCATION: 53384
<223> OTHER INFORMATION: unknown
<221> NAME/KEY: unsure
<222> LOCATION: 54684
<223> OTHER INFORMATION: unknown
<221> NAME/KEY: unsure
<222> LOCATION: 59215
<223> OTHER INFORMATION: unknown
<221> NAME/KEY: unsure
<222> LOCATION: 59235
<223> OTHER INFORMATION: unknown
<221> NAME/KEY: unsure
<222> LOCATION: 59242
<223> OTHER INFORMATION: unknown
<221> NAME/KEY: unsure
<222> LOCATION: 63290
<223> OTHER INFORMATION: unknown
<221> NAME/KEY: unsure
<222> LOCATION: 66614
<223> OTHER INFORMATION: unknown
<221> NAME/KEY: unsure
<222> LOCATION: 68660
<223> OTHER INFORMATION: unknown
<221> NAME/KEY: unsure
<222> LOCATION: 68697
<223> OTHER INFORMATION: unknown
<221> NAME/KEY: unsure
<222> LOCATION: 68718
<223> OTHER INFORMATION: unknown
<221> NAME/KEY: unsure
<222> LOCATION: 68733
<223> OTHER INFORMATION: unknown
<221> NAME/KEY: unsure
<222> LOCATION: 68739
<223> OTHER INFORMATION: unknown
<221> NAME/KEY: unsure
<222> LOCATION: 69785
<223> OTHER INFORMATION: unknown
<221> NAME/KEY: unsure
<222> LOCATION: 79134
<223> OTHER INFORMATION: unknown
<221> NAME/KEY: unsure
<222> LOCATION: 79198
<223> OTHER INFORMATION: unknown
<221> NAME/KEY: unsure
<222> LOCATION: 86336
<223> OTHER INFORMATION: unknown
<223> OTHER INFORMATION:

<400> SEQUENCE: 3
tcttctctct gaaagatgaa aggttagctc tctttcacat tcttaactgc ccttttttct      60
taccttgtcc atgtatttct aacccccttt cctcctaata tgtttatgtc ataattttgg     120
ctagattagt gtatacgatt tacataatta ttactctgta aatgctttt atgatctctg      180 agccatgtag tatattatgg ctatttttct ttcttatcta tttgtatttt tattgttatt     240
acctaaaaaa aaattttcta tgtcttatca ctaattcttc cctaaaattt cccacaattg     300
tgtaaactta cctcagtata ttcatagata tgagacattc tatcaatttt accctcttaa     360
agatgcagaa ataatgcatt atgtttcatc ccaccatctt taatgagaag cttccatctt     420
agattaatat tagagaatgt taaaatactc tgcaatcagg taaggacgct tgaaacttca     480
tcataatgca aaagttttct ttaacacaat aaatattttg aacccctttt gtgtcttgta     540
ttcataggag ttcagataga ccactttatt tactattttt tatagagagt gaacagaaat     600
```

```
cccatttcta gtcaccagtc cttaatctgt aaatcaggca gataatctgt aaatgattgg    660
ttgaaatcac attgaattcc actttgtgcc agggacttaa gttaacgaac aaattattct   720
tacaaaaagg tataaatgta aggttttcat tccgctaaat atgtttgtca aactgtgttg   780
tgatttgttc tcagtgtgtc atagctacca tagctttttgg aatgggcatt aataaagctg   840
acattcgcca agtcattcat tacggtgctc ctaaggacat ggaatcatat tatcaggaga   900
ttggtagagc tggtcgtgat ggacttcaaa gttcttgtca cgtcctctgg gctcctgcag   960
acattaactt aaataggtaa aaaaaattta ttgttttac tcttgcagat ttctttcttt  1020
cttttccatat aaacctcaaa agtgtttgag gctatttcca gtatcccaag taatttgtga  1080
gtgcatttaa agtaaaaaaa aaaaaaaaag aaaaataaaa cctccccaaa tccagaggac  1140
atgtaagaag aacatttgtg gtaagagttg ccacttggag atgagctaat ttcagcatgc  1200
cttagttagt gtgaggaatt aactaaatca ggacaatact tgggcctgtc acagagatcc  1260
tatggaatac tttcctacca ttgtgcatta atgaacaggt tcttttcctc tcctcagatc  1320
ctgtcaagtt gcgatgtctt cagccatagt tacttcaact accactgatt ttgttactga  1380
ttctttcttc ccatgctaca gtggtgatta ttccagagga tttctctcag tccctatttg  1440
actcttgtta ctatttgttt tcttggttag ttccatgaga ccatgccagt tctccttgac  1500
tgtgtatgaa tcattgtgtt gcactgtact gacagactgc cgtaagtcaa tattaagtgt  1560
tcagtatcta agtgcaggag aacctttcta cttaagtact caacaagtag tttgttggca  1620
cttaagttct atgagatttt ttgttgtaaa ggaaaacatt atcttgcaaa gattttgggg  1680
cagcatttac caatactttg ttccttcatc cgtaggaaaa agaatctcag gagaaaaacc  1740
tatacatggt aaccaatggg gctgccaagc tgatgaagta ttttcagagt acacctttgt  1800
gtagctgaat aaattgagat cttgaatgga catattagct cattttagta aaatgataag  1860
agagtgcctc ccactacagt ttttgttttt atgcatcatt aaacaatgtg tttttgattg  1920
tccactgtgt tccatgaact atgctatgtg tgggagatat agtagtaaag aaaagcaaag  1980
tacctgcttc catagaattc agtataatgg gaatggtaat tctttagaga atcacataac  2040
tatggataca taggcttcat tttactgttc tccttttgtg tttgaaaatg tcaacaatca  2100
aaattttgta aaaaggaat catgcaacat atttaaaatt ataactgtgt taagtgtaat  2160
gaagggaaat tgcactgagt agtaagaata tataatggtg tgtggtattt cccaagttaa  2220
aaaggtcaga taaggcttcc ttgtggaagt gatagttcaa atctgaaaga agaataggaa  2280
ttaattaggt aaaaatgttt gatgcaaatt ttaagatttt ccttctgagt agtcagtagc  2340
ttttccttct taacatagaa gatgacaaaa ccatcctttt tttgtacata acaattcttg  2400
ttttccttta gacagttgta tctgtcaagc ttcttatgat ctaatttaaa taattgggat  2460
agaacacagc tgtacatgtt actattaaat atggaatata tcaaacataa gttgattcct  2520
accagttctg attttatttg tgtattttgt taaaggtact gaggacatta atatccagtt  2580
ttatattgtg catttgaagg ttcatcaata aatacaattc ttgtttctct gggtcttaaa  2640
agatatttta aatggttatc tcattaagat ttaacaggaa ataacagtga ttcaaatcaa  2700
atagtggtgc cagaaaccca tacttgaatt ttgggtatag acaggttacc ctttgcatca  2760
atcctgagga aactaaaact ataggattaa tcaggataaa aagaattga gcaaggattc  2820
aggagggatc tgtatcatcc tggtgacaac cctcttctag aaaaaactag aaagtctaag  2880
aataaatgaa gttgctggtt ctcacctgga aaggtcagtt actcacaaaa ttttagagt  2940
ctatcttatg ccataattct atcactgaga gaagaaactt gtccagtcat catgtaatct  3000
```

```
tcatgtaaat ttatgttttt aattgcagaa ttcataccac aggcaaagtc ccaatgtctg    3060
catttgctgt taccttaaat agtcaaaccc caaagttatt gtaatctttt tttaacagag    3120
aataatttgc agagtaatct cggtccggta gatctttcag tggatcccaa atgattgcca    3180
tgaatggttt agaatttttt taattttcaa gttgtttta ttctgtggaa tactggactt    3240 attttttgtag tcccaaaaga aaaataaata tttatttatt tgccgttaag agttgtagtt    3300
ttgttttctc aaatttgtcc tgacactgac gagattagtt aaatgtaggt catctgaacc    3360 aaaatacaagg aaggaaggac ccagttctga agagtgtggg catttctttt cttgtttttt    3420 ttttttttttt ttttttttttt tctataggag gggaacgagg tgaactaaac aaacaaaata    3480
aagcaaaaaa gaactgattt ttatcccttg aggtagaaag aatgagatta cagtggaccc    3540
ccttgtctgc attttcactt tctatgtttt agttactcac aaccacgtcc aaaatgttaa    3600
atagaaaatt ccagaaataa acaatttata aattttaaat cagtggtggc tttgagtact    3660
gtaatgaaat tttgtgccat cccactcagt cggcctcgac ttcccttaga atcatcccctt    3720 tgtccggtgc attcacgttg tatttactcc ctgtctgtta gtcacttgtt gcagtatcac    3780
agtgcttgtg ttcaagtaac gcttatttta cttaagaatg accccaaagc acaagagtac    3840
tgtgcctaat ttataaatta aacttttttca taggtatata catataggaa aaaacataat    3900
acatacagga tttggttggt actattctgc ggcttcaggc atccactgga cgtcttggaa    3960
tgtatccctt gtggataagg aggaactgta tatggttaac ctaggagcta gagtcaacag    4020
ttggaagaga ctttggggat aattacatgg aagggcatgg tgggtggtcg tttcagatga    4080
caagaatgtt tttgaataac ggatcatttg tgtcttcaga cttttccagaa ctccttgaga    4140 attatgcaga ggtatttaat cagtcagaag gttgaatagt caaattatta gtgagtgaag    4200 tctatttga tgaggattt actaatgctg tcccttagat gttataagta aatcgttgtt    4260
ttcttttgaa atatctgaaa cctagttaac atggactttc atttgttctt gtaaagatat    4320
gcaaagctat ttgggagatt gtcatcatct gatatttgat attcatgggc tttcttcaca    4380
gaagactaga aattaacaga gtcatgatga attatggctg cattgacttt aaaaaacaaa    4440
cacctcctta atgttattta acaattttga ataaatttga tatggcaaac aaatcagtta    4500
taatcgattg agaaaggaac ttaattctaa tacttgactg gtgtcccata ataccccata    4560
atactaagag acagttttgg agggcgagaa gtcctgaaga gctgatagag ataaaggttc    4620
aaatttgagc ttctttcagt gttccttacg tcaatgcttt tagtttctca tacaaaataa    4680
aataaagaat aaccttttta ctgggaaaag gtaaaaatta ataaattgta gaagcattgt    4740
ttgaagccaa aaagtgtgtg acatgtaaat tgaaatgaaa aaccttagag tttttgatac    4800
tttttcaaag cagctaaaga attgatactt ggacacagga agaatttttt ttcaaaagca    4860 attttttataa aatcagaaaa atgtttacct cttgttgggg gcattgactg gaaaggaata    4920
caacagaact ttctgagatg ctagaaatgt tttttttatct tgatggggtg tgggttttgt    4980
agataatgaa aaataaacag taaaaaataa gtaaaaaaaa aagtaagaaa gttgccaata    5040
cagttttaca tattcctgtg atgttttttaa tcgacaggca ccttcttact gagatacgta    5100
atgagaagtt tcgattatac aaattaaaga tgatggcaaa gatggaaaaa tatcttcatt    5160
ctagcagatg taggagacag tatgtattat ttattttatg ccaatagtat ggatttatgg    5220
atgatgctct tttaagacaa caatttggct aaataattat cagtattttg aaaaaatatt    5280
ttgttgctgt tacatgtgtg ctgaattttt aaggctaact tctttgtgtc tgagtaaact    5340
```

-continued

```
gaagtcaaat aatgaagtcc caagtgaatc aattaatggt gatttaccct cattattttc    5400
aggaatgaac ttaacatata cgtttctgtt ctttattta atttaaaatt ttgtcttggg    5460
tagaatcatc ttgtctcatt ttgaggacaa acaagtacaa aaagcctcct tgggaattat    5520
gggaactgaa aaatgctgtg ataattgcag gtccaggtaa agatttctta ttatagatgg    5580
acattctaaa agtctttctt tctcttcctt ttcatgttta actgaattttt tgttgaatga    5640 taagtatttc agttttttaa acaaaacaat gaatgtgttt agatatgaga aagcaaacaa    5700
tattaaagta ttttgcttaa aaaatagata aagcaataaa atggtagccc taaatctaaa    5760
catatcaata gttatgttaa atgtaaatga tctaaaatat tatttaaagg cgtaaattgt    5820
aagaattggt ttaaaaacat gaccctgttc tgtacgttgt ccacaagaaa tccactgtaa    5880
ttatatagat aggtttaaaa aagaatgaaa cattacattc catgaaaaca ttaatcaaaa    5940
ggaagttgga gttactttaa tatcagacaa tggacacttt ggagcaaaga atattatcag    6000
gataaagaag gatattatat gatgtaaaag aatcatttca ccaatgtatc agtcagggtt    6060
caccagagaa ataggacgat tgatattatg gagatatata tatatatata tatatatata    6120
tatatatata tatatatata tatatatata tatggggagg gaaaggaaga acaaatatgg    6180
ggagagaggg atgaggcgac tgattttgaa gaattagctc acgaaattgt gggggttggc    6240
aagtctgaaa tttgtagagc aggtcaatag gctggaaact caggcaagag gtgatgttgc    6300
agtcttgagg cagaatttct tctctagcaa acctagtttt tgcccttag tcctgccact    6360 gagtggatga ggcccaccca cattattgac aataatctcc tttacttaaa gtcaactgat    6420
tataaatgtt aatcacgtct acaaaatatt ttacagcaac atctagatta gtgtttgacc    6480
aaacaactga gcatcatagg ctagccaagt tgatgcataa tattaatcat cacaaccaag    6540
aagacatcat cctaaatata tatatatatc tacttaacaa aaagactgac agaactgaaa    6600
ggagaaatag agaaatctac agttacattt ggtgacttcc agcatctctc aataatcaat    6660
aaaactgaca gaccaaaaaa tcagtaagaa gacagaagaa atgaacagga ttatcagcat    6720
gctggatctc attgaccttt ttagaacatt ctacccaaca acagtagagt acacattcaa    6780
gtgcagatgc agtattcatg aacatggatt atattcagag tcataaaaca aaccttaaca    6840
aatttaagaa tcttgtattt gtatattttt tgactagaat ggaattaaac tagaaaacaa    6900
taacagaaag ataacagaaa agtctctaaa ccttagaaat taaataacac acttataaat    6960
aaatccatga gtcaaagagg aagtctcaag gcaaatcaga aaatgttttg aactgaatga    7020
aatgaaaata caaaatgtgt gagatgcagc taatgcaata ctgagaagga aatttatagc    7080
attaaatacc tatgtaataa aagaagaaag gtctcaaatc agtacctaag cttacatctt    7140
aagcaacaag caaataagag caaaataaat caaaatgaag taaacataag gaaataacaa    7200
agaacataag tcaatgaata gaaaagctat ggtcatacca ctgctgtcca gcctgggtga    7260
cagagtgaga ccctatgtca aaaaatttta aaaacaaagc agcatgcagc attcattgtc    7320
agtgaataga aaatgggaaa acaatagaga aaatcaactc aaaagctcat tctgtataaa    7380
gatcaacaaa attgatataa acttctaaca agactgacgg naaagangaa aagacacaga    7440
agaccaatac caggaatgaa agagggaatt tcactacaga cctcccaggt attactaggg    7500
atgataaggg aacactatga acaactcaga acataacttt aataatttag atgaaatgga    7560
tcaatttctt gataatctca agctaattaa acttacagtg aattagataa cctgcatagt    7620
gttacaacca ttagagggat tgaattctat gttaaaaatc tctgaaaata aaatcccta    7680 gcccaaagaa tttcaatgac aaattctacc aaacatttag aagacaaaat aataccaatt    7740
```

```
ctatagcatg attccattta tataatagtc tttgaaacat aaaactatac tagagggatg    7800
aagaaaagat cagtggttat tagagattgg gggagggaga aggtatgatt ccaaaggata    7860
gtacaaggca gtattttgga gtgatagatt tatcgtgccc tgattgtgat gggagttaga    7920
tgaatctatg gatatcttaa aatgtgtaga actttacaca tacatacaac caatttgcct    7980
atgttaattg aaaaaataaa ataaaaacaa attatttacc tggtgggtta gctacgtacc    8040
taagttcaat agctgcgtta ctgtaagaca aagaagcat tattagggat ggagttgttc     8100
tctgtgtaat gacaaatact tccttcacta agaagacaga attgttttat gcacctttaa    8160
aaaaaaacaa aaacaaaaaa aatacaacca caaacagta acttgctggt gcggtggctc     8220
acacttgtag tattagcact ttgggaggct gaggtgggag gatcacttga gaccaggatt    8280
tttaagacca gtctgggcaa aaaccgaga ctgtgtctct acaaaaataa aaataaata     8340 aaaaaatta gctaggcata gcattatgtg cctctagtcc cagctactct ggaggctaag    8400
gtggaaagat cgcttgagcc tggaaggttg agactgcagt tgcagtgagc catgatggca    8460
ccactacact ccaggctggg catcagagta agactctgtc tcacataaaa aaataataa    8520 taatgataaa aactagtctg gcatggtgg ctcacacctg tagtcccagt cctttggaag     8580
gccgaggcaa gagaattgct tgaacccaag actttgagaa cagcctgggc aacatagcaa    8640
gaccccatct ctatttaaaa aaaaaacaa acttaaaaat ccagcaaata cataaagcac     8700
aaagccgaca gaagaggtgg agaaatcaac aaatccacca tcaaagtggg agaatttgat    8760
ataattttaa gttattggta gggtaaacaa tccaaaaatt agtacactgt agaaaatttg    8820
gtcaacatag taataagttt gcttattact atttatcagt atacatagta tactgattta    8880
tcagatacat agtatatgga gccctagagc aagcaactat agcagtgtat ctcaagtatt    8940
tttacttcat gacccacata gcaaatgata tgtgtatata acacactggg ctaattgtca    9000
gagttcagtt tctgtccaaa accctaagat ctggagtgat taacctttca gcactcttag    9060
aactcacttg tttgtagcac actgattgag aagcactgaa agacttcact cctcaaacat    9120
acatggaata tttctaaaaa ctatgtattg ggccgggtgc agtggctcat gcctgtaatc    9180
ccagcacttt gggaggccga ggcgggtgga tcccgaggtc aggagatcga ccatcctg      9240 gctaacatga tgaaacgccg tctctactaa aaatacaaaa aattagccgg atgtggtggc    9300
gagtgcctgt agtcccagct actcgggagg ctgaggcagg agaatggtgt gaacccagga    9360
ggcggagctt gcagtgagcc gagatcgtgc cactgcactc cagcctgggc aacagagcga    9420
gactctgtct caaaaaaaac caaccaactg aacaaacaaa aaaactaaaa aacaaaaaca    9480
aaaaaactat gtattagagc atgggttggc aaactatggc ctgtaggcca aatctgcatg    9540
ctgttttatt ttttttattt ttttgacata gggtcactac aggctgtcac acaggctgga    9600
gagcagtggt atgatcatag ctcactgtaa cctcaaattc ctgggctcaa gcaattctct    9660
tgcctcacct cagcttccca agtagctaca ggcatgcact accagaccca gttaattaaa    9720 acaattttt ttttggtaga gacagtctca gtatgttgcc caggctggtt ttcaaactcc     9780
ttgcctcaat cagtcctcct acttcagcct cctaaagtgc tgggattata ggcctgagcc    9840
atcacgcttg actaatgttt ttgtaaataa agttttctca gaacacagcc atgccttttg    9900
tttatgtgtt atgtagggct gcctgagtta agtagttggc tacaaagcct atcatggcct    9960
ataaagcctg aaatacttac tatctggtcc tttatagaaa gtgttttctg accctgtact   10020
agactagctt gtctcaaaat tcttcaatga atttggaagt tttctcacca cattttctga   10080
```

| | | | | | |
|---|---|---|---|---|---|
| ccataatgca | cttgagttag | aagtaaataa | gcagataaac | aacaaaatcc | tcatgcattt | 10140 |
| ggaaattaaa | aataacactt | aaataattca | tattcaaaga | aaaatcaaa | ctggaaatta | 10200 |
| aaaaaaattt | taaacctaca | gataactaca | ttaatatgca | ttaacatttt | tagaacttag | 10260 |
| ggatagttac | aatgatatac | attaaaactg | gtaagaggct | gggtgcgttg | gctcacgcct | 10320 |
| gtaatcccag | cactttggga | ggccgaggct | ggggatcac | gaggtcaaga | gattgaaacc | 10380 |
| atcctggcca | acatggtgaa | atcccgtctc | tactaaaaat | acaaaaatca | gctgggcgtg | 10440 |
| gtggcacgcg | cctgtagtcc | cagctacttg | ggaggctgag | gcaggagaat | cgcttgaacc | 10500 |
| tgggaggcgg | aggttgccgt | gagccgagat | tgggccactg | cactccagcc | tggcgacaga | 10560 |
| gcgacactct | tgtctcaaaa | aaaaacaaa | aaaaaaaca | aaaaaaaaa | ctagtaagag | 10620 |
| gtcccagtgg | ctcacacctg | tcattctagc | tctttgggag | actgaggaga | gaggatcagt | 10680 |
| tgaggccagg | attcaagacc | agtctgggca | acataacgag | accgcatctc | tacaaaattt | 10740 |
| taataacaac | aacaaaaaaa | ctggtaagag | gcaacattga | atagtacttt | gtgggagttt | 10800 |
| attagcttga | aatactcata | atagaaaaga | aaattaatca | gctaagcatc | tcactaaaga | 10860 |
| gattaggaga | ataaacctaa | gcatagtttt | tttcccccaa | acattattat | atctggaata | 10920 |
| ttgaatgcat | tcttattgct | atttcaaaga | tacttactct | aaggaaagca | attgaattag | 10980 |
| gtagttgaac | tctatagtag | attttcttta | atgagtcctt | ttgttctcaa | cctacttaaa | 11040 |
| taattctcat | ttgaatttat | gatagtttca | gatctaccca | aagggtgact | taggaattta | 11100 |
| acttctaaat | ctatttaaat | gaaaggttta | taatctttgt | gtcatatttt | acagtcgtta | 11160 |
| gcgtttaaca | atttatagca | taggatttgg | gtttttttt | ttttcatttt | aagaagaag | 11220 |
| tttatttaag | caagacactt | gactaaggga | agactatctt | ggagttatta | ttactagagt | 11280 |
| aatttatttc | tacttaaaga | cagattgccc | cacaagtaac | agctacataa | aaaacagttg | 11340 |
| taaaattgtc | cttggttta | caatgataaa | tgaaaaacat | taaaattctc | taattgaaca | 11400 |
| aggtatgcaa | ggatttttat | attgttttt | gctaaaacta | tgacagcaaa | ataacatcct | 11460 |
| ggagtataaa | gataagagct | gaatgagcag | gccactaggg | gacaaaggga | gtcttttcac | 11520 |
| agaaccaatg | cttcttttgc | ccaccccatc | tccatcgaag | tcaatctaaa | catattattg | 11580 |
| gccatttagt | taaaaaaga | aagaaaagna | aaagcaatat | gcttgtggac | atacaccagt | 11640 |
| tactttatgt | gcaataaaag | agtaggaagg | ggaaggtgaa | agaatagaga | aaactatgta | 11700 |
| gtcaggatgt | ggtggaacca | aattgcaact | ttcttttttt | ttttttttt | ttttttgag | 11760 |
| acagagtttt | gctcttgtca | cccaggctgg | agtgtagtgg | tgcccaatc | ttggctcact | 11820 |
| gcaacctccg | cctctcagat | tcaagccatt | ctcctgcctc | agccttctga | gtagctggga | 11880 |
| ttacaggtgc | atgccaccat | gcctggctaa | tttttgtatt | tttagtagag | atgggttttc | 11940 |
| accatgttgg | ccaggctggt | cttgaatgcc | tgacttcaag | tgatccaccc | gcctcagcct | 12000 |
| cccaaagtgc | tgggattaca | ggcgtgagcc | actgcgcctg | gccaaattgt | agctttctaa | 12060 |
| ttgagactgt | cttcttggtc | tggaagagca | gagttctgca | gtaaaataac | aggtcccct | 12120 |
| tttagtagac | atctccatgt | ctgctgctgg | aacacatcag | ttttgtctta | agcctcactt | 12180 |
| ccaaatgtgc | agatgtgtct | ggttcattga | ttggctgcct | gtcaaattga | aacctgatct | 12240 |
| gcctcattgg | caaaccgtgc | cccttacaat | aggctttcat | tggtttacta | agcggtgtgg | 12300 |
| tgcgtggctg | ttcatcttaa | actgcaccac | agtttaagat | gaaccttcaa | atgaacatta | 12360 |
| tccttgttct | cagtcttgac | tttccttggg | cttttttgtgg | accctggtga | gtgtggcagt | 12420 |
| ctcctcagct | gctgcttcac | aaaagaggta | ccaggtctgc | cccgaatgag | tgagccccta | 12480 |

```
aacaggacca ggagtggcag aagaaagagg cagcaactga gatgtgtttt ttctaagctg   12540
aaaggctttt ttttttttt  tttgcaacac acctttaaca ctaaagtcca atatttatat   12600
aattnggtca agtaagtgga gctgttctag ctataaatat ggcaactctg cttgctcgtc   12660
ctattattga cattattcct ttctgtggtc tgaggtgcct cccatgaaac ttgcttctag   12720
gacactagga ttgagaacca tncagcgtaa catatctgtt acgctacaat agtttatttt   12780
catattttag ctactttaca tactcgggta taatgaactt tattcatagc ttctgaagca   12840
gttggcacat ttgagatatt ttttacttgg ctaattgtta tgctaaatct tttgatttct   12900
aaagatacat gcctttgcta agctttcttc aaatgttatt attttttattt agattggatc   12960 attgctattc catggatgac tcagaggata catcctggga ctttggtcca caagcattta   13020
agcttttgtc tgctgtggac atcttaggcg aaaaatttgg aattgggctt ccaattttat   13080
ttctccgagg atctgtaagt atatatctgt gaattccctt catagatctt cttttacttc   13140
tattacactt ttcttcagag gtttgcagta ttatgattgt aactttgact tcagatgggt   13200
gactaggaac tcatagagtc ttactaagtt ccagttaaac actacattca ttactttgga   13260 taaacccgt  gtgtatggca tcttctgctg ttttcatgtt caagccgatg ttcagctctg   13320
cagctcagtc tggaagcatt gtgttaattt atcacattgc atttgggtga atccctagac   13380
tagtcttgct taggataatt aggaaaagtt aactttcatt gtatcaaggg acaggtagaa   13440
caaaattgtc cttttgtcca ggaaactatt aaattcttca aggaaaactt tagttatagg   13500
gattattttt taaatgtcta atttcagtaa caatatttgg gacatattta ttttccttc    13560 tgtttcctat cagaagtatt taagttata agaaaattgt ggttttgcc  tttactaatg   13620 aataaataat caattaaatt cagttacttt tttttggagt gattgatgtt ccagtattct   13680
tctaaacaac cacgggtaca aatgtgaata agataggacc gttgcagtcc aagagcttgt   13740
tctgtagtcc tttcctttat atgattttt  ccctgattt  agaagtctat aaagcaaagc   13800
taagtattac acactgataa tggctgaata aatcaagagc aagagatagg atactttgca   13860
aatatgcata tttattaaaa atgtacttta aaatagagat taaaattctc gtattgaatg   13920
tagaataggt aagcatttat ttgtgaaata ctcgaatgct tcatgtaaat actttctgag   13980
tttgtatttt tagaaaggaa cattttggag gctgaggcag gagaatggcg tgaacgtggg   14040
aggcggagct tgcagtgagc tgagattgtg ccactgcact ccagcctgcg cgacagagca   14100
agattctgtc tcaataaaaa aaaaaaaaga aacatattta ttaaattagt tgtgaaatat   14160
ttttaatgaa atatattgaa aacttctgtt gattttcat  gtactgatgt ttttagattc   14220
taaatggagt ttaaatttt  gtttgtaaat cacaagttgg attagaaatt taatagtaga   14280
agtgttgcct aaggactatt ttaggtgctg tgagtgaaac tgtattttt  ataacaagaa   14340 ttttagttgt aagggacagc ttaaatataa ttgagatctg tgaaaatgta ttctgtctct   14400
atcaccttca gaacctgtgt atctcagttg aatgtataat ttataaaaat tattcttgtt   14460
ttaatttggt gtaatccagc catatccagt atcaacaaat aagtctaagt aggctccttg   14520
acaaacttga actggccaca agagagatca gatttcacct attaaaaaac caaatcagac   14580
cacttacact gacagtctct tctgggagtc ctcaaattaa gaagtctatc ctttgtgaaa   14640
tattacacta cccttgctag ataaaacttt tctaaaagta ccacttaatg aaaatctgta   14700
gacactaaat gcaatgaaaa taaggcattg ttttttttttc tccccatttc agtgatcttg   14760
gtatcctggg atattgtttt taaaattatc gttataattc ctttgagaat ttagtgaaac   14820
```

-continued

```
gttcccttta accaacttag gaaaaattaa tatctttgta catgattttg agctgtaaaa    14880
taaacatttt aaactgggaa taattggagt ttagttaaag agataatgta tataaatata    14940
taacatagta gcagcatata attctgtctt acacaagatt tttctgaata gtataaacag    15000
ttatgtagcc tatctaggag tttgtgaata gagtttaaaa ttttgttttg aagctgcaaa    15060
tttgattaga aattaaacag taaagttatt acttaaggaa cttcgtttta gctgtctgaa    15120
caacttactg tataaaaatc tttaaacatt ctgtataaat atgtgataag atatgcaatg    15180
accttaattt tatagattag aaaataaaaa cacactcatt aatttacata actgacagat    15240
taagtgaaac ttctcttctg atcacgttag cagaatgcca aatcttgtcg tggcactaga    15300
attagacggt agttttgata atacatgatt tgactataga catttgttga aactattggt    15360
agttttaatc actcttgtaa ttttcaaact atctaacggg agaggattat ccatcctgtt    15420
ttctagacaa actgtttcat ctgaatgaaa tatattccta gagataatta tcactacttc    15480
atcttttggt tttattttgc acatagaatt atagttcaca atgactttct gaagctctaa    15540
agttgcagct gtgagcttct ttggcctgta gggactggga aaaagcaccc ccgtcctccc    15600
ccaagccccc ccaccaaaaa aagttaaagt gttttttaaca atagctgtgg gctttttgta    15660
gtttcagaac ttaggagttg cccaggctgg aatgcagtgg tgtgatcata gcttgatgca    15720
gccttgaact cctgggttca agcaatcctc ccacctcagc ctccagagta gctgggacca    15780
caggtgccac cccacccagc tattttttttt attttttaat tttttttgtag gtatggggtc    15840 tccccatgtt gccctgcctg tctcaaactc cagggctctc agtgatacc caccaccctt    15900 ggcctcccaa agcaccgaga gtcactgtgc caggctgagt ttaaaatttc ttgagttgga    15960
gtttatggct attttttcca ctagttatta aacatgtatt tttgtataag gcactgtatt    16020
acattttgtg gggggattca aagctaaatt agatgagacg catcatctat tatggaagat    16080
gttacttaag aagaaatgag tgtaatgtag cagagaatta gataagggac gtatgaatac    16140
atataaatgc tgttgaagtt ctgaagagag agagtgtta gagaaattag aggagtcttt    16200
gtgaagttat cactagaact tcctattttt gtggaatata tagtagattt tggtgtgata    16260
ctgtggattt ggacattcac tcagagaagg aatgagggaa gaatggtgga gaagaatggc    16320
attcacagta caaaaagcaa ctgtgacttt taaagaagtt aatatggaga agtggcaagt    16380
cttttcttct ctcttctctt ctcttctctt ctctcttctt tttcttttt cttttttct    16440 ctgtcagata ctgttgtaaa gactttgctt ttaccggaaa ctgatacgtt gggtcatgta    16500
ccctggccag tcagttctct ttattctaac acttagccga tcaattagat ttccacattc    16560
catgatatgt cagttttggt gacccttatt tttccacctg gttataaag ggaaagaatg    16620 tgatatgtca cccaggctct ggagtacagt ggcatgatca taggtcacag cagcctcaaa    16680
gtttccagtt caagcgatcc tacctccttg gcttcctgag tatgtggcac tacaggtgca    16740
tgccaccatg cccagctaac tttttttgtag agacagggtc tccctatgtt tcccaggctg    16800
gtcttgaacc cctgacctca agtgatccgc ccaccttggc ttcccaagat attggcatta    16860
caggcatgag ccactgtgcc ggcctgaaaa tttctctttt gagatggcat cccacagaag    16920
tatacctgct tagagctaac actggtaaaa agactattta accctattgc cttattttac    16980
tgtagttgag attgagttaa actgaaagct gaatgacctg tcctaggtca tactgttact    17040
ttgtgccaga gtcaggatga gcaaatggat ttcctgcctg ctagtctagt gtcttttcta    17100
tttattgtgc tgtaacatac agttttaaat ttgtattttt atgcccaatg gacatggtag    17160
ctcacacctg taatttcagc acttttggga agccgaggtg gggggattgc tcgagaccag    17220
```

```
gagttcaaga tgagcctggg caacatagcg agactccgtc tctataaaaa aaaatttaaa    17280
aattagctga gtggtgatgt gtgtgcgtgt agtcctcctt gtgggaggtt gaggtgggag    17340
gatcgattga atctaggaat tcaggactgc agtgagccat gattacacca ctgcactcca    17400
gcctgggtga cagagcaata ccctgtctcg aatgaatgaa tgaatgaatg aatgaatgaa    17460
tgaatgccca atccgtaag ctatgttctg tatagcagct ttttcatcat aggcagtttt     17520
tactcttatc agtggacaac ctacaaaatt aactaaacac ttaagcaatt aacagaggag    17580
gccttgttca gagtgagaaa tcattaagca tttgttgttg aaatttctta ctgtactctg    17640
ttttaattct gttttttttt tttttaatg ttacttgttt tagtttggat tcctagttga     17700
aagggaata tgattccttt aaacaaaga tactctgctt taaagcaaag gtatatcatc      17760
ctcttcatgg tgattgccat ggaaacaaga caatgtaaat ttattcaaat agtacacagt    17820
ttttatagtt attgatcatg aggggaaggg acagttaatc cctactgatc agataaaacc    17880
tcattgtttc atactaataa atggttttt tatgcttatg aaaggaaaag ccagaagggt      17940
aatttttagt gtttagagag ctagtgattc tagttaggga acttaatacc tttgaagtta    18000
ttagtttgca agcaatagaa tctactacta ccaaggtgac ccctagcaga tgtagagtac    18060
cattaacaag tgttccaggg aaggaaagcc aactagatac caagtcatgc ttttactct     18120
tagattaaga aattcaggtt gagttaaagg atcagctgtt aactaataaa aagcagatta    18180
atattacaga gccaggctct gtcctggtta tggacttaat cttcacagca tcctcaagag    18240
ataaaaatga atatacctgc atattagatg aggaaataga agataagtaa cttgccagag    18300
ctatgacgtg aactcaggta atgtagctta agagccccca catgtatgta tattgggtgt    18360
gtgtgtggag ggggtgcgtg tgagtgcttg tgcatgcgtg tggtataata agaaaaaatt    18420
agcatttatg cctgtaatcc cagcactttg ggagaccgag gcacgaggat ctctcaaccc    18480
caggagttca agaccagtct aggcaacata gcgagaccct acctctacaa aaaagtttt     18540
aaaaatatta gcgggcatgg tggaatacac ctgtagtctc agctgcttgg gacgctgagg    18600
tgggaggatc cttgagtcca ggagattgag gctacagtga gctatgatga cacctctgca    18660
ctccagcttg ggtgacaaag agagaccctg tctccaaaaa aaaaaattag aactagttat    18720
ctggaggcct gtgttctagt cctagcttta gtacggctac acagtgacac attaggctac    18780
catttaacat ctttgaacct ctgataattt gttaacaata tgggtaaaaa tgactaagat    18840
aaatcaagaa gctccagcat tccctccagc tctgaaattc tatgatgttt tatcttattt    18900
tacttacaaa aataaattat attatgtata tttaaagtat acaatttgat gttatgggtt    18960
acctatagta aaatgattac tataatgaaa ctaattaaca tatccatcat cttatattgt    19020
taaccatttt tttgttttg tggcaaaagc agctgaaatc cactcattta gcaggaatcc     19080
caaatacagt tcagttgtat taattgtaat tctcatgttg tacattcgat ctctagactt    19140
gtttatgcta catatgtttg acttttaaac attctactca aatcaaccct aagtcagggt    19200
tagcacagac aggacttgtt aacaaggtag aaggtgccac attgtacctg ggtgtttata    19260
tttctctaaa tcttgttctg atcatatttt aataaatata atcatcagga caccaaaatt    19320
cattccttag ctattaaaaa attctattct attttattgt taagatttag gagagcatgg    19380
tacagattct cttaactata cctatcagaa gcctatgttt taagtccaat gtataggcac    19440
tgctctgttt gtctctggtg ggaacttacc ctgctttacc taatttcatc ctagcttcct    19500
ttttgtgaaa gatcacccct tgcttagccta ttttttggca aatctacacc ttggaaatag   19560
```

-continued

```
tagtaaatga cataagcata ttaatatttta tgatgtgatt tattttttgtt ttcaagtcat    19620 atactgggga agattctcaa atattaaaac aatgtatctt tacatttatg tatgtcgttc    19680
ttgttctgtt ttagaaggct tgtatttgca tttttaacat tccaaaaggt aaacctgtaa    19740
tcataatgtt ttcatcaatt caataaaacc attacgtttg taatagagag ccctatagtt    19800
gccttagtta agtttgctgc aactcatttt atatattctt ttaattttga tccctggatt    19860
tttaattgat tattaaacct tcattaggat atatatgaaa tgtaaaaata ttgagttata    19920
atctaccgtt ttctaaaatt ttatactgca tttttatata gaaattcaaa ttgctcataa    19980
tcattctagt gaatttaagt agaaaggtat ttattactag gtattaaatg gcttataata    20040
ttgttgacaa ggttccactg caaaatagtt caccaaggga gctgtggcct cttctgtgat    20100
caagaagcca tctgtcaact tgggaagctt ccactatagc acctaacccc agactacatt    20160
gagtaggaag ctgtaataat caggaagctt ctacctttgc atgctctgca aaccaacgtg    20220
aacctgctgt aatttgtaac cacaaaatgg atgcctgttg atacttacga agctcatcat    20280
tgtatgctgg gttctttgct aatactttct tataaaaatt aaatacctcc acaatcatgc    20340
atgctagcag aaacagcaga ggagtagcct tagcctcact tcctgcttat acctgtcatg    20400
cagatataca gaacccagaa ccctagctga aagggagttt gagaactagt atttgtattg    20460
tcccagattc tgcagtggaa gaattcatag tggatggaag ttagaatgac ccttgaatta    20520
caatcggcca cattcatcac aaatacatta aataagagta atttgccata aagctctatg    20580
tttgtatact tctttgtttt ttttttttttt ttttttttttt tttgagacag ggtctcactc    20640
tgttgctcag tctgtagtgc agtggtgtca tcatagctca ctgcagtctt gatctcctga    20700
gctcaaacga ttctcctgcc tcagctcctg cttcagcctc ctgagtagcg aacaacagg    20760 tacacaccac cacactttgc taattttttta tttttttattt tttgtagaga tgtgggtctc    20820
actgtgttgc ccaggatggt ctcgaactcc tgggcttaag tgatcctccc aaagtgttgg    20880
gattacaggc atgaaccact gtgcctggcc catatactac atatatttaa aagtagtatt    20940
taaatgtgta ggatgaatga agaggcagt aagagaacaa agtgaatgaa aaagtatttc    21000
tatatgaagt gaaagcagga gagtcctctc tgttagagaa caacagaatt gcatatgaca    21060
gactagcttt cttaatatttt ctagaacttg atggctgtga agagcgtccc gtaggaattc    21120
tcccttcact taggaaaaca tacctcaaaa ccatcagctg tttagcatgc acctgctttt    21180
cctggtatat ctcagtgaag cagctaaatt gtaaatgatt aagtaaactt tgcagtgtat    21240
catgtgcaaa agcacagtaa aaacaaaaat gcattggaag ctgtgagttg ttgcactgca    21300
ctcatggatg aatagctgtt ggttcgcatt gcgtttttt gtttttgtttt gttttgtttt    21360 tttgagatgg agtcttgctc tgttgcccag gctggagtgc agtggcgtga tctcggctca    21420
ctgcaagctc tgcctcccag attcacgcca tcctcctgcc tcagcctccc gagcagctgg    21480
gaccacaggt gcccgccaca cacctggct aattttttgt attttttagta gagacggggt    21540 ttcaccatgt tagccatgat ggtctcaatc tcctgacctc gtgatctgcc tgccttggcc    21600
tcccaaagtg ctaggattac aggcatgccg cattgcgttt tatataattc tcatggttct    21660
agtctcgagc tgtaggattt tgatcactgt ttcaaacaat aatgtgagtt tgctaagagg    21720
tctaaataac aaaagctaag tgtccaaaca catatccaaa cctatacact gggcaatgca    21780
tctgaattat atgtgaaatt tcctgccatt atttaagaca caaaaggaac attattttga    21840 taatgtatt atttgtgagt ggagtgttca gaatgagcac gatgggtata acattttgt    21900 aggttttaa agttgaaatt tagtgtaaat ccaaagaatc aatagacaag tctgtgttttt    21960
```

```
acttaaccta tatgtttaaa ttagcatttt tagatactga ttttattcct aatttcagaa    22020
ttctcagcgt cttgccgatc aatatcgcag gcacagttta tttggcactg gcaaggatca    22080
aacagagagt tggtggaagg cttttttccg tcagctgatc actgagggat tcttggtaga    22140
agtttctcgg tataacaaat ttatgaagat ttgcgccctt acgaaaaagg taaacagtgt    22200
aggagtctgc ctgtttgact taattttgtt tcccactcca cattaaaaga tccttttgc     22260 ttttaatagg gtagaaattg gcttcataaa gctaatacag aatctcgag cctcatcctt     22320 caagctaatg aagaattgtg tccaaagaag tttcttctgc ctaggttcat ttttcagttt    22380
ttttcttgta acttctgcat tttttgttgc tatttatgtg attcaaatta taccagttta    22440
taggcctctc acaagtaaaa tgaattgcct gtttgttttt gtatgcctat tttagtcagt    22500 ttggggaag ggatctgtga ggaaggata agtcatagag cacttttctt ttttaagaga      22560
cagagtctct ctgtgttgct caagctggag tgcagtggtg cgatcatagc ttactgcagc    22620
ctcgatctcg tgggcccaag taatcctcag ccacctgagt agatgggact acagacatgc    22680
actactatgc ccagctaata tattttaatt ttttgtatag acagggtc ttctagtgct      22740 tcctaggctg gtcttgaact cctgagctca agtgatcctc ctgcctcagc ctcccaaact    22800
actgggatta caggcatgat ccaccgctcc cagccagaac attttcttgg ttgatgggaa    22860
gtagctgacc atggtattta gaaaacttct ttctcatcga ttaaagaagc agtactgaaa    22920
tcaatgcgga ggaatccata tatcatattt acttctggtg tgtagaagtg aaagggaat    22980 acatttgttg cttactttt tgtacccttta catgtgattg atcacttgtg agttttttct    23040
ttcaaacatc ttaaagcttc cagagctttt tctagaaaaa aaaccagtt ttaagaatca     23100 ccagttctaa aagggtaata tcttattcat ctttctgaga atggagtatc atgattcatg    23160
aattagatac ttgcatctta acatttgaaa taatttaatt ttattatttt ttagttcgaa    23220
aactgtatct tcgggcacca aagagcattg ttataatcaa gtaccagttg aattaagtac    23280
agagaagaag gtttgttta aagaaattgt tctgacttat ttcattcttt attgattcaa     23340
attctgttta aaattttata ttttaattcc tttccaatta aagagaaaat ggcatatata    23400
acaaagcata aaattcggcc agggaagtga tgtgaacaga ctaaaattta ttgtatataa    23460 tttctgggc taataaagaa ttggaggtat ttgagaaagg aattaatttg ggttctttta    23520
aacctatctg ctaactcatt tggcttagag tagtcacatg ttataatact tatagttgat    23580 caaaaattg attcctaagt gttcttatta agacacaca cacacacaca cacacacaca    23640
cacattcttt ctctctctct ctctcacaca cacacatg cacacacact tatgtacttt      23700 cttgctttt ttgacctaag atcttagata actattacag attaaatact aatccactgg     23760
cagacttcag ctaattagaa cactggaata ataggcaagc atagtgaatt acattttctg    23820
gtgaactttt tctgctttat tgaagtatgc agaatgtaaa tgaattgttt ttataacttt    23880
ggcacttgct gtatcttaga acattctttt gatgatttat tttctgtagt tttgggagag    23940
ataagacatt ggaatgcgtt tctaactacc tttagaactt tagaaactga aatttagga     24000 ggttatttc aggtgattaa tttgacagct tgattaggca agaaaaaat tgtgattttg      24060 agattttgt ttcttatttt cttcacattt aaaagttttt tgaacttttt tttaatggac    24120
ctttatatgt ttaaatgcag tctaacttgg agaagttata ttcttataaa ccatgtgata    24180
agatttcttc tgggagtaac atttctaaaa aaggtacag agttccatat ttctatgttc     24240
tatacttgct ttatgagtac tttttttttct aaagagaaag aactgtcaga tgttgggcta   24300
```

-continued

```
tttcattggc aaaaggaagt taaatttaaa acataagctt ttcagtatta gaatgatcaa    24360
agtgagctat aaaagaataa tgttaattta atagctaaca cttcttggat attactgttt    24420
gtcaggcatt atgttaaatg ctaagaactt tatatgtgat atctcattta attcttacaa    24480
gagtctaaca gctgttacta tttatcgcca ttttatagtt gaagatacca agggttaaga    24540
agttgacaaa cttgttcaag agcatacagc taatggccga gctggctttc aagtctatat    24600
ttgtctacct ctagcatcaa gacactattt atttttcttt gtatgaaata tatacaggca    24660
tactttgttt tattgtgcct ggctttattg tgacttgcag atattgcatt tcttataaat    24720
tgaaggtttg tggcaaccct gcgtcaaaca ggtcatatta gccccatttt ccaatagcat    24780
gttctgttgt catgtctttg tgttatattt tggtagttct tgactggcca ttcaccattt    24840
ctctccctct cctcgggtct ccctgttccc tgagatacaa caaaattgaa attaggccaa    24900
ttaataactc tataatagtc tctaagtgtg ttttttttt ttttcgagac tgagtctcac    24960
tctgttgttc aggctggagt gcagtagcac aatctcggct cactgcaatc ttcgcctccc    25020
gggttcaagc gattctcctg tcttagcctc ctgagtagct gggactacag gcgcccccg    25080 atcatgtctg gctaattttt gtatttttag tagagatggg ttttgccgt gttggtcagg    25140 tggatcttga actcctgaac tcaggtgatc cgcctgcctt ggcctcccaa agtgctggga    25200
ttacaggtgt gagccgctgt gcctggccca tctctaagtg tttaagagaa aggaagattc    25260
acatgtctct caatttaaat caaaagctaa aagtgattag gcttagtgag gaagccatgt    25320
cgaaagctga gataggccaa aagctaggcc ccttgcacca aacagttagt ttgcaaaggc    25380
aaaagttcct gaaggaaatt aaaaatgcta ccccagtgaa taaaacaatg ataagaaagc    25440
aaagcaggct ttttgctgat atggagaaag ttttagtggt ctttatagga gattaaacca    25500
gccacaacat tcccttgagc caaagcctaa tccagagcaa agccctaact ctcttcaatt    25560
ctctgaaagc tgagagaggt gaggaagctg cagaataaaa gtttgaggcc agcagaggtt    25620
ggttcatgag gtttaaggaa agaagccatc tccataacat aaaagtgcaa agtgaaacag    25680
caagtgctgg tatagaagct gtagcaagtt atccagaaga tctagctaag atcatcgatg    25740
aaggtgcctg cactaacaga ctttgaatgt agaccaaatg ctttctacca gaagaagaag    25800
ctgtctagta ctttcatagc tagagagaag tcaatgcctg gcttcaaagc ttcaaaggac    25860
aagctgactc tcttgttaga agctgatgca gctggtgact ttaagttgaa gccagtgctc    25920
aattagcatt ctgaaaatcc tagggcccct aagaattatg ctatatctac tctgcctttg    25980
ctacatacat gtaacaacaa agtcttgatg atacctgttt acagcatggt ttcctgaata    26040
ctttaagccc attgttgaaa cctgcttaga caaaagattc cttcaaaat gttattgctc    26100 attgacaaca cttagtcacc aagagccgta atggagacat acaaggagac taacgttgtt    26160
ttcatgcctg ctcgcttaac atccattctg tagctcatgg atcaagaagt aaattaacct    26220
tttaagtatt attatttaag aaatacagtt tgtaatgctt tagcttctgt agatagtgat    26280
tatcagagat gggttttaa gaggttttcc agaaaacctt ctggaaaata ttcactattc    26340
tagaagtcat gaagaatatt tgtgattcag agagtaggt cagaatatca atattaatag    26400
gaatttggaa gaagtcgatt cttattaaaa tcaagagttt agtgatagac atactgagtt    26460
tgggatacct gtggagtagt ccagaagtta atttaaatat atgggcttag tgtacagaag    26520
tgagcagggt gcttatatat gaataaatat tattttaaga tatatttaaa ttttccttaa    26580 aataataacct atacttgata taaaaagtta attggaaatt agtggcttat gacaagcata    26640
ccagcccaca ctcttcccaa acccacttg ctcttattca tagaagctgt catcttcaaa    26700
```

-continued

```
tcttccagct gatttccctg gcgtgtgcct tcttatttct gaatgacacg cttagagtac    26760
tatttttttg acttagcaat tttagaaatt ttctactcat ctcctattat ggtagatttc    26820
ccctccttca ttcctcctcc aatataatta tatttcgtca tattaataat ttgtttatat    26880 atattttttaa tataatatga taatattgta tttatattat taaaactaca caaatattat    26940
atacacacta ctaacccaac cgtgttatta tggccaccac tacctttatt tttttccttg    27000
tgttagtgat tgtctttgtt ttatttttctt ggttttgagt attccttttta ctaattttct    27060 tttttcctat ttcaatctct cattatttgt ttactcattt ggagtgttcc ttgactttta    27120
tcccctctta cctagtgaca ttttaatttt agttatcaaa ttttttaattt ctaagaatgc    27180 ttcttgttct cttcttgttt cttcttcccc accagccaaa atctatgat gttatagcaa    27240 ggatcataca ttgtttccca gtaggttaag aaaccttggt taaaacctgt tgtatcccag    27300
taagttaaaa gacgttaacg tgtcatcttc agtatggatg aaagaatatt ttcttttcaaa    27360 agcagttggt tgaggaagag aatgggacaa atgctctttt taaaacacca attttgtgat    27420
gaactcaaat tgcaatttta actttaccat tataatgaat gtatttgatc caaaatgttt    27480
aaaatctagg ctgttgtcat ttaaataaca aattaccta ctggtatcat gaagaataaa    27540
tgtttgtact gatttggaaa gacattctca tttaggggat gaaatagaaa gtcaatgagg    27600
agaaagaaaa gcttttatta tttatttttct tttaaatatt ttagtatcat ggtacagtca    27660
ccagaaaaag cttacagttc ctcacagcct gttatttcgg cacaagagca ggagactcag    27720
gtaaggcttt tgtaaaaagg taattagttt atgataggat agttatgatt ctatgtatgc    27780
ttaaaattct gtattttgcc agcattttaa aaattgttct taagctaaga gtctgagttt    27840
atatttcagt ttatattcat tctaaggaaa aatgtggtat ctgaagctct aaaaataaag    27900
gactagatct tttaagtaca ctttaaaaag tgttgtttct ttgttttttg ttcagattgt    27960
gttatatggc aaattggtag aagctaggca gaaacatgcc aataaaatgg atgttccccc    28020
agctattctg gcaacaaaca agatactggt ggatatggcc aaaatgaggt aaactatctt    28080
ttgcatgtgt tctcatttat ttccttctaa caaaatagat ttggaaaata tatctaagtt    28140
gataatatga ccatagcttc cactgtcaca tctgggaggt gactcagatt ccccctgctg    28200
cgatgcttat ctcttttgcca agcttttagta ccgtgtttct gtatgaataa aaaccagtta    28260
cgttttcagc aatcatattc aatatttata aaatctaact cattatttac ccaccctgca    28320
ttttatccaa atgccgaaac tcctcttttt ggattcttta tttttgatta tcttaccatc    28380
acatttgtag tcagaggttc ctaatgctta aaacctctga tctgaatttt ctctcctcca    28440
atataaaacc ccttcgtctt cctcttcttc ttcttcattt tttttttttt ttttgtctga    28500
agacttgtct cactgtgttg cccaggctgg agtgtagtgg tgcgatcact gctcactgca    28560
gccttgaccc cctggactca agctatcctc gcacctcagc ctcccgagta gctgggacta    28620
cagaacatgc caccatgctc agctaatttt tgtatttttt gtagagacag gttttgcca    28680 tattgcctag gctggtcttg aactcctaag ctcaagcaat cttcccgcct cagtctccaa    28740
agttctggca ctacaggtgt gagccactgt gcctggcctc tttttctcat ttaaatactt    28800 ttcataccctt ttgtaaaacg ggttccttgt tgcctgtcta tgccttcctc ctccttctta    28860
atgacaccac gttaattctg actgttttcc cttggcctgt tgcagaagcc tcttaactat    28920
taacccttca ttctctctct ctgtttcatc tgatatatga gtaccaaact aaatcttcct    28980
ttatcatatc ttacttctgc ttaaatgttt tttttctagc ttagaattca aggccctcta    29040
```

```
tttatgaact taaacttact tttccctcta agttacagaa tttgaaatgg tttatcttac    29100
ctggattgtt tatcacttgt tgaagatcca ttttcaactt ccatatattt atttacagtg    29160
ttgcttctcc ttgtagtttc cttgattcct caaaactcct tttaagaatt cttgaagatc    29220
tcgctttatt actatttctc gctttattac tgtaaagact atgagaaggt ctttcatgat    29280
cttatcagca aagtaattcc tctctcttga attcatagag gactttcaga tgaattctaa    29340
agatgcttct gtagcactta ccacacaatn gctatatttt attttttttgt aattagtggt    29400 aaacaagtat tattatatct tnctagattt taaactccaa ataaagatac tagctcctta    29460
cctttttgtg tgtctcctgt agcacctagc acaatgcctc ataaacagga ggtgatcatt    29520
aaatatttag aagaaattat tcccaagaa tagttgcttg gtaattgtat ttgtcttta    29580 cttccttta aaaaattgtt tctgtcacta aattgcatcc aatagatgtt acttgagtgc    29640 agaatttct aatgacatta cacagtgcta catctgacac taattctttt gttaaaaaat    29700
aaatattctg gccgggcgct gtggctcacg cttgtaaatc ccaggacttt gggaggccga    29760
ggcgggcgga tcacgaggtt aggagatcga ggccatcctg gctaacacgg tgaaaccccg    29820
tttctactaa aaatacaaaa aattagccgg gcgtggtggc gggtgcctgt agtcccagtt    29880
actctggcgg ctgaggcagg agaatggcgt gaacccggga ggcggagctt gcagtgagcg    29940
gagatcgcgc cactgcactc cagcctgggt gacagagcnn nactccgtct caaaaaaaaa    30000
taaaaaataa aaataaataa atattctaag accatacttt aatggagtg tttttttgttt    30060 tttttttgttt ttttttttttt ttttttggtga tagagttctc actctgtcac ctaggctaga    30120
gtgcagtggc gcgatnctcn ggctcactgc aacctccgcc tcctgggttc aagccattct    30180
cctgcctcag cctccggaat agctgggact acaggtgcgc gctgccaccc ccggctaatt    30240
ttttgtattt tagtagagat gaggtttcac tgtgttgtcc aggctggtgt tgaactcctg    30300
agctcaggca atccacccgc cccggcctcc caaattgttg ggattacagg cgtgagccac    30360
agtgcctggc ccagaggaga tatttaatga aaaataataa tcattagata ggcagatttt    30420
tagaaggagg gcatcgaatg ggttcttgga tattggacac aataagaaat attgagctaa    30480
aagtctgaag gaattggcag atatactgtt acaggtaaac actttgtaga agaaaataat    30540
gaatgagact ttcttttgag attttcttag cctcttagtt gttcccagtt aaagcctcat    30600 attttttcctt ttcatgacaa taaaaataat aataaaatca gtaataaagt gaatatatga    30660
gatgttaacc tgttccttta tgacaatgtc ctgtttacca attaacagtg tgtttttgtg    30720
gtgatggggg caagacaaat ctttaaatgg tggaaagcaa agaaagaaat tataaaacat    30780
gattagttgt attatacgtt gttttttggtt gttggaaaaa ctatacattt attgagagaa    30840
tcattaggaa gctgaacatc agctatattg ctggagtgat actgtttcag tggtttcttg    30900
acctttttgt tgttgttgtt gttgttgtta aacacagacc aactacggtt gaaaacgtaa    30960
aaaggattga tggtgtttct gaaggcaaag ctgccatgtt ggcccctctg ttggaagtca    31020
tcaaacattt ctgccaaaca aatagtgttc aggtaaaata ctgtggtttg caggagctct    31080
tagagaataa gcatttttttg taaccatttc aaaagtaccc tccagaagca acatttgctc    31140
actttatttg catttccata ctggacactt agaaaatgaa ttaaaattgt ttttacagtc    31200
aatcnntgtt gtaaaaacat gtcagttatc tacttttaaa gatgatacta aaaagtagtt    31260
gtccaggctg ctgatgtctt tctatttcat tgggaggttt tgttttttaaa ttggaaacat    31320 tattttaggt tgataaaatta taattttaca ttcaaatgtg gtagttggaa tttaaagctg    31380
gaaagttatc cttgctatga gttggtcagg agctcagcca ctttctttttg gtttagcatc    31440
```

-continued

```
ttctctaatc tccctcccct tccagtaatg ctgtcttttg atagtaagtg gatttcatat   31500
tattctcttc agttttaata gtgtttcctt catatccttt tattattgct tgttctgccc   31560
taagtgacca tttccagaaa tgtcatttag gnattttctc taaactccac gtagcagact   31620
ctataatgca tactctgcag aaggtgaggc agtgggaggt agaggggaga ctactagact   31680
aggagtcacg gaatcaggac tttagttctt ccttacagtt gttcacctgg tgaacctgca   31740
catgtccttt aatttccttg ggtctccatt tcctcagcta taacatggaa atgcacttc    31800 ctcccccaca tccaggaaac aacagatgac attagaaaat agaagacatg ggataagtat   31860
aaaatgttga aagagttaaa cacattcaag gcaatattaa gggattattt tttacttcca   31920
agaagctcct ggaagctttg ggcaggcaca gttggatcct actttagaaa aatctttctc   31980
taactataag tagaaaaccc ttctgctttt tgaatgtagc atttccctct tttgatatag   32040
agtatctttg gcaactttga attttctttt tcatactctt atataagaca tcatgtgaaa   32100
attcttattt cttactgagt ttttggaaat gaattataa tgtcttaata gtttgagaaa    32160
gaatatcata cctaccagcg gtaattgagt aagttccctc tctttggaca cttgaaagta   32220
gtatcttctt tcatgaatta gtgatattat ttaataatga atgagtgatc tctcctaact   32280 cccccttcaga agaggaaaat gaagtagggg aaaaggtaaa ttccccaagg gataggtatg  32340
aaacctttat gaaccttctg gatagagaag atgactgctg atttctgtga ttagaaatta   32400
tacttgggtt attctgcaaa ttgaaatgaa ttatttaaaa aaaaacaact ttaatgttta   32460
ttaagcaagt tttgttattc atgagtttca ttagccttt atttttttt taaattttga     32520 agtaaaattt cttgctgtca caatacacat taaaaattac aaatatgaca catattaaac   32580
acattaagat ggccgaatag gaaaaatatg ctaaatatt tttatataaa tacatttttt    32640
gagaattttg agaatttctg gaacaaagta atgatataat ccataaatgt acaattaaag   32700
agtttaagga tatccaaaat acttggcaaa gtaatctgaa ataatactct taggaaggta   32760
gggcaagaat gtgattctag taagcaaaaa tgtaatcaaa tcgtattcta gtcccagcta   32820
ctcgggaggc tgaggcagga aatggcgtg aacctgggag gcggagcttg gagtaagccg     32880
agatcgtgcc actgcactcc agcctgggcg acagagcgag actccatctc aaaaaaaaaa   32940
aaagactata tgaacttgta tggcataaat atgtacaaat attatttatt ttaaaaaaat   33000 tcagggggtag ggacagggta gttagaaaat atctaaggat gttcatgaaa taatactggc  33060
tatgaatgac agttgatgaa accgggtggt gcccnatctt attccctcga ctcgtgtata   33120
tgtttgatat atcccacaat aaaccttaaa aaaaaaagn atgagtggtc aattatagga    33180
agatataaat agaaaaggca ataaggacaa aagttggcaa agcttaccta agcactcttc   33240
agataaaaag acattttttgc taactagatt tgaatattat agtttaattg tcaaggaaaa  33300
tgcctcaact taatctttgt taagagacta cttaaggcac tatcagaagt tccctcatgg   33360
caaggtgcaa tccctcatgc ctgtaatccc agcactttgg gaggccaagg caggcaggtt   33420
acctgaggcc aggagttaga aaacaacctg ggaaacatag tgagacccga cctctacaaa   33480
aacaatttct taaaattagc caggcatggt ggtgctagcc tgtaatccca gctatttagg   33540
atgcttaggc aggaggattg cttgagcccg gggatttgag gctgcagtga gccatcattg   33600
tgccacaata ctccagcctg agtgatagaa aaaaaaaaa aaagtgtctt tgttatattc    33660
caaacttgtt ctcaactttc aggtgagctg gcttcctgta taactcttgt ataggacaga   33720
acatactggt tggggcaagt gaaactgtct agttgtatgc ctcataaatt aatgaatttc   33780
```

```
ctttctaata tatacactga tatttataca cacatacaca taaaaccaag ctcaatagat    33840
gggtagtgca gctctattcc ccaaaaccca actaccctgt aacaagacac attagacttt    33900
tgagattgca aggatgagga ctgaaatgct ggcctagacc atggtgttgc catagtgggg    33960
tgaccagtct gaatagccaa caatgcttcc tcagtaaata cccatttttgt cttggtggga   34020 tttctacaaa ttgcaaaatg cagctattat gaagctgtaa aagagaaac angaaacatg    34080 taacacctgg gactgtttta ttaggcccac cgtatgctca gaacatgaaa tctccactgc    34140
tagggttatt tgattgaaat tatcttttgt gttgatgtga gagtttagct ctgagattct    34200
tccacatgta aaatgtaatc ccccaaagta tttggcaagc acattttatt gccttgggtc    34260
agataattga aacattaggc atcatatata tagcatgtaa aaagtaaaac agaaacattt    34320
atgtttctca ccaagcagta aattagtact caactaataa atttcttaaa ctccctaata    34380
acagaatatg gaaacaaaaa ataaatcttt ccaaaagaag agctcatgga cacatttcct    34440
catatatgta tacataatat agtagaacac atgataaata acctataaaa atgataccaa    34500
tatcattcat caagagacga ggctcttctt taaattatta atttcatctg ttacaggttt    34560
tattatgact gtagtatgct gttttcatct acctttatg tgtagttaaa aaaatagttt     34620
tctatctctt tacctttatt tcagccttta aaaagattcc attatttttt cattaatctt    34680 gttttcagt ttttcccatt ttttctttta aacatttctt aaggaaccat atttaagatt     34740
ttatagaata cttagatttc tagttgggat gtatcattta aaattagata tgtagagaga    34800
gtgttatgat atatttcctt acgatatatt agtggttata gtacctaaat ttgaatagtg    34860
attctgttca ttcattcatt cattcattca atattcactt ccaggagatt ggggacttat    34920
ttaaagacag agtagttcac attatagttc ctttttttag tccttcttat tcgttaaaga    34980
aaagactagg aaatgtttgt tattacaaat attttattaa aattttgtgt gctctagcat    35040
tattttacct tttaaaatca atatgttaaa aatccaactt ctttttgagc tccccataaa    35100
aagggaatta tttgttgctt atgggtttaa cttgtgttat tttttttctta atggctaatt    35160 atcatacata tattctatta ttgtattgat attactgatc atttgtgcta cattaaaaat    35220
tctgtagaca gacctctttt caagtacaaa acctcaagaa gaacagaaga cgagtctggt    35280
agcaaaaaat aaaatatgca cactttcaca gtctatggcc atcacatact ctttattcca    35340
agaaaagaag atgcctttgg taagtgtgac tttcatgtta cagggaattt ttttagttta    35400
cttaaacttg tgttttatca gctttttagt attaaagttc tgacttggga tcaatttcct    35460
ccaaccctac aataaatctc agtttatctt taattttaaa agagaatgtt gttttctttt    35520
tctgttaagc ctccctgtta agtaatagca gcaagtttag tttggccatg aatatcttct    35580
agagattgta tcggggtact gataaacaca tttatagctc agggatactg catcagccat    35640
attttaaaat gggactaaca gtttaaaaac tataaatatt cacagtgtta agaaacaatc    35700
tcaagatgca ttaagaaaaa ggaaggtgca aaacagaaaa acaaacgtaa acgtgtgtgc    35760
atatgcatgc ttatatagtc acatattctt gtatgtgtac aaaaaataca cactggatct    35820
ctgcaagcat agccaagcaa ctggaaatat gttttaaaa acttgctttt cattctatct     35880
cttctagtac tgttttgatg ctctttgaaa acaatctaat tgctgtaaca aatgaccata    35940
cgtaggccgg gtgtggtggc tcatgcctgt aatcccagca cttcgggagg ctgaggcagg    36000
cagatcattt gaggccaggg atttgagacc agttggacaa catagggaga ccctgtctttt  36060 actaaaaata caaaaattag ctgggcgtag tgacgcatgc ctgtaatccc agatacttgg    36120
gaggcggaga catgggactt gcatgaaccc aggaggcaga ggttgcagtg agctgagatt    36180
```

```
gcgacactgc attccaacct gggcgaccga gcaagacgcg gtctccaaaa aaaaaaaaaa    36240
aaaagaccat atgtaatgtt tcttcattgt tctaagataa atctttaagg ctgttgaggt    36300
tttttgtata caaaatggag agtaagtttt aatgggatgg gacaaaatga ggcttacagt    36360
tgagtttaat ttgagttcac atcctgttga cattaagttg atttggaaca agtgatatgg    36420
tccaatgcct gcttttctat tgtctgtggt tccatccact agtgcctgtg ttacacacct    36480
cttgttcagg ttttatcatt taaaataaat aagaataaac agtccatagc ttatcttact    36540
tactgaataa atgctctgat ttgacagtca tgtttcttaa agttccttac aaaggccatt    36600
gcccaagaaa ccaaataatt ccattatact attttttgaaa tagaacacat aataaatggg    36660
aattttaagt tcagtttctt atgtaaacaa taacttctat gtacatgtta aatatgcctg    36720
tatataccta atttgaccat gtatgtatag tagaaatgaa aacagttact aagaaaattt    36780
gttattggct ccaaattttc tgaattaagt gtattnctaa tgctcagcca taatatgggg    36840
tttcatgtgt tagtttatgt attcatggtt aaaaatgtga agactgttat atcttcattt    36900
gtgtcttttg gtattatttg gttgtatttt attgtgtgat atggtggtat aattatcctt    36960
acctcccagg agtttgagag ggtcttgcca gttaaccgca gaattaaaca tgcctaggac    37020
taattaatca ggagcaatac tacaattaat tggaggtaat ttgaaacctg gtttcaaata    37080
accctgatat tatgcacaca tggtgcacac ttttctagta gacatttaat gaaagtaatt    37140
taaaacctac ctttgaagga tgaaaaacat tgccttaaat gctctattct gtgaaagtat    37200
caacatttat gcaaatacag tctaaattca gactttgaaa atgtattgaa agagaggatc    37260
atgaaataag ttagagctga gtgacaaagc tttctgagtg tttaaaagaa tgttttacct    37320
aataaatatc tgaaatgtat ttggagccac atttgtttaa agaactgtat aaatatgtag    37380
cactgttcat gtgaagttca atagtaggaa aatgctgaca gcccttgtgg aactgtggtt    37440
attattattt tatgaataga gccaatttca aacacctatt agagtcttct caggaacatt    37500
ttatagaatg catctggagc cttatgttat ctctaagcat tttaggattt gtcttcttgg    37560
aaattcatgt aaccaaacca ccatgtgtta tttcaagtgt atatagtatt gggttacagt    37620
ttactatgtt ttcagaaggt tgtgacaact attagactta cagagaatga cttctctgcc    37680
actaacggct ttctaaagtg aatagagagg ggcgaggatt gaattcttcg gtaaagctgg    37740
gtgattttgt tttattcaat acagtataat aagtataaaa agtagaacct atagagagct    37800
ataatggggg tagtttttaaa gaaattctga aaatgaaaaa cttaagtaaa ggtttagttc    37860
attgtttatt tcacactgag catttactac ctgaatgttt tggacatttt atttccatga    37920
ctggagtgga cacttttaca actcactggg ttctttgctg atctttctct agaagagcat    37980
agctgagagc aggattctgc ctctcatgac aattggcatg cacttatccc aagcggtgaa    38040
agctggctgc ccccttgatt tggagcgagc aggcctgact ccagaggttc agaagattat    38100
tgctgatgtt atccgaaacc ctcccgtcaa ctcaggtgag aggcatggcc tagctctgca    38160
cccttaatga cttgatgaag taaacaagca atccactata ttttttcactg ttaacagcat    38220 taatccttta tgctattatg aaaaccttac ttttgtgatt cttttttcttg ttttaggaaa    38280 acaatctttc ttcccattat cactcagagg aaagtatact gagaaatttt tttgttttgt    38340 tttgttttt gagacagagt cttgctctct tgtctaggct ggagtgcagt ggcgtgatct    38400
tggctcgctg caacctctat ctcccaggtt caagtgattc tcttgcctca gcttcctgag    38460
tagctgggac tacaggcgtg tgccaccatg cccagctact ttttgtattt tttgatagag    38520
```

```
                                          -continued acagggtttt ccatgttggc taggcaggtc tcgaactcct gacctctgat gatccgccca   38580
cctcagcctc ccaaagtgct gcgattacag gtgtgagcca tggcacctgg ccaatacact   38640
gagaaatttt tattttcctt ttcagcttaa ggttacaact tccccaccat ccaaaacgtg   38700
cactttcatt tttttttctaa tttctatctc atcacttgca aaaccatat ttttctccac    38760 attcattccc agtagcttcc tgactcctag ttcttcccta aatccttctg agtccttgtc   38820
attggtttcg cttgagtagc ctttctaatc aacacagtca ttggtatcag ttactgtgac   38880
atggaaggga cagaccaagt tctgtgggcc gctacgtaga aggatttcct gtcactttgc   38940
tgcagaacct cagctcgcgg agagcaagcc cctttgcttg ccctgtagaa atattttaaa   39000
ttattatcct tttttttttn aacagaagta aataggagat acgttagagg attttctctc   39060
ctagatgtgt aaatacaaac ttggggtctt ataactcaat aaatctgata aatttctttt   39120
gactgttagg atagagcagt ggccatacca atagcctcat ctccaaagct gcagtgaaga   39180
tactttttac taccttaaag tctttcccat ttgtgaacaa cttgtgaaca attccccccca   39240 agaatttgga agatcactct ctgaaagcac agtcaatact gtacttaaat ggatctgagc   39300
aaaaataagt cacttagaag acaggattat ttctagactt gagtgtgact tgactgaagg   39360
tctaaagaac aaacagctcc ttcacttcca ttgatcacgg tggaagcaca gggaaaggac   39420
agacacggag gcaagttgga gtagtgctca tctaagttcc agggatgcgg gggagtggcc   39480
aggggacttc aggtatagta aataaataac ctatttataa gttatgtcaa tgtcatgttt   39540
gaaatagaaa accaaatact gcatgttctt acttacaagc aggagctaaa gttggtgcat   39600
atggatataa aaatgagaac aggccgggcg tggtggcttg tgtctgtaat cccagcactt   39660
tgggagacct agatggaagg attgcttgag ctcaggagtt caagaccagc ctgagcaaca   39720
tagtgtgacc cccatctcta caaaaaataa gaaaattagc cagacgtggt ggcatatacc   39780
tatagtctca gctacttggg agtctgagtc aggaggagtg cttgagctca ggagtttggg   39840
gttataataa gctgtgatca tgccactgtg ctccagcctg agtgacaccc agagtgagaa   39900
cctgtctcaa aaggagaaaa aaaaaaagt aacagtagac gctgggaact actgagggga    39960
gggaaggaac aatggttgaa aaggtgggaa gggacagtgg ttgaaaaact acgtgttggg   40020
tactatgctc actatctggg tgatgggatc aattgtacct caaacctcag catcctgcaa   40080
tatactaatg ttacaaacct gcccatgtac tacctgaatc taaagtaaaa gttataattt   40140
aaaaaaatta taataaaatc agaaataaaa ggtctgagat ggaaaattaa aagaccaaag   40200
ccacccataa gcacaataaa tccctccccc caaaaaatta tatctattaa aaaaggtgt    40260 tgcgccaggc actgtggctc atgcctattg cctataatcc tagcactttg ggaggccaag   40320
acgggcagat gacttgactt gaggtcagga gttcaagacc agcctggcca acatggtgaa   40380
accctgtctc tactgaaaat acaaaaatta gccagcagtg gtggcatgcg cctgtaatcc   40440
cagctactca ggagactgag gcaggagaat cgcttgaact ggggaggcgg aggttgcagt   40500
gagccgagat catgccactg cacttcagcc tgggtgacag agtgagactc tgtctcaaaa   40560
aaaaaaaaaa aaaagacct tgtaccctga caagttttag tttgtgcagg aatgacacaa   40620
tctagaatga ctcaagattg gaaaaatctt taaatgttaa ttacacaata agggtaaaag   40680
gagaaaaatt acctaatgtc atctgagcaa caagaagaag aaatgaaagg cattaaaaat   40740
tgggaaaaat ttatatttga cagtatctta acaacgaatt ctgcttctat atcacttcct   40800
agctttctga tgataacttc ccgtgcagat ctgtatgtaa ggaatggacg tagtagtcat   40860
gctaatctga gtatttatct gtgtgatact tacgaattaa cgatgtaagt taataagtta   40920
```

```
gcatttcgtg aacctggtta ataccatttg ctaaggttaa attagccaaa tcctgaagta   40980
agctgtaaaa catccaaggt agggtagaga ggcatcttat gagaaagctg gccaactctc   41040
ctggtcacct tctaatcttc ctaacttcag aaatcaaggc agagagagga aaatagtaat   41100
tactttgtag gattagattt atggttgtcg aaacctttgt ttctccagtg cagaatgaga   41160
tagcgtttta gggaaagcca aagactcaga tgtcttcttc atgctcatcg tgtggaattt   41220
ttcttccttt agaaatgtat tgtctctcag ggcttaaagc aatttgcatc tttcgatgag   41280
acattgagta ataggcaata ttctctgaaa taatttgtgc aggctgggca cagtggctca   41340
cacctgtaat cccagcactt tgggaggccg aggcgggcag gtcactgagg tcaggtgttg   41400
gagacgagcc tgaccaacat ggtgaaaccc cgtctctact aaaaatacca aaattagctg   41460
ggcttggtgg cacacacctg taatcccagc tacttgggag gctgaggcag gagaattgct   41520
tgaaccccca tggaaggtgg aggttgtggt gagccaagat tgtgtcattg tactacagtc   41580
tggacaacag agtgagactc tgtctcaaaa aaaaaaaat agaatttgtg cagttccccc   41640 caccccttt ttttttctg ttggcatttt tgctatcatt tagctgcctt ctttatatcc   41700
tgaaacttac aggtggtgtt ggtctagtca gtaagagcaa aggctttggg aatagataga   41760
tctgtattta gaccttggct ctagcatctc attgttatgt gacctccatc aagtgaccta   41820
atttccctaa tattcaattt cctcatctct aagacaggga gttaatattg cctctcttat   41880
agaattgtga gaaatatagt catgtgtcgc ttgatgatgg ggatgaattc tgagaaatgt   41940
gttgttgggc gatttcattt tgtgggaacc tcacagggtg gacttaaaca aacctagatg   42000
gtatggccta ctacacacct aggctgtacg gtatagctcc tgtcttcaaa cctgtacagc   42060
atgtgacttt actgaacact gtaggcaatt ataacacagt ggtatttgta tatataaaca   42120
tagtgaaaca tagaaaaggc ccagtagaaa tacagtgtaa aagnatttt taaaaaagct   42180 gggcatggtg gctcacgcct gtaatcccag cactttggga ggccgaggca ggcagatcac   42240
ttgaggtcag gagttcaaga ccagcctggc caacatgatg aaactccgtt tctactaaaa   42300
gtacaaaaat tagctgggcg tggtgttggg tgcctgtaat cccagctatt caggaggctg   42360
aggcaggaga attgcttgaa cccaggaggt ggaggttgca gtgagtcaag attgtgccac   42420
tgcacttcag cctgggagac agagcgagac tctgtctcna aaaaaaaaa aaaaaaaaag   42480 agataaaaag gtacatctgt acagggcact taccacgaat ggagcttgca ccctgggagt   42540
tgctctgggt aagtcagtga gtgagcggtg agtgaatgtg aagacctagg actgtgcact   42600
gctgtagact ttataaaccc tgtgcactta ggccacactc acccctgtga tacgagtcta   42660
cctactgtat aacgtacctg catatgtacc cttgaaacta aaacaaaagt taaaaaattt   42720
atcttctttt gccaataata aattaacctt agcttactgt aatgattttt ctttatgaat   42780
taaaatcttt ttactcttt gtaataacac ttggcttaaa acacaaacat attgtacagc   42840
tatacaaata tattttcttt atatccttct tctctaagat ttttctgtt tttgattttg   42900 ttaaatttgt ttttacttt tacatttttt ttgttaaaaa ccaagacaaa acccacaca   42960 tcagcctagg cctacatggg ctcaggatca tcagtctcac tatcttccac ctccacatct   43020
tgtcccacca ggtcttcagg ggcagtcata tgcatgggc tgtcatctcc tgtgataaca   43080
atgccttctt ctggacacct ccagaagggc ctgcgtgttt tacagtgaac ttctaaaaaa   43140
taataaaatg tatagtatag caaacacata aacatagtaa catagtcatt tattatcatt   43200
ttcaagtatt atatactgta cataattgta catgctagac ttttacacag ctggcagcaa   43260
```

```
ggtgagtttg tttacaccat taccaccaca aacacatggg tgatgctttg cattgtgatg    43320
ttacgatggc atgatgtcac taggtggtag gaacttttca gctccatgat aatctaatgg    43380
atacttgttc ctgttggctg cccgtcgttg actgcaacat cattatgtgg tgcatgactg    43440
taaattagat actgttcaga aagctttggc acactggtaa tagcaaatgg tggtggcaaa    43500
tatgatgatg atgatgatga tgattgaaga catagatggt aaaattttat ggtgtcttaa    43560
aagtaccctc taaatatgat tatttttata gtctgtcctt ttgaataggc acttaagaat    43620
gtatgaactt aataagtata taagaaagaa tgttccccaa aatatatctt acagaggcat    43680
acaatttaag aattcaaaca ggttgtaatg gggtgtgtgt gtgtgtgcac acgcgcacgc    43740
atgcgtgctc attcacacta aagaattctt gggcatatgt tcctgaatgt cctaaatgga    43800
cattctaaca tcacttcatt atgggcagag ggaaatggta agaaaaatt tcatattata    43860 ttattcagcc acatattgac agcatctgtt ttatttgcct atggtaaaga attgaagcac    43920
tgttaatttg cttttttaaat catgtaggca caaagttatc gaactttaga tttagaaatg    43980
aaactggaaa tcattacact ttcccttttcc tatccccacc ctgttttgga gagaaagagt    44040
gtgaggctta gagagttata aaactgtttt aataccatgt ctaagattaa taactgaaca    44100
agtttctctt tttactcgtg ttaaagttgt actgccaatt aacttaaaag aaagaaatat    44160
gcaatttcta atcctgatat aggatatggg tatataaact ctaacttgat gagtgaaaca    44220
aattaactta tttataatca gtttcatatc tttatttatt gagtgtcttt aaatacccct    44280
tacctttaaa gtaagaaata ttaaaatcaa gcagaatata ataatgaaaa attcttaaga    44340
tatacttact aaaaacttat cgttcggtta atacactgta tgtaggttgt acatacaata    44400
tgaaaaagta tattttttgta gcctactttt aaatccagaa tagaggaggt taagaaggtt    44460
gtgataacca tgagctcttt ttttttttttt tttgagacaa ggtcttactc tgtttcccag    44520
gctggagtgc cgtggcacaa tcatagctta ctgcagcctt gaactcttgg gctcaagcaa    44580
gccttccact tcagccttcc aagtagctgg gaccacacct ggctaatttt taagtatttt    44640
tgtagagatg agttctcact acattgccca ggctagtctt gaaccctag ccttaagcga    44700 tcctcccacc tcagcctgcc taagtgctgg gattacaggt gtgagccact gagcccagcc    44760 ctctttttatt tcttttgata gtacactcat aatcattaaa ctatcatttc tggatgtgag    44820
attgtgcttt tggattctta ttttttcttt ataaaatact ttttgttctc ttactggaga    44880
aaacattgtt ggattataaa tgatataaca aggaatgagg atatacatac tataataacg    44940
attcagatat gttatttttca tattttattt aactgtagcc atgccacaat aatttagagt    45000
tttaaagaac aagtttgatt gaaatctaaa ctttgtacaa tcctgaattg agaagtttcc    45060
tgtattttat tatgacacaa tatttaccta aaaatagggt aattatgaat tgagaaaaca    45120
tagctattaa tttcatactc ttatttgtta agtagatttt gtctggaaaa ctgttcatat    45180
ttaaaggagc tttgtacctt tgtattcttt ttgttttttcc ttgtttatat aatttttaaac    45240 tctgtttatg gatttgggat tctaactatg ctaaataata aattaaggca ttgaatgaag    45300
tacctagaca gtattttgat taattttatt cccccattct taatgtgcat gtaactggaa    45360
aattaagagt ggcttccaag ggatctacta caaaagtaag gttaatatga tctcttttaa    45420
aacactgaag gcgtgtagcc agtgttgtca ttaattctgc agtagatatt ttcagcactt    45480
atttacatgg gaagttagag cagagtaaga tgcacctgta aagctaaatg ccacttattt    45540
gcatatatat aaaacgcagg atgaatttac catagaaata taagggtac ttatagaaat    45600 gtattagaaa aatatatgaa ttttttaactt atatctagaa gttaaccttta tacatttaac    45660
```

```
tttaaatcat taatagtggt ttaacaccat aagcggatgt ttatgcatca tcattttatg    45720
aacaaaagac attctaattt tagaaataaa gtgattcaaa agagaataaa atatcttact    45780
ttttctttta aaattaattt gtttagcgca ttacatgata atagctcaag cttgtgtgat    45840
ttttccctaa aaaattggtt tataaatatt acatttatag tatgaagaaa ttaatcatac    45900
atagtttatt tatctaattt ctaaataccc atggaagaaa atgaatttaa tggaatgtag    45960
ttgtgtatta cttggtttcg agtgtgggaa aatttatatg gtctttctaa aacagcactg    46020
tcagtagaaa tacaatgtga gctacatatg caattttaaa ttttctagta gccacatttt    46080
aaaaagtaaa tggatgcaat ttattttgat aatataattt aattagtcta ctatatttaa    46140
aattttatca tttcaacatg taatcaatat gaaaattatt aatgagatat tttacatact    46200
tttttctgta ataagccttt gtaatcaggt atgtacttta tatatacaac aaatcttctg    46260
atgctaaatt ttaactggaa atacttgatc tgtgtttagc ttttgtaaaa tttactgttg    46320
aacaacgtgg actaatgtgc ctaagtggtt ccaaacatat tttaaaattt gaagacaaat    46380
aaaagggaac tcaaagtaaa ttgggataca tacatacaac agaatactga gccattaaaa    46440
aatgatgaaa tagtaaaatt gggggaattt tgatgatact aggatgatat aatgaccaag    46500
agacaaatac aattttagtt tggttgagag atgtgatcat cacgttgctg attttactat    46560
gtatagaggt tatctttttcc tttctaagat tttgaaactt taattagtta acccacttac    46620
ctagtttcta ttagctgtgt aactttctct tcctgttttt tgttttgttt tgttttgttt    46680
tttgcttttt aactgcagta ttttgaggag tcttggagta gcaagctaat ctttggaaga    46740
aaggaaaata taaacctgaa aactaataat ttaaagaacg tcttttcagg ttgtcatttg    46800
aaaaatanct tgatttctga tcnacntgat ttgaattgag tgtcaaatat ttgatatgtt    46860
ttgtaaatta ggtgaagatg agtgagtagg ttctaaactg cttgggttta ccgcactctg    46920
gagcattgca ggagaatgtg atgttggaag gaagtgctga aacataatta ttggcttgcc    46980
tataggaggg tgctacataa ttttagaagg tgtcaagaaa ttgacacagt ctgaattagt    47040
tctgttgagt tgcaaaaaat gtaaagtttc ttgattctga aaataagaaa tatgttccca    47100
gaaatctcat ctagttaatg tgcttttaaa atcattgatg tctcttgtta ttacaataat    47160
agccattgaa agaatctttt ttattagaat gttatttaca ggtacgatta gcttctattt    47220 aaataaaatta tttttatact tgatcttagg caaaaggcca acaagtgatc agaataaatt    47280
attttaagag naaaactaat tataattgat atttggaatt ggaagcacaa tttccttag    47340 aacaattcca cgaatggttg ttttgattct caaggcagcc cacaaaagac agtttgaaac    47400
acaatttatg cagtgtcaat agtactgacc tgactttgga tcttggaggc aggggcttca    47460
ggtgataccc gagtggagtt tttactccat ttccattccg taaggctata ggcatttgaa    47520
agaggaaact tttctttggc aaccttccac cttcctttct acagaatatt tcagtatttc    47580
tagctcatag gttttctaaa atattctctg taatttattt tgaaatggag tttttttatc    47640
gtttacagat atgagtaaaa ttagcctaat cagaatgtta gttcctgaaa acattgacac    47700
gtaccttatc cacatggcaa ttgagatcct taaacatggt cctgacagcg gacttcaacc    47760
ttcatgtgat gtcaacaaaa ggagatgttt tcccggttct gaagagatct gttcaagttc    47820
taagagaagc aaggaagaag taggcatcaa tactgaggta ttaattatat atagaatttt    47880
cataaagtgt cagtttgttc aatttgcata tcctagtact agaatgctgt attttttga    47940 actgttatga attctgatat gattactttc tctatgtgct acatttcctt tgcttttcat    48000
```

```
aaatatgatc tgagaaaagt gattaaaaaa aagacagtaa aagggaggtt tagtccatct    48060
gtttagctta ttatgtagaa tgtcagctta aattttacct gtacctcata ttgaccgtat    48120
agcctggaaa atctttcgga ggtatagtta atggatttaa gcatatggca gtttatgtag    48180
ttaatgaaag tgaaaacaaa ttgtattata aatacctccc aaactggttt attatcattc    48240
tatcattctt catgctctgt tagtatgata ttgaatatct gaggtaccag gattattgtt    48300
gcttgtggct ctgagcattt cgtagtgctt ttgcatgatg agagaaagat tacaaattta    48360
gtattatgtt agatggtacg ttttattaaa atcaaatgct tcaaaaataa ttgctctgtg    48420
tatggcatga gataaatagc aatcagatat attgtttaat aatatgactc tattaaatga    48480
tggcataaat ttgaaaattt gaccttcggt atcttccggg tctaaaatta tatgactcca    48540
ttataaatat tttggaaatg attaactaaa aaattgtttc aattcttagt tggtaaattc    48600
aatgtggtag taggtggtgg tgattatttt gtattagaga attaggaatt acacttagtt    48660
ctaaggtaat ctttatagga tgtccagcaa ttaaacccct acttttttga attgcttaaa    48720
aataagggaa ctgatctttt taaattctgt acttgagtta cgtctgtata tatagtcatg    48780
tcctagataa tctaatggaa cttaattagt tggaaatctt tatattgttt ataactgaac    48840
tagctataag aggaacatta aagaaaacat attttgagtg gaggtaatga aatttagctt    48900
ctaatgctca gccttttatt tctgtaatct ataccagata cctaagaccc tcttattgtt    48960
tcccagcttc aacctgtcag tatagaaaac ggtgtaactt actattttt ctcaatattg    49020 aagcacattt gtagtgaaat attattttaa ctatatattg ccattttgc ttttttccta    49080 tttcagtaac atttttcgct atttcagtaa cattacatgt caacaagaga atggtgggta    49140
ttttgggggg ggttgggtgg gaagaaattt tactaagctt gctagattct aaaaggtata    49200
ccttatttgg cccctttcc ccatttaggg gaacaagggt gttggggctg ggaagtagat    49260
aagaggtgaa gtaagtcatc caaagcatat gtcttcatta gcctccctgt atgaaaagct    49320
gatttctgta gagtgttgga ggcctacttt cagaatctgt catatgttaa cattcatctt    49380
ctctactgac ctgattata tcccttagtc tatttcattt tataattatg acaaaggata    49440
aagtcattag aacaaattct ttttattagt tgacgtattg ttgtgtttat atctcttgtg    49500
tttgttatta agatggaagc tcaatcatgt ccttgtttaa cagaaaggtg atgtcttggc    49560
attgataatt ctgattcaat atccataggt acatggtgga ttctttaaat atttagtatt    49620
cttttatttc tggaaagttt tcttaaatga tagttttttt aaaatttcat ttctataaag    49680
ttttcttaaa tcatactttt tagtgtttta ttccattact tcatatttct tcttcaggaa    49740
ctcctgctat acatgtatgt tggatcttca ttacccagct tcaatatttt tcacttttca    49800
tgcattcttt ttatttcttc atttctcttt aaattttttt cttccttttc accttctatt    49860
tctcttttaa cataattgta tttatttctg tattccacat agcttagtat tcacttattt    49920
taaaattatt ttaaaacgtt tttagattt aaaaattctt ttttattta tatatacata    49980 ttttattttt accaaaggag caacactatt aactgaagac ttctataatt tttttctttt    50040
atttctgatt ctttcttcgg ttttcccct cagttttgaa cttttctaat tttgatttgt    50100
gatgtccttt tgtattttag ataatttcc taatgttttc cagctcattt ggaaaggcta    50160 cagtttatt ctgtacctaa gcaagtcttt ctggtgtcaa agatttgacc ttgatacttt    50220
tcttttgctc attttcgtat gagattagtt ttcctgtact ttcaaaagaa ggcgtggttc    50280
aagatggctt tcccaatttc acatctgtct ctaatgtttt tgtgtaatgt ctaaaatatg    50340
gaaacttggt ttatgagatc tactctgcca tttttatctg ggctttctct tccttttgtc    50400
```

-continued

```
tctgttgtac ctgtcctgct tggttctgat ttaacccag tggtttctcc tgaatgtgga   50460
gccttctcct agaaggcagc ctcggctagt cccagggttc agagtagcca gctgctctct   50520
tcacctaaga gaccactgtg gattccttgt actcacttgc tattggcttg acaaaagcc    50580 ctcccatttt cagatgctat tatcagatta atctctcatt aatctgtctt tccagtgtat   50640
gcctgtgggc tatcttgggg ttctcttgtt atcagacacc tccctgctgg cctctgcttt   50700
ctcccgtaca gatgtcagta ctgtgcaggt cttaattgct gttggtggtt tgcccctaca   50760
ttcttacagt tttagtttcc caaggatacc tttaaacttg gttttattgt aaatgtcgac   50820
aatggatttt gggttttact atctagttct gtcttaattc tggaattcag aaagattaaa   50880
agctctgttg ttgcagctgc tgccacctct tcccagtacc ctctcctcct atgtcatttt   50940
tttcttctta tttttcttga ctgtataaga gagaatgtat gacatttcct gcttgaccgc   51000
tgagtttgat tataaattaa aatacacaat attttataca aattgttttg tagaagattt   51060
atttacagat gctcattcac aggtaaaatt gacttatgaa aatagttttc atgacaaatg   51120
tatcaggctc ggtaactaaa tatatggatt gatcttgttt ataaatgaaa ttaaatgtga   51180
atgtaactta catatttctg tatttgctta catccgtatg tacacatata atcagcaaat   51240
gagttgatgt ttcctattcg taacttaatg gtaatagctt ggtaacagag ttgggagtat   51300
taaaaagatg taaagagccc cttaaaattt tgttgctggg aattttagtg ttctactgat   51360
gaaggaaata gacactggaa ggtgttgttt ctattaggta acttagatat catactgaag   51420
acttcaaata cttattgttg acactcaaaa gacacactta gtgtaagtaa gcatttcccc   51480
gcttttccca atgaaataag atcattatta taattccatt ataaatgctg atgatcatat   51540
ttatagaaat atagaagata agacttgaaa tgatattcgc taccaattaa tgagtttgaa   51600
gaagaaatca ggatgtgttt tgctatttta catttattct tatttaactc caaagaattc   51660
agtgatgtta tgtactatta tttccatttc tctgtgaaga cgttgaagct taagtaacac   51720
gcataataag gtcatacatt tagcaagtgg ctcaattaaa gttcaaacct ggttctgcct   51780
ggtttcaaag tctgtgctac tccatggtat taggctacaa catgacttag ggtttcttcc   51840
tctgctctat tgctgttcag atgtactcct cttttggcag agtgggagaa aatttttgca   51900
atctatgcat ctgacaaagg cccaatatcc agaatctaca aggaacctaa acaaatttac   51960
aagaaaaaaa aaaaaacatt aaaaagtggg caaaggactt gatcagacac atctcaaaag   52020
aagacattta tgtagccaac aaacatatga agaaaagctc aacatcactg atcattagaa   52080
agatgcaaaa tgccttttct gtatgccacc ttatatcccc agtatttatt atttctaagt   52140
catagtatct tacagtgtat ataagtctca tccgttcttt tgattttctc ttccctgctt   52200
gcaattgggt acctaggaac aaagttgcaa tcttagccag ttttttcttt agcctttgct   52260
gatgtgtgaa aagcccttt ttctaccctg gatttctgta cttaagctgg aacagctaag    52320
ttttaccttt ttttaaatat aaagtttcag agtcttctgc caaggatctt ttgctgtttt   52380
cctactgtta aatatttcaa agccttttt aaacataggg aatataatca acatagcaa     52440 gcagctgatg aacaatatct agatagtctt cattattgaa atggaataaa tggtattttt   52500 gtatttagg ctaacagaca ccttgtacct tagataaggc caaccttctc ataaaatccc    52560
tcagttactt ttattaataa taaccaaatt aactctggat tccagggtgt actcatgatg   52620
gaatgatttc tctgtcatgt tatcctgagg atctagtact ctgagataac ataagtgtat   52680
gacactttag gcttatgaaa cacttagcta cttaaattat ttaatttttt ttcatgtgca   52740
```

```
gatggtattg tacccaaaca ctacctttgt gtgtgtgtgt gtgtgnncgc ctgtgtgtgt   52800
gtttttgaga cagggtctta ctctgctcag gctggagtgc agtggcgtga ttatagctca   52860
ctacagcctt gacctcctgg gctccagtga tcctgccaaa gtgttgggat tgcaggcgtg   52920
agccacctca cccagcctta aattattttt ttttcaagga tgtttaacct gagggttaga   52980
ggctctttgg cacgtgagct gctgaaatgt gtgtgaaagt gttgtgcacg tgtatgtttc   53040 tcttttttc tgggaagtgg atctgtagtg attcttagat gagtctatga gacaagaaac   53100
ttttattttt ttcatttatt tagcgaatgt ttgttaagcg tactatgcct tggccactct   53160
acagggtgct gattggacca gtctgtctac ctaccgttgt agatgttaga agctatattc   53220
ttttcacatg cctaatataa ctctttgtgt atgtatacat gcccaggcat gttccttcct   53280
cagaacatta aattcaccat tttggtcaac tcaaagcaag taccatgg gacacagatc    53340 tgaaataatg tccagatttt tacttactga atgaggtgtg ttgnagtgta taagactaca   53400
tgatgagatg gcaagtaatt gcctgaagaa atgatgtagt gattttgtgt gtcttatatt   53460
tatttacttt ttgatccaga aataaattat atagatacca ctattttgtt tggatggggg   53520
agaaaggatg ggtgtgtatt caggaactta tgttacttt ttgcaactaa taccccttct    53580
cagtagtaca aagatttgat ttcttttttct ttctattttcc tacagacttc atctgcagag  53640
agaaagagac gattacctgt gtggtttgcc aaggaagtg ataccagcaa gaaattaatg    53700
gacaaaacga aaaggggagg tcttttttagt taagctggca attaccagaa caattatgtt   53760
tcttgctgta ttataagagg atagctatat tttatttctg aagagtaagg agtagtattt   53820
tggcttaaaa atcattctaa ttacaaagtt cactgtttat tgaagaactg gcatcttaaa   53880
tcagccttcc gcaattcatg tagtttctgg gtcttctggg agcctacgtg agtacatcac   53940
ctaacagaat attaaattag acttcctgta agattgcttt aagaaactgt tactgtcctg   54000
ttttctaatc tctttattaa aacagtgtat ttggaaaatg ttatgtgctc tgatttgata   54060
tagataacag attagtagtt acatggtaat tatgtgatat aaaatattca tatattatca   54120
aaattctgtt ttgtaaatgt aagaaagcat agttatttta caaattgttt ttactgtctt   54180
ttgaagaagt tcttaaatac gttgttaaat ggtattagtt gaccagggca gtgaaaatga   54240
aaccgcattt tgggtgccat taaatatggga aaaacatgt aaaaaatgta aaatggagac    54300
caattgcact aggcaagtgt atattttgta ttttatatac aatttctatt attttttcaag  54360 taataaaaca atgttttttca tactgaatat tatatatata ttttttagct ttcatttact  54420
taattatttt aagtaccttt attttttccag gatgtcagaa tttgattcta atctctctta  54480
tgtagcacat gtgacttaat ttaaaaccta tactgtgaca cagagttggg taaacgatga   54540
ttatttaact ttaagcagtt caccatccat ttcaaagcct ttgattggct tttttgtaaa   54600
taaaaataac ttgttaagaa acaaatatat ctgtcataga agaactagaa aatccaggga   54660
agtgagaaaa atgaaaataa aaantcattc atagtttac tagtagctaa tcacagtcaa    54720
cctcttttgt gtatcccacc agactttttt atattcattt gttttaggt aaaatataaa    54780 agtctcgtat attcccattt ttctgcattg cattaccaga aggtagtggc gcctattaaa   54840
tatgtgatat gttgttgtcc agccatggct tctgcatttg catgcttttg tgtgtgcatc   54900
tgcaataccc tgtgaatatc ctgtgtgatg gagtggcaag tacgcacaga cacgtctgct   54960
gcatgcctag gtacgaggct gtctccagga gaagcacttg tttgattatt tgagttgcca   55020
attgaatttg ctgcttttttt tcatggcttg ccatttcac tgaaaagaat gactaatgaa    55080
aaacgatgat tggttattag atttggatgt ttggcagaca ttttctcaaa attgaactaa   55140
```

-continued

```
gttggcctct tcacggaaaa caactggtat ttgttgtgcc aatgataaaa ttggagattt    55200
ctagcaaaat gtataatttt ggaaaagttg tgttcctcca ctggaagctt gacagctttc    55260
cttaacataa agacttctct ttctcttcgc tttcactact actactacta attcttcttc    55320
tgattcttct tcttctcctt cttccttctt ccttccttcc tcctcctcct ccttcttctt    55380
cctcttcctc ttcttctttc tctctttcct tccttccctt cccctttccct tccttccttc    55440 cttccttcct gcccgtccga ccgccctgcc ttccttcctt ccttcctccc tccctccctc    55500
cctccctcct ttcttttttct ttctctttct ttctttcttt ctctctctct ctctctttct    55560
ttctttttct ttctctttt ctttctttca agcagtcctc ccgcctcagt cccccaaaat    55620
agtgggatta taggtgtgag ccaccatgca cagccttaca taaagccttt tctaatgaga    55680
tggatagtaa ttaacaaatg tgagtttttg atattatata aagattttt ctgtgtttcg     55740 aagatccgta taactcagtg aatcagtatg ttctggatga ctaatatgtg atgttaagaa    55800
atcatgactg aggccgggcg cggtggctca cgcctgtaat cccagcactt tgggaggccg    55860
aggcgggcgg atcacgagat caggagatcg agaccaccct ggccaacatg gtgaaacccc    55920
gtctctacta aaaatacaaa aattagctgg gtgtgttggt gcgtgcctat aatcccagct    55980
actcgggagg ctgaggcagg agaatcgctt gaactcagga ggcggagatt gcagtgagct    56040
gagactgcgc cactgcaccc cagcctggcg acagagcaag actccgtctc aaaaataaaa    56100
aaagaaatca tgactgggta aaagatctgt tcagagtaca agatggacca atggatttga    56160
tatatttgaa tataacagag tatgaaaaag tttattgata tagtttcaga ttacacactg    56220
caactaatct ttaagaaact attacttgtc cactttttgg taaaatttca gagaacaatg    56280
tccaccatta tctgaacagg ctattaaaat actcttctct tttccaacta cgtgcctgtg    56340
caaagtcaga ttttttttcat atacttcagc caaaacagca tatcaaaatg gattgaatgc    56400
agaagtagat ctgagaatac agccactttt gttaagccag acaatgagat ttgcaaaatg    56460
taaacaatgc tgctgttctc agttttttaaa aatatgtttt ttaaaagtat ttatgttaat    56520
gtgtacttgg tttactactg ctattttttaa ataaaacaag aaacatttt aaatgtctgt    56580 tttaatttct aaagtggtag tgatagatat aacccatatt aataaaagct ctttggggtc    56640
ctcagtgatt ttttttttaag agtatggaag ggttctcaga cctaagagat tgagaaatgc    56700
tgatgtaatg ttttattata aagtgtacc atgaattatg taccttactt catattgttg    56760
gacattaaag ttgctttcag ttttttttgtt ttaaacagca ctgctttgac cttttttaaa    56820
aaatgagtca gggtcttgct gtgttgccca ggttggagtg cagtggctat tcacagacat    56880
gatcatagca tgctatagcc ttgaattcct gggctcatgt gatacttctg cttcagcctc    56940
ctgagtagct gggactatag gcgtgcacca ctatgcccag ctgctttgaa tattcttgaa    57000
atgaaatatg gtatagtctc ataccatatc atagccagag ggggagagag agaattttgt    57060
tgttgttgtt atgttatctg tagtggactt tatgccttcc cagcataaat tctctctttc    57120
cccatttttc gtgaccccttg attttttgttg gggttcgttc caaggagaat aatttccatc    57180
tggatattgg attggcacct gtgacctctt ctgagctaga ccctagtaac agcgtttgga    57240
tctggggtag gtgtgtggcc aactgagctg ctggttcatg cctttcctga aatgagccct    57300
acctctgaat atttcagaaa catgggacat taacttccct ttacttacgt taaacccctt    57360
tgaatgagga gttgttttttc acttccagtt gtgttcagtt gtcacagaag cacagcgatg    57420
tgattggtgg aaggacccgt caacagaccc agaagatgta aagtgttttt aatctcaaag    57480
```

-continued

```
gatgtggaat ctcagagata gttacaccga gtagaggatg aagcggctcc tggatggagg    57540
cagaggcttc ctggatcttc aagttctgta tgggttgttg tatgaggttg gtgcaaaagt    57600
gaggcaggag aatagggtct ggaggcaagg aaactaaggc cgattcacac tgacttccta    57660
gaactaaatc aaaaggaaaa ccccaatttt ccagacctaa ataacaaaag taccagatgg    57720
ctcctccctt tcaactgccc ctcccccaca cctttctgcg tgacacatgg aaaattgaaa    57780
gtatctctgg ttgcttctgc gtaggaatgt aactttgtaa ccaatcagac ggatcgcagg    57840
ccaagtcgcc tgcatagaaa tgtaacttg taacttcact ttagcctctg attggttgct    57900
ttccacaacc aatcagatgc ttgcataggg tgtacctgtt gtgacttcac aaagtggtgg    57960
aagtggtgga agtggtggaa gggtggaagg gctatttaaa tttttattca tcctctgatt    58020
ggttgtttca cttaagcctc taattggttc ttgagtcctg gagcctgtga agggtacttt    58080
attttcagta aatgcatgct ttttttgctt cattctttcc ttgctttgtg cattttgttc    58140
agttcttagt tcaagacacc aagagcctgg acaccctcca ctggtaacaa aagtaactgg    58200
tgtttttgcc attagaagta atggcacaga acaagtacat gagagcgatt tcttatggaa    58260
aattaaatgg cgcataagtc gtgtgctcag gtaagggagc tgggaaccgg tagaggaagg    58320
tctccaaccc acaccgtggg gatctctgag tctttgaaag tccgtcctca ccctttgtga    58380
agaatgggag cacggctgga ctcgtcaccg ggggttttgg ggggctgaac ttgtcatttg    58440
agggtgtagg gaggttggat gaatcgcagg ggtgcaggga gggggcccac tggagctcca    58500
ccaggacccc agcaccctag atccaaacct ggtcatgctt cccatgctca gaggcaaatc    58560
tccctcccct tggggggcgg agtcagacga gacccctct ccatcctttt ccaggtccgg    58620 tggggcggg actttaaagg taaaacagc aattactttt gcaccaactt atcttctaag    58680
tttcgctccc taccacctga gtgtgtttgg aggctctggc tcattgtacc tgcctgatca    58740
ccaggtgcaa gtagctgggc cagaaggacc tcggcacgtt acggaatatt tactacagga    58800
acaggtgagc tgaaggcgaa ttccccaggt gtagcctgtg accatagatt cagacaaagc    58860
cctgactgtt gcctggaatt caaaaaagct gtagccctac cagatagaat aagaaaagaa    58920
tataggattc ttcctattca aataggttgc atataattaa gagcatgaac gatccaatgg    58980
aatgaactca aagtagtttt tgagtgtaat agacttgaag tgtcttatgg aaaagaattg    59040
caaaaccaca gaaacagtga agaaggttag ttatagcctt gatggggtag ctgacttcag    59100
cagtctcagc tatctgaaaa gttatttacc agattttggt tgggaacata tccctaaat    59160 catttgagat aatgtacttg tttccttact gggtaaatgt gtttaaacct tgagnaaaat    59220
gtagacataa gtagnaatat angaataaat taaacctttg gtagttatgt tttaggatta    59280
aggactaata agtacatatt tgatatttaa gcatttgtaa tgcttgagat aatttatcct    59340
actcaagtaa cagattactc ttgtgactcc aatgtaaaat atatcattga aaattagta    59400 tctgcttgtg attttaagt agaaaccctg ccatttgaaa ggtatttgcc tttattattg    59460
gagatatttc atatgaatgt ttaactttgt tattgcatag aagtatttaa acagatttca    59520
cttgcaagag aaagatatct aataggttac tcttaatcag tactaaatta ctacaattac    59580
tatattctat taatatcgat tcattaaaac ccagagcttt aattatgtct cagaaaatta    59640
attaaacttt agcctcataa tcagctttat tttctaactc aatgtttaaa aattgacaag    59700
tatgtattat acttatttat gtcttcattc agtaaacatt tgcatttgta gcatgcaaga    59760
caacatgcta gacacacgaa agatggaata aatggaagaa aatgcaacac agatctcatg    59820
cttaagaggg acagatttac tctgaagatt caatgaaaaa acatccacaa acaacttttc    59880
```

-continued

```
tacaagaaac aaaacatttt aagaaaaca tttacttcag ccgggcgcgg tggcttacgc   59940
ctgtaatccc agcactttgg gagggcgagg tgggtgcatc acgaggtcag aagttcgaaa   60000
ccagactggc cagtatggtg aaactgtgtc tctactaaaa atacaaaaat tagcctggcg   60060
tggtggtgtg tgcctgtgat cccagctact caggaggctg aggcaggaga atcgcttgaa   60120
cctgggaggc agaggttgca gtgagctgag atcaggccat tgtgctccag cctgggcaac   60180
agagcgagac tccgactcaa aaaaaaaaaa aagaaaaaaa aaagaaaac atttacttca   60240 cataataaga tatgagaaaa aatggactct ctgaatgaaa aaagaggag atcatgtgaa   60300 agatttgcgc tttttttttt tttaaagtta tggactgaaa cactcctaat cattaacatt   60360
tgttatttta ggggagtgga attggaaagg tggaaggggc tatttacatt tttataatct   60420
ccatgtcttt taaatcaata tatattgcat ttattctttt agttaaaatt ttaagaactc   60480
tataaaaaat agacagggg actcccttg ttacccaggc tggtctcaaa ctcctgggat   60540
taagtgatcc tcccacctca attagaaggg tggaagggcc agctgtttaa gtttctataa   60600
tctctgttaa atcaaatgta tattgcattt attattttaa attttaaaaa ctttttttaaa   60660 aatagagatg ggatcttcct atgttgtcca ggctggttgt gagctcctag gatcaagtga   60720
ttctcccgcc ttgacctttc aaagagctgg gattacaggc atgagccacc atgcccagcc   60780
tatttatttg tttatttatt tttagaggca gggtctcact ctcactagac tgaagtgcag   60840
tggtgtgatc atagctcact gcagtctcaa actcctggac tcaagcaatc aactagcctc   60900
agcctctgag tactgagatg acaggcatgt gccttcatac ccagctaata tttttgtaga   60960 gatgggtct tcctgtgttg cccggaagag tctcaaactc ttggcctcag cctcccaaag   61020
cactgggatt gcaggcatga gccacaacac atggccctgc ttttaaaaaa tatatagtgg   61080
gccaggcttt ctgggatgat gggcaaccat tacatttgct ttctctccat tctgaatgtc   61140
agcctccata cacctctctt gagccatctc ttgatgccca ggactggcag gcaagcagga   61200
tgttagggtg ctggctggag ggctggaaag ccccagggca aggatatgaa cgtgaaggat   61260
tttaaggaga ttcttggacc tcaagggaac ttttggtcct ggtttcctag agtatgttag   61320
atcttcttgg ccccccaaga atcaaggaaa agctgaatag gtggaccgaa tccttttccag   61380 cactgaggct gggagaactc tatgacacca gtgggtgctc atcctggtgc tgccatggac   61440
ctgactacct acttccgcta aactctccag cagctgagcc ttcaagagaa gacgtcctcc   61500 acctttttcca tgagatgaag aatccttggg gccagggat gtgctcacta gctcacacct   61560
gtctccatcc tctagaccat gcttgcagta cacaggaccc cagaatgcct ggcccaaaca   61620
ctcgtgagcc tccaggggct gcaggggctt ctggccttgt ttccccatct gatgagttcg   61680
tttcttggtc tgaaagattg tgacagttac tacgagactg aatgaagggg gatgaatgca   61740
gaaatgaaaa cttaagacaa aagtaacttt taatgagagg ggccgaggga agaagaagag   61800
ggctccctgc ttctaatgag caaaggcagc caccctgagc ttctacagcc cttcgtatttt   61860 attgagtaga aagagcaggg aggaggaggt aatgattggt cagctgctgg attgatcaca   61920
ggttcatatt attgctaaca ggcttcagat gtgcctgatc acaagaaaca cttgcgcctg   61980
ggcatgactg ccctcagcat tccttctggg cggcagatgc agtttgtcag tttgctaaca   62040
acctgctttc atgagaacag tttgctgctt acttacacag ccaccagtga tttactgagt   62100
tgatcacgac cctcactctt tcggcctcca acaaaagacg atcaaagaat ggttgtttgc   62160
agaggttatg gacaagactt gatgtccagg ccgagtgtcc gtatgcacag gagcctcttg   62220
```

-continued

```
gtggtgcaga gtgaagccag aggaggagga gtgggttgtg tccatgggct gattctccct   62280
gcaccaacag gacagaatcc taaggaatcc gagcatttga aattcaaatc tggtcttaca   62340
ggttgttatg tatttgtcta ggtaggaggc tagaatgtat tgaaatgggg ttagcctgac   62400
atatttatat atttcatatt taggcttcca tttgttcctt tgtcttgggt cccaaaaata   62460
tattagaggt gggcctgtct gttctcttgg acacgaggac ctcaacgagt ttccactgtt   62520
ctctgaatgt ttccttcctg gttttctgtg tatacaataa ttcctagttt tctgttattt   62580
acaattttac ttccactttt taaagacaaa aatgtatgtt tttttagtca atattgatat   62640
agtggaccaa tatattttac cgttattttt gcttactgtt tttgttttt tgccttcctc    62700 atcttctcac taagtttgtc tgactacagc cacacaccat tcattcaata ccaactcttt   62760
tttattttta ttttttggag agagggtctc actctgtcac ccaggctgga gtgcagtggc   62820
atgatcttgg ttcactgcag tctcaaactc ttggactcaa atgttcttcc tgcctcagcc   62880
tcctgagtag ctgggaccac aggtgcacac gaccatgcct ggctaattaa aaacaaaaca   62940
attttttttt ttttagagac ggggtctcac tatgttgcct aggctggttt caaactcctg   63000
gggtcaagtg atccaatacc aactcaacac gtggtgagac ccagtggtct agacaaacag   63060
ccacatagca atatgttttt ctccatgatt catatccatg ttcgtttgtt acaaaataac   63120
aggcatgaac attttcttca gagagggaga tccccactta tccattaatg actcatttgg   63180
tgtccattcc aaactattaa actgcaaaag cagacatgag aaaagaaact taagtcaatg   63240
tttttatcac atgttggtgc cagcctccca tagtggtgct aaatttatgn aaattgcaac   63300
aaaacaaaaa cccaaacaac ccaacaacga aaagctattt agtgaacacc gtgactaaca   63360
agcttattag aactgcttat cagagctatg tgtggatttt gtaggggaa agattttctt    63420 ccctcgtaga cattttgcaa aataaaagta aaatattacc tttatgtacg tggtagatag   63480
aattccacaa gcttcaaatt caacgactca aaaatgttgc ttttactttc catatctcag   63540
aagtcacttt tcttttattt attttttaga gatagggtct cgctctgttg cccaagctgg   63600
agttgcagtg gcacaatcat agctcactgc agccttgaac tcctgggctc aagcagtcct   63660
cttatctcag catcctgagt agctgggact acaggcgcat accaccactc ctagctgatt   63720
tttaaattct gtgtagacat aggatcttgc tgtactgccc aggctagtct tgaactcttg   63780
gcctcaagtg atcctcccac cttggcctcc taaagtgccg ggattgcagg tgtgagccac   63840
catacctgcc cagaaatctc ttattttaaa ccccaattcc tcctgatagt aaaaaaaaaa   63900 aaaaaaaaa aatgtcatct tggtgtattt tgggtaggct ggatcacttc aagtttcccc    63960
ctcctcctga agctccgaca gaggcctgca agccctgctg ggatctgtcc tcagtccctc   64020
tcgggctcat cttctaccat cttgctgtca ctccatctcc ctgtccttcc ctttgcttca   64080
cccataccag accctgtact gtttctggaa gacaccaggc atgctgtgtc ttaggggaga   64140
atgtgatttc accaactagt gccgcccaag taacatgcat ttgccctgac tgctcttttc   64200
acctgctgtg ctgctccccc agataaccac aggcaaaccc cgccaactcc tagtttattg   64260
aactatacca tgagtaactt acttaaaatc tccataccdt gtcccattct ctcttacctg   64320
ttccaatact tatttatgat gttgatagat gatctccctc tactagactg gaagctcctt   64380
gacagcgggg attcttgtct gttttgttca ctgctgtgtc tttagcacct ggagaaatgc   64440
ctggcacaca gcaggaactc agtaaataac tgctgaataa ataaacatga ataaatcaat   64500
gaatggggat gcctaagtgc ttcgggattc tggtcaaagc tttggcaact agggacgcac   64560
agggaccctc atcatctctg cctcctaggc aggtatccac tgagatccgc aatcccatct   64620
```

```
ggtccttgga ccagttaccc ttcatgttgg cctctgttaa gatgtccagg ttgtatctgg    64680
tctcccacac agcatccctt tattactacc cctggacctc agcagtcagc cacacattca    64740
gtaaaggcca cagctctgcc atctcctagc taggggactt tggacaaatt acttagacac    64800
tctgagcctc gtttgtaaca tgcagagacg ttgctgggat tagacacaat gcctgtagac    64860
catttaacaa ttgctgtcac acatggttgg tattcactca gctgtcgcta tggaattagc    64920
agacagaaaa ggcacagcgt cagtggctgg gtgtccagag agaagcagcc tgtctctcta    64980
gataatactt ggcaaaatca cagcagtccg gtgtgtggcc ctttactgac cttgattaaa    65040
aatcgggtgt cagcaccccca agtggatcct tcttacaggt gcagattcag actcattatc    65100
caagttgaca gagacagaag taaatattca acaaatattt attgagcact tactatgtgc    65160
caggcactgt tgttgtaggt gctggaatac agcaatgaac aaaaaaagtg aaacattctt    65220
ccttagatgg tggtaaagcg ataggaggac acagcaggga aggggtttgg actatttcaa    65280
tttgggacag gaaacgcctt gctgagagag tgagggttga gctctggaat tagcctgagt    65340
ttgaccacat gtaactgcaa cttgagcaa gtcgatccac tgtaagtctc ttttattaac    65400
accattgtgt gtaagaggaa atagaaactc agctaaagtc gttggagaat tgaatgtggt    65460
gcagcattta gcacagcgca ggaataataa agccagctg ttctcatcct ttgcccatag    65520
aaaagctatc cgggaagcca cattatagtc tgaaggctgc ctactggttt ggtcaaagaa    65580
agggcagtta gataattttc atgtttaatt aagggcacgg ggctagattt cttgaggtgc    65640
cagagtaatg cttgcttttc atgaacaacg gatacaagat atgggcattg cagaaccttt    65700
aaagaacata actggaataa tcaaataacc gaaagttcat gaaatattct ggctcatgaa    65760
ttagttatct ggtaaatcac agtctgaaag tcacagaata caaattactt taaatttcct    65820
ccaaagctta ctgagtaagg ggagggacat ttaagatgcg gaggaagcgc tgaacttgca    65880
agaggaacaa ggaggacggt ggctgctgga actctgtaac ccttagagaa gatgtgggtg    65940
ggatttggca agccccctag actctctttg ttttgggtct taatagggac agtttattat    66000
ttttaatgac tcgcgtgaat tgtatactgt tttaagcatc caccaaaagc ctttcggctt    66060
tttccctaat tagactcatt ctcacacaga gaggaactga acttttttacc tctttggttc    66120 aagagcacca tctactggtc agatttggta atttcgggtt tatggcactg gaaaatcaaa    66180
gagcattttg atttggttgt gtttggtttt ggtccattta tcaatacagg ttttttggcg    66240
gacaaaataa tgtgaaaatc aggggaatca ggtgagggca ttggatgtct ctgtcacaga    66300
cgatggggag ctcagccgat tttaagcttc taacctcagc tggtctggag aagagcaaac    66360
ctgacaacca gcacgaagaa agtagctctg cctctgtggt gtgctggaca ttctggttac    66420
atagatggga agacgaggcc ctttccgaca aatatgcaaa tcccccacat ctccaaattt    66480
ggtagctctg gggcttaggg cagcttctgg aaacagaact cagacctagc ctgctggagc    66540
aggaagggct tctgagaaga tgatatctgg accatctaag gagtgtaaat aagaaatagc    66600
cgccaggcat ggtngctcac gcctgtaatc ccagcacttt gggaggctga ggcgggcaag    66660
tcgcttgaca aagtcaggag tttgagtcca gtcgggcaa catgatgaaa ccccatctct    66720
acaaaaaata caaaaattag ctgggtatgg tggtgcatgc ctgtagtccc agctactctg    66780
gaggctgagg tgggaggatc acttgagcct gagaggttga ggctgcagtg agtcgtgatg    66840
gctgcactcc agcccgggca acagagtgag accctatctt aaaaaagaaa gaaaaaagga    66900
agaggtcagg agtttgagac cagcatggcc aacatgatga accccatctc ctactaaaaa    66960
```

-continued

```
taaaaaaaaa atcagctggg cgtggtgcat gcgcctgtaa tcccagctac tgggaggtt   67020
gaaactggag gattccttga acccgggagg cggacgttgc agtgagccga gaccacacca   67080
ctgcactcca gcctgggcga tagagcgaga ctccacctca aaaaaagaa aaagaaaaa     67140
gaaagaaaaa gaaatagcca gatggagaac aggggaaagg ccagaagagc agggcgtaa    67200
aaggcgtgga atggcatgcg ggggagtaac aaggttttt tttttaaac ggagtctcac     67260
tctgttgccc agtttggagt acagtggcgc gatcttggct cgctgcaacc tctacctccc   67320
gggttctagc gattctcctg cctcagcctc ctgagtagct gggactacag gcgtgtgcca   67380
ccacacctgg ctaatttctg tattttagt agagatgggg tttcatcatg ttggccaggc    67440
tggtctcgaa ctcctgacct caagtgatct gcccgcctca gcctccgaaa gtgctaggat   67500
tacaggcgtg agcaccgtgc ccagctagta acaaggtatt gactgaacca gagtggggtg   67560
tgtcaagatc gggaatcagc aagcagcaca ggggtgtcc tggtggga tctgggctc        67620
aggtcttcct gctatcctgc tacccacctg cacacttgtt cgttttcttt ccactcattt   67680
ttctcccttg cccagacttc aggtctacca gctacacttc ttgatttctt tggccttcaa   67740
aattcggttc aataaggaaa gttttagcat tattttcata taggtccttg acatttcttg   67800
ctaaggttat cattagattt ttttttaatg gtgtaatagt tcaggccttc actcaaatgt   67860
catctctcta gagaagcctt ccttaactac cataccaaaa acggttccag cgccgctacc   67920
gtctatccca gcctatcctc tcacgtcctg tggtcctgag gttctgtgat aatgttctat   67980
aattctgtgc tgtccaatat ggtagccacg agccacatgt attcatatcg tcgttattga   68040
gcactatata atgtggctag tgcaattgac acactacaat tttagttgaa tgcaatttaa    68100
attaatttac attgaaatag ccacatgttt ggctcacacc tgtaatccca gcactttggg   68160
aggctgaggc gggtggatca cctgaggtca agagttcggg accagcctgg ccaacatggt   68220
gaaaccccat ctctactaaa aatacaaaaa ttagccgggt gtggtggcac gcgcctgcaa    68280
tcccagctac tcgggaggct gaggcaggag aatcacttga acctggaggg tggaggttgc   68340
agtgagccaa gattgcacca cttcactcca acctgggcaa aagagtgaca ctctgtccaa   68400
aaaaagaga aatagccata tgtggctggt ggctattgta ttggacagca cagctctgtt   68460
tctcccacta gaatgtaatt tgatgagggt ggggacttgg acttattcac agctgaatac    68520
ctagaatgga acataactgc tatgttttga atgtttgtgt cccttccaaa atgtatgttg   68580
aaacttaatc ccctatataa gagttgaaga acctttagaa aggtaattag gccatgaggg   68640
cagagtcctc atggatgggn attagggtct tataacagga cttgagtcct ctataangga    68700
acggagagtt cacctttncc ttcccttctg ccnatgtgna ggacacagcg tgtgtcccct   68760
ctgaaggaca cagcgacaag cctccatttt ggaagcagag agcagccctc accagacact   68820
gaacctactg gcgccttgat cttggacctc cagcctccag aactatgaga ataaaactac   68880
tgttgtttgt aaattgccca gtctgtggca ttttgttatg aaaacagcaa aaacagacta   68940
agacaaatca gttctggcac atactagtaa ctcagtgatt ctttgtagag tgagcaaacg   69000
tgtgaatgaa tgaatgaata cattgtcatg cgcagctttc gtgggtcgtg agtacaaatg   69060
agaaaatacg atcatggtgc cattgcaatg gcttgaaacc ccagcactta ctggcaggaa   69120
gtctgtcatt ttttgcaatt ctccttccca agtgtttcca gactcccgag aagtgcacat   69180
gtatatttag gaatcagttc tcatctgcta gaacatggga agggagttag ttgatagcag   69240
ttcagctgct tcaaatgcag tcctagctga ccctggagga tccaggtacc tatgggtgcc   69300
atcacggcca cctttgcact atcctgtgag aaactctctc ccatccttgg tgatgtcctc   69360
```

```
ctgtggtaac ctcagtgaga gaactccatt gattccctaa accagaggtc cccaacctttt  69420
ttggcaccag ggactggttt tgtgggagac aattttttcca tggaccatgg gtggggaggg  69480
ggggatggtt ttggaataat tcaagtgcat tataatacgt ttattgtgta ccttgttatt  69540
attattacat tgtagtatag aataattata caacacacga taatgtctaa tcagtgggag  69600
ccctgagctt gttttcctgc aactagacag tcccatctgg gggtgatggg acacagtggc  69660
agatcatcag gcattagatt ctcttaagga acatgcaacc tagatccctc gcatacacag  69720
ttcacaatag ggctcatgct cctgtaagaa tctaacgctg ctgctgatct gacaggggggc  69780
ggagntcaag tggtaatgtg atggatgggg aactgctgta aatacagttg aagccgctca  69840
cctcttgctt tgtggctggg gcctgggtac ccctgcccta gacagtagac ttctcaaggg  69900
gaggggaaag aatgggccaa ggaactgtgt cagtcaagag ggccccccact caacggaaac  69960
agaccagcca ctggtctcac agtgcaagtc aaggaagctg gtctcagagc tgtcctcaga  70020
ggggacgcgt gataagcaga tcacacccgg gaagactcgg catcaagatg gagaggaggg  70080
aatgcgatgc gcctggtggc agccgtagga tctccttcca aggccgcact ggaggagagc  70140
tgcctcctaa gaacaggaaa gtgaatcaga gtgaggctgt cattatagta agataaagaa  70200
agatgagtgc ttgtttggga atctggacag aattagcatc tgcttgcttt aggatagtgg  70260
cttcttttct ctcttgaaca aaatactctc cttaataact gcagacccag gataacatgg  70320
agtcattgtt caaattcacc ccgttgcaga attctccagt tatcagcatt tgtgtgtgtg  70380
tgcgtgtgta cctacatgtg cacagatgta tacacacaca gataaacaca ctccaggctt  70440
tggggaaatc gtattcgtag atgcctgtct ctacctttat tatgttaaag agaattctga  70500
ctctcaggtc gtggacttca ttcattgtgt tgctcacatg caggaaaaaa aaaaaccaga  70560
atgcaataag gataattcat tgatttgtgg ggaaagagaa aattcattgt tttggggggga  70620
aagagagaat gtattgattt gtggggaaag agtcaataag tgaatgtttc ctgttctagg  70680
actggctttg ccttgtcaat aattgatttt gttgttgaga atacatttca aagcctttaa  70740
agcagtgtgc agttaaggat gatattttg cttgaaatga ctactttgca tcatgtgaaa  70800
ggaatagtgt ctttttaaagg caacagatgc aagtctagga ccccagagct ttagaaggct  70860
ctgggcttcg ggtatgtgtc tgatgtgttg agagttgcag gggacgggag ggatgtccac  70920
tgtgggccag tttctaccag ccaccgagaa gctggaattt gtttattcat ttatagagca  70980
acaggaactg gaatcgaaat ctgtcagtcc ctatgtgcag ggtgtaattg aattgacttc  71040
tctgctctca attggaactt cctttgacct gtagtgagaa catttttatgg ctccctctaa  71100
tctaaaaagg gtttttttt tttttttaac tttccttcct attcccttgt ctgctaacca  71160
acagagaact cagcccacag cctcacagac agaatgagag caatgcttaa tccttgttca  71220
gtgaatctca tggcctcctc tagtcttcaa acttggattc caagtgcctt gaagagccaa  71280
acacagtggc tcatgcctgt aatcccaaca ctatcggagg ctgaggcaag ggtggatcac  71340
ttgagatcag gagtttaaga ccagcctggc ccacatggcg aaaccctgat tctacaaaac  71400
atacaaaaat tagccagtcc tagtggtgca tgcctgaaat cccagatact ccagaggctg  71460
agggaggaga atcacttgaa cctggaggt ggaggttgca gtgagtggag atcgcactac  71520
tgcactctac tctgtctcaa ataataataa tatatatttt taagtgccta gaagaaagaa  71580
ctgcacttct gcagagagcg cctccaaagc tcagggtaag tgcatgctg cttaccatcc  71640
tagaatggaa ccaggccacc catccccagg tgggacaact gcactcccag gataacccct  71700
```

-continued

```
gagttatggg cagacttgtg tctctcccca gttcagatct tgaagtccta gacccagtgc   71760
ctcaggatgt aactgtagat tctttaaaga gtgaattaag atgaggccat tactaaaagc   71820
ctagacctga ccactatgca atctatgcat gtaacaaaat tgcacatgta tcccatctct   71880
acaaattaaa ataaataaat aaaactacgt cattacagtg ggtcctaatc cagtatgact   71940
agtgtttttg tgtttgtttt tgttttgaga tggagtctct gtcacctagg ctggagtgca   72000
gtgacacgac ctcggctcac tgcaacctcc acttcccagg ttcaagcaat tctcctgcct   72060
cagcctcccg agcagctggg attacaggca cgtgccacca cattcagcta attgttttgt   72120
aatttttttt tgaagttttt attttttatt tatttatttt taatcttttt ttatttatt    72180 ttattttttt actttaagtt ttagggtaca tgtgcacaac gtgcaggtta gttacatatg   72240
tatacgtgtg ccatgctggt gcgctgcacc cactaactcg tcatctagca ttaggtatat   72300
ctcccaatgc tatccctccc ccctcccccc aacccacaac agtccccaga gtgtgatgtt   72360 cccttcctg tgtccatgtg ttctcattgt tcaattccca cctatgagtg agaatatgcg   72420
gtgtttggtt ttttgttctt gcgatagttt actgagaatg atgatttcca aatagagaca   72480
gggtttcatc gtgttgccca ggctggtctc gaactcctga cctcaagtga gttgcctgcc   72540
ttggcctccc aaagtgctgg gattacaggc gtgagccacc actccccgcc tggtgttatt   72600
agaagaagag attaggacag agacacagac acagaggaaa ggctgagtga ggacacaggg   72660
agaagacagc catctgcaag ccaaggagag aggcctcaga agaaaccaac cctactgaca   72720
tcctgagctt gggcttccag catctagaaa ctgtgaaaaa ataaatgtct gctgtctaag   72780
ccacccagcc agtggtattt cgttgtggta gccctaacag actaatacat gctgagtctc   72840
tcattgttca aatcatcctg taaaactgac tcaacaggct tttttgagc agggttttct    72900 attcatgtac tcattaattt tccttaaatt aaaagttgca aatacaatat acaaaattaa   72960
aagttcaatt agaaaaatga gtttctataa tcagcctact cagaattaac catggtttca   73020 aatagggggtt tgctggtgt ttttgtttt gttttgtttt gagagaaagt tttgctcttg    73080
tctctcaggc tggagtgcaa tgacgtgatc tcatctcact gcaacctcca cctccgggtt   73140
caagtgattc tcccgcctca gcctcccaag cagctgggat tacaggcaag cgccaccatg   73200
cccagctaat tttgtatttt tagtagagac ggggtgatct gccctccttg gcctcccaaa   73260
gtgctgggat tacaggcgtg agccactgcg cccgttagct gttttgtttt gaaatcaact   73320
ttgaaaaatg ttttgatatc tcatcatgtc cccaatgcca tttgtaatgg tcacacagca   73380
ttctgttgta tgatgtacca tgctttatct aacctgtgtc ctattttgg atagttcgaa    73440 ttttcctatt tcttttcact attagaagca aggctgcaat ggacatcctt ttaaatactt   73500
tttaaaaaca aaaaccttgg tacaagtacc tgtatataga cttgcagggt caaaacttcc   73560
catttgatgg ctattgatat gtactaacaa attgtcctcc agaaagtggt cttttcctca   73620
ccctcatcag ttcttggtgt taccaccttt ttgcattttg ccaagctgat aggtaaaaaa   73680
gtgtctctta ctattgtatg tattgaatta aatttattta tttatttatt tagacagggt   73740
ctggttctgt cccccaggta ggagtgcagt ggtgcaatca tagctcactg caggcttcaa   73800
ctcctgggct ccagcaatcc tcctgcctca gcttcctaag tagctgggac tataggtggg   73860
cccagctaat taaattttt tttttttttt tttttaaga tacaaggtct cactacttcg     73920
cccaagctgg tcttgaactc ctgagctcaa gacatcctcc cacctcagcc tcctgagttg   73980
ctgggattac aggcaggagc cactgtgcct gcttattata tatttcaaaa taacgaaaag   74040
agtggaattg caagttcctc acacaaagaa atgacaaatg cttgagataa tgattatcat   74100
```

```
aattatcctg atttgatcac tacaacttgt atgcttatat caaaatatca catatttata    74160 ttttaaaaa  ttatatttat atttatgtga tattttgata tattttgtaa tgatcatttt    74220
acatatgaac atatttatac atatatacaa accaaataaa ccatacatat ttatacatat    74280
gcacctatgt acaaaccaaa gaaattggga tatagctatc ccagttctat taaaaaattg    74340
agattttttt cttctctatt gatatttcct acttttttt  tgttttgaaa ataaatttat    74400
ccttgagtca gttgtgatga tttatacctg tatagagatt actagtttga tcaaaatcat    74460
ttcatttatt gttaaaaatt gtataatgat attatctcct aactgaaaat tttcctttat    74520
ctctgtgatt atattccatt tctcattcat catattttca tttcattcca gttttccttg    74580
gttagacttt cctatgattt gtgtctttta ctgttctttt caaagaacag ccttggtatt    74640
tatttatcaa ttctatttct ttttaatttc acaattaatt gttttctgtt tttaccatga    74700
ctaattccca ccactgcttt catagattaa ttttgtgttc tttttctaat ttcttcaatt    74760
aatttatttt cattttttaa aaacttaata ataaagttc  ttaaagtcct aaatctttttc   74820 ctgagtactg tgggattctt tccatgtgct tctgcatgta gtatgactat tgcaattggt    74880
atagatggta ttacagttct tactccttct tacatccagg gattactaag gagactgatt    74940
ttaaatttgc aagaagtttg acttctaaaa gtgccaggct cctttttgat gtcaagtctc    75000
acctatttct tctgtttttc tctagtaact gagctcaggt tttgttgaag gcagcaaact    75060
actggctaaa actgctcaat gttttccagc taaaattgct caagtatttc ctgcagctag    75120
ttagggcaag ttacctggct ctgtctagag agatggaggt gcaggtcctt ggagacagag    75180
taccctctga acaaaaaggc aaagacttac cagcagaaaa cccatttgcc ttttcccttt    75240
cctcctcact gacatgcaag ggttatgtct ggaggtacga gaaaaggaaa gcataaggat    75300
aaaatctaac aggctaagaa tgacagggca gaaagataga aaggatctgt gtccccgatg    75360
gcatcgttgt accagcaaga ctgatgatca tgatgtaagt caaatgaatg cccagctgct    75420
gctggctgtg tttttgtta  tttgcggctg aatgcattgc taatgtaaac attaccttgc    75480
agccagagaa tacggcttgc caaaagtcta gttttgtatg ttaatcatga tacaccagcc    75540
agacagagtg gccctcagct gtaatcccag cacttgggga ggccaaggca ggcggatcac    75600
ttgaggttag gagttcgaga ccagcctgac caacatgaca aaccccgtc  tctactaaaa    75660 atgcaaaaat tagctgggca tggtggctcc tgcctgtagt tccagctaca cgggaggctg    75720
aggcaggaga atcgcctgaa tgcaggagga ggaggttgca gtgagccaag atggtgccat    75780
tgcactccag cctgggcgac agagtgagac tctgtctcaa aaaataaaaa taataataat   75840
aatgatatgc caactgctat agcacctaga ctgcaaaatg tacatcacaa cagtccgatt    75900
ctctgttctc tttgttcagg gtaagcatg  gagcttaatt ttgatctatg agtcaacgtg    75960
ggaagtccgt taggttagaa gtgcttctgg tcaaggtttc tttgcttcta aaagaggaat    76020
gtgaggaaaa agtccctgtc ttggtgtgga ttttggtgtg ggggatgta  tataaagcct    76080 gtagctattg aagccatctg gcaaacttga agggagcagc tgactctgag ctggtagaat    76140
atagaaatgg aaaggattta gatcttgatg tggttgagag gctgccctcc cttgggactt    76200
cttttttgtg tgtgagttaa caagttttcc ttattgttaa gttgctttag tgggtttgct    76260
attacttgta gtcaaaacat ttattatggc atcatctact ttattctatc cttctgcttt    76320
ccttattaca agtatattta caagctcatt gtcattcatg tcatcatttt aatcagcacc    76380
aacaacagca tcaccagtaa catttattga gtgttttaa  gtgccaggcc ctgttgttgt    76440
```

```
catttaaatc ttacaccaat ccctactgct cagatactat tcttttttaaa aattattttt    76500 ttttttaggca caggatcttg ctctgttgcc caggctggag tgcagtggca taatcatagc    76560
tcactgcagc ctcaaactcc tgggctccag tgatcttcct gcttcagttt cccaaagtgc    76620
tgggattaca ggtgtgacca ctacccctg tcctattatt attgattcag atttacagat     76680
gaggaaaata aggcttagga aggctacata atttcctaga ttgcttattt agtaagcggc    76740
agagccagga ttcaaaccca gacctgaggg actcctagac tagtccatgc cactgtgata    76800
tggcctttca catctcttct ttcatccgtc atcatgatat ctttctcctc tgagttctgg    76860
ggaagtttct caagttggac tgccaatttt ctgcaggatt ttcctgtgat atataactcc    76920
ttcatttact gcttccattt tatttcatat cacctacaat ttcccttatg tctaaaacca    76980
attgctccta tatctaagat gcaacgtcct tctgaattat agtgttaatg caatagggta    77040
ttttgaaggt ttctgtatgt tttctgtaga aaagttatct caaggggga tatatacttc     77100 catttcccag tggtctactt cttttaagcc acaaataggg cactttctct tgttagttta    77160
atcctacggg tatataattt tcagtatttc tagtgttaga atttgagatt cagagaacta    77220
tgagtctctg ttttaatctt tcagtcctag gaaaaggaga aatagggctg cctatctttt    77280
ctgtggtttt attttgccat ttaatttcta attgactgtg agatgtatca agagatctgt    77340
agctcaaggc agttgaatgt cccagagctt cacagctgag ccaagtgact tcttttccat    77400
gtttattgtg gcagccaagg tcagcagatg ccatgcctct tgctctgagt gcctggacca    77460
cccccattaa gagcctccca cagcaacaac tccacttgac ccacgataag tgaggttggc    77520
actgtgtctc tctctttgta cattttgttt tctaagttgc ttgtagggcc aagctttgag    77580
tccttgttac catcagctta agctccggcc tctctgaatt ggaggatttt gtttgtgttt    77640
gattagagcc tgttggcaga agcaagtgcc aaagtcagac ataaaacaga aaactctaat    77700
gtggtgtcaa gtcttttcca gatgttactg atcctctttc ttttccttct ttttttttc     77760 tttttttgtta tttttgatcc ccttccttttt tgcttccctt aggttgacct ttgctgtcct   77820
acgggcagta caaagattgg gtcttttctgt ctctgcctct cctgccctcg gactcctacc    77880
atgggtcttt tctttttta tagagatagg ggtctcactt tgtttatcgt gttttttttt      77940
ttgtttgttt tttgaggtgg agtcttactc tgtcaccagg ctgcagtgca gtggcgtgat    78000
cttggctcac tgcaacctcc gcctcctggg ttcaagcgat tctcctgcct cggcctcctg    78060
agtagctggg actacaggtg tgtgccacta tgcccagtta attgttgtat ttttactaga    78120
gacaaggttt caccatgttg gccaggatgg tctcaatctc ttgaccttgt gatccacccg    78180
cctcagcttc ccaaagttct gggattacag gtgtgagcca cagcgctcag cctgaacttt    78240
tacttttaag acaattgtag attcaaatcc tgtgtcctct cttacacagt ttcctccaat    78300
gggggcattt tacaaatata ataaccagga tattgacatt gatacatttg atacagtcaa    78360
gttacatttt catcaccaca aagatcctgg tgttactctt ttatagccat acctgcctcc    78420
ttctcccctc cccatcccct cacgccggca accactaatc tgttctccat ttctacaatt    78480
ttgtcgtttc aaaaatgtta tgtaaacaga atcatacagt ttctcatctt taagattcgt    78540
tctttcctgt ttttttttc ttttttttct tttcttgtt ttttgagat ggagtctcac        78600 tgtgccaccc aggctggagt gcactggtgt gatctcggcc cactgcaacc tccgcctcca    78660
agttgtgggt tgaagcgatt ctcctgcctc agctcccaa gtagctggga ttacaggtgc      78720
ctgccaccac gctcggctaa ttttttttt gtattttag tacagacaag gtttcaccat       78780
gttggccaag ctggtctcga gctcctgacc tcaggtgatc tgcctcggcc tcccaacttg    78840
```

```
ctgggattac aggcatgagc caccgcaccc ggctgagatt ggctctttca ctcagcataa   78900
ttccctggag acttcatcca agttgttgca tgtatcaata gcttgtttct tttcattgcc   78960
acctagtttt caatggtatg aatgccgcat tgcttgtttc atcagtcacc tggtggaaaa   79020 catcaggggtt gttcccagtt tttaactatt atgaataaag ctgctatgaa catttgtgta   79080
caggtttttg tgtgaacata ttatcatttc tctgagatga atcaatgcca agnaatgca    79140 atggtatgtt tagttttata agaaactgcc aaactgtttt ccagagtggc tatatgantt   79200
ttgtattcct actagcagtg tatgaataat ctagtttctt tacatcctca ccagcatttc   79260
atgttctcag tatttttttt attttagtta atccgatatg tatgtagtgc aatatcactg   79320
tggtcttaat ttttagttca ccagtgctaa tgatgttgaa tatctttcat gtacttattt   79380
gccatctgta tatccacttg gtgaaatact tcatgtcttt aaagaagacc caggatttct   79440
aaaaaactgt tgagttttga gaatttaaga aatatattct agatactggt actttgttgg   79500
atacatggtt tgtaaatatg ttctcctagt ttgtagcttg tcttttcata tgtgttaaag   79560
cttatctccc attttattat ttgttttctg tttactttgt ttcttattcc tctattctca   79620
ctttgggtgg attatttaaa tatttttttaa ggtttcatct tgatttattt gtagcatttt   79680
gggtacatct ctttgtacac ttttcttagt ggttgccctg ggtgttacca tatacatatg   79740
tcaagagtca cattctgctg gtgtcagtgt ttttccagtt gaaggcaagt gtggaaaact   79800
tacctccatt tagattcctt tactcttccc attttttaaaa catgtgtctc aagtattccc   79860
tctacattca ttgatcagca cactagagag tgttattttg gctttaacct tcaaatataa   79920
tttaagacac tcaggagaat aggatcatct attatgttta cccctgtctt tgcctgtttt   79980
gatgttcttc attcttttct aaagtttcaa gcattcttct gttatcattt cctttctgtt   80040
taaagaactt cctttagtcg ttctttaagg acagatttac tagcaacaga ttctcagttt   80100
tccttcatct gagaatgtct ttatttcccc tgcattcctg aaggatattt tcacctgata   80160
tggaatttgt gagtgatagt tcttttttcct ctaagcactt gaaaaatgtt atgccacttt   80220
ctgctgtctt ttatggtttc cgaagagaaa tccactttca ttcaaactgt catttccctg   80280
taagtaatgg atgttttctg tctagttgcc ttcaagactt tgtctttagt ttttacaagt   80340
ttaattatga tatgtcttgg tgtgaatttc tttgagttta tcctgcttat gatagttcac   80400
acagcttttt gaaactgtag gtttatgtct tccaccaaat tttactgaat ttcttcagtt   80460
ctatggtctt gctcctcttc ctgaagtatt ccaatgatac cgtgttctct tttgttacgg   80520
tcccactggt ctttgagact ctctgttcat tttatttcgg tctttctttt ctctgttgtt   80580
cagattgggt aaattccatt gatctacctt caagcccact gattctgtcc tctatcatct   80640
ctattattga gcccaaccac acagttttaa ttttgattat tgtatttctc agttctataa   80700
tttccatttg gttattttc aatgacttcc attttgctg aaattttcac ttgtttcaag     80760
agaatttgta attacttgtt gaagcacttt tataatatct gtttaaaata cttgtcatat   80820
aattccagta actaattcat cttggtgttg acatctgttt attgctcact taaaaataaa   80880
aaataaaaaa cacctagact ttatttttta tagcagttta aggttcacag caaaattgag   80940
aagaaagtaa agagtgtgcc cagaaaaata gtacccctat gcagaacctc cctgatattg   81000
tttggctgtg tccccacca aatctcatct tgaatggtag ctcccacaat tcccacgtgt    81060
tgtgggaggg atccagtggg aggtaattgg ataatggggg cgaatctttc ccatgctgtt   81120
ctcatgatag tgaataagtc tcatgagatc tgatggtttt ataaagaggg gttcccctgc   81180
```

-continued

```
acaagtcctc tcttgcctgg cgccaggtaa gaagtcccct tgctcttcct tcatcttcca    81240
ttatgattgc gaggtctccc cagccatgtg gaactgtaag tccattaaac ctccttttct    81300
gtataaagta cccagtctca ggtatgtctt tattagcagt gtgagaatgg actaatacac    81360
tccctatcaa catcccctac cagattggta tgtttgttgt aatcgatgaa cctatgtcaa    81420
cacagcgtta tttcccaagc tccatagctt atatgaggat tcgctcttgg tgtttacatt    81480
ctgtgagtat tgacaaatgt atgatgaaat gtattgacca ttatagtgtc atacagaata    81540
caggatagtt tcactgtctt aaaaaatctt ctgtgctccc cttattcatc ccttccttct    81600
gtgtaagccc tggcaaccac cgagcttttc actgcctcca ttgttttgct ttttccagga    81660
tgtcatagag atggactcat acagtaggta gccttttgaa attgacttct ttcacttagt    81720
aatatgattc ctccatgtct tttcatggct tgatagctaa tttctttata gtgctgagta    81780
gtattccatt cacttataat tccttgaatt cattgtttgg aatattttgc agatgatatg    81840
ctattcccta actttatgca tcttcactca caggattgtt ttttctcac caatgcttat     81900
ttatataaaa gccatatcaa caaaatttta cacatcaaaa attttcagac ttctggttgc    81960
tccaaagaag gaatgacccc attcttctca gtcctcttc ctcatgacta aaaaactctg     82020
aacaaagcac agaaagttgc ggaaggctct gaaaggtgaa aggaggtgga ctgcctaggg    82080
acctcaggac ttggaaaaca actcagtggg gaattccgtg gatttcctta tcacctccct    82140
tatatcctgg acacggagct gcagaagact ccaacctaca gtcaccaatg cgcatagaag    82200
aaaaaagctc caagaaaagc cttttcctcc tggccagatg actggacaag gtggcctga    82260
caacagaaaa cccacaacaa ggaattacag gtaactccag agaggatcag cttgagtggt    82320
taaaacaagt acatggaaaa caaaagaag cattttctt tttttgtaaa agagcttgta     82380
ctgtaataac tttgattttg tttttgttt ttgttttt gtttttttt tgagactgag       82440
tctcactcta ttgcccaggc tagagtgctg tggcgcaatc ttggcttact gcaacttttg    82500
cctcctgggt tcaagtgatt ctcatgtctc agcttcctga gtagttggga ttacaggcat    82560
gcaccaccac accaactaat ttttgtattt ttagtagaga tggggtttga ccatgttggc    82620
cagactggtc ttgaactcct gacctcaaat gatctgccca ccttggcctc ccaaagtgct    82680
gagattacaa gcctgagcca ccgcacctgg ccaacttgga cttatttta taataagtag    82740
atattgttca ctgtagatat tgaatcaatt tttatttaat cttgattttt tttcttgagc    82800
tgcattagaa attcattaca atatttcaat ttataaatct tattaaaaat tactactacc    82860
tagatctcat tgttttcttt tttctttttt gagacatggt cttgctctgt caagcaggag    82920
tgcagtggga caatcataac tcactgtagc ctccaactcc tgggctcaaa cgatcctgct    82980
acctcagcct cctgagtagg tgggactata ggtgcacgcc acccatgtgt ggctaatttt    83040
ctttattttt ttttgtagag acaaggtctc actgtgttgc ccaagctggt cttgaattcc    83100
tggcttcaat caatcctccc gcctcagcct cccaaggtgt tgggatttca gacgtgagcc    83160
actgcacacc tggcccccatt ttttttcctt gaataaagtg tactggtaaa ttttaggctc   83220
atgagggtat atatgcatta ttttcttcaa atcaagcctg aatcaaagaa acttctgctt    83280
tagttttagt gatatttgtc ccaaatgttt aaagactgta tcattctgat gaattggata    83340
ttcccattga gagatattca ataggccttg attgaaatgt tcttcatttt cttttttaaat  83400
tctatttaca gtagtctgca tgtgttagaa ctttcagaaa gggagagatt tctgtctggg   83460
ctgtccccac cagccagaag ggtctgagag gcactgactt gccctgggt gatatttctg    83520
caggactttg ctcctctgta ggaagacagc ctagaacaga ggtgaaggat gcctcgggcc   83580
```

-continued

```
tgcctagacc aacagccatt ccctggtgat gctgtagtgt gaagaccctt gtctttccca    83640
acacctgtga tagcttttcaa attattcttt tcagacaaac tttatgcctg tttctttatc    83700
tctattttgc atcctaacag aaaaagccaa tcacctagaa gggaaagtca gactggtccc    83760
tgctgctttc cccacatctc cactgccccc aatattgaat gccgtgacaa tggaatgaaa    83820
ttccaatgtc catgaaattc tgaggggaga cattttgact caagattata tactcagtga    83880
agatgtcctt tatttattta ttaaattaat tttttttgag atggagtctc tctctgtctc    83940
ccagtttgga gtgcagtggt gcgatctcgg ctcactgcaa cctctgcctc ctgggttaaa    84000
gtgattctcc tgctgcagcc tcctgaatag ctgggactat aggtactcac caccacacct    84060
agctaatttt tttttttttt ttttttttttt tggtaaagat ggggtttcac catgttggcc    84120
cgtctggtct tgaactccag acctcaggtg atctgcccgc tttggcctcc caaagtgctg    84180
ggattacagg cgtgagccac cttgtctggc caaagacgtc cttaactaa agacttctgg    84240 tgtatgttac cttaaaaata taaatataaa agcatgaaga aaatacaacc tccatggaat    84300
ttttttgcca atgaatctag aaaaataaga attgattcaa ataatgaat agggaagctg    84360 taataaaatg acttgagggt tcattgagtc catttaaata tatatctctt actaaaatca    84420
ctaagggtca taattagaca atgaagtaag tgccataaat ctaaacaatg taaataacaa    84480
tatatctaaa aaaaaaaaac taaggagttt ggagagagga tacgggagga tgtgttcttt    84540
catagtaggg aattagttaa tattctttaa aatggaaaca tgtaagaaaa aagaccctaa    84600
tgactgaaaa ctaagttttc ctcaatcttt ttttcatatc ctttgaaggc tattttaaga    84660
aataatatct aaagaacatc gatttgatgt tcacaattcc agttgatttt ccttctgtga    84720
aattcaaatg aaattaaata aatatgtttt gttaaaaatg gtgtcatccc atttaagtaa    84780
atgtcctttc ttttacctat ttatccatct ataatctgta tctattcatc catcaatgga    84840
tacatgtgca cagataaatg gcccctttgg tgaagggctg agagggtatt gttttctaac    84900
cccaacctgt gacggcttcc atgaggccaa tggaatcatt ttgaaatgtg tttaccacag    84960
cagggagaca cagaagactg gggtctcaca cctgtgtggg aactccagag ggtgagaaaa    85020
gggccaatga actgctccgg tgacacagca gggagggtgg ctgccgtgct gggtgcggcc    85080
tgccttccta gagaatgtca gggaaaggga tgtggggtca tttcctgtgg acacatttaa    85140
gccaagtagg ggagaggtct ggtatggggt cctcttgggg cctgttggac agggttgacc    85200
agcagagaga ggatgcccaa ggattgaagg aggagtgggg aagaggttct ctaggtcatg    85260
ggaacttctg aatttcccat ggaaagcacc accataatct gtgtgcaatg aacagccaga    85320
cccacgtggg aattctaggc cagcaagaat cccttacttg ctcactggct gccacgtggc    85380
tctgaccatg gagaggtctg gaactgtagc ttcccagtgg gggagaagta ggctgggaga    85440
gagaagggga cagaggaacc acaccctcct tccccacctc caaacagaag ccagtaaaaa    85500
ttgagggatg gagaaaaata taaggctaaa ttaagttttg gaactttggc atgatcaagg    85560
ctcactgcag cctcaacctc ctgggctcaa acaatcctcc cttctcagcc tcctgagtag    85620
ctgggactac aggcacatac aaccatgctc acctttttttt ttttttttttt tttgtagaga    85680 tggggtattg ctatgttgct cagggctggt ctcaaactcc tgggctcaag caattctcct    85740
gcctcagcct ccaaaagtgc tgggattaca ggtgtaagcc attggccctg ccaagtttaa    85800 gaactttttac agtataaga gactagatat tttaattatt attattattt tttagacaga    85860
gtcttactcc gtatccaggc tggagtgcgg tggcacaatc ttggctcact gtaacctcca    85920
```

-continued

```
ccttctaggt ttaagcgatt ctcctgtctc ggcctcctga gtagccagaa ttagtagaga      85980
cggggattcg ccatgttgat caggctggtc tcgaactcct gacctcaagt aatccacctg      86040
ccttagcctc ccaaagtgct gggattacag tagatatttt aatttttttg catggaggct      86100
atttttacta ctaaaagtga atgaagtata ttttgtatct tccaggagtt tggaaagtca      86160
agtctatttg cacccagcca cgtgcctgcc atggtgcccg cggcctctca atttttgacc      86220
tttgtttatg ctgctctgtc tacccagaat gctctccatc gagggaaacc tactctctct      86280
tcaaggccaa attccagcat cacctccgcc atgaagcctt catagatcta ctcaangtag      86340
aaacttctta acccctctaa actgtcttag catcttggtt gtagtattgg tttagaatag      86400
cacaaattct acccaaaatc tcactaagtc tattctaagc aaatcttgga taatttgcta      86460
acactaaaat taaacctgtt ctcttttggt tttttgctaa caatgaaaca aacttggtct      86520
tactcttttg ctcaagctgg agtacagtgg tgtaatcatg tctcactgca gccaggaatt      86580
cccggactca agggatcgtc ctacctcagc ctcctgagta gccgggacta caggtgtgca      86640
taaccgtgcc tggccagttt taaaattttt atttagggac agagttttgc tatgttgtcc      86700
aggctggtct tgaactattg acctcaagtg atcctcccac cttggccttt caaagtgctg      86760
ggattagagg tgtgagctgc cacacccagc ccgttctct cttttgcatc tatattagtc      86820
tctgtgctct tgggaaaagt ggaccaatat catttcaaaa cttgatgaaa agaaaatta      86880
aaatctcatc ctcgggaact gaaatcacaa accaccagc aaggtccaca cctctaggag      86940
actggcattt agaagacagg accacagttg aagcaacggt tctttcttta ccctcctgc       87000
ctgtgacaga ctgcatgtgc tgattatccc tgcgttttct gcagagcttg ccttcctggt      87060
gatacagtac tttattttat tctgagggcc ccttcctgcc aggggatatc tgtcaggga      87120
Utacataaac tgcacaaaat ggaacaagtt ataggtcata taaatttca ggacattgtt       87180
gagaaggaga agttgctaaa ttggagacac catgatgtga atcccaggg tcccagaata      87240
ttgatggaac tagtatgttt ttcttatgta atattttatg gtgtctggga aatggagttg      87300
cctaagtgaa ctcatttttt atgtctaggg aatagcaac ataactatca tctaacacta      87360
aataaagagg agcaaaatgt gctacattta gaaagtgatg gtattatccc cagctgaggc      87420
agacttagtg atggtgttag aaataaagta tggtaggagg ctgaggcagg tggattgcat      87480
gagctcagga gtttgagacc agactgggca acatggcgga aaccccatct ctacaaaaat      87540
cca                                                                    87543
```

<210> SEQ ID NO 4
<211> LENGTH: 19
<212> TYPE: DNA
<213> ORGANISM: Artificial Sequence
<220> FEATURE:
<223> OTHER INFORMATION: PCR Primer

<400> SEQUENCE: 4
atcccaagcg gtgaaagct                                                   19

<210> SEQ ID NO 5
<211> LENGTH: 24
<212> TYPE: DNA
<213> ORGANISM: Artificial Sequence
<220> FEATURE:
<223> OTHER INFORMATION: PCR Primer

<400> SEQUENCE: 5
ggtttcggat aacatcagca ataa                                             24

<210> SEQ ID NO 6
<211> LENGTH: 22
<212> TYPE: DNA
<213> ORGANISM: Artificial Sequence
<220> FEATURE:
<223> OTHER INFORMATION: PCR Probe

<400> SEQUENCE: 6
cccccttgat ttggagcgag ca                                              22

<210> SEQ ID NO 7
<211> LENGTH: 19
<212> TYPE: DNA
<213> ORGANISM: Artificial Sequence
<220> FEATURE:
<223> OTHER INFORMATION: PCR Primer

<400> SEQUENCE: 7
gaaggtgaag gtcggagtc                                                  19

<210> SEQ ID NO 8
<211> LENGTH: 20
<212> TYPE: DNA
<213> ORGANISM: Artificial Sequence
<220> FEATURE:
<223> OTHER INFORMATION: PCR Primer

<400> SEQUENCE: 8
gaagatggtg atgggatttc                                                 20

<210> SEQ ID NO 9
<211> LENGTH: 20
<212> TYPE: DNA
<213> ORGANISM: Artificial Sequence
<220> FEATURE:
<223> OTHER INFORMATION: PCR Probe

<400> SEQUENCE: 9
caagcttccc gttctcagcc                                                 20

<210> SEQ ID NO 10
<211> LENGTH: 98844
<212> TYPE: DNA
<213> ORGANISM: Homo sapiens
<220> FEATURE:
<221> NAME/KEY: unsure
<222> LOCATION: 24962
<223> OTHER INFORMATION: unknown
<221> NAME/KEY: unsure
<222> LOCATION: 64383
<223> OTHER INFORMATION: unknown
<221> NAME/KEY: unsure
<222> LOCATION: 65468
<223> OTHER INFORMATION: unknown
<221> NAME/KEY: unsure
<222> LOCATION: 65469
<223> OTHER INFORMATION: unknown
<221> NAME/KEY: unsure
<222> LOCATION: 65470
<223> OTHER INFORMATION: unknown
<221> NAME/KEY: unsure
<222> LOCATION: 65471
<223> OTHER INFORMATION: unknown
<221> NAME/KEY: unsure
<222> LOCATION: 87130
<223> OTHER INFORMATION: unknown
<221> NAME/KEY: unsure
<222> LOCATION: 89049
<223> OTHER INFORMATION: unknown

<223> OTHER INFORMATION:

<400> SEQUENCE: 10

| | | | | | |
|---|---|---|---|---|---|
| tttttgtatt | ttagtagaga | cggggtttca | ctatgtaggt | caagctgatc | ttgaactcct | 60 |
| gacctcaaat | gatctgcctg | cctctgcctc | ccaaagtgtt | gggattacag | gtgtgagcta | 120 |
| ccatgcccag | ccaatatctc | ttttctcttt | ttttttttgtg | agatggagtc | tcactctgtc | 180 |
| atccccatgc | ttggttaatt | tttggaattt | ttagtagaga | tggggtttca | ctatgttagc | 240 |
| caggctggtc | tcgaaaccac | ccttggaacc | ctttgtgatc | cacccgcctc | ggcctcccaa | 300 |
| agtgctggga | gtacaggcgt | gagccaccat | gtctggccca | atatctctaa | ttttaaagca | 360 |
| gtgagttcaa | ttgctgatct | aaagaaaagt | actgtaggct | gggggtggtg | gctcatgcct | 420 |
| ataatcccac | cactttggga | ggccaaggcg | ggtggatcac | ctgaggtcag | gagttcgaga | 480 |
| ccagcctggc | caacatggca | aaaccctgtt | tctaccaaga | atacaaaaat | tagctgggcg | 540 |
| tggtggcacg | cgcctgtaat | cccagctact | cgggaggctg | aggctggaga | atcgcttgaa | 600 |
| cctgggaggc | agagtttgaa | gacaaaaaaa | ggtactataa | acacagtaca | gtatatagtt | 660 |
| cctccattct | atacgtacag | agaggataca | ggaagatggt | aaaaatgcga | tatgctttta | 720 |
| gaagaaatta | gtatatttct | caccatttat | atatcttgag | ataatcagca | atttaagctc | 780 |
| tagcctttaa | attctgttta | cttagcgtat | tctagtaact | atgaacaatt | tgagctacat | 840 |
| gatgtatgtc | acaaaatgga | aaactaaggg | attaaattaa | ttccaaggtc | ttttaagtcc | 900 |
| taatatttaa | tagtcattaa | acttgtatta | ataattctta | ggtagagaaa | ttgttcactt | 960 |
| ttctttacca | agatttatat | actataatta | caaaataaat | taaaaatatg | catcagtctc | 1020 |
| catatattta | aaagctaagc | ttttcacatg | aggcttcata | actgttaatt | cctatcagat | 1080 |
| ttctctcaag | atagctgttg | aaaaatgaga | gggaatcaga | aaggttattc | aaaagggaag | 1140 |
| aaaataattt | tttacaaaac | tctggtcaac | ttattaaaaa | gttgcttgtt | tcaagatttg | 1200 |
| taagcttgtc | aaggcagaag | aaggagtagc | tctcagtctt | ctttctaccc | agatacccta | 1260 |
| gttgttttga | ccgagttttt | ccatcactat | cttctgtagc | taaggtaaaa | tctcatcagc | 1320 |
| tgacagcagt | gtggttctta | aagtgcggtc | ccctagatc | acagcatcca | ctctccttag | 1380 |
| gactgttaga | aatgcatatt | cttggtcttc | tccccacctc | accagtccta | ctgaacagaa | 1440 |
| actctgagct | ggggccagca | atctgtggtt | taacaaacca | tcaagatgat | ttgtattcac | 1500 |
| actgaagttt | gaaaattagt | gccctatagt | aatggggaaa | aatatgtatc | tgtaaatgga | 1560 |
| gaattatctg | tttattgtac | tggaattaag | agaaagagga | ggaaatttgg | taattaaata | 1620 |
| tgaaaatgag | tggaatgata | tagggaggag | tatggcagga | aaagttgtga | gacatcaata | 1680 |
| agatggcagg | aaaaagttgt | aagaaatcaa | taaaacttcc | aaaaatattg | ataagattta | 1740 |
| ttttgaaact | aagataacgt | aaccagttgt | ttttggttca | tgaaaatgaa | attgtagacc | 1800 |
| catggtgaat | agtaatttgt | ctcctctctg | cccttaggga | tgaaactgtg | aagctcttct | 1860 |
| acattcttat | gatctgatcc | ctttaaaaag | ttatgatccc | tttaaaaagt | ttattggaaa | 1920 |
| tagttgatca | agattagagg | ttttatctgt | aaactaaaga | tcaaataact | tgtatttatt | 1980 |
| agcaccaact | ttaccaatg | gaatcctcat | ataagccaag | tgtctctttg | gtgagactag | 2040 |
| tcccacatat | agggatggt | tttggataaa | ataattccaa | gtaagctgag | gcagatgtat | 2100 |
| agtggcggct | gggggtagac | tgtgctttat | tagagttgga | aggatcagct | tcataggaaa | 2160 |
| tctgaaaggc | agtttggcct | aactgaacgg | gcacaatcgt | tggctttggt | gtaaatttgg | 2220 |
| gttcaaatac | attagttctg | atattctgaa | ccagtttata | aacctctgga | aaatcatatg | 2280 |

```
aaaatgggga taatagggtt gttataagga ttaggaatag tagctataag gggcccagct   2340
atgtctagta tacagtgggt ggtccataag caatagttat tactactaat aaatcttaat   2400
tgactcttcc tttctttacc acctgctctt ttaaaatggt catggtgaaa cttctctagg   2460
gaccaaattc atttctttct tttttttttt tttttgaga tggcgtctca ctccgttgcc    2520
caggcaggag tgcagtggtg ccatctcagc tcactgcaac ctccgcctcc taggttcaag   2580
cgattctcct gcctcagcct tctgactagc tgggattaca ggagcgtgcc accatgcctg   2640
gctaattttg tattttttag tagagacgga gtttaaccat gttggtcagg ctggtcttga   2700
actcctgaac ttaagtgatc cgcccgcctt ggcctcccaa agtgctggga ttacaggcat   2760
gagccaccac acccagccta aattcatttc tgaaattacc tgtcaatcat gctcgtcaaa   2820
aatattttct gaagatgcac tgtgtattga aaagctggag gaactgacct ttcagttcat   2880
gtcatcccaa gtcaaatctg ttttctattc atcctaaact gtcatataga aatctggcaa   2940
gagcgtggag aacagttcag tgaagtagta acccttcttt cttacagtct atagatcaag   3000
ctcacagggc aatttctaga ttttcaaaga gcagctctgg tctctattat gtttcaattg   3060
tcttctgaac aaataaatag gatggagtgg gtccatgtga tagtgaaaga aattaatgcc   3120
cttacccact tccaataggg tacagtgtac aggagggaag aaggaaagag gattataatg   3180
aatggaattt tagaattcta ttttttacaac tgattataac atgagatacc cttttggaa   3240 catttactaa gcagcaaaag attttgttct attgacattc tagactgaca aatcattgga   3300
ataaaccaca ttgctagttt gaagaaccaa gaaataaaat acaacagtct ctgaagtaaa   3360
ttagcaaatg ataaggaatg ttgtgaattt gggtgtctgt atatatcttt atccttactc   3420
ctacatcatt ttctatggct ctgttgtttt attttgctcg gcagttttgg cacgtaggtg   3480
acttcttttg gtaaagttgc ttagaatatc tgatgggaag ctgaggaaag tttctacaaa   3540
atggcaaggg taaagaactg ccaaactaaa ctattctctc aaatcccact tagatttcaa   3600
acaccactga aaagaagca atcaaggatt taaaatgtat ctgctatttt gagaagaggg    3660
aggagaaaag agagaaaaca ttttctaaca acagccaatt cattctatag aatttgttga   3720
aaacagacca accaaattgc tattttgaac caccaccagg gcaaagatta gttatcatat   3780
ggaatgtttc cgtaatggaa tttatgtgca cagaaacttt tgaaattagc aaaatacaca   3840
tgcatatgca cttgaaaata cacttcagtt acccttaaat ggagtctctg ataaacaaat   3900
aggcactaaa agagaggtct agggagaaac atgtcactct tttttaagcc tcttcactgg   3960
cagtggcggg gcactgcata gctgaggact ggggtgctta aatacatgct tctctgcatt   4020
ccagcctggg cgatagagtg agactgcatc tcaaaaaaaa aaaaagtaa taataaataa    4080 ataaataaaa taaatgcttc taagacaaaa cccttgtgtg ctgcttcttc tctttccaa    4140 tcaccatcct ttgacgtttc ttaaggctaa aaaaacccc caaaccatta gatgtttaat    4200
ctttgcatac cctagtagtt acaagtcctc taaaacagaa ccatacagtt cacaggtcag   4260
tatcctttct gatggtcttt gtcagacatc attatttcta gcataggata ttggacagga   4320
tcaacaaaaa ggaatcgaag acagtaggga ccactaccat gacagctgca gtattatttg   4380
gcaatgtgat ctatggttat tttaggaaaa atggcatttc aggaagtgat attaatctgt   4440
aaaattcctt tgccatgcag aatataaaaa atgattacag aatatgcaga aaaagcaat    4500 gctccttcca ataatgaga tatttgatat aataaggaga tgggaaataa tcaatattta    4560
aaaatattcc ttttaaaaaa ttaaagtttta ggatagttac gtagttagta tacaacaact  4620
```

```
tggtcttaat aaggactaga aacaaaattt tattttgtgt ggctaaagaa atacatacat   4680
attataaaac tgacattttt ttgcattgtt ccgttgggta tcatcacagg ttgctgcatc   4740
attatagttg tttttaatgt aaacagataa actctcacac tttccaactc tggtattatc   4800
catctatttt tcctttcaca gtccactgat acagaatttt aaacatttag agtaggaggg   4860
aaccttagct tccagcacaa tactgttcat ctttcacatg aggaaatcat ccaacagaag   4920
ttgaatgatt tactcagggt caggccgcac cttggcagaa ttacgtctta ttattctttc   4980
tcaaatgctc ttttaaaggt taaacagagg ttgagttttg agaatgactt atttctctta   5040
gatgaatttc gttacagaca agcaaaataa tcagccactg tctttctctt ttctattttt   5100
tcttttctgt ttgccacctc taggcaacaa cctcattgaa tccacaacaa aatcctgaag   5160
atttctgtat tatccaagag aaccattttc tttaagaaaa ataaatact aaatatgttt   5220 tgaatataaa agtttctgat aaagtaatc ctgactttaa tcagatcaag taagataatc   5280
agatttatac cattattttg ataaagacaa aaaaaacaac ataagctttt tttccccagt   5340 cttacactttt gagcaactct tttaaatact ataaacactt tcattaggg acaattttc   5400 cctttcccta ggaaaatgaa aaccgaatag aaaaatttt tgcaaaaatt aagtttaaga   5460
gggtaaaatg tgaagacaga gaactgctac ttaatcagaa ataagtaaac aatattaaac   5520
aggaaagtat atattccatt taaatgagtt tttttcttca tattcatatc acaaagtaac   5580
ttcactatag cagcactaat tcattatgtt tttatttact ggtggatgtc actggcctca   5640 ataaaatat gtaattttc ataagaaata ttcaaaagaa cataaagttt gaaaaatata   5700
atttaccaga aagcaccaac atgggaagct cttcaattaa ggatgggaaa ttattaatat   5760
gctttagcct aaatttaagc aaaattcatt cctaaagatg aattttttaat gaattttata   5820 atgaattatt cagcatgaaa ataaagggag caaacttta tgctttttaaa atatgtttaa   5880 gaggatctta tcttttaaca cacctctttt cattttgtaa acaggacatt atgctaccaa   5940
atatagagtt attattctaa agtttaaagc aatgctttaa attttttaaac cttatgacat   6000 gttcataaaa ttcacggata ccaatccatg aaaaaattct tcttcctcaa cccacatttt   6060
taaagatatt tacaattgta ttggatctttt tactctggtt gctttaattc atagttagat   6120
agcatctttc aggactcaag tatgggatct ttcattttttc agataatttt ttcttggtgg   6180
tcaatagaaa agtcatatca aaatgcactc ttgatgggaa tgaaaagaga attatgattt   6240
ttggggacgg gtgctcacaa aactattaag gcagcttttgt ttatgtttat aggactagta   6300
ataatgctaa cttcattaaa aaattatatt gaccatttta tattcttcca ccagagagac   6360
agtttagctg tacttgtaac ctcacagcac tccagttttt actcattccc caaatcatcc   6420
cactgccttt ggtcccaaga ctactgacag actcttggtc cttcagtgaa aaatcaatgc   6480
tttaaacaat cgggtctaga gttacctatt tgcttaaact tggatttgat gaggttgcta   6540
aatgaacatt ataccttttct cataaagata aaggcttcat gctaataaag tatttcaaca   6600
gaaatatacc tttttactat agttctaata ctcatttgct cttataaggg caaggtctttt   6660 ggataaagat aatagtaaca gaattagtaa aaattgactg aacgtgatac tttattaaag   6720
cttttaaata tgggtgtttt tcattaggga atacggtttta agataacact tggttaaatt   6780
atttaatatc ctggcactcc tgaagtgcac tacttcagga aaaagaccaa tatatttgtg   6840
aggggaatac aggaaggcaa gatggctagg aagagagaaa ggaaactagt aggatgaact   6900
gaatatttgt atatttaaaa tacacatata tttgcacttt aagtaaatac caatgggatt   6960
cattcaaaat ttccttgata tttccttggt atagttaata tatttcaaat taagtgatat   7020
```

-continued

```
gttaactagc tcaagtatga tatctaagtt aaaaaaaagt cacttaaaat gacagatctg    7080
aaattgaatc tactaggtac aagatagtat atataatatg ttttcatctg tatgttttaa    7140
aaagaatata tatatatata tatatataca tacatacaca tatacttgta tatgcagagt    7200
aactctagaa ggatacacaa gaaattgcta acattggttg ctacttttca ccctctaccc    7260
atctgtactg tttccatttt gtactatatg tatgttttc cctattcaaa aatattgatt     7320
aaaatctcat taccaaaata aatttaaatg atttaaaata gcatgtcaaa ttaataacaa    7380
gtacggattt tttccattat acatgaaaat atatacttat attattttc taagctctac     7440 ctactaaatt tgggtatatt ttctttacga cagagttact gtgatctgaa acccaattt     7500 tcacatgata ttaagttggg aaaaacacat tttccctgaa cttcattgct acagtatggt    7560
ggactatgag ttgtttcaac agcatgttaa catacttatt ctttttctct gatgggctag    7620
ccattagcca ccatttctct ttgaaattca agaaatattt aaggaatttt cagaaggatt    7680
taagatcctt ttcaggccgt gataaatatt acacctgtat tattctgtag gcatagaatc    7740
aatgttaact cctctttgta tgttgtcaaa gatgtttggt gttttagtaa agacagactt    7800
caaactaagt ggtgactaag caaaccccctt acataaagct ttgaatagga tttcataaat   7860
attccaatga aaaacatttg gagataagaa ggaaaaaaag ctcacactta tgaaaaaatt    7920
attttcagaa aaccacttaa aattcaaatt aagtcctatt catttaaata ttaaaatata    7980
ccataaaccc aaatttaaag gaatgataat acatacatca gctttcaatg gtagctgctt    8040
atttaaaatg agcatctgag ggtatattcc agtttcatcc tcttcaaatt gtgcagctca    8100
gataaatgtt tattttatgg aaaatatttg caaaattaca atataaatac atgattatat    8160
taaggtagga tgactatata atttattctt atctatagat ataaaatgaa ctcagtaaat    8220
atagcacact cttgatgaat tgttagtaca cagtgtttct cagtaaagta ttattaagca    8280
acagttatct agttttcaaa tgtacatctt aagaagcttt taagatggaa ggatacacta    8340
aatcccccaa tacccttttt agttggggaa ggttagtact tctgtgaatt ctgagatatc    8400
atatttgtgt tagtgactgt tcataggttc cttgcatttc cttaacttga aaccttactt    8460
ctttagtctg aatgttcttt aaataatgcc acatcagcta accacacttt taatttgagt    8520
ataatattat gtactgcata tttattcatt acttaaacac atatcaacaa tgaaacaatg    8580
attgaaaaaa attttgtcta gacaaattcc ccaaattaac tgtcagggca ctgtggggaa    8640
tctcaactaa atatagtctc aactgtaata agaatttggg ttagaaatag tattttattt    8700
attctagttc ttaagacatc aaatgtgaac tctactttaa aattctttgt taaatatact    8760
gggatttgtt tcaaaagcat cttctaccct tctccattac actgatttaa tggaaacctg    8820
ttacaacaac agttccaaca caaacatatg catgcacggg atcaccttat agattctagc    8880
tacatagtta ttgaaacaca tcccacctgt caagtggcat aaatgtacat cttctatata    8940
caaaaggtaa agtgcattat taaattagtg aactgacaga ttgtctgcct ggaccataca    9000
gctttcaaat agacaaatgt gaaattctca tattagaacc aattatttca agaggttcca    9060
actagctttt ccaccctgtc atttattttt ttggccatgc tctttagtgc aaataagctt    9120
gtgtttgact caagtttcag ggacatggca gtctggggct ttaacaagga aaattataaa    9180
atgtagagga actttaatat ctttataata cattgcatct tttgcataaa gcaacagatt    9240
agtgctgctt tcgattgcta ggagcacact gccaactatc aagaggaacc cgtttccaaa    9300
tttcatacta ttagcttata ttactacagt ttgagcctgt accacattat gcttggatta    9360
```

```
ttaggtgcaa acatcatcag tgttttagaa ttatacagtg aactagtact tttggttact   9420
aactttcatg ctcatttttt aacttctaac ttccagttgc cttaagagtt taatgtcttc   9480
aaggcaggga ttctgttatt ttgaaggata ccatgaacac ttgcagctcc atgtatgtta   9540
caaatgacaa taaataaaat gcatattgca cagataagaa tagtagctta ttttataaga   9600
tacatggcaa tacatgtcct aagaccagag ttttgaactg gatcatattt aattacggct   9660
aatgaattct tgggaatttt aagtatcaaa aagtcatagc atcatctcat ttttgaatga   9720
ttaactatga aaaaaatgaa acaaaaggac tggcagaagg cttaataatt ttagagtata   9780
ctcaattgcc agtatatatg catctattta atctgcagct ttgagatggt aaaaactttg   9840
aagtatacat acaaagtaga aaatctggct gcttaactaa ttctttactt aaataattaa   9900
tggaaaacta aatttaataa tgtttatata caatgagtta aagatattta tctttaagtc   9960
tgacatggta ttgtatgtat gtatacacac atatatatgt atacatgtat atacatatgt  10020
ctgtgtgtat atatatagat atagacacat acccaaatct tatcagaccc aaaaggtaaa  10080
aggaaatcat ttagacctaa tggatataaa tattttagaa aggaagactt taagagagtg  10140
tatacactca tagcaatagc gataggaaca atcaaatact agaatattca cagctccagt  10200
ttgccaaaat ctgacaggtt gattattatt aataggcact atgatgggca gcaataacaa  10260
tcagtagtac agtaattcaa gtgcacatca ttccttcata gaccaaaaac tactttttta  10320
gcaagcctac atagttattt tacagttagg actgttttaaa aatccttgct acttttagag  10380
tctcaacacc caccatgtgc tattagctct agtactaaca ttatctccta accttcagtt  10440
gttccatagt gatccagatg gtccacaatt ataatgaact aatgagattc cttcacgcta  10500
ctagaggaaa tgtgaaatac aatctgcaaa ccaacactag tatatatgtc ggggttactg  10560
attgcttgtt cttaagtaac ataaaccaat gaaattaatt ttttttaattc ataccatcaa  10620
gttttcttag tgacctcacg taaggtatt ggggacaaa actctggaag aaaaaaatcg  10680
ctgatataat tttaaattac ttttagcata taaaagaaga gctacattct gatttgaatc  10740
catgcagcca gctctcatca atgagagtga tatttggggg ttgaaatcag tgttctggct  10800
cttaaatatg attagatgga cttattgtgt gggaggtgaa taaagccaag ataaaagaca  10860
ataatttcat tcagaagaaa atatagctga atagatgtaa tttcagtcaa ttaatacagg  10920
atgggttggt acacatataa cactatatcc acttatttaa aaaattgctt aggtgttgaa  10980
aaattgctgt ggcacttcct ggaaagtaat ttttaataca ggtaaatggg tgagtcttgt  11040
gtaaagtcag aaagagcacc ttggaaaatg cctgaatttt cctttcaaat atatttataa  11100
ccaatcttca aataatattt ttctcagact ggaaatttgt attctaaatt ttttttagaa  11160
aaaaaaaatc cccaccccct ccagaattaa acacctgta aaatacagga ttatattgga  11220
agtgttgaca tggttttaag ggtagcaatt gcaaagtgc tactaaaata tattattaca  11280
ggtatatttt tatatcagtt aattggtaca ccaaccttc tgaaagagtg ttaaagaaga  11340
agcataaagt ataacacctt gagtccatga tatattttgg ggaagaaacc tcttgcaatc  11400
tttaaattag catgaaaagc tacaccacca agatttccat agcaaagcca ttggatgaag  11460
cctcccactc aatgtgacat aaaagtaatt cctgaaactt tggaaagtca ataaaaatat  11520
atggaacatt aagtagaggt aaagaaggga ttgtaactaa acttagaata acgaattaaa  11580
actctcccat ggctttgata tggcaactat aaaatgtagg gttaccacaa agtttgaaat  11640
tatagaatac tatagtattc ttaagaaata ttatgacatt atattttaa ggtttaatta  11700
ggtaataaga tttgatcctt tgatggtata ttcagttatt caacggacaa tatacgtcta  11760
```

```
cttgtactttt tataagtaaa tatttatata taccggaggt caatttctgt ttctgtggta    11820
actgccctac aggtaagctt agcagctttt aatgaagtag aattgaaata cttttggggg    11880
aaagtcacac ttctatttaa gtatatgtat cttttttcgg gattatgtca tagtgcaatg    11940
taaatcttag ttatggtatt tagaatgtca gaatgtcaca ttttgtgctg atttgcatac    12000
ttcaatagtc tggagcagtt gaagcagcta aactatttag ctctgggaag gttggaattc    12060
ccgtaagaat tatagtgatc tatgtgtaac ataacatgag aatcagactt cctgaagtat    12120
caactactag aggtattact aataacaacg ggccaaaaaa gaggaaaaac ttcttcaaag    12180
gataatggat cagtactttt agccaatttg tgattttaaa ttttgcctga tggagttcaa    12240
tttcactcta gtcgaggcat tcttgttctt caccactggc ctttctgcca tccattctct    12300
tttctttatg gctgttgcaa attttcctca tctcttcttc atacttgata aaattctccc    12360
caaaccttgt ccaagctttg aatggaacag taatagtatt acgtaaggt ggtctcacct    12420 cacttacctt caggaaaatt ccatatttat tagagcccac atcaaagtag aacctttat    12480 tgtccactct gaaagaagtc ccctctggga gttcaagcgg gtcatcgtct ccacctcttc    12540
gttcttctat gtctccttcg ccatagtctt caatcagctg aaccaaggca tcacgaaact    12600
caatcattcc ttgtgctggg aggacaatag tctgttcttg gcccaaactg tggccaaaat    12660
aacctatcat gccagtcccc cgcatcatgg tttgtctaat ccgtaggaag cgaccccgct    12720
gattttcctt taggtctagg taatatttcc tattgtccct ctcgatatag tctgttttca    12780
ggacactgtg aggatgctct tcggacccca ccgagactgg tggggagggt gccgagtgct    12840
tctgcctcct tctggagcct tgctctttgc tgtggccatg ctcttgccgg tggccttca    12900 ggcccaggtg ggcatagtgc tcgatgaagt cccctagaca gtccttcagc tccgctgcca    12960
cagacaggga gagggtcagt ttactctttc tgatgttgtc ctgccggcct ctccctatcc    13020
agacttcggc tatctttagg aagcggcccc gggagctttg cttcacgtct aggtaaaacc    13080 tcttttctg gatgtccact cgtttggagg ccagctcctg gatttcggct gcgccccgg     13140 cctgattagg ggtggctgag gccgcgtagt gggggtagtg ggagtgctgg gcctggggat    13200
agagtctact cttgcttagg ccagagcccc ctacattctt gcctccgcgg ccgcggccgc    13260
cgccgcctcc ccttcgcctg gctctttcca tcttcagctg caagtaacaa acagacacac    13320 gggatgggt gggggagggg tgttgagaac aatcgcagac gcccctcggc ctgaccgccc    13380
cgccgccgcc cgcgaccccc acgccgggcc cggctccccc ggcgccgcag cgcggggctc    13440
cagccactgc cggccggttg gcggccgccg ctccggctct gcccgcgctc cccgcatccc    13500
tccgccgccc ccggggccgc tcccgcacgc cgccgccgcc cgtcccgcgc tccgcggccc    13560
caggtctcca gccggcgggc actcacatca tctctgccat caccgccgcc gccgatgccc    13620
ttcacgacca ccgccgccgc caccgccagc tctcggcccc tctgctgcag ccgccgcagc    13680
cgccgccccc cgcctcctcc cccgccgccg ccgctcgcac tgcccccgc cggagcagcc    13740 gggcaggggc atcgcccgcg gcgcccaccg cagccgcccc tcctgcggcc gctgcggggg    13800
ccgccgcctg acttcggaca ccggccccgc acccgccagg aggggaggga aggggaggcg    13860
gggagagcga cggcggggg cggcggtgg acccgcctc cccggcaca gctgctgag       13920 gggaagaggg ggtctccgct cttcctcagt gcactctctg actgaagccc ggcgcgtggg    13980
gtgcagcggg agtgcgaggg gactggacag gtgggaagat gggaatgagg accggcggc    14040 gggaatgttc tcacttctcc ggattccacc gggatgcagg actctagctg cccagccgca    14100
```

-continued

```
cctgcgaaga gactacactt cccgaggtgc tcagcggcag cgagggcctc cacgcatgcg    14160
caccgcggcg cgctgggcgg ggctggatgg gctgtggtgg gagggttgca gcgccgcgag    14220
aaaggcgagc cgggccgggg gcggggaaag gggtggggca ggaacggggg cggggacggc    14280
gctggagggg cgggtcgggt aggtctcccg gagctgatgt gtactgtgtg cgccggggag    14340
gcgccggctt gtactcggca gcgcgggaat aaagtttgct gatttggtgt ctagcctgga    14400
tgcctgggtt gcaggccctg cttgtggtgg cgctccacag tcatccggct gaagaagacc    14460
tgttggactg gatcttctcg gggtaaagtg tcttcctatt cccgttttcc cagctccgtg    14520
ccccggggta tctatagtgc taggcttctg agacacgtgg aggcgcttag gcccgcggag    14580
caggcccctg ggctgtgttt gggagattct ggaaaaacag actttctccc ttttcctttc    14640
ccctctggag cagctgggaa aggcgtctct cggagcttcc gccattcaga aagtgtttcc    14700
ccgccctgac ggccccagct tgatgtttac cttgcgcgct tagttaggat tgctcttttct    14760 agtacggcct ttattatggc agaaattgag ccactacagg tctgcacagc aaagtcgagg    14820
gaataaccct gctgtctatg atttagcaag tgatgatgga tatttttgag ttcaaatcac    14880 tcagtctttta atggattttc ttttcttttt ttcctagttg aatctcagtt gttctcaggc    14940
taggtttgat atgaaaaata ctactcccta ttgaagaggg taatataatt cttaggatgc    15000
taatacagga gtctgtaagt cggagtactt caggcttttt atggttcggt acatttcttt    15060
ttaggggtgg gatattggga taagtaggac agttcagatc ttgatgtcat tgaatagtgg    15120
tgtctaccta aaaggaagag gctggggcac aaaattataa tttaaagtgt ttacttcagc    15180
caaaatgagg acagctgccc aggactcatt tcccagttgc cttggggagt gctccttcag    15240
ccttggttac aagcaggttt ttaaaggcga aggggaagag tgggctgaga caaagttggt    15300
caggaattgt tattggttta cagagatacc attgcttagt gattggctgt acactgtaac    15360
tcatagggta tgagttatcg tgtccagcat atggcatttt atggcttctt ggttccagtc    15420
tagagcccat atagcaggtg ggctttaaga gataattatc cagctcagac cgggagtgag    15480
acgggactgt tttttcattc taatacctct ctgggcctga taatttaaag gggcttgcat    15540
tcttcagcta aaattttatt ttcttttatt ttttttcccc cacagtggtc tccctttatt    15600
aatccaacaa atgtttatta aggactgctc taggcactag atataccaac aatgaacaaa    15660
acagacaaac atctctctcc ttttggagct tacattttag tggaaagaga caggcaaaaa    15720
gtaaaattat aggatgacag aaggtgaaaa tagagattaa aaaggaaagg gggatgaaga    15780
gtgtgtgtgt gtgttgtggg tgggggctg tagggagctg cagttttaca ataagtggtc    15840
agggacgtcc tcgctgagaa gggaattttt gagtccagag ctcaaggaag tgagagaact    15900
taccttgacg ttctctggag gagaagaaag tacaaaggcc ctgggggaac ctgcctcttt    15960
atgttcagag agcaacttaa gaggcctagt gagctggagc agagcgagag gaggtcagag    16020
gtcaggccag aaagggaaag gggccagaat gtgtaggact ttatgggcta tattgaaaat    16080
tggggctttc attctgaggg agatgggaag ctgttgagga gttgttaggg aaacgtgatc    16140
tgaattatgt ttctaaaaaa ttggagtaag atatcataaa atttgccatc ttagtctttt    16200
ttgtatctgg ccaattccac tcagaattct ttttaaaca gctttattga gataataatta    16260 atatatcata tgattcactc atttaaagtg tgcaatacaa tggttttttag tttgtcttca    16320 gagttgtaca acctttatca caattacctt taggactttt tcattaccca aaagagaatc    16380
tccataacca ttagtactca atcccacccg cttttcctagc aatcacttac ctattttttt    16440
gtctctatat agctctcaaa ccctatgata ttccttctat ctaactgtat ttttgtactc    16500
```

```
attaacagcc tctcttcatt cccaccaccc atccatccca gcctctggta atcaccattc   16560
tacttactac ctcaatgaca tcaaatttt tagctcccac atataagtga gaacatgcga   16620
tatttgtctt tccctgcctg gtttatttca cttaacagaa tgtcttccag ttccattcat   16680
gttgctgcaa atgacaggat ttcattcttt attatggctt aatactattc cattgtatat   16740
gtatatcaca ttttctttat ccactcatct gttgatggac agttagcttg attccatatt   16800
ctggctattg ttgaatagtg ctgcaggaaa catggaagtg cagatagctc tttgacatac   16860
tgatttcatt tcccttgaat atatacccctg tagtggattt gctggacccg cttgtagttc   16920
tacatttaat attttgagtt atttccataa tgttagtaat aatttacatt cccaccaaca   16980
gcgaggaagg agttcccttt tctccacatc ctcgccaaca cttatctttt gtcttttgg    17040 taatagccat tctaacaggt gtgaggtgat atctcattgt gattttgatt tacatttccc   17100
tgatggttat tgatgagcaa tgtttcatat acttgttggt tatttgtata tctccttttg   17160
agaaatgtct attcaggtct tttgctcatt ttttaaatat ggttttttaa ttttttatt    17220 tttttgctat tgagttgttt gacatcctta aacattttgg aaattaacct cttattagat   17280
gtatagtttg caaatatttt atccgattct gtagattctg tcttcagtct gttgaatttg   17340
ctgtgcagag aagcatttta ttttgatgta atccctttgt ctattttgc ttttgttacc    17400 tttgcttttg aagtcatatc caaaaaatca ttgcccagat cagcagtccc caacctttt    17460 ggtaccaagg actggtttca tcgaagacaa ttttccatc cacaggaggg aggggatggt    17520
ttcaggatat ttcaagcgca ttacatttat tgtgcacttt gtttctatta ttattacatt   17580
gtaatatata gtgaaataat tatacaattc accataatgt agaatcactg ggagccctga   17640 gcttgtttc ctgaaacttg agggtcctat ctgggagtga tgggagacag tgacagttca    17700
taaggcatta ggttcttcta aggagcatac aacctagatc ccttgcatgc gcaattcaca   17760
gtaggttttg cgctgctatg agaatctaat gccaccgttg atgtgtcagg aggtggagct   17820
caggtggtaa cgtgaggaat ggggagcagc tgtaaagaaa aatgaagctt cgcttgcttg   17880
cctgctgctc acctactgct ttgtggcctg gttcctaaca ggccatggac tggtactaat   17940
ctgtggccct ggggttggga acctctagcc ctgaccaatg ttagggagct ttttcctgt    18000 gttttcttca agtggtttca tggtttgggg tcttacattt aagtctttag tccatttga    18060 gttgatgctg tatgtggtga gagataattg actactttca ttcttttgca tatggttatc   18120
agttttccca acaccgttta ttgaagagcc tgacctttcc ccattgtggg ttcttggctc   18180
ttttgtcaaa aatcagttgg ctataaatat gtggttttat ttcttgggtc tctgttctgt   18240
tctattatct gtgtgtctct ttatgccagt accgtgctgt tttaattact agagtttagt   18300
atattttgaa gtcaggtagt gtgatgcccc tagctttgtt cttttagctc aacattgctt   18360
tggctattca gagtctttg tgaggataat gttttcaagg ttcacccatg ttgtggcatg    18420
tatcagaact cgatttcttt ttatggctga ataatattcc atttgtttat attatatata   18480
tgccatattt atttattcat atgttgatgg acacttaggt tgtttccacc ttttggctat   18540
tgtgaataat gctgttatta acattggtgt acaagaatct gtttgagttc ctattttcaa   18600
ttcttttggg aatataccta cgtgtggact tactagatca catggtaagc ttttagttta   18660 gcttttaag gaactgctaa aactgttttt ccatgggagc agtgtacaag tgttccagtt    18720
ctccatatgc tcaccaaaac ttaatttcct tttttaaaaa ttatagctat cctagtaggt   18780
ggtgggaagt ggtatcttac tgtggtttta ttttgtattt ctttaatgac taatgatgtt   18840
```

```
gagcatcttt taatgtgctt attggccatt atatgtcttc tttgggaact gtctattaag   18900
tcctttgccc atttttaat tgagtttttt tttctgttga attgtgggag atctttatat   18960
attctgaata ttaaacccct attgggtgta tgatttgcaa ataatttctc ccattttgtg   19020
ggttttcttc acttttgat attgttcttt gattcacttt taaattttta tagagtccag   19080
tttatctgtt ttttcttta ttacctatgc ttttggcatc atacctaatt cccaaatcca   19140
atgccatgaa gattttctgt tatgttttct tttaatagtt ttatagtttt acttttttcta  19200 ttggagtttt aagtaaattc ttgtatatta gtgtgataca ttttaagtta ttttttgtata  19260 tggtgtgagg taggggtcca acttcactgt tttccatatg gagatccagt tgtcccagca   19320
ccacatgttt aagagtctat tctttcccca ctgaatggac ttggcacccct gtcaaaaatc  19380 aattggtggt aaatgtatgg atttactcct ggaatctcaa ttctattcta ttgtatttat   19440
atttctgtcc ttatgcctgt accacactgt tttgattaca gtagctttgt agtaagttta   19500
gaaattggga acatgagtc ctccaacttt gttcttcttt tcaagattat tttggctatt    19560
tggggtccct tgcaattctg atgagtttga ggatcacctt ttccatttct gcagaaaagc   19620
cttttgatag ggattgcatt gaatctgtag ataactttgg gtagtattga catcttaaca   19680
atattaagtc tttctatgca taaacatggg atatctttcc atttatttgt gttttctttta  19740 atttctttca gcagcattct gtagttttca gagtacacgt ttttcacctc cttggttaaa   19800
tttattcctt ggtatttat tcttttagct gctattgtaa atgcagttac tttcttagtt     19860
tcctttcaga ttgttcattt ctggtgtata acaacagctg atatttcaac gttgatgttg    19920
tactctgaaa ctttgttgaa tttacttatt agatctagta gctttctttg agatttttat    19980
atgggattat gtcatctgta tatagagata gttttacttc ttccttttcca ttatggatgc  20040 cttttatttc ttttccatgt ctaatttctc tggctagaac tttcaatatg atgttgaaaa   20100
gcagtggtga aagtgggtat ctttgtcttg cttcctatct taggtggaaa gctttcagtc   20160
tttcaccatt aagtatggtg ttagctgtgg gttttcataa atgcccttta tcatgttgag   20220 gaaatacccct tttattccta gttttctgag tttttatcat gaaagggtgt tggattttgt   20280 caaatgccctt ttctgtgtca attgaaatga tcatgtattt ttcctcccctt atcttaatgt  20340 aatgtgttat attgattaat tttcttatgt tgaaccaccc ttgccttctct ggggtaaatt   20400 tcagtcactt atgttatata gtccttttaa ttgtgttatc ttataacaga atcactctgc    20460
tactgttttg agcataggcc atagggaaaa gcagtaaaa ggtaatatgg cttgaaccaa    20520
cattgtagca gcggaagtgg tgagaggagg tcgaattttg gctttgtttt gaagatagaa    20580
ccaacagtat ttgctgacag attagatgca gaatgtgaaa ggaggagatg agtcaggatg   20640
aatccaaggc ttttggcatg agcaaccaga aagatgaagg tgacttacta agatgggaaa  20700
tatacaaaag gagcagtttg gggaaacttt atatctattg agtggaatat gccaattaga    20760
gattcaaata tccagtaaat aattggctat caaagtttga agttaagagg aatggtctag   20820
gctgtttata taactttgga agtcattagt gtataacagc taatttaaaa gccagcagac   20880
tctaagggag tgagtgtaga gggagaagag tagaggtctg tgacttgaat cctggaatgc    20940
tgtgatgttt agagattggg gaggtaagaa ggagcagcag agtatactga aaagggattg   21000
ttatactgaa aagggattga tatagatgga gactcaagaa ttatcacaga aacctgataa    21060 aatgttttcaa gaagatgggt gtgattaatt gtgtcactta ctgccggtac attgactcag    21120
atgagcgttg agaattggct ataggatttg acaacataaa agtcattgga aaccttgaca   21180 tgagccctttt tcgtggagtg gagtggttac agtgggttta agagaggatt aaaggagtgg   21240
```

```
aaacagagat gctattatag atgactcgtt tgagtagttt tcctacaaag gggagaataa    21300
taatggagca gttagccaaa agttgagttt tttttctttc ttcttttttt tagttggaaa    21360
aaattgcgta tatgttgatg ggtcttttct ggcagaccag tagagaggaa aaagttgatg    21420
atgtaggaga tgggaaaatg tctttgagta gatgtctttg agaaaatgtc tttgagtaga    21480
tgagaggttt gcacacatgg agaggttgga tgtaggagta ctgatagttc atccatagtt    21540
acataagaaa aggtagatgt attagagttc tcctgagaaa cagaaccaat gggagatctt    21600
tatatctctg tgtccatctc tatctgtatt tctgtctctg tatctatgaa gagattataa    21660 aagtttaag atctgccagg agacataccc acgggagcta atggtatagt tccaggccag    21720
ttgtgaaggc ctgagaacca ggagagccta tggtgtaagt tccagtctga gtccaagtct    21780
gaaggcagga gaagaccaat gtcccagctc aaagacaggc agagggagca gatcttccct    21840
tacttagcct tttatttat tcaggccttc aacaaattga aggcccaccc acattaggga    21900
gggcaatctg ctttactcag tctactgaat caaatgttag tctcacccag aaacatcctc    21960
acagacacac ccagaataat ggttagccaa atatctgggc accccatggc ccactcaaat    22020
tgacacataa aattaaccac cacagtagag tatatgggta caaatataat tatgtgatat    22080
agatttcagg gtaagagcct gtggaaattc atttttgatt gcttctagtg aaatcggaag    22140
caagatcatc agctaagagt gacgatcggt ggaggagata tgaagtttaa gtggagagga    22200
gaaggtataa aatagtctta ggaggggagg atagtaaata gattagggaa aagttgtagg    22260
attgccagga agtagtaagg gcccacttga ggctggtggt cacaaattta aggtgagacc    22320
agtcaaaatg gttgtgcttt tcacctgctg cattcattca gctgcatagg tacaggcaca    22380
gagtaggtca agagttcttt tttattcggg gttagagttt tgccaggaga tagtaataaa    22440
gccagaaggg caatgaattt gagggagtat gcaaggaagt ggctgttaac ttggagttta    22500
aactagtcaa gaagagaatt aaggactgcc caagggtga ggacaatgat atggtagcag    22560
ggcccttaaa agccccagtt agatgaaaag attgttggaa ttgagtttct agagggaatg    22620
aacttgaaaa acaggaggtg ttggttggag agtgggatat atggaattga gattatggaa    22680
ggattcagtc gttggtaata acatagtatc tttgtaggaa taaataggtg gagcaggatg    22740
cagacaagat cactggagga gggctggtca gaagactggg aggcactatc tcccttggat    22800
attatacatc aaagcttgtg atctactaga caagtagtgg ggaaagggta ggatatagat    22860
attaatggct atagttttga tggtgatggt catggtgatg atgatggtcc attaacactc    22920
aactcaaata ccatcaattt gatttatatc taacaccaca aagttaggtg ttgagttaca    22980
tgtggttata ttgtaactaa tagtcaaccc ttcatggact tctattcttt gatgagactc    23040
ttcttgtagg agtagtaggt gccttaaagc accttttcat agttgtcaga ttgaaatcct    23100
tcaccagtgt tttaggttaa ccctgttact gtggaagttt ctcttggctt tctgtgtggg    23160
ctgcttcttt gtctagtttt accttttggg gttagcatac tattgtgaat aatttattgg    23220
tgagaaggta agcagagaag tagagtactc tatgacctag taatttcata tctaggaatc    23280
tatcctatag aaatgatagg aatgccttac aatacccaca tatccacaag ggtattcatt    23340
gaacgttatt tttggtgaaa ttcgcaagca acctaattat catcaatagg gaattgttaa    23400
attatgatag ataaaatgga attctattca gtcttcaaaa agtcagatca agaagtggtc    23460
ttacatttta attatcccat cctgtcaaca agagtgtctt cagttgcaag taatggaaaa    23520
accattcaaa ctgacttcag caataaaagg ttatttattg gtctgtttca tggagacatc    23580
```

```
tgaggtagag tggccttcag gcaagttcac tcagggatcc gactattttt ctggccttat   23640
tcttggccct cttctatgaa acaccttca gggtggtttc ttgtatgctt gtaagatggc    23700
tacttgcatc aaccatgacc acatctagca ggagcaaaag catcctttcc cgtaccagag   23760
gagagtcccg aaatttgttg caattggact gccttggaag caataattat ggccaggaga   23820
tggaggctag agaactgaga cctgatcata gctcctatcc ttgaatcagt tgtatagcaa   23880
ggggaattgg atttccttaa agacagttgg atttcacctg tagtcttggt gatgaggtca   23940
gttccatcca taaaacttg ctgttacaca ttttgggatg gggtgaggag ggctgaatgg    24000
agattaggat gctattgaaa tttgctgtac acaatggatc attatcgtct tctttcttag   24060
tgttaaggta atcagcctct ttttcctcct cctatgcttg actttactaa aaccatgaga   24120
catgtttaac ctcaggactc caatttgaaa aaatatagac tgttatttac tttattactt   24180
acagaagccc ttcatactac tctcagcaag aaagaggtag gcagggagtg agggaggggg   24240
gatcatgctt actgagaaac aaactatcga gtattgaaac tcccccttca tatgcctgac   24300
ctcagtccca ttcagttacc agtaggggcc cctattaatt ggtacctcac cagcttttgc   24360
tgttcgttca taaaactgag tcattgaagt acagtagaaa aataattgga ctacaagata   24420
acttatttcc ttccataatt gcaaaatatc tgattttttct tcttgtttgt attatgtaaa   24480
cttaccctgt ctgagggtcc tcctggattg ttctttgcat ttatatatac atagaatttc   24540
attttctttt ttcttgtttt tttttttagac ggagtctcac tctgtcgccc aggctggagt   24600
gcagtggcac aatctcggct cactgcaagc tccgcctccc aggttcacgc cattctcctg   24660
cctcagcctc cccagcagct gggactacag gtgcacgccg ccacacccgg ctaatttttt   24720
gtgttttttag tagagacggg gtttcaccat gatagccagg atggtctcaa tctcctgacc   24780
ttgttatctg cccgccttgg cttcccaaag tgctaggatt acaggcgtga gccgcttgcc   24840
cgaccttctt tttttttttt tttttttttt tttgagacgt tgagatagag tctcactctg   24900
ttgcccaggc tggagtgcaa tggcacgttt tcagctcact gcaacctcca cctcccaggt   24960
tncaagcgat tctcctgcct cagcctcctg agtagctggg attacaggcg cccgccacca   25020
tgctctgcta atttttgtat tttattaga gatggggttt taccatggtg gtcaggctgg    25080
tctcgaactc ctgactacgt gatccgcctg cctcggcctc ccaaagttct gggattatag   25140
gcgtgagcca ctgtgcccgg ccaatttcat ttctatttt gaaatttaaa ctaccactga    25200
cacttcgttt tccctctgtt ttacttagca tttatcttag agaataatct taatatgtat   25260
agttctattt tattctttta ctggcagctt agtatgccat attttggatg tgtcattgtt   25320
tatttaccta ttaatttacc ctataactgc ttcccatatt tttgctttta caagggatg    25380
taatgaacat cctttacata cgtctttgtg catatgtgca aatatttcca taggatagat   25440
gtaattactg acttgaaggt tatgcagatt taaaattttg atgccttcta tgaaacatct   25500
ttcaaaatgg tgatgccagt ttcttctctc gtaattactg catatggtca atcttttaaa   25560
tttttgctgg taatgatatt tcaaaattat aaccagtttt ttggcctcat ttcttgaata   25620
acttgttttt tctcaaagat aagaaatgtc tccttcatcg tatgtcaaat tccatatttt   25680
acatggatct atttctggac atggcaagtt ttatttattt attgtatgta tttacggtgt   25740
acaacatgat gttttgatac acatatacgt agtgaaatga ttcctacagt caaacaaatt   25800
aacatgttca ccaccttcca tagtctctgc agtcttcaag gttttctcta tatgggatta   25860
gacatgctat gtctgatctg ttttttgtatt tttacaccaa ttccacacta attttttttt   25920
ttttttttgac tgggagtctc gttcttattg cccaggctgg agtgcaatgg catgatctct   25980
```

-continued

```
gctcactgca acctccgcct cccaggttca agcaattctc ctgcctcagc ctccctagta    26040
gatgggatta cagcactcgc tgccacacct ggctaatttt tgtattttta gtagagatgg    26100
ggtttcacca tgttggccag gctggtctcg aactcctgac ctcaggtgat ctgcccgcct    26160
cggcctccga agtgctggga ttacaggtg tgagccacct cacctggcac acactatttt    26220
aattactgta gttttaaaag tttcatattt agtagggtga gttttccctt gttggtcttg    26280
tttttcaaaa aaaatttgct gctcttgagt attttctctt cccagtgaac tttaatgtaa    26340
actcacgtgg ttcaatgaaa aattctgatg actttttttc ttggtattgc ttcttgagtg    26400
tattgattta attaatatat ttacagtttt gggtctggct gtgccgaaac gcagtgtgtc    26460
ttatccagtc cttttttaac tgtcttaata aaatttgctg gttatcttta aaatggatct    26520
tgtatatttt atgttaggtt tattcccagg caggttgtca tttttgctgt tactgatttt    26580
ggatataaat tttggatata attgtataat ttggacttgg atataattgt atttgattct    26640
gtcttatata taaaaatgag ataggataat aatttatcct aggataaaaa taatttgagt    26700
atccttattt tgcatctggt accttacttg ctcctgttaa acaaatagat aaaattactt    26760
gtcttcaaag agatcctgtg gaaaaattat ttattttagg agactttgga gctttgataa    26820
aaattaggct tatcttttgt aaaagctggt tagtgatagc aatcagactc ttttaaaggt    26880 gattttttt tctttccttt gataaaatgc ttaatatgag ggaggattaa gaaagaggat    26940
ggcttttgaa cagtttcttc atggggaaat aagaaattaa aataatttca tgttctccaa    27000
aaaaaggaga aaaatgacct tccctcctga gcctacttca agcctctgtt tctttctgac    27060
tctattgttc tcatctctgc atttttccaa tctcttctac tgttagtgtt ttaggctagc    27120
tcctcagtgg agggcagaaa ttccccttct ctttagctgt ctttgaaacc aagaagatag    27180
aggtatgaga tcttcgtagt ctgtagtaag aataatagaa gccatcagaa aaaaatatca    27240
aagctttgta gctgctcctg gaagttttga tgtgaagcag gagacatcac ctattggtac    27300
ctgacttgct tttgctgttc attcataaaa cagagtctct gaaatacagt agaaaaataa    27360
ttagactgga ggataacttt tttccttcca ggaattacac aatcacaaaa ttgctgattt    27420
ttcttcttat tcatgttaca taaacttatc ctgtccgaaa agactgtatt tgaacttact    27480
atgtaaaatt tgcttaggt aaatttatgg ctgcttccag aattgtgtat taattttcca    27540 gtttctttt taccagtctc cacttttacc ttttccctctt cccctatac ttaaattggt    27600 cttactgtaa aatttatgcg tttctctttc tacctggcaa tgctgatttt tttttttttt    27660 ttttttgag gcaaggtctc actctttcac ccaggctata gtgcagtggc aagatcgtgg    27720
ctcactgcaa cctcgaatcc ctgggctcaa gcgatcctcc cacctcagtc tcccaagtag    27780
ctgggactac agatgtgtgc catcgcacct ggctcatttt tgtatttttt gtagagatag    27840
tattcgccat gttgcctagg ctggactcaa gccagcctcc tgccttagcc tcccaaagtg    27900
ctgggattgc tggcacgtac cactacgtcc agccagggct gagtttctga atcatcattg    27960
cagcaagaga aattggatta ccttagacc actggctcta ctgtgggctg ggagtgggac    28020
accttcctta aagcgcattg gacattggct ttgtgggtaa ctgatctta cctgaatgaa    28080 atttatcagt actgtattaa gggtctaggg tggaatggat gctagcaagg caaccgttaa    28140
catccactta ctgatgaatc ctataaaatt ttatttcagg ccatacgaag taacagtaat    28200
aaatataaaa ggaaaaatag acaacctaag caactttta aattgactta cttgaaaact    28260
ttccctgcaa tttcccggtt tataatggtt gatttcagct gactggctat agctacttag    28320
```

```
agaacagagg aaattcatta aaaataatga attattcagt tgggtagtga aatccagtta    28380
taaagcactt cgctgtgcca tggattcagt tcaggtcaag tgatgttcct ggtttatggg    28440
cagtgtggct tctcactatg acacagcaaa gaacgtagct tttatccttt acccttgtta    28500
ctaactaaaa ttaatggcat tttattgtgt ttatttgttt gattccattt acagtttatt    28560
tcacttggtt ttattagtac aaaattgtgc tttatataat atttgacagt taggaaaaat    28620
tgttagatac ctataaagaa acaagtctct caaaaatcat cctactactt ttaaaaatta    28680
catcgtctta ctacagttaa cctagatgtg aatgggtagt tttatttagc ttttctggtt    28740
tgtttgcttg gtctgtttgg agggaagtta agattagcag aaatgtagta atagattcat    28800
gaaagtcttg aaagcttctt taattagaga atttaatgag ggctttggca tgcattcttt    28860
ggtttttctc tgttttcctc taccccttct tattcttttt ggttcattga aaagtagaaa    28920
gaaattctca aaaccgtac aggagaatac cttataaatg atatcttctg caataaacta    28980
tagattgtat atatgtatat gtatctagat acacaatctg tgtgtgtgta tatatatgca    29040
tgtgtgtgta taaatgtata aattagttac tagtatatac gtaagtataa aaactcaatg    29100
tgcaaggtta cattttcaga aaatatgtaa tataataaaa gaaatcaagc ccagaatttt    29160 taaaagttt attgcgcttt ctgttaaaaa tgaaaggctt tttgactgga agctgcttct    29220
cagtaaaaat aacataattg tgttggtgaa gcccaaagat tctaatgaaa attagggtat    29280
tgacaaccaa acggaattgc tggagtactt aagctgcttt ggttttgtaa tctttctgtg    29340
tcagaatatt tgaaaacac ttattaatcc agtcttgtaa cttatccttg aaatctcttt    29400
tttaatattc ttttccacac acatgaaaag ttagatgagt gtatgaattt ctgttgtcag    29460
actagttgta aacctcctaa atatagtttc tgcagtatag ttaaagagaa agaacatcct    29520
ggctaacacg gtgaaaccct gtctctacta aaaaaaaaat acagaaaatg agccgggcat    29580
ggtggtgggt gcctgtagtc ccagctactc cggaggctga ggcaggagaa tggcgtgaac    29640
tcaggaggca gagcttgcag tgagccgaga tcacgccatt gcactccagc ctgggcgaca    29700
gtgcgagact ctgtctcaaa aaaaaaaaa aaaaaaaaa aaaagaaag aaaataggcc    29760 cagcaaggta gctcacgcct gtaatctcag cacattggga ggctgaggta gggaggattg    29820
cttgaggcca ggagttcaag accagcctgg gcaacatggt gaaactccat ttctacaaaa    29880
aatacaaaaa ttagctgggc atggtggcat gtgcctgtag tcccagctac ttgggaggct    29940
gagtgggagg attgcttaag cctggggagg ttgaggctgc agtgagctgt gactgagcaa    30000
cagagctaga ctctgtctca aaaaaaaaa aaaagagat gggttttgaa attcagtact    30060 tttttttgagt gaggtccaat gggtcagaaa gaagcattgg ataaatgaat ccattttctc    30120
ttctctgttt gaatttgtaa tttgaaagaa tattctacct ataaagtact tcagtgctta    30180
attagctgtc agtgaattta tatatctttat ctaattcata tggatttgct attttttatct    30240 gtacctacag attcctgacc tctctaaggg gatcccagta tactataggg aatgaggtat    30300
aatagaagta aaagacctat cactagtcct gtcatcattc caactcatgt gtaattatag    30360
tttaaaagaa gtgacatcat gtgtattgct gtttatcttt acattaatct tgtggtcaag    30420
aaagcaaata ctataatata taataattat ataatcat aagacaagta atataatat    30480 gggaatataa tcccatttta caaatgagga aatgaaaatt tagagaaata aagtgacttg    30540
tccagggtca catggatact aagtgaccaa gtgtcaaagc agaattttcc aaataactta    30600
aagataattc ttgtacaaat atagaacgaa cacatgtcat atgtgttgtg ttaatgaggg    30660
aaccagaagg atgacaacat tggttcagag agatgcaaag ataaatatag acattggagg    30720
```

-continued

```
aaaaagttgg aaataagatt gttaggttag atacaaagct gtgttatagg ccaataaaaa    30780
ccatagactt tgaggttatc ttttttactg gacaggattc agttacacct ttatgagacc    30840
aaaatttatt atttaacatg tggatattag agtctgagtt ttaaaattat tagtaaatga    30900
ccgtcaaata aagatatgtc ccctaatgaa atactgataa tcgctgggtg agcttgtgct    30960
cctatatgac attgaaatga catactgccc tctctttgtc ttctaagttt tggatacttt    31020
tttttttttt tttttgacac aaagctgcat tagaacctag gtttcttgac tttcagtcca    31080
gatttctttc cactctactt cctgcttctt catagtataa ttttcaacac tagagcagtc    31140
tgcataactt ttgcaaaatc agctagtctt tcttattagt tttcctttgt gcaaagtgat    31200
gtagatacag ctttcttctt cagagaaaca ttgtgaaatt caatgaatat ttgtaaaatt    31260
tgcatacgtg cccaatgtga gaaattgaaa ttattactta agtattgcaa ctgttctttt    31320
aggatatttt gtttgcaaat ttcagagtaa ttataaatat tcttgcattt ttattgtaat    31380
cagtatttat aaaacagtgt atttcatcac attaacctt acatattttg aataaaatag    31440
tattgaacca ttttaaatag taagtggaaa ttttttccaca ttaaacagta taacgggcta    31500
acagagttaa gcattgcatt atttaactaa taatttttc ctgaacttca gattattatc    31560
tgtatgtgtc atataacttg acaatttttt ttttttagtg cttttttaaaa agagtgggat    31620
actttattca gtttagccct caagcaatta ggcaagtcag ttaccatggt aacagtaggt    31680
attaattcc ttacctagtt agaggtttta tgaacaaaga aatctctgag ttcatccacc    31740
aaaccccaac tttctcttga gactggcctc ttgagactgg tgttaaattt gtctatttc    31800
tagaagatga cactattcta agtggaaaat acggttctct tgaggtgaat ttctactcta    31860
tcaagagtga agtagagtat ggcttaaaag ttaagtgatt aaaaagctac cctttcttag    31920
ctaatttgta atgtaattgg tcttaatttt tctaaattcg ttctaaccaa aatcttattg    31980
gcgtgatttc tattgacatg aactagaagt gacttcagca gacaacttgt cccaatatct    32040
aaatgctgtc aaatagaatc acttaagatg aatttcttcc aaaacagagt tcacaattt    32100
gacagataat ctcttagcat ttaattgact agtattacca accttatgga ataggtccac    32160
tcgtttagct atcatgagga ccattttgca actaacttat caaaaagcct tcaccaagaa    32220
gttgcatatc ttattgatat tttagaatgc gattatggag attaaaaatc accacaatgg    32280
gttgttaata acgccagcct tgaacttca gttttagagc attttatctg tgttctgtag    32340
tcaaagttgg taaggtgtcc agtgggtcat gtttgacttg ctgcttgttt ttgtactgtg    32400
tgctaaatgg tttctacatt tttcagtggt tgaaaagtca aaagaagaat aatattttat    32460
gaaatttaaa taaatccagg tttcagtgtc tataggtaaa atttcattgt aacgttgtta    32520
tgcttaagta ttgtttatga cttctttgct atagtgacaa acttgagtag ttttgacaaa    32580
gatcatctgg cctgtaaggc ctagaatagt tactgtctaa ccctttagag aaaaaaattg    32640
ctggcccttg ttctatagta tgaaaaaata tagccttgat tattcattaa aaaattattt    32700
tcccattta ttgacatact tttgtcccct gattgttaaa aggaatgcat gttcttatag    32760
aaaagttgga atatatagaa aagtataaag aacaatatga aaaccatttt gcaattgtga    32820
gataaccact aatgttttgg tatacattgc tccagactta cacacaaaca cacgcgta    32880
tttatttat acaattagag tctaattttt tttttgagac agtcttgctc tgttgcccag    32940
ggtggagtgc agtggcaaga tttcagctca ctgcaacctc tgcctcctgg gctcaagtga    33000
ttcttgtgcc tcagcctctt gagtaactgg gattacaggc gtgcaccacc atgtccagct    33060
```

-continued

```
aattttttgta tttttagtag agacggggtt tcgccatatg cccaggctgg tctcgaaccc   33120
ctggcctcaa atcatcggcc tgccttggcc tcccaaagta ctggattac acacgtgagc    33180 cactgcgcct taatttttta atttgctttt ttcacttgaa taattataag aacattattt   33240
ttaatgactg tgtagtgttc tgttttatgg atgtaccata cttaattatt tagtcataat   33300
ttattattat gaggttgata aacatgataa tcagattgag ctcaagaagc tagttatagg   33360
gttgcacaat taatgaatcc caggtacctc gctgggttgc tgaggctgct attttttcc    33420 tgcctgtttg gaacactgtg tttgggacca atgaggcaaa agaaattgaa gagctgccat   33480
tttcaattat tctattagaa gatacattga agatttgtca aatgacatag acacaacact   33540
aatccagaag attatttaat caaaaaggca ttcatttcag atatgaattc ataaacattt   33600
gtaacgatcc tcagtttgaa gaccatatag aatccctgaa gaactggaag acactatttg   33660
cttggcaaag agaagtcccc agaccaactg gggatgaaat attcaaagag ataaatgaat   33720
actttgaaac atacaaggta ctatggaaaa agagtggaag tttgggacag gtaatgacag   33780
gaagatataa aagctttaca ttaagttcaa tctaaaactt tattccaagt aacaggttgt   33840
cttattcatg gagaagcagt tgtaaattaa aacttgcctg tggtttggaa tttcacatta   33900
aatgattaca ttaaaaattc aaatggtgaa cctaactaaa tccaagctcc tacagtacct   33960
tcttttcacc tttaggtgaa gaaatgcggt gagctatttt attactgatt atgtggacag   34020
tccaaaggaa ggttcataag cgaaaggaa aaatttaaat tattccatgt gagcgattct    34080
tactttgcag atttgttgaa gtgtagttac tggcttcaaa aagtggtatc cttaactgac   34140
attttgaaca cttgaattca ctcaataaaa aaatgcagtg atcatgtgga aaatacatta   34200
aggtatatga cagagtttat ggattcagag caaaaattca gctttggaaa agtgaagtta   34260
aaatggtttt ttaagtgatg tttaatttgt gttatttgaa tcctaaagaa gaattaatag   34320
tactagtaga ggaaagtcag tgtgtctgtg acaaagcttt agtattattt tgaaatactt   34380
gatataaaaa agttcacgtt tactcaaagc ttacttaaat catcagaata aattaacatg   34440
tttcttaatt aaagaaaagg agaagctatt agacttaaaa aattttttgca cccttgaaat   34500 acatacaatt tgaagagatt aagttgttgg aatactggtt aatggtgaaa aaggagtttt   34560
cagtctatga aagcaaagcc ttctcctttg ccatttgctt ttttgtagtg gttgctatgt   34620
agaattcgaa gaaatattg ttaaaaagtc ttggtcagga gtagagtgta gcatgaaccc    34680
aatgcatttt aacgttaata atgaggaaaa agggaatgca tgataatttc atcaagtcag   34740
aaaaaaatgg aaaaagaaaa agaggaaact gaagaaagta actgatgaaa gtaaggtgaa   34800
agggaaaaca acttttttata ccacctgtga atgagattaa ttttcgtttc catactgaaa   34860
gacaaatata ttccaattaa gccattcaaa ataaaaaaca attttttttt ggtaagagat   34920
gggatctcac tatgttgacc aagttagtct tgaactcctg ccctcaatca gtcctcctgc   34980
ttcagcctcc caaagtgcta ggatttcagg catgagccac tgtgcctggc caaaccaaa    35040 attaagcaac aaaacaacaa caacaaaaat tccagacagc cttttaaaata atgataaagg   35100 ttgaaaaatt gtagatagtg gtaggtagat aagatttcag gaaaagtcca aagcaaatca   35160
taatacgtta tttttaaggg gggtttaaaa tccttttaaag gtacaatgtg aagcattatg   35220
aaatgataaa atacatgttt tttaaaaaca ttaatttttat tttaagttcc aggatacatg   35280
tgcaggacgt gcaggtttgc tacataggta aatgtgtgcc atggtggttt gctgcaccta   35340
tcaatctgtc acctacatat taagcccgt atacattagc tgttttttcct gatgctgtcc    35400 ctcctccagg acccagtgtg tgttgttccc catgtattct catcgttcgg ctcccactta   35460
```

```
taagtgagaa catgtggtat ttggtttcct gttcctttgt tagtttgctg aggataatgg    35520
attccagttc catccatgtc cctgcaaagt acatgatcgt gttcctttt atggctgcat    35580 agtattccat tttatatgta ccacatttc tttatctagt ctatcattga tgggcatttg     35640
gtttttttcc atgtctttgc tattgtgaat agtgctgcag tgaacatgaa catgtgtgtg    35700
cttgtatctt tataataaaa tgatttatat tcctttgggt atatacccag taatataatt    35760
gtataaccca gtaataggat tgcagtgtca aatggtatt ctggttctag gtctttgagg     35820
aatcgccaca ctgtcttcca caatggttga actagtttac attcccacca acagtgtaaa    35880
agcattccta tttctccata gccttgccag cacctgttgt ttcttgattt tttaataaac    35940
gccattctga ctggcatgag agggtatatc attgtggttt tgatttgtat acaaaaaga     36000 tttgtatttc tctactgatc agtgatgttg agcttttttt catgtttgat ggttgcataa    36060 atgtctttt ttgagaagtg tctgttcatg tcctctgcct actttttaat gggattgttt     36120
gttttttttt tcttgtaaat ttgtttgagt tccttgtaga ttctggatat agacctttgt    36180
cagctggata gattgcaaaa attttctccc attctgtagg ttgtctgttc actctgattt    36240
gctgtgcaga agctaaaaga catgatttta gaaaagaca tgtcaaagtc atacatgctc     36300
aacgacatag cgagtacata tgtaaataaa aaattatttt atgctgtgaa tttgaccgaa    36360
aataaccttt acctcgtcag gaattacaat cctcacgtat ggtaaaggat ttccctattg    36420
caaattattc cacaacatta atgttctgtg tgcttttat ctatcccaag atacaagtaa     36480
atttgacaaa gatattaggt ttgtaaacaa atttacgttc aaatctttgc ctggaagtat    36540
ctagatagaa ttttgcatgc aaaagagtat ttacatctaa aaaattacat atttcaaatt    36600
aaaatgattt tagtgttata gatagaagga aagagttatt gaagtttatt tctgttttgg    36660
cagtgtaaat gaattactta caaaatttta gaagtctaca ggtgttttta taagtttgt     36720 gttatttgtg gaaacctcag ttttctggca ttttgccaat gaggtctact ctaagtatag    36780
cagaaatttg ttttccagct ttataaatat atattttaag attaagaact gattttactt    36840
atataatctg ggatcaactt ttggcttctc ctgtcaagga ttttgaattt gtgacaaaat    36900
atacacttat tgataaccag tgacatatat aaaatgcttt acaattaata aagcatatgt    36960
attttacata ttttttcact acatatgacg catgtggcaa ccccaagagt tgagttgtac    37020
ccatcggcaa actttgatca tgattctgtg aatataggca agcaccaatt gcaggtagaa    37080 cattctttt ttgagtccca aaccgtgaga acaaattac agaaatgtac ctttcttttg     37140
cattaggaca cgttgtagtt ttgtatgaac actctagttt taagcagtat gtgcaaaaac    37200
attgcacaaa ggatttgtgt gttgattttg ggactcctgt attattaatt atgtggttta    37260
tttgactacc ccacatttc aagcataaat taataaatcc ataattccag cttattaac     37320 aataaacaat ctagatagtt gaactcttc ttgctaacat tttctagata tggactgttt     37380 ggtattttc tactaataaa gacccttagt aagctgcctt ctggtttgat gtcattggga    37440
tgtttactgg gaactttggt ggagatcttg cagtctctct cccccagtgg tgaaagaatg    37500
agttacaaac cagctttcct tcccagtgta caatagcgat ggagtttgtt ctatatggaa    37560
aatttgtttg ataaagtat tctttaaaat tttttgttcc ataaattatc agtatttca     37620 gtttctgatt catgcttggg atagttgctg catattgttt aattttgtca gaatttatat    37680
tgttaaatat caaatacgac agactaccct caaatcataa gtagtaatg taattaacat     37740 cctgtttcat catgagactc ttcagtgtta cattaaaaac tgctacctcc tgggccgggc    37800
```

-continued

```
gtggtggctc atgcctgtaa tcccagcact ttgggaggct gaggtgggcg atcggatcac   37860
gaggtcagga gattgagacc atcctggcta acatggtgaa accccgtcgc tactaaaaca   37920
tgcaaaaaat tagccgggct tggtggcggg cgcctgtagt cccagctact caggaggctg   37980
aggcaggaga atggcatgaa cccaggaggc agatcttgca gagagctgag atcgtgccac   38040
tgcactccag cctgggcgac acagcaagac tccgtctcaa aacaaaaaac aaaaaacaaa   38100
aaaactgcta cctccttatt acaaatagga actaaagttg aagtttgagg aatttgctaa   38160
gaactaagcc ttgaactaag gctatttttat ttgagtatga gtcatatcag ggtacggatc   38220
cattttacta ttaacaaaac aaatatgttc tgtttttttt ttttaaatgc acacaccacg   38280
tttgagagat tcttattcac tgtatttttct ttaattatac ttgaatttg gtttacattg   38340 aggagtgccc tcaaagatat aacagatttt ttaaaaaatc ctctaaaaaa ctcattctta   38400
gggaaatttg ttcacttact aggtgaggag caaaataaaa atccttaata tagaagagct   38460
attatctgtc ttcaaaatta agtctttgag tagatttgtg aataaatcta atagttttgc   38520
tgaatttact tagatcttaa gacagaataa tcatgtagaa aatttaaaat gtcaggaatt   38580
cataatgatt catatacccca aggattttca ttgatagtga ggtaaggtta ttcttgagaa   38640
agactcaaag tcataaaata atagaatttc gaaactacca gaattataca agtcaattaa   38700
aatgactgat ttgttttaag aggaagaaat actaaatgta taattattag atgcagcata   38760
ttgtatctgt tttgttttgt gattctagct cttataacct atgcttggac ctaggtgtca   38820
taacttactt taaatatgta tgtttggttt tcattcatat tgacagtact acctctcagt   38880 tttcttttcag atattgtttt gtatttaccc atgaagacat tgttttttgg actctgcaaa   38940
taggacattt caaagatgag tgaaaaaaa ttggaaacaa ctgcacagca gcggaaatgt   39000
cctgaatgga tgaatgtgca gaataaaaga tgtgctgtag aagaaagaaa ggtatgttgt   39060
tcattgacta ttctttcggg tgagaaattt aatttatatt tgactgtgca aagagtcagt   39120
tgttacttgt aaacttcaag tcattgttta ggtcagagtt gctgttgtct aaatgcacca   39180
ggacctagtt gttgaaaggg taaactggaa taaactttaa ttgggtttac aaaatgagaa   39240
ttcttactgt atattttctc ttttttcgggt tgacttttacc agtttgttct agttcagata   39300
atttagacaa cattaacttt gttgaatttt ttgtttgcca gccggtcttc agcattttaa   39360
ggcaacatta ttattacagt tgtaatacga atataattac cagagaaaaa actcaggaaa   39420
ataaatgctt ttatgaaaat gggattagag gtttgaaaat aaacttgtta ggagaaataa   39480
tttcacaatg ggatggtttt ttctttgtta agttttcttt atgacttcat tagtttataa   39540
aacattaatt gataaaactt agaactataa attgaatgct tcagtgaact ttattatttc   39600
agtgaacatt tgttatttga tgtgaacttt gtgcctgttt tgaaatttac taaactcaag   39660
gcatgtgttc ggaagagtgt ttttgaagat gacctcccct tcttagaatt cactggatcc   39720
attgtgtata gttacgatgc tagtgattgc tctttcctgt cagaagatat taggtaagtg   39780
atttgaattt cctgatttta tttgaatttg gaccccttaga aggtactatt atggtaatgt   39840
ttgtgaatat actgagtttt acaggtgagg tgtgttcaat agataattat ttctatgtat   39900
acactatcac caagttttac atttcaaata aaagtcactg aattaatttg taatctgtca   39960
gtttgttcat tcataagctt ttctattact tcagacagtt ttttttttaac tttttttaata   40020 tatgtgctgc tgaagcgagc acgacagttt tttaactttc agtacttaag atgttatata   40080
tagagctact gaacatactg tgtttatttt accaatttag ggaaaaagtg caaaaattat   40140 ttaacctttta aatgcacctt tatatttcat taaaaatatc aacatagtaa tattgaataa   40200
```

```
tggctatgat cggctctgtt gtgtgtaatt agtaacagtt gtagcaaatg atccttaaaa    40260
aatgttctaa ctaaacatta gaggccaggc gcggtggctc aggcctgtaa tcccagcact    40320
ttgtgaggcc gaggcaggtg gatcacaagg tcaggagatt gagaccatcc cggctaacat    40380
ggtgaaacac cgtctctact aaaaatacaa aaaattagcc aggtgtggtg gcgtgcgcct    40440
gtagtctcag ctactcagga ggctgaagca ggagaatcgc ttgaacctgg gaggcagagg    40500
ttgcggtgag ccaagattgc atcactgcac tccagcctgg gcgacagagt gaggctccgt    40560
ctcaaaaaaa aaaatccaa aaaacaacc ccacaaacaa acaaaaaaca ttagaaatgt    40620
ctgttagtac ttttaaaggt tgccttgtaa aattaggact gcaatagtgc aatctaaggc    40680
tctcaaagca taaacaagt aataaggaat tcattcagat attttccgag gtggttatac    40740
ctgtctttta aaaaaaaaat tttgttatat attgggttaa aaaagcaga ggtgctgggc    40800 acagtggctc atgcctataa tccctacact ttgggaggcc aaggcaggag gattgcttga    40860
gcccaggagt ttgagaccag ccatagtaag acccccatct ctacaaaaaa atttaaaaat    40920
tagccaggtg tctgtggtcc cagctactca ggaggcctag gttttgggcc cgagaggttg    40980
aggctgcagt gagccttgat cacaccattg cactccagcc tgggcaacag ggcaaaaccc    41040
tgtctcaaac agacaaacaa acaaacaaaa ggcagaggta ggttaagctg tttattaatg    41100
gtcttctact ggtatagata aagctagaa ataacattca agtgttttta cttttactac    41160
agttatctgg ccactttggg actcattata ctgaattagt ttcacagagg aggtaaaatc    41220
tgttgtttat gattacatat taactctacc attttacctt cagcattgct atagtatgtc    41280
atatctgaag gcaattagca caagtgactt gaagaattgt agttttgatg acttatatgt    41340 atttttataaa aggcaggcag agttttttgtg tttgctttcc cctcctctgg acactttaaa    41400
tttttgctac cacaggtttc caacaatttg attatgatgt gcccttgtgt aatgtggttg    41460
gtgtttattt ggcttggagt tcgttgaatt tttttgatct gtgtgggctt ataccttttaa    41520 tcaaatttga aaaatgtctt cagatccttt ttcctcccat cctgttattc ttttctcttt    41580
ctgggactct tagtacacac aagtttgatt gcttgatact gtgtcacagg ccactgaggc    41640 tcttttccttt cagtcttttc ttctttcttc cttttttttct ttctgtgctt cattttgaat    41700
agcttgaata gttttgtttc ctgtcttcaa gttcacttat attttttttct tctgtagtgt    41760 ctggtctgtt tataccatcc tgtgaatttc ttttttagat actacatatt ttgtttatct    41820
ctagaagtcc catttggttc ttaatttttt tttccatttt ggctctcatt attcatgttt    41880
ctttcaaaat tcttgaacat atttagcata ttttttaatag ctgttttaat gtacttgtct    41940
gttaattcca ttattctagg gttttttttct ttctattgga tgatttttct cctgattatg    42000
ggttatattt tcctgtttat tcctacagct gttaatttt tttttttttta attaggcatt    42060 gtgatcttac tttgtggaat gttagatttt attgttttcc tttaaagaaa ggaactttgt    42120
cagacatcta agttacctga agatcaactt tatgttttga agcttgtttt caagcttgat    42180
cagggaaagt ctacgtttgc ctttagtcta aaggtaattt agccctataa taagatgtga    42240
cccttctgga gtctttgtag actgcctctg gtgatcaacg atctcttctc tgacttttca    42300
gaacgttaat gcctcttacc tttgtgtaag tccgtcctaa gaatcattca gcttatggtt    42360
gtttgcccag ccccatagag ttttagtcta tgcatgcttg tcttcgtatt ctgcaaagac    42420
caaaggagtc cctagggag atttctggag ctcttttcct gcctagcttc ctcctctcca    42480
gaactctgcc ccgtgagttc caggtccttc agcttccagg gctctgaact ctgtctcccc    42540
```

-continued

```
aactcagtgc tctccttggg attcttctcc ctgttctgtt gtctgcaatg ggtcccagga    42600
agaatgtggg gcaactgtaa ggttcaccct tcatttccct tcccttagag atcatagtcc    42660
tgtactgcct gttgtctagt atctgaaaca gttgttttat atgttttgtc caagtttaga    42720
tttgtttgtg gtgggagggt gagtctggcc tcccttgtta tatcatgttg tcctgaagca    42780
gaagctgagt ttcttttatt ttttaaatat agtttcaatt tttaacaact attaaatagg    42840
caagtatcaa caacaataga taacaatata atagatatgc atattcctcc cactttatca    42900
aatcttaatt ttcttcaatt tttttttttt tttttttaat agggtctcac tctgttgctc    42960
gtgctggagt gacagtggtg tgatcttggt tcgctgcaac ctccgcctct gggctcaag    43020 tgatcctcct gcctcagcct cctgagtagc tgggactaca ggcatgcacc atcatgccca    43080
gataatttat atatatattt ttttatagag atggggtttt tgccatgttg cccaggcggt    43140
ctcaaattcc tggactcaag caatctgcct gccttggccc cccaaagtgc tgggattaca    43200
ggcgtgaacc actgcgcctg gcctgttttc ttcagttctt tattaagaaa tgaaacagta    43260
aaatacagct gaagcccccgt gtttgttctt tctgattctc cctctgtgcc cctctgagat    43320
aacttctatg agttttgtgc attttttttt cttttttaata aaaacagggt cttgctctgt    43380
tatccaggct ggagtgcggt ggcgagatca tactcaatgc agcctcaacc ttatgggctc    43440
gagtgatcct ttcgcctcag cctctcaagt agctacaact actggtgtgt gctgccatgc    43500
ctggctaatt ttttatttat agttttttaaa gacagggtct cactatgttg cccaggctag    43560
ttttgaactc ctggcttcta gtgatcctcc tgccttggtc tcttacttaa agcactggga    43620
ttacaggtgt gagccactgg ctgctcacat gttttttata atagtactta ataattttat    43680
gtctgaaaat attatataat gttatttttgc ccatttaaaa actttaaaaa atgctaacaa    43740
actgtgtact ctgtaacttg tcttttttac tcaacactat gtttttgaga attttcttg    43800 ttgatctgtg tagttccatt ttaactgtta tatcttacta tgtttcatta tgcaacagtt    43860
ggttcaatcc attctcttgt taatggaaat ttagtttgtt tctaattttt gccagtagga    43920
acagtgttgc aatgcatatt cttaaacatg tctgtacaca tctgagggtt tcatttattt    43980
gtgacaaaac ttgccaggtc atagtgttta tgcaccttca actagatatt gtcgttgtca    44040 aagtttttt ccaaaaggat tttaccaatt tatacatgaa ccaccgatag atatcctctt     44100
aacacgtggt attctgaaac ttaattttta ccaatcagat agatgtgaaa tcacgtagac    44160
ttagtttgca tttctttgac ttctagtgag aagtagtgtc ttcacatatt ttttggattt    44220
ttaaaattta ttttttattt ttgttttttct tagagacagg gtcttgaact tttacccagg    44280
ctgaagtgca gtgatgcgat catagctcac gctaacctcg aactcctgga ctcaagtgat    44340
cctcctgcct cagcttcctg agtagctggg actacaggtg tgtgccacca gcccagcta    44400 atttttaatt ttttttttg tagagacatg ctgtgttgca caggttggtc ttaaaactcct   44460 agtctcaagc agtcctcctg ccttgacttt ccaaagtgct gggattacag gggtaaacca    44520
ccatacctgg ccatatcttt tggatttatt ggtcatttgg attttctttt gggaattacc    44580
tgttcatatt tttctccatt tttctgctga ataatttgtc ttttcttact tattttcaa     44640 gaaattttac atattttctg gctgttcatt gtcagttgta tgtgctccag ataacttgaa    44700
cagtctgtgg ttgccttta atttttgaat tatgtcttta gttatgcaga agtttaaaat    44760
tttaacataa attaatttac actatttttc tcactttagc atgagtctat cagatgggga   44820
tgtggtggga tttgacatgg agtggccacc attatacaat agagggaaac ttggcaaagt    44880
tgcactaatt cagttgtgtg tttctgagag caaatgttac ttgttccacg tttcttccat    44940
```

```
gtcaggttgg tatctctaca tttcattttt atatggctga taattgtaat atgtcaactt  45000
tatccctata aaattaagtt cttttattag ctggccgttc tctcattatc tcaaatttat  45060
ttaagtattt atgttctacc tgattcactc acattccttg ttttatttaa ttttcacaac  45120
atacctgtga ggcattgaca tttttctgt tttagagaag agaaaactga aattttaaga  45180
ggctaaatga ccaggatatg tactgctatt gctagcagga gtggcattca aactgattat  45240
tttttcttgt catttatcaa tcaggactgt ttgctttagt taagaaatac tcaaggtcaa  45300
tgtgtttctg aatttaaaat tactgttaaa tacaaattta tacataaaca tggtatgtat  45360
aagaagtagg acataaatcc atcatacttg acagaactta tggaaataac aagaaaatgt  45420
tacagttttt ccccagggat taaaaatgtt gcttgaaaat aaagcagtta aaaaggcagg  45480
tgtaggaatt gaaggagatc agtggaaact tctacgtgac tttgatatca aattgaagaa  45540
ttttgtggag ttgacagatg ttgccaataa aaaggtaaaa gcaatatata tataattttc  45600
atgatgaaga ttattttgtg ttacacagaa tgtactttct atctgaatgt tagatttttt  45660
tttgaaaaag cttgttatat aatgttttg tagcaataaa aaagttccaa gtgaatgttc  45720
tttaatgaaa acctttattt atttatttat ttttaacttt tgtttcaaga tcggggtaca  45780
tgtgcatgtt tgttacacag gtaaacttgt gtcatggggg tttatcatac agattatttt  45840
atcacccggg tattaagcct ggtacccatt agttattttt cctgattttc ttcctccctc  45900
ctcccaccct ccacctccca cagtgtgtgt tgttccctc tgtgtgtcca tgttttctta  45960
tcatttagct cccacttata agtgagaaca tatggtattt ggttttctgt tcctgcgtta  46020
gtttgctaag gataatggcc tccagtgcca tccatgtccc tgcaaaggac atgatcttat  46080 ttatttttt tatggctgca tagtattcca tggtgtatat gtaccacatt ttttttaatg  46140
cagtctatca ttgatgggca tttaggctga ttccatgtct ttgctattgt taaatagtgc  46200
tgcagtgaac atatgcgtgc atgtgtcttt gtaacagaat gatttatatt ccttttggta  46260 tacccagt aatgggattg ctggggcaaa tggtatttct ttctttaggt ctttgaggaa  46320
ttgctacaca gttttccaca atggaaagcc tttagttcta atccatgtct ggcatagag  46380 tttcttttct tttttttttt tttttgagg tggagtttcg ctcttgttgc ccaggctgga  46440
gtggaatggt gtgatctcag ctcactgcaa cctccacctc ctgggtttaa gtggttctcc  46500
tgcctcaggc tcctgagtag ctggggttac aggcatgcac caccatgcct agctaatttt  46560 gtattttag tagagacggg gtttctccat cttggtcagg ctgatctcga actcctgacc  46620
tcagataatc tgcctgcctc ggcctcccaa agtgctgaga ttgcaggcgt gagccaccgc  46680
acctggccgg cagacagttt cttttttct ttttgagaca gagtcttgct ctgtcgccca  46740
ggctggagtg cagtggtgca atcttggctc actgaaacct ctgcctcctg ggttcaagcg  46800
attctcctgc ctcagcctcc cgagtagctg gcactacagg cgtgccacca cccagcta  46860 atttttgta tttttttag tagagacgag gtttcaccgt gttagccagg atggtcttga  46920
tctcctgacc tcatgatcca cctgcctcgg tctcccaaag tgctgggatt acatacagtt  46980
tctttaagca agccttctct tttccttcct cccagttctt ggtactcttt cactttcata  47040
tatttgcaaa tgtaaaattg tgttttaggt gtatattttt aatccatgta taccagtaac  47100
ttaaaaaaaa attttttttt ttttaaggga gagcataatg gagctcttgt gatacggtgc  47160
tcttagtgga agtttggcta tcaattccat cacctgtatt tcacatattt tattaatgaa  47220
gttcttaaat taaattctca tatttagcca agtattcatt tggctgggag gtagaaagcc  47280
```

-continued

```
tactaaccaa ctttttttca tgaacaatat ttttaaagtc caagattttt aatacctaca    47340
ttagggaaat tctagaatta aattcttaca atgtggactg catatgaggc ttttagtgac    47400
agggaatttg ttgaaggcta tctgtgggtt gtattttggt ataacatttc ctaattttat    47460
ttgtggtatg ttcatttgat atcatttggt aatacctgaa aacaggaact gattttactg    47520
tgttgctttt tcatcatttc tagctgaaat gtacagagac ctggagcctt aacagtctgg    47580
ttaaacacct cttaggtaaa cagctcctga agacaagtc tatccgctgt agcaattgga     47640
gtaaatttcc tctcactgag gaccagaaac tgtatgcagc cactgatgct tatgtacgtg    47700
cttaaagatc tttagaaatt gtgatgtgtt ttaaaaacat tattataaat gactttagaa    47760
aaattttatt atagtagtgg cagaaactct accaaaatat tttatatcaa tttggcattg    47820
aaaaatgctt aggaagacat ttagtgaaac tattcatttt cgatattaat tagcaagtac    47880
caatcaacag attgttcaat gctagtttat tttcattgtc atgaagccaa attaatgtct    47940
aatttgtatg ttaaaaaatg tgaacttgct gaaaacatga aaggctaata aatccaggct    48000
gagcaagcat aaatagtact gatgatggat ttgatatata aacaattcag aatgaaaata    48060
attatagtac agtttctatt ttaaaactgg ccttatttct tatatataaa atgtggtgaa    48120
attttagaaa aattgcctcc aaatttagct tgttgctgcc attagatata ttttttatatt    48180
tacatgtttg tatgtagtga aatctgggct tatctttata tatagcacta ttgtgtgttt    48240
tttaagaaat gtattttatt ccacagtgaa tttgttttct cctaactcat gctttcattt    48300
gtagatgaat atttttattgt ttctcctttg catctatcaa aggaatggaa actcctttga   48360
attgtaacca gcaaacaatt cacttttgtt agggaaattg gatgataatt ttcctttaaa    48420
agataccgcc aaacttgaga ctaacattct cagctgattt aagtaggatt tctcttacta    48480
gattgcattt tgttagattc cattttaagt tatttttattt ggatattgtg tgtaatattg   48540
agtgtgaaaa agtgaaaaca aacttttaag gctcaggcac ctttctcaat tttcacaatt    48600
ggtatgatta ttaaatgagg acatattgat atttgtgtca cataataggt tgaattccat    48660
gtttgggtgc tttgtgaatc attctcttcg attttttctga agatgggact tactgtttta   48720
tttcggtgat ctttagcata cttttttaaat ttttctgttt ttttataggc tggttttatt   48780
atttaccgaa atttagagat tttggatgat actgtgcaaa ggtttgctat aaataaaggt    48840
atgttaagat ccataaataa aatgtgaatt cactcttttg tgaggtttat ctccaaaaaa    48900
ggcaatattc acatatttgc aaagcattta gtactataac ttcttgaatg tctgagcagt    48960
cctgacatta gggtgggatc catcagggcc caagatgagt gtttcatctt tgttacttgt    49020
ggcaaagcag ccccttacttc ttttttacttttg tagcattgct atgtatttgg cttctagagt  49080
tggggctttg tggctttctt attgcagtga cacaaccagc tttctcctag tctggagatt    49140
atacatcctt gctataagta tttaaaatgc tttctatata atgctttaaa acatgtaaga    49200
tggcttatcc ccaagatggt agctaataaa cactaagtga taaagtaggt aaagatctat    49260
ttattcattt attaaatatt gttggtcatt ttacagtgct ttctaacata ctgatttaca    49320
tttctaattt tcttctgtca ttttttctcca aaaataatgg tcatgtcatc caacctcagt   49380
gctgttttta gaggtcttga taagccagtg agagcagaag gagccacgta gtagagtggg    49440
tgagcccagg cttttttgttg cacagaccaa tgtgaatccc agccatgtga cctgggatgt    49500
acctgtttct ccaaacatgg aatgtagata ctagcataat gtccgttta ccgtttata      49560
gaataattgt gaagacttaa agggacaaac tattcgaagc atctgtattg atataaagtt    49620
atcactattc tcgtagcttc cttttggaga ttttaaatga ttgtgtttgt taagatgtta    49680
```

-continued

```
attaaattag gccattttgc taaatgctct taaaaatatg gcatgactgc ctcatataaa    49740
atgatatgat attctttata attgtcgttg agcctctgtg ggtggcaggc cctccttta t   49800 atgttaaggt agaagagtct ttattcttac ttctcctccc tggagagcca cttcctatga    49860
atgcctgctg gttctctgta gtcagaggtc ttgtggctgt aacttagagt cagtctccat    49920
atccctgggt tctgcatctg tggattcaac caaccacaga ttgagaacat tcaagccaaa    49980
aaaaaaaatt cacagtttta aaaaggaaa  agttgaattt cttgcatgga gtaccacatt    50040
gaatctatat gaatgaagtg atgcgtaggc attttataag gtattataag aaatccggag    50100
atgatttaaa gtatacagga caatgtgtat agattatatg caaatattgc agcattttat    50160
ataagagact tgatcatcta tggatttgat atcagtggga gggaggttcc tggaaccaat    50220
ccctcaagga tacagaggaa tgactgtatg ttaattaact gaggcaggtg atcggttttt    50280
taagctgatt agggaaacag tatataagaa cttacttaac tcataataaa actaaaattc    50340
aacaggggag agttatgatt ttttggcttt atggttgtgg aattgcatgt aggttacatg    50400
tacaattttg ttacatgtgc aattttgatg aaaatgcttc caaggaatgt ttatgatatt    50460
tttcactaaa gtaacatata ttaataacac agtactggaa gtcctggtat ctgtgtactt    50520
gtcattgtaa tgctacatta tttgaccttc acttttttc ccctttatta cattatatgt     50580
gtgagtatat tgtgacatct tgactcagat tccagtgaat tgtattaggt tggtgcaaaa    50640
ataattgtgg ttttggtaat ttttaatggc aaaaaccaca attactttg caccaaccta     50700 ataactaaga ttaccatctt ttttttcttc cttcctccct tccttccttt ctgttattca    50760
gccagaagta tcagcatcac tgttctctta tttt cttcat gtacatatgg atgatatttt   50820
cgaatgacca ctttttctctt ttgctttta ttattagact gttttttttct tcttgttaaa   50880 ggataaaagg attagaacat aaaaggatat ttacacattg tttccccatt gacttattcc    50940
caagatggta gctaataaac accaaatgat atagtagtta aagatacatt gactcattta    51000
ttaaatattg ttgagcattt tacgatatgg gaataccgta gtgaacaagc caggcatact    51060
ctgtttcctg aggggcctac agttttattg gggatataga tgagtgaaga aagcaattgc    51120
agtgtaggga gatgagtctt acgtcatggg aaaacaaggt gctgtagttg acacaccgag    51180
aggcatctga cacattgggg gaaatattct agaatatttc ctggagaaag tgcaggtaaa    51240
agccagacct gaaacctgag caagagttag ctaaggccag gtgcagtggc tcacgcctgt    51300
aatcctagca ctttgggagg ccgaggtggg tggatcacct gaggtcagga gtttgagacc    51360
agcctggcca aaatggtgaa acaccatctc tactaaaaat acaaaaaatt agctgagtgt    51420
ggtgacgggc acctgtaatc ccagcttctt gggaggctga ggcaggagaa tcgctttaat    51480
ctggagggtg aaggttgtag tgagctgaga ttgcaccatt gcactccagc ctgcacaaga    51540
gcgagactct gtctcagaaa aaaaaaaaa  aaaagttag  ctagctgaag agtataggaa    51600
agaatgggta caggaaatta caggtgccaa gttacagagg tgagagaaat tatggtatct    51660
ataggtaatt gaaagtaatt cagtatagtg aacattgaat agggctgggc ggatgaaggc    51720
aaagcagaaa aaggaaagca gatgggccat ggtaaggagt ttatatctcc tcccaagagc    51780
aatcgaagtg actgagagtt ttaaacacag cagtgaagtg aattcacatta aaaaaataag    51840 aacttgggct ctagaataaa aaacggatat aggaggaagg caggagtcac agtaggaata    51900
tcttttggga ggctgtgaca ataatccaag tgagaagtaa tggcaacttg agtcggttaa    51960
ttgtgttgag aatggagaga agttgacagg ttcaaaattc atttttcttc ttttttttgag    52020
```

```
tctcactctg tcacccaggc tggagtgcag tgatgcgatc ttggcttacc gcagcttcca    52080
cctcctgggt tcaagtgatt atcctgcctc agcctcctga gtaactggga ttacaggtgc    52140
ctgccaccac gcccagctaa ttttttgtgtg tttagtggag atgtggtttc gccatgttgg   52200
ccaggctggt ctcgaactcc tggtctcaag tcttccgccc acctcagcct cccaaagtgc    52260
tagaattata ggcatgagct accacacctg acctcaaaat acatttaata gagcaagcat    52320
gagccactat gcccagcctc aaaatacatt taataaacca atggaatttg aggtaatgat    52380
gaaagacaca tgtcaaggat cattcctgtg ttgttggcat aagcaacagg gatgaaaagc    52440
attgaggaag agcaagattt tgggatgcgt tgtcacacag ttgattttag gtatgttaag    52500
ggagggagac ctgtaagaca gcaaagtgga ggtggtgcaa gaattagttg tgttggctgt    52560
agcacagagg acagtttgag ttaagagagt tgggactgag aatcccgagg aactcttagt    52620
gttgaacatt tgcgtggagg agggacacc aaaggagttg ccatagacat cgaggaaatt     52680
aggaggtgtg gtgtgcagaa agccaagtga agaacatgtt ttaagtagga ggatgctatc    52740
aactgtttta aattctgctg agagtttgag aaactgagga cttagaattc atcattagat    52800
ttggcaatgc gccaatcatt tgtaatcttt taaacaatag ttttgctgta ctgggtagca    52860
aaagagtgat ttgaggagtg gtcatttgga gcatatgcta ttcaaacaga gaagagtcca    52920
cgggctttgg taacatgaag gtcctataac catagcaaga gaatgaggtg ggtggaagtc    52980
atattaacgt gaatagagga gtaggttaga tctgaggaat gtgggaacag agacagggtc    53040
tcattatgtt gcccagcctg gctcagactc gtggcctcaa gcgatcctcc tgcctcagcc    53100
tcctgaatac ctcgggtttc aggcctctgc atctggcttg aaaacaacat tttctcagaa    53160
gcttgtttta gttgttttag aaataacgaa ggcatgtgta acaactgtt ctagaagctt     53220 agtttggaaa gggaacgttt attgatgcat ataacactta tatgttgggt gcttatgtgt    53280
caggcactgt tagagttgct cgggaaaatt tacaaaccaa gcaaaccatg ccccttcatt    53340
tcctttgggt gaagtgaggg agccatgtgg ttatctgaag gaagagctta gcaggattag    53400
agggaagaaa gtgcaaagcc tcctagggtg attggctggc tcttttggag gaacagtacc    53460
tataactgaa tgaaatgagt gagggtaaga gtggcaggaa atgaggctag aaaaggagct    53520
tgggccatat cacgtagggc ctcgtaggct gtgaatctga cttcatttct tattaatgaa    53580
aataaatacg atgatgggtg atgggaaacc catagaggat ttggagcaga agaatgatat    53640
aattaaaatt ttatttttaga aatatttttc tggttgtcgt aagaggaaaa atatttagcc    53700
ccagggcatt ttggcagaga gttaggaggc tattgtaaca gcccaagcaa tagacaataa    53760
ttgtttggat taggcgggta gcaatagagg tgatgagaag tcgtagcttc tgtaggtatt    53820
tggaagatat atattgtgaa ggatttgctg atgaattccc tgtaagggt gagatgtaaa     53880 gattcataga acattaagat attttggtca gatcatctga tcaatggaaa ggtcagttat    53940
agtggacaga ttatgagaag aacaggtttg ggtgagaaaa ctttagattt cagtgttgga    54000
tatcctaagt tttagatgat tattgatatc caagagatat caatatttgg gatcaatttg    54060
ggaaatatga tcccaaagtt caaggttgag gttggagatg taattcagat ccgatggtag    54120
ttaaagcagt gagactgaat gagataaaat agggagtgaa tgaaataaag agtaggtgtg    54180
atattgacct caagggcaca ccagcattta gaggttggga agatgaggag agagcagcaa    54240
agaggactgg gagggccact aatgaaggag ggaagtacag gaggtgttta gttctgaagc    54300
cacctgaaga aaatgtttgg aataggaaga agttgtcagt tgctttaaat cattcgggga    54360
ggttgagtga gatgagagtc tagaactaac agttaggttt gatggtgtgg aggccatcag    54420
```

-continued

```
taaccttttc tttcttttttt tttttttgaga cagagtcttg ctcagtcacc caggctggag    54480
tgcagtggcg cgatctctgc tcactgcaag ctccgcctcc caggttcaca ctattctcct    54540
gcctcagcct ccggagtagc tgggactacg ggtgcccgcc accatgcccg gctaattttt    54600 ttttttttt gtattttag tagagacggg gtttcaccat gttagccagg ttggtctcga     54660
tctcctgacc tcgtgatcca cccgcctcgg cctcccaaag tgctgggatt acaggtgtga    54720
gccaccgcgc ctggcccaag agtaaccttt tcaaaagcag ctttgctcta ctgatttggg    54780
taaaagctta gttgcagttg gtttgggagg aaatgggagc agaaaatttg agagagtgag    54840
tgtagacaac tctttcaagg aatttcgcta taaatgggag tagagatctg aagactgaat    54900
aattagcaaa ctgaaaagtg ggaagacgta attctcttat tatttcattt ttcttagtga    54960
aataagaggt gaagttctct gagtaatagg agggtcaaac aggtgttaga agttcacaaa    55020
gaaaggaaga ggtttgaaat agtcattttg agagtgggaa atgtagaaga attaacagtc    55080
attgctgagg gtgcgtttga aatctgtcat gagtttaaaa taacttgtgt catcatcgat    55140
gtgtttattt tcaactatat tcaactgctt gggtgtaggc atcaggtagg taaaaaagt    55200 gggttttatt atgagtagag gttttgccac gtaattacca tggagggagg gaagagcaaa    55260
ggagttgaga gtatagatac aaaggaatga ttactgtaat gtgggtaaga gaggaatgga    55320
aggctcagtg ggcagtggga gtagggatgt tgataggtaa ggaaaaggtg ataggatcaa    55380
tgcatttggt tctgcaagtg tcaaagtatt gttggggaaa gcatgctgga aggaaagata    55440
gggatgctgg tgttctcagg gtggaaggct tacagttgta gtctggaagt ggtgatttta    55500
ttggcaatta taaggtcaac ggtatgacta tggaattgag tggctaaggt ctgttgaaga    55560
aaagattgtc ggaaatgcag gggtcaagga actggcctgt ggatgttgaa gtcactggca    55620
ctgatcaagg aatagtagtg gagtgaaagt agttaatgaa tcaggcacta agatctccaa    55680
gggatgaaag gatgcagttt ggagatgaca agataactgt agtaatcagg aatagcaggt    55740
tttgtagctc tgtctcatag gcctcagagg agatgggctt ttgaaggaca agagaaatga    55800
tgatgaataa attctaagca ggggaagtgt ttgggaaagc agggcaggct ttgtgctgtt    55860
gatggcaaat gatgtaccag acaggatgaa gttgagaatt tggaagttga tcactgatta    55920
gaaaggctta cattttattt tggccggggg tggcagctca tgcctgtaat cccagcactt    55980
tgggaggcca aggtgggcgg atcccttagg ccagaagttg gagaccagcc tggccaccat    56040
tgcgaaacac tgtctctact agaaatacaa aaaaaaaaa aattagctgg tcgtggtggc    56100
acatgcctgt agtcccagct actccggggg ctagggaatg agaatagctt gaagccggga    56160
ggtggaggtt gcagtgagcc gagattgcgc cactgcattc cagcctgggt gacagagtga    56220
gactctgtct caaaaaaaaa aaaaggaag ggcttacatt ttattttggt gctgactggg    56280
aatgaaggca atgagggatg actgttggag aaggctgtgc ttactaaaca gtattattaa    56340
gtagcagcat acatggtgtt atactgactt ctgattttgc aatagtacag acaggttcag    56400
attctcattt ccaccttctc cttccgccta ggtgaataac tgctgggtta tagtacagat    56460
gactgcagat catttggaat ttactttaaa tgtaaacagt aaaaatttga aagagaggga    56520
aagtgattga ggcaatttgg ggattgaata agaaggtctt tttgttggaa ttcatttaag    56580
gaaagaaaat gaaaatttga tccctaatat tatttaatga agtggctaaa tgaatatctc    56640
tgctttgtgg tttgaaaatt aatattgatt tttttccc ctagaggaag aaatcctact    56700
tagcgacatg aacaaacagt tgacttcaat ctctgaggaa gtgatggatc tggctaagca    56760
```

```
tcttcctcat gctttcagta aattggaaaa cccacggagg ttaaatatta ccttttttt   56820 ttttaactta aatcaattct gtttatttt ttatcacatt ttcctatatg tgaagaatac   56880
tattcattaa ggctgactca tagaaatttg cttgaataca cacacacaga ctgatgcata   56940
aatttgagaa atatctttcc agttgttgaa tagtgaatcc aaaggtttaa gccttttctg   57000
tctgctttgt aggatgtttt atgaaacaaa ggaatagaaa ttgtattcat attatacatt   57060
ttgaaattat atctatatta tattttttgt caaagcaaaa taaattatac attaaggaaa   57120
atatttaaga ttcaaagttg tcattttctt tctgttaatg agtatctttg atttaataac   57180
atttatagtt tggtcacttg aaatctatag tgaccaaaag caatgtcata tttagtagcc   57240
tcatttctgt tactatctga ttattactta agaattctac ttaattaata gattattaga   57300
acaaaaggca ttccaatttt agagattctt ttatggttaa agcactaggt aacttaaaaa   57360
atttggatca aatgttatac agattaatag accttggaat acaggggcta tgtcttttg    57420 gaatcagacc ttgtcctggc cttaattgca ggatgacttc cttattaaat ctctaaaagc   57480
aggaatgctc tggaacaatg aacaattaga atgtggtaat gtaattttgg gccaaaaaat   57540
actttgtaga aatgtggatc tcttacttgg aatagaaaga attctgactc gaaaaagtgc   57600
agttaatgta tgcttttctg ggtaagattt gtgatagatt ttgattgaga tttaaaacca   57660
tgatatataa atttagcttt tttgtcaaag taatttgcca ccctagaatt tgtgttggta   57720
atttttaatg caacttggac aatttctgaa agatgtaact ttcttttttt tgagacgagt   57780
ctcgctttgt tgcccaggct ggagggcagt gacatgatct caggtcactg caagctccgc   57840
ctcccgggtt cacaccatta tcctgcctca gcctcccgag tagctgggac taccggcgcc   57900
cgccacccca cctggctaat tttttttta ttttagtag agacgggtt tcaccgtgtt    57960 agccaggatc gtctcgatct ccggacctcg tgatctgccc gcctcagcct cccaaagtgc   58020
tgggattaca ggcgttagcc accgcgccca gcctgaaaga tgaactttaa aatggggaag   58080
gatactagta aagccatttc ttactcatgt atacattttc ccctccatga aattaaagca   58140
gccacctttt acatgacttt tacatgcatt tcaaatttt gtactaacaa ttaaaatatc    58200
tactggatgt aaatcacatg tgcttaatgc tttgcttcat aatatctgtt gaagtcaatt   58260
aaaatataaa gacagatctt taaattgaac atgttttatt tgggaagcaa gaattaaatt   58320
tgaggcatat acacagactg ggtgtccttg gtatctctga agaacaaagg gaattttgga   58380
ggttatagaa aaaggaaaat gtgacattgt ttttccagaa agttctttgg cactagtaaa   58440
ttttggggag ttggaagctc tgatgggtta gtgactgtgg tgggtaaaac tagtcttaga   58500
gtcacaacag gttgtttcag tatctattag ataaaacagg ttttaggtta caataggcag   58560
tttcagcagc taggcttgca gaaaattaca ttcttagagt aatgttatgt gccttgagtg   58620
cttttttccc cttggcccttt gactctgatt tagttgggta tgacaagaat tatcaattta   58680
tataattact ttttacatat tgaagctgaa taggttttct taaaacttgg aaatgggaaa   58740
tactgggtct tgtgaagttt tagtgtgaaa acgataacta gtctcttatt tcatgctctt   58800
tgtaacaagt ctacagtaat acctaatgta tctagatgac acctcagaac caggaggaa    58860 caaaaaagac ctctgagcag tcaaataat gctataagca tgtattccag cttactttcg    58920
gcatttctgt ggagtgcagg aggccacatt ttgttcatag atccagtttg acaagcttgg   58980
gtactgagtt aaagtgaaaa tggtgtaaat aagtaatcat attcacatga cagtaggtgg   59040
aagtgacagc tgacaatctg aaagagtgga caaaactata aaaattagaa ctaagaactc   59100
ttaaaataga acggtttgaa gtttgttaca gaagggagca gctttatgct tcagtggact   59160
```

```
ctgaaggtat tggcagtgta tagtactgct tagtcattga tttaaattcg gtatatatct    59220
cttctattgc tgtcatgtac ttgacattct gctgggtgct aaggctgtct gcaggctact    59280
aatatgcata ataacaatcc tgaaaaagaa ggaaaagtat actgtgcctt actgaagaag    59340
gcaggacagc ctttggtatt tgttagagta aatattagtt atcttacata aagcatgtta    59400
tattccctga tgtcagggcc tgataaatga gcccttacac tcttgatagt caatctgtgc    59460
cactgttgct gtgtttgtat gttacaccat ttcctgtcca tgtaacagtt aaactgtatc    59520
acatatctgt tcctactaaa ctatttgcat ataattttaa catttgagtg gctgtatata    59580
aagctaaaag ttctttataa gatttatagc atcttagaat gtttaaatta gataacatta    59640
gtgtgctttt agtttttgaa tttaattttg ctcttgattt tgtttgtgtt aatgtagact    59700
ttgtctacgt aagcttgagc ccaactttgg agtggtgttt tcagtgatgg aagtaactgg    59760
aaataactca tgaaaccact tagtactttt gatagtttat tcccatgaag gatcaaattt    59820
ttacttgagt cattaatata aaaatttaaa agacatgtca gattttatta agcatggatt    59880
ttaaatatat aaatattaga agacctaaac aaaatcgcta atgaaagagt aaaacatgtc    59940
cctgcctatc atactcccct cactttcact gatttctgct tttatgaagt actttaataa    60000
gctctacaac aaataaacaa gacattgtgc ctcattttac actctagcag tggttttcca    60060
ttccaactaa ctagattggg tttataatat agtcatttaa acttacttag ttaaaatgtt    60120
atacattagc aactgcaatt aaggagctaa gaaattcagc tcgtatttat ttatatgcat    60180
cttatccata gtttctcact tgttatattt gcctactgat ggcaaattga ttttttctgt    60240
tccaaaaatg tagtgttttg agattttttgg agatgcaaaa cagcatcatt ttcaaattag    60300
atcacaaaca atcttacttg ttgcagttga gactagtaat tgatcagtga ggtgaaaaaa    60360
ttaggcaaaa cggtatcatc aaaatttcct ttctttttt tttttgaaac agagtattgc    60420
tcttgtcgcc caggctggag tgcaatggca cgatctcagc tcagctcact ggggccccta    60480
cctacgggat tcaagggatt ctcctgcctc agcctcctga gtagctgaga ttacaggcgc    60540
atgccaccaa gcccagctaa ttttttgtatt tttagtagag acagggtttt gccatgttgg    60600
ccaggctggt ctggaacttc agacctcaag tgattcacct gcctcagcct cccaaagtgc    60660
tgggattaca ggcatgaacc accgtgcccg ccccaaattt tcttttaact taaagtgtta    60720
atgtttgttt gttcccaata ttttatata tgtcaaggct ttttcattat atacaggcca    60780
gctctttgga gttctgcata gtgttttcttg tttaaaccac acctataatg taccatctac    60840
aatttccaat tctttaagac agagtgaaaa attaagacac ctgaagcaat ctgagtgcgg    60900
agtcctaggc attatgattt tccttgacac ttttagggtt cttttatcac agtttatcaa    60960
acaccttttt ttttttttaac aaaaaacaaa tttacaaaat cttttccatgt attcaactta    61020 gaatttaatg aaaataggggtt ttttttttt tggtggtcat gtatcatcaa ctttctttac    61080
atttaattaa attaatcaac aaaaaacata tagttgacat aaacaaattt gggaccaagc    61140
actactgact cttagtaaac atacaagtca actgttggtg cagaagtgcc ttgatgctag    61200
agagtagcct gcaagctgta attatatatg ggcattaggg aatgaagaac agccttaata    61260
ctattgatct tttaagtgaa ggtcagctta gaaagctttt acttgttaaa aagcttcaca    61320
gtttgtcctt gtagttaatg caattgaagt tgaattaatc tttcttaatt tttttttag    61380 ggtttctatc ttactaaagg atatttcaga aaatctatat tcactgagga ggatgataat    61440
tgggtctact aacattgaga ctgaactgag gcccagcaat aatttaaact tattatcctt    61500
```

```
tgaagattca actactgggg gagtacaaca gaaacaaatt agagaacatg aagtttaat    61560 tcacgttgaa gatgaaacat gggacccaac acttgatcat ttagctaaac atgatggaga    61620
agatgtactt ggaaataaag tggaacgaaa agaagatgga tttgaagatg gagtagaaga    61680
caacaaattg aaagagaata tggaaagagc ttgtttgatg tcgttagata ttacagaaca    61740
tgaactccaa attttggaac agcagtctca ggaagaatat cttagtgata ttgcttataa    61800
atctactgag gtactaaata aagaggaagc acattttag ttattagtag gttctggcag    61860
actttattcc cgtaaagaga cagatagtaa atattttagg ctttgtggga catacagtct    61920
ctgttgcagt aactcagttc tgttattgta gtgtgaaagc agccacagac aaatgtaaac    61980
aaatgtgcct gtcttccaat aaaactttat ctagaaatac agatagtggg ccacatttgg    62040
cttgcgagct gtagtttgct gttcctgact tagtatgata tgcagcattg tgtagtggaa    62100
agattttata gtatcaacag acatttgtag gagtttgcta ttttataatt tcgtatgctt    62160
ttttcataat agatgtctct gcttttgtg gattctcttc atatctacta gtgtttactc    62220
ttctgacttt gattttgggg ggtgtatttt atttctttat acagaatttt ttctttttt    62280 cttttttttt ttgagacaag gttttgctgt gtcaccccag ctggagtgca gtggtgggat    62340
cttggccccc tgcggtcttc aactcctggg cttaagcgat cctgtcacct cagcctccct    62400
agtagctggg accacaggcc tgcaccacta cactcagcta atttttgtat ttttttgtaga    62460 gatgggttt cgctctgttg cccagactgg tctccaactc ctggactcaa gtgatccacc    62520
tgccttggcc tcccaaagtg ttggaattat aggtgtgagt cactgtgcct ggcccagaat    62580
ttctttactt gctcatgtga gagagtttct aataaactcc tgatgctttt gcttgacact    62640
atagttttac tgtcatctca gagtcagatt ttttcctaa tttcttcatt aaattgattt    62700
cttaatttct catttgtttt gcattagttt acaaaattac ttaagatgcc tatattctct    62760
gaaattttat attttatttc acgataaata agtttaaaaa attagatttg accatttaat    62820
tagagttatt tccccatcat ttttctaatg gcaacaataa ttttagcatt tgagcaattc    62880
tctgtatttt ggtaactatt agtaatcact tttatcagta taaacatgca tttcatttta    62940
aaatggtttt caaaatattc tcataccaac cattcataaa agatgttccc cttctgggaa    63000
atatcagttt ttgctaacat ctgcatttcc ctttgatttt ctaggaattt cttattaggt    63060
atacacttta agtgatatgt ttcatataat attataggat tatcaggatt tcatgatttt    63120 tttttttga gatggaatct atctctgtcg cccaagctgg agtgccgtgg cgcagtcttg    63180
gctcactaca acctctgcct ccccggttca agtgattctc ctacctcagc ctcccgagtc    63240
actgggatta caggtgcccg ccaccacacc cggctaattt ttgtattttt agtagagaaa    63300
gtgctgggat tacaggtgtg agccactgca cctggccttg gatttcgtga tttgactgac    63360
atcttttaca ccaattattg ccattttttt attgggtact aattattagt attgctttct    63420
ttattcgtta aataagaagt aaaagaactt ttaaaaaata aataactttt ttttcctagt    63480
acaaagctta ttttcaattt ttttttattgc ttaaattttg caggttaatt aaggctgtac    63540
ttctttttcc tacttcctgt ttaaatattt ggcattttt gagggttttc tttctatgga    63600 ttttgtggg ggatcccatc tcgttggaca cttggttcct ggagattgcc aaattattga    63660
aaagtttcct catacccaaa cattggcaat agactgaata aataacatct ctgacattat    63720
ttttcaatta tatagagaat gcttttgta aaatactgat ttatttaaag atattacaat    63780
catagtagtt ttttgcaatc tttttaaat cagtggatgt caaggaacaa ctattgttct    63840
ttgtacggca tttttcaaca ttgtgaagag ttcttatact caaaaagttt gggagacaca    63900
```

```
gtgtgacatt gtttaacctg agttgaactt gtcattttgt attcttgttt agagcaggga   63960
ttttattttg tctctttatc taactttgta ttcctaacta tttctttctt tctctttggt   64020
tctttgtttc tttgttcatt cttctctctc tcccttttt atctatcata taaatatgta   64080
aatatatatt atatatccat tagggaagag gaagttgtct aaagatatct agtatatagg   64140
agctttgttc tgcagaaaag aggatatgaa gtcaattata ttggaaatta atgcttaata   64200 cttttttaa agcatttatc tcccaatgat aatgaaaacg atacgtccta tgtaattgag   64260
agtgatgaag atttagaaat ggagatgctt aaggtatgtt tacaattata aaatattac   64320 ttcaagttct ttccaaagga catttaatta agtaaaatat taactaattc taaactaggt   64380
tcntaccaca atgaaattgc tactaattat gtaacattag atttcacatt ttccaattca   64440
tgtttctttc atgtagtcta taaataatgg gttagaggta atttactaat tttaaatgtg   64500
ctttccttgt tccttcttat ttttattt gaagacaggg tctcactcta tcacccaggc   64560
tggagtgcag ttgctccatc tcggctcact gcaaccttca cctcctgggc tcaagtgatc   64620
ctcctgcata agcctcccga gtagctggga ttatgggcgt gcaccaccat gcccggctaa   64680
tttttatagt tttagtagag acagggtctc accatgttgt ccttgctggt ctcgaactct   64740
ttacctcaag taatccaccc gccttggcct cccaaagtgc tgggattaca ggtgtgagcc   64800
accacacctg gccttggatt tcatgatttg actgacatct tttacacaaa ttattgccat   64860 tttttattg ggtaccaatt attagtattg ttttctttat tcgttaaata agaagtaaaa   64920 gaacttttt ttaaaaaag aactttttc ctagtaaaaa gcttattttc aattttttta   64980
ttgcttaaat tttgcaggtt aattaaggct gtgcttcctt ttcctacttt ctgtttaaat   65040
gtttggcatt ttttgagggt tttctttcta tggatttttg tggggatcc catcttgttg   65100 gacacttggt tcctggagat tgccaaatta ttgaaaagtt tcctcatacc caaacattgg   65160
cagtagactg aataaataac atctctgaca ctatttttca attatataga gaatgctatt   65220
tgtaaaatac tgatttattt aaagatatta cagtcagtag ttttttgcaa tctttttaaa   65280
atcagtggat gtcaaaaaca gctattgttc tttgtacagc attttttcaac attgtgaaga   65340 gttcttatac tcaaaaagtt tgggagacac agtttgatat tgtttaacct gagttgaact   65400
tgtcattttg tattcttgtt tagagcaggg attttatttt gtctctttat ctaactttgt   65460
attcctannn ntttctttct ttctctttgg ttctttgttt ctttgttcat tcttctctct   65520
ctcccttttt tatctatcat ataaatatgt aaatatatat tatatatcca ttagggaaga   65580
ggaagctgtc taaagatatc tagtatatag gagctttgtt ctgcagaaaa gaggatatga   65640
agtcaattat attggaaatt aatgcttaat actttttttt aaagcattta tctcccaatg   65700
ataatgaaaa cgatacgtcc tatgtaattg agagtgatga agatttagaa atggagatgc   65760
ttaaggtatg tttacaatta taaaacatt acttcaagtt ctttccaaag gacatttaat   65820
taagtaaaat attaactaat tctaaaccag gttccaccac aatgaaattg ctactaatta   65880
tgtaacatta gatttcacat tttccaattc atgtttcttt tatgtagtct atgaataatg   65940
ggttagaggt aatatactaa ttttaattgt gctttctttg ttccttcttt tttttttt   66000 tattttgaga cagggtctca ctctgtcacc caggctgggg tgtagtggtg ccatcttggc   66060
tcactgcaac cttcacctcc aggctcaag tgattctcct gcatgagcct cctgagtagc   66120
tgggattaca ggcgtgtgcc accacccg gctattttt gtatttttg tagagatggg   66180 gtttcaccat gttgcccagg atggtcttaa actcctgggc tcaagtgatc tactggcctc   66240
```

```
agcctcccag cgtgctgggg attgcaggtg tgagccgccg catccagccc tgtgttcctt    66300
cttgtgttac tttcttgtaa tttttttcctg gaatatgggt agtgatttgg ctctccagta   66360
ttgaaattga gtttcctttc ttccaattca tgtgtatcca tttttatttg gaagttttgt    66420
ttttatacat tcaataatca tctttacttt ctttggtatt atttactatg gatattttat    66480
attatataat tttcaaatgg attaaatggt tcagttttac tcttattatt gagattgaaa    66540
atactagttt ataatttata tattttctat tcctttacct ctaatttctt tgtcaggtgt    66600
tactaaccaa agatgtataa taagaaaagc caatgtagct aaattaagta aaaaatgaag   66660
aaaaacacag aagttcccca ttatgcattt ttttattcct aatctttagg ttgatgagat    66720
ttttttattt ttatgaaatg agattaattt attgactttt ttagttttga ggccaagtaa    66780
tgagtagtga gtaagaatgt atattctagg gccaggcatg gtggctcact catgtaatct    66840
cagcactttg ggaggccgag gcaggaggat cacttcattc caggagtttg agaccaacct    66900
gggcaacatg gcaaaaccct ctctctccag aaaaatacaa gaattggctg ggtgtggtgg    66960
catgtgcctt tagtcccagc tacttgggag gctgaggtgg gaggatcacc tggggagcct    67020
ggggaggttg aggctgcagt tagccatgac catgccactg cactctagcc tgggtgacag    67080
agtgagaccc tgtctcaatt aaaaaattaa aaaaaaaaa gtagattgtg aattcagatg     67140
taggtttgta tcccagcttt tccagttagt atctgtgtga ctttggggaa gtttcttagc    67200
atctttgata ctcggttaac agttgtaatt attatttaag gtattgcttg agaagagctt    67260
agtatagagc ctgacattta gtaagtgttt aatacatatt agctaacagt aaaactagaa    67320
cataaatact gaattgtatt ttgttattaa ttatccattt ctctgagaag tactgttcca    67380
atagtacatt tataggaaac ttgtggacgt ctacaaacgt atacattaaa tctcttagaa    67440
ggcaacctgg atgcccatat tagagaactc tattttaaac atgcattcta agtatgtttg    67500
tggacttgaa taaaataaaa caaacagaaa cacttctttc ttctgccttc aggcttgaaa    67560
tgaacatact tttttttaaa aaaaaacctt caaaatgaaa atattaaata aaagatttaa    67620
taaaagagaa agtaaaaac tgtagtttaa taaagtcttc ctgtctcttc atagttaaaa     67680
aatgttatag atgaaacaat tttgaaatat tcttgaaata gataatcttt atttagggga    67740
gaatgtcaga tactgtcaag ccaaataaaa acaaataac tttatttcat gtttgtaaaa     67800
ttccttttct aaaatgattt gaatcttttg ttgttttgac aattccaaaa cacatttatt    67860
gtttgctcat agtttcagcc ttattcagaa agaatgcgac tgacacatga tatagagaaa   67920
cttgttccaa aaataacatt aaaatccacg tttactactt gagaatcgaa atatattgagg   67980 tgcaataaag aataaaatgt tttaaattat ccaaatttaa aatttatgat agctttcccc    68040 agggggcagtt tattatatgc tattaatgag ccttgtttat gctggaaatg ttccatcttt   68100
ggccttgcgc cttagaaacc attcatgagc acatatttaa accggagcac acatgttctt    68160
ttgtagtatg gcttgcacat ctgccagctt tcgacaaaat tgtaggccct gttaataata    68220
gtccttttgt gtttggtgaa aaagatacga cactgtcagt ggttttgctt ttaagatttc    68280
ttttaaactt tcagtcttta gaaaacctca atagtggcac ggtagaacca actcattcta    68340
aatgcttaaa aatggaaaga aatctgggtc ttcctactaa agaagaagaa gaagatgatg    68400
aaaatgaagc taatgaaggg gaagaagatg atgataaggg taagcactga agtatgtttg    68460
aaatgactca cctgtgatac ctaccactga ctttaactta ggatccagtt ttggatggtt    68520
tggaggtcag ggactttgtg gcatatagtt aattattgga tccttataag cttttgtctc    68580
cttagtgctt ttgtctccat aaagcacaat cttactactt agaaaaatag agtaatagca    68640
```

```
ttatgatgat aaaaatatct ttccctttgt ttttttgtat ttctccaaat cattatagct    68700
ctcatttaga attattaaag ctgagaactc taacaatgaa cttttattgt ttagtggtta    68760
attatcttga ttctttgttt tgcccttct  tggccactca ggaatctttc aagctcactg    68820
tggacaggga aagtgacttg ggtagagcta acataacttc attgtgctgt gcagttagaa    68880
ttttgaccaa agatgtgggt aactaacttt tcctaactaa atgacattta ggtaactaaa    68940
ctaaacgaga ttttcgtaac taaattttgg tgtaactaca tttagcttta ggtaactaaa    69000
acgaagattt tattttatct gtggattttt ttagtgcggg actaatgtaa tttctgatta    69060
ccattaattg aaggttggtt atattataac atttggattg gtatattgct tgccatggtt    69120
tgttctaaat gttagccttt agaagtattc ctgattctaa aacatcagtt ttttttaata    69180
gtcctggcaa agtgtgaatc acaacaaaat tctaatactt aaaagtaatc caagtgtcac    69240
agatggtacc cagaagacca gtttgtattg gaattaaaaa atagaaaaca ttaacccatg    69300
gtagctgtca ctgtattctt tcaaagaagc caatgaaata aactgttttc tccctctatg    69360
tggtgttttt ctacttgaac ataaatgcac attttatttt atttccagac ttttttgtggc   69420 cagcacccaa tgaagagcaa gttacttgcc tcaagatgta ctttggccat tccagtttta    69480
aaccgtgagt ataatctcat ttaatcaaat cacatatttta gtattctctt taaaacaagg   69540
gaaaaggcaa ataacctgtc tgcttaacag caacagcaca acttcactat agttatacat    69600
gccacacggt attttctgtg tgactacaaa attatttcaa agtgatattt atataaaatt    69660
catttctgca aattgttttt ataagtgagg aaaaatggtt ttcctttaac tgagcagttc    69720
tgagtagaaa ctagtttaaa gatacttata aataaatgtt aatttaatac tgacttgttt    69780
ttcattaaac gagtgtctat gtgcctgttt tgtgtatatt acccagaaca tgcagatgta    69840
ctagaagttc ttaatacaac aatttgagga atagtgataa tcttatctat tttaatgtac    69900
tcaaaatttg tttacatcta acaggcacat ttttgtgagg attaaatgag atgaataaga    69960
atgagatgaa caagtaaatg tgaataaaac taataagcct gtgaaaatct agactggatt    70020
tttcctattc tgagaattta aaatataatc cactgaagta tttctttcct ttttctttt    70080 gatcttaaac attttttatt tatgtcttac atacagaaaa gtgcacatgt tgtagagatc    70140
aatgaattgt cataaactgg gcaccctgtg gccagcactt agttaagaat aggtcagtaa    70200
cagcatgcca gaagaccacc tctccaattg attttttccca tgatatttta ttaagaaaat    70260
tttctaagat gtagtaaagt tgaaagaact tttttctgtg catgtctgta ttcccaccac    70320
ctaaattcaa ctatcattac tatacttgct ttatcacata tccatccatt catatgtctc    70380
tatccatcca ttcattcatt ccagttttaa aatgcatctc agggtcaatc gaggacacca    70440
ttacacttcc acctaagtat ttcagcatgt aaattattaa cgagttaaat atttacttaa    70500
cagttttttc tttggtgtaa aatttgcacg taaggaaata taaaacttta agtgtacatt    70560
tgcaaatttt aaatatacat gtgcataccc atgtaaccca aattcttatc aagagatatt    70620
attatcatca ccacacagag ttcccttatt tccctttca  gtcagtcctt gtccctgagc    70680
atttctctta ttattttaaa gtattgattc ttttggatat ctagtatgaa gcttagaatc    70740
tgttttttac tttagatgta tgtagtgaaa tttaatatat ataccaaatg gtagttgtta    70800
gttagcttga atgggacatt ggtcaaatgg cattgtttgt tttaaagttc caggtttgtg    70860
catttatgta tgaagtttga aaataaattc tatgagagga aatgaaaaat tgaatggatt    70920
ttaatttgta ccttgggttt cttattaata aaacaaaata gcttttttgct tttcaccttc    70980
```

-continued

```
aagagttcag tggaaagtga ttcattcagt attagaagaa agaagagata atgttgctgt      71040
catggcaact ggtaagttgt acttaagcaa aaccaaatcc tttaaaaaaa taaaacataa      71100
agagtttgaa atgcttaatc tttcattaaa ctctcaaaat acaaatgcaa ctacaaatga      71160
tgtaaactat agaagagagt gaacaaagaa cagatgctca gatttatgta tcaattagct      71220
tttaggaaga tagcatacta gtattgacca ttcatctgta taagtacatt gtaaaaagaa      71280
atgaaagcat caaaggttta ttttttatttc tatattttttt tcatttttatt tttatatttt      71340 tttcatttca aggatatgga aagagtttgt gcttccagta tccacctgtt tatgtaggca      71400
agattggcct tgttatctct cccccttattt ctctgatgga agaccaagtg ctacagctta      71460
agtaagtcat gttatcattg ccacaatatc accctctttt tttcttctgt gggtgaaaca      71520
tctgatccat catgcatgtt aaaatctagt tcacaataac acatttctgc aggtattgct      71580
ttatctttat tggtaataaa tgacccttta gtggaagagc ttccttctt tcttgtgttc       71640 tctgtaattc aaagctacca ggtggccctg ataaaatttt tttaaaaaac attattactt      71700
tatgctggtt tacattgaat atctcaaaat tcttttctct ttttgttacc cttgcttttt      71760
agcttgataa gaagtgtata catggaagta tatttttttat ctatgaaaca cttttcagct      71820
tcttcaacct gagcttgcaa tctgtttttaa attgatacat aatatcttta catattcatg      71880
gggtactgta gtattttgat acactcatat caaatacact tgatcaaatc agggcatttg      71940
ttcatcaact tgaacattta tcatttcttt gtgctgggaa catttctaat cttttctttg      72000
agttattttg aaatacacag tgttgttgtt aactatagtt accctactgt tggttaatga      72060
gtacaaacat acagttagaa ggaataggtt ctagcaacct attcctttac cccctgtcat      72120
cccctgctgc cctgagcttg cagtctcttt caaagaccca ccttaaaaac ttgcattctg      72180
ataaggccct tgaaggaatt tgcttatcaa gttagtaagt gacaaaaaag aaaattgcaa      72240
agaacaggaa tataaattat tatatttctt tattctttct cacttaagag tgaaattgat      72300
atgtgtaatg tgtacatggt gccagaatat ttgttttttct tcttatagaa tgtccaacat      72360
cccagcttgc ttccttggat cagcacagtc agaaaatgtt ctaacagata ttaaattgtg      72420
agtaattttt ttccctcaac ttttattttg gatttatggg ggtgcatatg caagtttgtt      72480
acgtgggtga attacatgtt gctgaggaag ttgtgagtaa tttatgtcat ttctaatcat      72540
gtggtcagat gtctgtggta tatgagagaa ttttgtatac aaacaaattt tactaaatgc      72600
atgaaaaaaa aagtccatga ttttaaaatg cactttcttt tgtaccttttg caggactgtt      72660 actttttaaa tccttcaaac ttgaagaaat ctgttattct cggttcttgg gctataagat      72720
tagcattgta ctcatagaat tataaaaatt ttggttttgg aagagaagtt ggagaatata      72780
aagatttgtc tcattttata gatgagaaaa ctgaggctca gagacaagta atttgcccaa      72840
aatcacacaa tgactggctg agcagggact ggattctagg tctcttgccc aaccaattct      72900
atcatgatgt aattcctaag gagaatgtca tctcagatac acatacacac acccattttg      72960
tgtgtgtggt gtgtgtgtat atgtacacac acacacaaac atatgtacac ttatatatac      73020
atacacacac atatattaat atatatgcat atatatgcat gttctaattc agaacatttt      73080
catcactccc aaaagaacac ccctgcccat taagcagttg cttctcttac gtatatatta      73140
gtatatacat acacacgaga tacacatata tttactgagt tttgataaat gcatacaaag      73200
atgtaaacca aacctctaac aagatacaga atatcactga cactctagaa agtttcttca      73260
tgtccctccc cagtctgtcc ttccatcctc catcctaggc aagccactgc tccgattttc      73320
tctaccatag tttggtagaa tgccatataa atgcagtcac acaatattaa ctcttttgtg      73380
```

```
taagacttct ttcatttgct gtaatgtttc tgagattctt tcatgctgtt gcatgtatca   73440
gtagtttttt gttttgtttt gttttgtttt tgttttttca gagtcagggt ctccttctgt   73500
catccaggct agagtacagt ggcgcaatca tagcttactg cagcctctaa ctactgggct   73560
caagctatcc tcctgcctct caagtaggct aggctgcagg tatgttccac catgcctggc   73620
taattattaa attttttgta gagacaggat cttgcttggt tgcccaggct ggtcttgaac   73680
tcctggcgtc aggattgttt ccagttttgg attattacaa ataaagctga gacacatata   73740
agtctttgta tggacatatg gtttcatttt attgatacat gtcaaggagt gggatgactg   73800
gatcgtgtgg tggatatatg tttaactttc ttttttctga gataaaatta gaaggcgatc   73860
ctcctgcctt ggctttccaa agtgccggga ttacaggcgt gaaccaccgc acctgatgca   73920
gttgttgttg tgttgttgt tttaatatct gattattatt ttattgtatt tcattgaata   73980
tagcacagtt tgttttaca ttttcttatt gatagacacc taggctattt ttctggtttt   74040
ggactgttac taataaagct gctatacaca tccttataaa aatctttttt gtgaacatgt   74100 tttcttttt tctaagcatt ttaaatcacc tttattgagg tgtaattgac ttcaaataaa   74160
ttttatatgc tgagaatgta taatttgata agttttgaca caggtatgca ctcatgaaac   74220
catcatcaca atccagataa tgaacatatt catcacccac aaagtttacc tttttgtttt   74280
aaccccagtc accgggtaac tgctgagctc cttcctgtta ctgtagacta gtttgcattt   74340
tctaaactta tatacatgga gtcattcata ttttatgtgc tctttttttgt ctgatttaaa   74400 taatgcagta taattatttt gagattcatt catgttatta cagtgattaa tagttcattc   74460
ctcttattgt taagtggatt acatttatg gatatccaac aagttgttta tccattcacc   74520
tgatagacat ttggatcgtt tccagttttg ggttattaca aataaaactg ctatgaacat   74580
tcgtatgtaa gtcttgtat ggacatatgt tttcatttta ttatatatga cggagcggaa   74640
tgactggaac atgtgatgca tatatgttta actttctttt ttctaattga gataaaattc   74700
acagaacata acttttacca ttttaatcat tactaaagtc cagtgggttt tggtatagta   74760
ataatatata accatcataa ttaattccag aacattttcc taactcccaa aagaaattcc   74820
atacccatta aggagtcatt ccctattttc ccttttcttt tctttctttt ttttttttt    74880 tgagtcaggg tctccctctg tctcccgggc tggagtgcac ttgcatgatc ttggttcact   74940
gcatccttga tttcctgggc tcaattgatc ctcccacctc agtctcctga gtagctggga   75000
ctgtaggcat atgttaccat acctggctaa tttgttttat tttgagtgga gatgagattt   75060
tgctatgttg cccaggttgc tctcaaactc ctgggctcaa gtaattgtcc cacctcagcc   75120
ttccaaaatg ctgggattac aggcgtcagc cactctgccc ggcctattat ctctgttctg   75180
cccacttcca accactaatc tactttctgt ctctatgatt tgcctattct ggatgtttct   75240
ataaattaac ttatacatta tatggccttt tgtgtctggc atcttccact tagcatagtg   75300
atatcagtac ttcattcggt cttttttat gactgaataa tattccatag tatgggcata   75360
cacattttaa aaattcattc atcagtgatg gacatttggg ttgtttcctt tttggctgtt   75420
atgaataatg atgctgtgaa catttgtgta ccaattttttt tatgaacata cattttcaac   75480
gcttttgcat atatgcctaa gagtggaatt gctgggctat atgctaattt tttaagaaac   75540
tatgaagctt ttgagagtga ttgtatcatg ggatattccc accagcagtg tatgagaggt   75600
ccagttcctc cccatccttg ctatcactta gtctggctga tctttaactt aagccattct   75660
aatagtatct cattgtatt ttagtttgct tttccctaat gactaattat attgagcatt   75720
```

-continued

```
tttcatacac ttattggcca tctgtatatc ttctttgagg gagtatctgc tcaaatcttt    75780
tgcctatttt ttacttagtg agttttgata gtcatttcta tattctgaat ataaattatt    75840
tatttgatat atgctttgca acatttcct cctagtttat ggcttttcat actttccaca    75900
cagttctttt gaagagcagc agttttcat tttgataaag tccagtttgt cgattcgttc    75960
ttttagggat tttgctttta gtgttttgac ccaaggtcac aaagatttgc ttttatgttt    76020
tctcctaaaa gttttatagt tttaagtttt acatttagat ttacgattca tttttagtaa    76080
atgttgtcta ttgtatgagg tattgattac agtttatgta tttttcacat attgttccag    76140
ctccatttt taaaaagact atgcttttac actgaattga ctttgtacct ttgtcaaaaa    76200
taaattgact acatatatgt gggtctattg ctgcactctc tattctgtgt tctgtggatc    76260
tatttgtctg tcttgattgg tgtcttgatt actgtagctt tataataaac ctggaaatca    76320
ggtagcgcaa ggcctcttgc tttgctcttt tctttcaaag ttgttctggc tattctatgt    76380
cctttgtatt tctgtgagca tgtcagcatc accttttcaa cccatatgcc tgctgggatt    76440
ttgaatgagt ttaccttgaa tctagatatc gaaacaatta gctgtcttga tagttattgt    76500
caccgtttta taccgaagaa actaggcata ctaaagtaac ttggctaaca tcacttacct    76560
tgtaagaagt agaactgggc tgtttgacat cagagcttat tctttatacc atttcctatg    76620
ttaattagaa tacaatatta atttcataaa ggtaaaggca tatctgtttt gttcctattt    76680
gattccttgt gaaagcacaa tgcctagcgc acaatagaca cttaaactta cctgttgaat    76740
ggacaggtga atgcttttaa agtctttcca tatagaaaat taagtttcat tacatttgac    76800
ttgatctagg ttttcatttc atagaatgga gagcagactc tgtaaatatt ttgcccagaa    76860
cctagcctta ttacaaacat tgtcttaatt aggattctgt ctacccagaa tagaaattaa    76920
ctcaagctag catgagtgta tattgaaatt tatattaagg ataaaggaat gtctcataga    76980
tcccactcaa aagaaattag ccagcccta ggaagagact ggaattgggt ttggaaaata    77040
caataggtct ttctttttat ctgtagtctt tagtgagtct tcctcatttt tctctctgaa    77100
gagataagca ttctctgcat atatatagca ttcttttaga ttttcgtgac ataaagtatt    77160
atttaaactt tcataaggta tcttgatttt aagttgtaat tccttgagat gattgttttc    77220
tttattgtta atatgtttcc cttcctgttt tttttttttt cttttttctt ttgtttgttt    77280
ttacagaggt aaataccgga ttgtatacgt aactccagaa tactgttcag gtaacatggg    77340
cctgctccag caacttgagg ctgatattgg taagtgataa agaaagatct ctgtaaatac    77400
ttactgagtt aatatttaaa gttaaaccta tggatggaca ctggatttca cttctgttaa    77460
agtttatttc aaacattact tcctccagga aatctctgac tctctaactt gctgtttcac    77520
ctatcttatc ccatgatact ctataattcc ttttgctata gaaattaggc tctgttatca    77580
taattacctg tttatatatc tgttttcttc tgctaggcta taaacttttc aagggaaaaa    77640
tatcactttt taaaatttat gtttccccag tgcagtgctt ggcatatagg cacttaaaca    77700
tattgttgaa tgaatgttga atcctaggtt ctgtgaaatt ttaatttact tgttttcat    77760
gttctgtatc taaattaagt cagtgtagtg gttttgtacc ctctttgttc ataagaatca    77820
cttttcaaac tttaaaaaaa atgtaggtaa ccaacaccca actctgaaaa ttctgattta    77880
acaggcctgg gttggcacct ggcattggtg gtttctcaca ggtgattctg atatatagcc    77940
cggggttggaa accacagtac ctttgattag ttgccactag tgagtatgat ttattacaaa    78000
aaccaaaaac ttagataagt cacagtttat ttcctagaac gtgtaaatat agaattagtc    78060
aaaagctgat agcactttt ttgtacttaa aaatatttta agcctcagta tagtgagacc    78120
```

-continued

```
tcatctctac aaataatttt ttaaaaaatt ggccgagcct ggtggtgcat gcccatagtc   78180
caagctactt gggaggctga ggtaggagga ttgtttgagc ctgggagatg aaggctgcgg   78240
tgagccaaga tcatgctact gcactccatc ctgggcaaca gagcgagacc atgcctcaaa   78300 aaaaatttt ttttcttctt ggtggttagg cttaactatc caagaattgc aatcatggct   78360
tctattgcaa atgccctat ttcccacctt cagttggcct aaccaaattt aattttcaa   78420 tatcatatga tcttttgta taattatgta ttcaaataat tccagatagg ttaggttttc   78480
gaattgcaac gtctcattta atggttactt tcatataact gtaggaaagc atttgataat   78540
ttttccaaca atgtaatgaa aacaaacttg tatcttttt attatgtgtt aaaaccaaca   78600
aaagaatgag ggcagcaatt aacatttcat taaatatatt agcaatgagt acatttatga   78660
gctcttaaac tcccttattg acatactgta tttttgcct ttaatggaca atgaatttga   78720
tatgtttcct aataggttgt atgaagttat tgtgaatatt tcactttgga ttaagaataa   78780
ctaccctata tataaattc atggttgtat tgcaaaagct ggggtctatg tccatagtgg   78840
tttgggtacg ttttactat ttgctttgtt tctgtgatag tgttaaatga ataataagct   78900
taagtattta agcaaatact taatacttct gacaagtagt tagaactctc tatttttgtt   78960
tttttgtaat ggatgagtta tggacactgc aattattaga gcagcgtact ttgcttatga   79020
tggatgaaaa tgttctctgg ttgactcagt gttgaataaa aagggataca tgaaataaaa   79080
attatttttg aaatattttc ctttgccttt tgttgcggga aattgtacaa tgcttgcaaa   79140
aatgaatata cgcaggatat tatttgtaca gcagtctgac atttagctaa tcagattcct   79200
catttttagg taaatgttaa attacttaag tagtctggat ttttaacaga aacagcaaac   79260
atagttttat agggaggctc cttaccaacc agacttttaa cttaagtgaa tgttggcaaa   79320
agcttgtcta aactgatttc cagggataag gtttagctcc attaaaagct agtttgtcaa   79380
acctgtaact aaagcttttt aaaaaatgaa agttttaaaa gagaccatca ttctgtttta   79440
acctatttaa tttaaaatct gggctgaagt aggagtattg cttgaaccca ggagttcgag   79500
accagcctgg gcaacacagt gagaccccat ctctgaaaaa aaaaaatgag ctgagcatgg   79560
tacctgttac agtgctagtt atgaaagaaa gaaagagaga gagagagaag gaaggaaggg   79620
agaaaggaag gaagggcctg ggagtggtgg ctcacacctg taatcccagc actctgggag   79680
gccgaggcgg gtggatcatg aggtcaggag atcgagacca tcctggcgaa catggtgaaa   79740
ccctgtctct actaaaaata caaaaagaaa aaattagccg ggcatggtgg tgggtgcctg   79800
tagtcccagc tactggggag ggtaaggcag gagaatggca tgaacccggg aggcagagct   79860
tgcagtgagc cgagattgcg ccactgcact ttagcctaag aaaaggaagg aaggaaggaa   79920
ggaaggaagg aaggaaatat cagtcactca ctcaggttta gtttcaaaag ccaaaacagt   79980
gataatattg aatttttcc agccactcag tagtacccag agaattttga tacaaataac   80040
tgactttgac cccatgttta gtaggttttt tttttgtttg tttgtttgtt tttttttt    80100 gtctttcttc tccacactct cttaggactg ttgtagcttg taatgttagt gaattgtaat   80160
tgtttatttg catgtctgtc tcctcttta gaattgtgaa ctcctcaggt catggattgt   80220
attttattag tcttttttatt cctagaaaag tgtttggata taatagata tttattaacc   80280 ataataggag tagtagcatt tttgtgtgtg tgtgccaggc cctatttag catttatgt    80340 gaatgatata atttaattt tagagcatct agaaaatgtt aggtaccatt attatccaca   80400
ttttacttgt gagaggactg agacttggaa agcttaagta acttgcttaa ggtaatacac   80460
```

```
atggcagatg gtggagccag gttctgcatc tgggcagtct gactttagag ctttttaatc     80520
atcctcctcc tagtgtccga acattattaa tgctcagaga agtatcaaag aatgatgata     80580
ctcattgagg gaaaaaatta ttcttaagta tcaatttgtt aattgaggac aaaagcacta     80640
ctgttactac tgtgaaaaat ctgaaaacat tgtcacggat gattttacaa taacatcctt     80700
ttctgacatg cattcaaaca cactattgat tccgtttcaa tgtttgtgtc tggtatgggg     80760
gcggagtgga gaggctacta caggaagaaa gaacaaataa catttcttct tactactttg     80820
tgcatcatgt gatttagctc ctcccatacc attttacatt agaaaatgtg gctgtcctcc     80880
tgtgctctag tactggcatt tcagaggact ctttgcaata tgatatgtga tcaatcatgg     80940
atggcgatgc agttaatttc agtagaaatt tgctgactct ttttatctct tttaatagct     81000
aatgcatgag ataaaattga aggtattacc aaggagaaat gcaggtggat agttttggag     81060
gcaaagtcac agtaagcaat tcatctctcc aaggaatagt gatgaaagct gagatccaat     81120
aaatgtcttg tttggattaa tacataaata tttccttttta aaattcttaa ggcttttatt     81180
catatatctc ccctctccct atttccaata atgattttttg gtgttaatat gatgatattt     81240
atgcttctgt ttttatagga accaaatact ttgatttggt tatttattct cctttggaga     81300
tgtagatgag tttattttttt cctttcgagc tttatctttt cctttatgtg tttttctttt     81360
ttacaggtat cacgctcatt gctgtggatg aggctcactg tatttctgag tggggcatg     81420 attttaggga ttcattcagg aagttgggct ccctaaagac agcactgcca atggtaagct     81480
ttgccaagtc tgatgtcccg aaattacatt cttaataagg agagcattca ggattgggga     81540
gtggtaaaga agctgaagac ttcactataa aagagcaaat ggataatgta aaaagagaac     81600 tatttttttta aaaatgctaa agttggtata taatctattg aggaatataa tagaacaagg     81660
cttgacaaac cttttctgaa aggaccagat aataaatatt tcaagcttta taggccacat     81720
gtagtctgta tcacatattc ctctctctgt tttttctttt agtaacccctt taaaaatata     81780 aagagttaca tttttcactg gtgggccata acaaaacagg ctgtgggcca tatttgtccg     81840
aatgtcttct cagtgatctt tcatccgtat gtccttttac tctaggatgc tgtgaaatcc     81900
tggttacccc ttcttgtatc acattgaaaa cctaaagttt gaactattct atagaaattt     81960
tattaaagct tttggtatta gaatttccct ttcttcccta attataaaaa atagcaaatt     82020
ttggccgggc atggtggctc acgcctgtag tcccagcact ttgggaggcc gaggtgggtg     82080
gatcacctga ggtcaggagt tcgagaccag cctggtcaac atggtgaaac cctgtctcta     82140
ctaaaaatac aacaattagc tgggcgtggt ggcaggtgcc tgtaatccca gctacttggg     82200
aggctgaggc agggggaattg cttgaactcg ggaggtggag gttgcagtga gccgagattg     82260
tgccattcca ctccagcctg ggcaacaaga gcgaaactct gtctcaaaaa aaaaaaaaa     82320 aaaaaaaaaa gtgaattttt acatgaatat tctacatgat tggcatattt acatgaatgg     82380
tttaaaaacc cacaataata gcactgtttt attttttatt ttgaaaattg tagattcaca     82440
agaagttgta aaaaaaaaaa tacctatata gaggtcctat gtacctttca tccagtttcc     82500
tgaacagtaa catcttgtgt gactatagta caatatcaaa actaggaata tgacatttgt     82560
acagtatcta gagtttattc ctatttctct agttttgtaa gtactctttt gtatggcatg     82620
tgtattgttc tatacagttt aatctcatgt acatttgtgt aactaccact gcagtcagga     82680
tgccaaatgt tcccttacca caaagctccc tggagctgtt cttcccaccc ctggccctag     82740
ccactggcaa ccacaaatct ggtctctatc tctaaaatat tatttcaaga atgttatata     82800
catggaatca tgcaatttgt caccttttgg aattagtttt tttcactcaa cataactacc     82860
```

```
ttgagatcta tccaagttgt tgtggtcat gtgttgccta acaacaggga tatgttctga    82920
gaaatgtgtt cttaggacat tttgtggttg tctgaacatg gacttacaca aacctacatg    82980
ataaagctta ctgcacacct aggctgtatg atagagccta ttgctcctag gctgtaaacc    83040
tgtacagatg ttactgtaat gaatattgca ggcaattgta atacaatggt aagtatttgt    83100
gtatctaaac ttatctaatg tagaaaaggc acagtaaaaa tacagtataa aagataaaag    83160
atggtatacc tgtataggt gcttcctgtg aatggagctt gtaggactgg aagttgctct    83220
gagtgagtga gggagtggcg agtgaatgta aaggcctagg acattactgt acactactgt    83280
agactttata catattgtac acttaggcga cactaaattt ttaaaatttt ctttaaaaat    83340
tttctttctt caataataaa ttaatctcag tttactgtaa ctttaattca taaacctaaa    83400 acatttttg actttggact cttgtaataa ttcttagatt aaaacatgaa cacattgtac    83460
agctgtacaa aaattttttc ttccttgatt aatgcattcc ataaggcttt attttaaaat    83520
tttattattt ttattttaa aacttttttg ttaaaaacta aaatacacac atatcagact    83580
agacctacac agggtcagga tcatcaatgt tgctgtcttc cacctccacg tcttatccca    83640
ctggaagttc tttaggggca gtaacactca tggagctgtc atctgtgata acaatgcctt    83700
ctcctagata cctcctgaag gacctgcctg aggctgtttt tcagttaact ttaaaaaatg    83760
aatacgtagg aggagtatac tctaaaataa tggaaaaggg tataggtaaa tacgtaaacc    83820
agtaacatac ttgtttatta ttcatcaagt tatatactgt atataattgt atgtgctata    83880 cttttaatg cctggtagtg cagtaggttt attgacagca gcatcaccac aaacgtgagc    83940
agtgccttgt gctaagacat tatgctggct atgacatcac ttggtgatag gaattttca    84000 gctccattat aatcttatgg gaccactgtt ccacatgtgc tctgtcattg acagaaatgc    84060
cgttaagcac cacatgacta ttttcggtg gtctgttcct tttattatt acagagtatt    84120 ccacagtatg gttgtaccac agtttaactg atcacctgtt gaagaacttt tgggttgttt    84180
tccagttttt gactattatg aataaagatg ctatgaacat ttgttcatat ctcaaaggtt    84240
cttttttttt ttttatttat ttttcttttt ttgagacagt ctggttctgt caccctggct    84300
ggaatgcagt ggcgcgatct cggctcgctg caagctccgc ctcctgggtt cacgccattc    84360
tcctgcctca gcctcccgag tagctgagac tacaggcgcc cgccactgtg cccggctaat    84420
tttttgtatt tttagtagag gcagcgtttc accgtgttag ccaggatggt ctcgatctcc    84480
tgacctcgtg atccacctgc ctcggcctcc caaagtgctg ggattacagg cgtgagccac    84540
tgcgcccggc cttcagagat tctttaatgg gtgaatggtt aaacaacctg aaaatataaa    84600
agttttcatt tctctgggat aaatgtccag gagtgtattt ttagttttta aggaattgtc    84660
acaaacctgt tttccaaagt ggctgtagca ttctacattc ctgtcagcag tgtgtgaatg    84720
atctagttat ccttgccacc gtttgttgtt gcaactgttt tttattttag ccatttcgat    84780
aggtgtcgag tggtatctca cttttaattt gcatttctct catggctaat gatggtgaac    84840
gtcttttcat atactaattt gcctctggtg aaatttctta cataattgga gtgcttgttt    84900
ttttctgttg agttttaaga gtttaaaaaa tacattgtag atatgagtcc ttggtcagat    84960
acgtggtttc aaatatttct ttcactttgt agcttgcctt tcattctttt taccgtgtc    85020 tttcacagag taaatattta acattttagt gaaatccagt ttatcatttt ttcttttatg    85080
gattgtgctc ttcacctagc cctagatcct gaagattttc tcctgtggtt cttccctaaa    85140
attgttacag ttttatgttt taagtctgtg atccatttg agttaaattt tgtataaggt    85200
```

-continued

```
gtgaggttta agtcaaggtt cattgttttc ccaatagatt aaaattgcagc agatcctttg    85260 ttgaataggc tgtccttccc ctgttaaatt gcgtttgccc ctttgttgaa agtcatgtgg    85320
gtgtatttgt gtgggtctat ttctgggttc tctagcctgt tatattaatt ttgaacgaat    85380
aaagttggct tatgtttaag ttttcttggt agtagcgagg caatggtgcc ttctgagccc    85440
aggatttcac aattttgtga gtaaactgtg ttagaaattg tttgttattc ttttggtagg    85500
ttgtctagtt caatttcatt gctcattaat cttgcttata gatagcaaat tgagaggcat    85560
ctcaaaaata gtatcttttg ttagcttatc tcacagagtt tggttggagc agatattaaa    85620
acagaacaaa ccaaaaataa attaaatata ctagttagca agtttatatt gagggaaaat    85680
caaaccatgt gaattgagct ccaatgatgt ggctggcctt gggtcagatt ttagtatcat    85740
ggttcaacaa ggtagctatt aaaatcttca tacttttct tgaaataatt ctttagtagt     85800 cataggac agcacacact catggatttc ttctttcctt actgtctctt tattctcagc      85860
ctcctgttcc ttctcatctc cctgaccttt taatgttggc cttccagaaa ctttagtctt    85920
tggacctacc tttgcactca ttttcttggt catttcaccc aacatacagt tttatgttat    85980 tttattttt tatttttgag atggagtttc actcttgttg cccaggctgg agtgcaatgg     86040
cgtgaactca cctcactgca acctctgcct cccgggttca gtgattctt ctgctcagcc     86100 tcccagtag ttaggattat aggtacgtgc caccatgcct agctaatttt gtattttag      86160 tagagatggg gtttcaccat attggccagg ctggtctcga actcctgacc tcaggtgatc    86220
cacctgcctt ggcttgccaa agtgctgaga ttacagatgt gagccaccac gtccagccta    86280
cagttttaaa tatcaagtct atactgagga ctcccaaatt tttatctcca tcatagactg    86340
atatcagcag tatatgagtg attcagttgt ttttgcctct ttgccagcat ttggtgttgt    86400
cactattagt tcattttagc catttaatag aatatatgta catatatatg tgtgtataca    86460
caggcacaca tctatataac tactcaacat gcctctggtg agatgaccaa caggtatctc    86520
aaacttaacc tcttcctaat tgacttctgc atagcactcc agatctgctc tttcctcact    86580
ctcctccatc ttgtttaaca gcagctccat tggccaaaat tttggaattt tcctcaatct    86640
tttctctttt tcttacactc cactgtttat ttaaacagta aggaaatctc gtgaggtctt    86700
cagaatatat gcagaattaa atcacttctc tcttgatccc tgccattccc caggtacggg    86760
ccaccatctc cttagggcct cctgctttca ctcttcccat ccctcattct gtttcaacac    86820
agcgtccaga gtgatacttt aaaaatgaag tctgatagat catgtcttcg gctcagaacc    86880
atctagtagc atgccatttc attctaaata aaggcaaaag tccttatgat gagttaccga    86940
tcctcatgta atctggcctt ccattttccc tctgatctca ttctctactg gtctcctcat    87000
tcaccggatg cagccacacc accctccttg tttttcttcg gacattccag gcatgcttca    87060
gtgcctgggc tttgcgcctg ctgcttcctc tccctgaata cgtttccccc acattgtcta    87120
taggatgttn ctcccatact tctctcagat ctcttggatt taggcctcct gggccaccat    87180
atttgaaata tcagattagt tccccctccc ccatcattca gcattcctcg taaatctttg    87240
ctgttttaaa aatagcacta tcactgtcta acttactgtg ttatattttg ttaattttct    87300
gtgagttctt cttcactaga atattctttg tagggaggag tttttgattg tttgttttat    87360
aaaatctgga acaatacctg gcttatagga ggtgctcaat ttataatggg gtgaatgaat    87420
gaatgaatga tgatgagaaa gctgagaatc agtaaagtga ctttccaaaa caggtagtgg    87480
gcagtataga gttgggccat aaaatagctgc accatacaac atcctgctag tttctaaagc    87540
aaatgatttg aaagaggcat aaaacataat ttctgccctc aggtagctca tagttcagta    87600
```

```
aaggagttta gattcatacc tataacagta gaagtaatag caccaaatga aatatggtat    87660
tatgaagtgg tacaaataat ataaaaagat gaacagtgtt agtagtacat gtttagaagg    87720
gatttctgtg gtgaaagtca ctaggcacag tgcacctgga ggaccgattt ccattccatt    87780
tagaatggtt taaagtaagc ttttggaaac taggaagatt actttctgta atcctttcct    87840
aggcctttga ttctagaagg attgtgttaa aggagtttta aatattttat acagttctta    87900
aacattgtta agcttgaatt aaatctttta ttatgtctgg ccatggacgt cattggatca    87960
ttttcatttc ttgggaggat taataaagca cattccttct gttgggcctc cagtgcgggg    88020
agggtgttgg ccgagcagtg gctgagaaaa cgttttccc ctggtgtttt caagaaccct     88080
ctttattagc taagtggtga gacatgccac ctggtggtta tagtagtatc attttctca    88140 ctgttcttgg tgcttttctt ctccttctga ttccagttat actaggacaa ctgctataaa    88200
cctggaatgt ttcacactat attatttcag taatttcaaa aacagcagaa atcactaagc    88260
tgtttggcac aaagattcct atttggaagg aatcagacaa agtgagtgtt gagaaagaac    88320
agccaggcag aaagctttgc atcagtctta aagttcttta catttcaagt aagaggaatt    88380
gtgaaatcca taagacatgt ggggtttttc tattactttc tccccagtat ctattacaaa    88440
gatcagcaca tagtaggtac tcagtaacta tttagaatga gtgcatgaat gaatgaagta    88500
tgtgtgatgt tatggagtac aaagttagaa ttagcaacat gacctgaatt tagaagcagg    88560
tgggatactt atacttttct cagtctgtgg gcaccacacc attgaagtat atgtctaaga    88620
ttaatttata tttggttgtt tgatttagca aaacttgctg cctgttaaaa aagaaattaa    88680
gacctgtcaa cttaaagaat acattttgtg agttaagaac taaatgacag tataatttat    88740
tacccaaagc agtttgcttc tgaaaattaa agagttcaag ctattaataa ttatgctgtg    88800
actgcaggca taaactggga atgtcctggc aaatgaggat gtattgtcac ctttctcagc    88860
ctgcctgtgt gttgttttta agcttcactc tagtttatat attttaaatg tcataaaata    88920
ccacatactt ataagagaaa aggttctatt cattgctgaa gtggaagttt atcattaatt    88980
tttatttatt tattttttt tccagttttg gaattcttat tactttgaac ccaagaacca     89040
ctgataacnt agcacaatcc agtgaaacag aggaagcagc agcttaatca aaggaaaaat    89100
acatttaaga ttataagtct ggttataagc ttaaaaagtg acccagaaag ggatatcatt    89160
gctaaaaaaa aaaatcccct tgtgacctgg gtacattttg caaagccaca ggtttgcagt    89220
gttacacaag ggccaaagga ggccatgagt tgtctttggt tgtggggccg gagggtaact    89280
gttcatgaaa atagtgagtg tctgaagatt aagaaaatca tgctgcagca gaggagaagg    89340
gagaggaagg caggaaggga aaggagatgc ctgagggtca aaagctgagc ccaagcctaa    89400
gcccaagctc aagttcaagc cccagcatgg cacaattttg tgaattaact caggctgagt    89460
tgcctccagt ctttggaatg tcatcttata ctggtactgc tgaggcagag ggcagtaatt    89520
ggttctttgg gataggagaa ggggcagttg ctgaaataca aaattaatag tcagcatccc    89580
aagttcctca attgcagcca aaatacatgt gttcaggcct tcggcagta ccgcccccag     89640 aactaccagc tgtagtgtgg tctattccca gacagcaaca tgcaagaata agtttacaat    89700
acactcagcc cttgtggctt aagatcaggg gctcagaggc tgtgacaact catgatgctg    89760
aaaatgtatc caatgaaaac gaagtactag ctcgtttagt agtaacgaag tactattaat    89820
ttttaatata gtctgatact ttattttcta attgtagaag caacattctt agctatatct    89880
ttctagaatg ttgaggcaaa agagtaaatt tatagtgatt ttcactgtta ccagattgct    89940
```

-continued

```
ggaataggga atttctggta gcaagatggg aattttttaag ttggaagggt ctaacacatc    90000
atatagccgt ctccatctca ttttttttgc tgaaaaaact gagcccttgc aaatgtcagt    90060
tgcaaatctg ggagtagtac tcatgtctct gaagttgtta tatagaattc ttttttattta   90120
ttttaataac aatatttatg atagttgaaa cttttttgagt gcttactata ttttatttca   90180
tgcattatgt tcagcacttt acatgtttta tctcacttga tattcacaac tttatgagat    90240
tggcactgtt attgtagcca ttttatagat gaggaaactg aagcttagag agttaaataa    90300
agagctcaaa atctcacatc tagtaagtgg caaaaacagg atttcagctc aagcaatctg    90360
attccaaaac agacttttttt cactgtgctg ccattctttt gcctggtttt tctgttaact    90420
tcttaaatat atgtcatgtt tcatgcttac ttcctcattt tcataaatat attacctgct    90480
cacttataca ttatattgct tagaaacaaa cccaaccctg ttttcttatg gactgtatcc    90540
tgaaaatcac tgttttttaat atgtggttaa acaagtgttt tattagtgca tttatataaa    90600
ttatttaacc aaaacactta accggtgaaa gtgctttact gtgagagtga gaatgtgcat    90660
gttctaagaa cctctaattt ttaaacctcc cttattctca gccttatatt tgttaaaacc    90720
tgtgtgttaa cacagatgca cccatgttag gggttaatta gagaaaccaa cctctttata    90780
gattagcttg ttcatctttta agttgctagg caggcactgt aaattcagag aacaatctga    90840
ttgtaagcca caaatcaatg aaattaattt tggggttgcc ttttaaaata gtgtcacaaa    90900
atttaaggat aaagaatgca aaaatgatgc caattatctc atcacattag ttttgattta    90960
atttttttaa tttgaaaaaa cctactctta aacttaattg atttttttaa ataaagtttt    91020
ggagataatt tttaattcag taaagttata gtgattgaaa aagtagttta aattttttaa    91080
taaattgatc ttgttttaat tttgagtcat attctagaag tgcttctttg caaattggta    91140
aattgcacat acatttccac ttatatacaa gataattgct atggttggtt tgtataatag    91200
atgcagtgca tctgaagagc tatttttatga gaatattgtt tcttgtatct gtcacgagcc    91260
aaaaagaata tttttaagaa agttatattc ttggtgatag aacagctgat aatttagaaa    91320
caactgtaag acagtccact ttttctgatt atgaaataat accatagtta agtgtaattt    91380
cctataatag aataaaaaca cgagatctag ttttagggga ggcatgttgt tactgtacct    91440
tagaatttct ggaagatgac atattcatgc ttttcctgat aactgctgag tctcctgctc    91500
tgtctgccaa tccagtcaag aagcctttgc tagcaatcaa ttaataatac gtttcattta    91560
tacatatttc ctatatatag tatgttattg attatctcag taccactgaa gagaggttat    91620
ctgggtcatt ggagctttgc ttctagattt gtgaagccat aaacctatat atttaaaata    91680
ggaggccaaa aaaaaacgac cattgcttta tatagttaga ttttcagtga attgagagtt    91740
tatcatttgt aattatacat taatcaaata taaggcataa tatacccccc tgcttatatc    91800
agcaccattt caaatgtaat gttaaaaaat aataaatgga gaagtagata gctaacaagt    91860
aggcttaatt taataagaca aagtaaatgg catttggaaa cctcatggat ttaatgtttt    91920
atttaaatga tttctgattt ttaaaaagta aatattgtat ccagaaggct gagaaacaag    91980
ttagtaggga gatttttttct ttgcaaaaaa attttacagt tgtgtcttta acattgtacc    92040
acaaactgtt gtcctaccag tctctttgta agaaagctat agacatgttg ggaatgaatg    92100
agctctttcc ttttttaaaat atcagtttta catcattcag gttccaatcg ttgcacttac    92160
tgctactgca agttcttcaa tccgggaaga cattgtacgt tgcttaaatc tgagaaatcc    92220
tcagatcacc tgtactggtt tgatcgacc aaacctgtat ttagaagtta ggcgaaaaac    92280
agggaatatc cttcaggatc tgcagccatt tcttgtcaaa acaaggtaag gatttaatgg    92340
```

```
ttgatgaatt ttggtaatga tttccttttt ttttttttaa caacttatgt attttatgtt   92400
atttacgatt tccttctaat gcatatttaa catatttcaa attccaccta gttttggttc   92460
aagtcaagca tgatgttata taatcaattc agtgattgag actagtgtat ttttaaaagc   92520
agaaaccaat tctcctaata ttttaatacc ccattctgtt gcttaaacag ggcatatact   92580 atttatttt attttttaaa attttactta tttatttata gagacaggt ctctctgtcg    92640 tccaggctgg agtgcagtgg tgtgatcaca actcactgca gcctcaaact cctgggttca   92700
agcagtcctc ctgcctcagt ctcccaagta gctggaacta cagtcttgca ccaccatgcc   92760
tggctaggac atatactttt aatgattgat aagtaaacaa gcaaacataa aatgactctt   92820
tcatctgaat tctgtctagt ttactaatta catgacttca gtcttaagga gcttagaaaa   92880 ggtcaccta caaacacagt ggagcctgta ttgtgttcca aggactattg taggcgcttt    92940
ctatataaaa tgatctaatt taatccctat aactgctcag taagttacgt attattttca   93000
ttttattgtt gaggaaactg gcattagtac ttttttctgt ttattttgtt taaaggcatt   93060
ttaaatatat atgttaagaa gttttcaaaa gcctatattt tacttttat aagcctttat   93120 tttactattt gagacagtgt cttgctctgt cacccaggct ggagtgcagt ggcgcaatcc   93180
cggctcacta caacttccac ctcctgggtt caagctattc tcctgcctca gtctcccaag   93240
tagctgaaat tacaggtgtg cgccaccatg ccaggctaat ttttgtattt tttagtggag   93300
acggggtttc accatggtgg ccaggctgat ctcgaactcc tgacctcaag tgatccacct   93360
gtgttggcct tccaaagtgc tggaattaca ggtgttggcc actgcgcctg gccagtttat   93420
aattttaaac attaaaataa atgcttcttg tccaatcatg gtgtctcaca cccataatcc   93480
cagcactttg ggaggcagac gttggagaat cacttgaggc caggagttcg agaccagcct   93540
gggcaacatg gtgaatccct gtctctacaa aaatacaaa aattagctgg gcatggtggt    93600
gcatgcctgt agtcccagct atttgggagg ctgaggtggg aggatcattt gagcccagga   93660
tgttggggct gcagtgagct gagatcacac cactgtactc caggctggat gacagagcaa   93720
ggccccgttt caaaaaaaaa aaaaaagct tctaccaata caaacacaaa acaagcatag    93780
acaaatagag tttaaagaac atcattggtg ttttcctcta aagggaatat tgatgctagg   93840
ccaaaaaaat cctggagtta ttcttgagga ccttaaggaa taattgaaat gtaggatttg   93900
ctcctggctt tcttgtccta tattcagaat aaaacaagaa tggatcgaat atattctgag   93960
tgttctggcc attctagtgc tctctgaagt gagtactcac tgtgtttcac ttcccttca    94020 tcctaaagag gaaagttct tttgaagaag gctgtttgtc ctaggttaga gtctccacag    94080
tcagatcatt atctcctcct aatctttgat cctgttcagt ctctatggta ctttccctta   94140
taataacact ctctatggca cttccctta taataacact ctccttttta aagcagtttg    94200
ccttttttgt gtgtaatatt gttctcctgg ttttctgacg tcctggtcct cttataatcc   94260
tatgcaaatg tttctttctg ttttcatgt tgactctgct aattgaggtc tttgttactt    94320
tttagccgag actattataa tttccccaac agatatccct ctccccagtg cccttgttg    94380 ctttctatgc agtttacaaa ttattgtctg caaacacatc cttaagtctg gaataccttt   94440
ctggaactcc ttactaggaa ataaagacca gactcagtgt aacattcaac agtattgaag   94500
atctaggtat ttaatatgaa tttttttttt aaggagatca agaaagattt ttgtacccat   94560
ttttaatcct ccaagaagac ttaggatagc aggaaaccat tgagagtcag aatgctttct   94620
acagatctta ggtgaacaga aactttcctc ttcatgagca gtgaggtaga gggtaattaa   94680
```

```
ggcttcagag cattgcccgt tatttccatc ttcttccctt cctttaattc tgctaaattc   94740
ctttaatttg tttatcagta ttcaagtatt tttatccatt gagctaaggt gtttcttaaa   94800
ctaaccctat tttgttaaag tcttaattat aatatattca tagtacattt aagtgagata   94860
gatgagtctc tcatataatt tagtggttag attagattag aattttctcc cctcagaaaa   94920
ttaagaggaa ataaaagtct gtagcaaatc acttggcaaa ataatggctc cttttgtaat   94980
aggaattttt actctttcga tttatctgtt acataagttc aaattttac  atattttcca   95040 cctttttttaa aaaagagtga tatgtagtca atatcaattt gagcaacact gttgcatata   95100
aattgaaaag gactccaatt ttctaattcc gtacctcagt tgtgatcact gttggtatttt  95160 tggcattttat gtagacttcc tttctctgac cctactactg tgcagatata tagttgcagt  95220
tttttgttgt tgttaagttg atacagaaat agttgcatac tatatccatt atttatgcaa   95280
attttttttc atttaaagta tctgctatct ttccatatat tgcattttct taaattagag   95340
ccttaatata taggatatta caatatctag gttttgttga gtagtttttt cttctttgaa   95400
aacatgtttt taaaataaga tttttttttt tttttttttt tttttgacat ggagtcttgc   95460
tctgtcgccc aggctgtaat gcagtggcgg gatcttggct cgttgcagcc tctgcctcct   95520
gggttccagc gattctcctg cctcagcctc ctgggtagct gggattacag gtgcatgcca   95580
ccatgccctg ctaattttg  tattttagt  agagacgggg tttcaccttg ttggccaggc   95640
tggtctcgaa cttctgagct caggtaatcc gcccgccttg gcatcccaaa gtgctgggat   95700
tacaggcgtg agccactgtg ctggccttaa aataagattt ttatacacta aaagaaaact   95760 tacattttttc actccattaa gtagttcact gtgaattttt gatattgaag cccatttggt   95820
tgctgtcaaa aatagatttg aacagattat tcagtatgac tcttgtagtg aaattattgc   95880
cttgtttcct ctgcttaagt tttcagtggc ttttgccaca gtccttaaag gtttttataat  95940 tttttttaatg tttaatttttt aaatgtttgc ttaatatttc ttagtatgag tgtagataat   96000
gatgaacatt tagatgactt tttactatta taatgttgca gtgaatattt gtttacattt    96060
atcttttggc caataagcaa atattttgt  aaattagaat cctaaaattg aaattggatc    96120
aaaagttata tgcacttgaa attgattaac ttttcctaaa tctaaaatag tatagtcttt    96180
tttatattgt cagcataaat gaatgcactt atgtaaatga atattttttag gcgttaagta   96240 aaatattcta tggaaattga acatttaagt tgtttatact tctatggaaa tcgtttacgc    96300
ttttaataaa gaagcacaag tttctacaaa atacattcta acagatgttt tctataacat    96360
tcagtctcaa gattactagt aaatacttct ttgaactgta aaagcaatct ttcaatatta   96420
taagaaagct cttgctttag taaacattta gaaactcagc tttattatca taagcaagaa   96480
taagaacagt gtaacaagtt ttatgcacac tcctttgtaa acccctcacca gactaattgt   96540 taatctggtg ccttgcattc cccaaagtat ttgtatctgt cgtttataag tttttatcaa   96600
ggtttcagct aaaacaaata aatttgtttc tggttttagc tttaatttga actgaaacag    96660
tcaaaactga gttttgggga cttcacacaa ttcattggga tatttgattc tccataatgt   96720
tttaaatttt catgcactta aatatatcat tatttttgat aggctttctt cctttagtct   96780 tttcttttaga aggtagaaag gaagaattaa ataagataaa accaaacggg tctgaagcat   96840
gtataaagta tatgtgtttg ctcttttgtt cttcttttc  tttagttccc actgggaatt   96900
tgaaggtcca acaatcatct actgtccttc tagaaaaatg acacaacaag ttacaggtga   96960
acttaggaaa cttaatctat cctgtggaac ataccatgcg ggcatgagtt ttagcacaag   97020
gaaagacatt catcataggt ttgtaagaga tgaaattcag gtatgaggat caatcatcat   97080
```

```
tgctctccgt tgctcatagt ggaagtggat atttctcaaa tgtttattta      97140
ccagatcttt
attgaatact ttctttgtgt tgaacataaa gcagtccctc tgataaatgt      97200
gggagaacaa
acttgcagat tagtataaat agcaatctgt acctagtgct taggtgcaca      97260
gaggagggag
gaatagctct gtcaaggtag ttgtgtaatg ggggtggtcc atccaggaaa      97320
attcaattag
agtccaaaca tgtaagtaga agtttttcaa gtatgccagg ccagtaggtg      97380
atgagggaa
aggaattggt tatagaattc caggaagaag gactagcagg tgcaaagaca      97440
ctttgatatg
agaacacata ctgggttcag gaaatgtgac tggtatggaa tggttggagg      97500
gaaagacaat
gtggggtagg aatggcacaa agtatggaca agaggcagg gtggaaccgt       97560
tagagacttg
agagaacagt tgaatgggtc ggttggccag gttatagatg gctttaaaac      97620
ttgcaaagaa
gcagtctggg cttggtatca tatacctgtt agttttcact gactacttta      97680
gccttagaat
ttttagttta gatacaattt tctgtaatag gtaaaacgga ttaaagtaga      97740
ataactctgg
ctgaagttaa tgtgagggaa aaggaggtac aagagtctcg tctctagacc      97800
ttgaagacac
tcctgtcggt gtcttataat ccttggagtg ccgcagaatc atttgaaaac      97860
catcttgatg
tactactctg tttttaaata agataataggg attatagaaa cattagactg      97920
gcagcaataa
gttggattga tttgaagaag agaaactgaa gaagggaaag ggtatcgatg      97980
cagctattgt
gaaattctac agttgagatt cctgacctga ttggactggc tcagtgggtg      98040
tcatagagga
tttatttggg aggatttaag ttcaaggcac atgagtaggt ttaagtcaac      98100
aacttgacac
tgtcaacatg aaatccacac tgtaactata agtccgagga agagccctct      98160
cctgaagtta
ggaatttaac ttcagctctt gcattttctg tcccaccggt catccatttc      98220
ttctctatcc
atctcctttt ctgatatcta gttgttatca gtgttgttga aaagcttaag      98280
tatgattcat
attcactgtc tataaagttc actacacata gtcatgctgt aatgcatacc      98340
cgcctgaaag
catctggtct ctcttttcct tctttccaaa gataagaata ccattcacag      98400
ctgtttagaa
tagaaatttt atccaaattc ttcagtgttt atattttgt tctgttattt      98460
cagtgtcttg
aatattgtca aatgacattt attagctact actggtacta ctgaatctta      98520
ataatcaatc
ttcaagccat taactgacca atggtttctt ctatcttaat gtattagtaa      98580
ttattcattt
agagtaaaac atctcccaga acatgaaaga atacaaactt tattcatgtt      98640
acgttgtgac
aggagacttt gttggatgcg cctgattttc ctgccaattc acagcttcat      98700
taaaacagta
atgctttgaa atatggctta ggaaacttca caatgatcat taattacacc      98760
taatttctgg
aagagtatat gcatgtatgt gttgcggtat tctcccttgc tgtggcagga      98820
tgtcacaaat
ttttatccac attacgaaaa ttta                                 98844
```

<210> SEQ ID NO 11  
<211> LENGTH: 5208  
<212> TYPE: DNA  
<213> ORGANISM: Homo sapiens  
<220> FEATURE:  
<221> NAME/KEY: CDS  
<222> LOCATION: (232)...(4530)

<400> SEQUENCE: 11

```
tgtgcgccgg ggaggcgccg gcttgtactc ggcagcgcgg gaataaagtt       60
tgctgatttg
gtgtctagcc tggatgcctg ggttgcaggc ctgcttgtgg tggcgctcca      120
cagtcatccg
gctgaaggag acctgttgga ctggatcttc tcgggttttc tttcagatat      180
tgttttgtat
ttacccatga agacattgtt ttttggactt tgcaatagg acatttcaaa      237
g atg agt
```

```
                                                          Met Ser
                                                            1
gaa aaa aaa ttg gaa aca act gca cag cag cgg aaa tgt cct gaa tgg     285
Glu Lys Lys Leu Glu Thr Thr Ala Gln Gln Arg Lys Cys Pro Glu Trp
         5                  10                  15 atg aat gtg cag aat aaa aga tgt gct gta gaa gaa aga aag gca tgt     333
Met Asn Val Gln Asn Lys Arg Cys Ala Val Glu Glu Arg Lys Ala Cys
 20                  25                  30 gtt cgg aag agt gtt ttt gaa gat gac ctc ccc ttc tta gaa ttc act     381
Val Arg Lys Ser Val Phe Glu Asp Asp Leu Pro Phe Leu Glu Phe Thr
 35                  40                  45                  50 gga tcc att gtg tat agt tac gat gct agt gat tgc tct ttc ctg tca     429
Gly Ser Ile Val Tyr Ser Tyr Asp Ala Ser Asp Cys Ser Phe Leu Ser
             55                  60                  65 gaa gat att agc atg agt cta tca gat ggg gat gtg gtg gga ttt gac     477
Glu Asp Ile Ser Met Ser Leu Ser Asp Gly Asp Val Val Gly Phe Asp
         70                  75                  80 atg gag tgg cca cca tta tac aat aga ggg aaa ctt ggc aaa gtt gca     525
Met Glu Trp Pro Pro Leu Tyr Asn Arg Gly Lys Leu Gly Lys Val Ala
     85                  90                  95 cta att cag ttg tgt gtt tct gag agc aaa tgt tac ttg ttc cac gtt     573
Leu Ile Gln Leu Cys Val Ser Glu Ser Lys Cys Tyr Leu Phe His Val
100                 105                 110 tct tcc atg tca gtt ttt ccc cag gga tta aaa atg ttg ctt gaa aat     621
Ser Ser Met Ser Val Phe Pro Gln Gly Leu Lys Met Leu Leu Glu Asn
115                 120                 125                 130 aaa gca gtt aaa aag gca ggt gta gga att gaa gga gat cag tgg aaa     669
Lys Ala Val Lys Lys Ala Gly Val Gly Ile Glu Gly Asp Gln Trp Lys
             135                 140                 145 ctt cta cgt gac ttt gat atc aaa ttg aag aat ttt gtg gag ttg aca     717
Leu Leu Arg Asp Phe Asp Ile Lys Leu Lys Asn Phe Val Glu Leu Thr
         150                 155                 160 gat gtt gcc aat aaa aag ctg aaa tgt aca gag acc tgg agc ctt aac     765
Asp Val Ala Asn Lys Lys Leu Lys Cys Thr Glu Thr Trp Ser Leu Asn
     165                 170                 175 agt ctg gtt aaa cac ctc tta ggt aaa cag ctc ctg aaa gac aag tct     813
Ser Leu Val Lys His Leu Leu Gly Lys Gln Leu Leu Lys Asp Lys Ser
180                 185                 190 atc cgc tgt agc aat tgg agt aaa ttt cct ctc act gag gac cag aaa     861
Ile Arg Cys Ser Asn Trp Ser Lys Phe Pro Leu Thr Glu Asp Gln Lys
195                 200                 205                 210 ctg tat gca gcc act gat gct tat gct ggt ttt att att tac cga aat     909
Leu Tyr Ala Ala Thr Asp Ala Tyr Ala Gly Phe Ile Ile Tyr Arg Asn
             215                 220                 225 tta gag att ttg gat gat act gtg caa agg ttt gct ata aat aaa gag     957
Leu Glu Ile Leu Asp Asp Thr Val Gln Arg Phe Ala Ile Asn Lys Glu
         230                 235                 240 gaa gaa atc cta ctt agc gac atg aac aaa cag ttg act tca atc tct    1005
Glu Glu Ile Leu Leu Ser Asp Met Asn Lys Gln Leu Thr Ser Ile Ser
     245                 250                 255 gag gaa gtg atg gat ctg gct aag cat ctt cct cat gct ttc agt aaa    1053
Glu Glu Val Met Asp Leu Ala Lys His Leu Pro His Ala Phe Ser Lys
260                 265                 270 ttg gaa aac cca cgg agg gtt tct atc tta cta aag gat att tca gaa    1101
Leu Glu Asn Pro Arg Arg Val Ser Ile Leu Leu Lys Asp Ile Ser Glu
275                 280                 285                 290 aat cta tat tca ctg agg agg atg ata att ggg tct act aac att gag    1149
Asn Leu Tyr Ser Leu Arg Arg Met Ile Ile Gly Ser Thr Asn Ile Glu
             295                 300                 305
```

```
act gaa ctg agg ccc agc aat aat tta aac tta tta tcc ttt gaa gat    1197
Thr Glu Leu Arg Pro Ser Asn Asn Leu Asn Leu Leu Ser Phe Glu Asp
        310                 315                 320 tca act act ggg gga gta caa cag aaa caa att aga gaa cat gaa gtt    1245
Ser Thr Thr Gly Gly Val Gln Gln Lys Gln Ile Arg Glu His Glu Val
            325                 330                 335 tta att cac gtt gaa gat gaa aca tgg gac cca aca ctt gat cat tta    1293
Leu Ile His Val Glu Asp Glu Thr Trp Asp Pro Thr Leu Asp His Leu
    340                 345                 350 gct aaa cat gat gga gaa gat gta ctt gga aat aaa gtg gaa cga aaa    1341
Ala Lys His Asp Gly Glu Asp Val Leu Gly Asn Lys Val Glu Arg Lys
355                 360                 365                 370 gaa gat gga ttt gaa gat gga gta gaa gac aac aaa ttg aaa gag aat    1389
Glu Asp Gly Phe Glu Asp Gly Val Glu Asp Asn Lys Leu Lys Glu Asn
                375                 380                 385 atg gaa aga gct tgt ttg atg tcg tta gat att aca gaa cat gaa ctc    1437
Met Glu Arg Ala Cys Leu Met Ser Leu Asp Ile Thr Glu His Glu Leu
            390                 395                 400 caa att ttg gaa cag cag tct cag gaa gaa tat ctt agt gat att gct    1485
Gln Ile Leu Glu Gln Gln Ser Gln Glu Glu Tyr Leu Ser Asp Ile Ala
        405                 410                 415 tat aaa tct act gag cat tta tct ccc aat gat aat gaa aac gat acg    1533
Tyr Lys Ser Thr Glu His Leu Ser Pro Asn Asp Asn Glu Asn Asp Thr
    420                 425                 430 tcc tat gta att gag agt gat gaa gat tta gaa atg gag atg ctt aag    1581
Ser Tyr Val Ile Glu Ser Asp Glu Asp Leu Glu Met Glu Met Leu Lys
435                 440                 445                 450 cat tta tct ccc aat gat aat gaa aac gat acg tcc tat gta att gag    1629
His Leu Ser Pro Asn Asp Asn Glu Asn Asp Thr Ser Tyr Val Ile Glu
                455                 460                 465 agt gat gaa gat tta gaa atg gag atg ctt aag tct tta gaa aac ctc    1677
Ser Asp Glu Asp Leu Glu Met Glu Met Leu Lys Ser Leu Glu Asn Leu
            470                 475                 480 aat agt ggc acg gta gaa cca act cat tct aaa tgc tta aaa atg gaa    1725
Asn Ser Gly Thr Val Glu Pro Thr His Ser Lys Cys Leu Lys Met Glu
        485                 490                 495 aga aat ctg ggt ctt cct act aaa gaa gaa gaa gaa gat gat gaa aat    1773
Arg Asn Leu Gly Leu Pro Thr Lys Glu Glu Glu Glu Asp Asp Glu Asn
    500                 505                 510 gaa gct aat gaa ggg gaa gaa gat gat gat aag gac ttt ttg tgg cca    1821
Glu Ala Asn Glu Gly Glu Glu Asp Asp Asp Lys Asp Phe Leu Trp Pro
515                 520                 525                 530 gca ccc aat gaa gag caa gtt act tgc ctc aag atg tac ttt ggc cat    1869
Ala Pro Asn Glu Glu Gln Val Thr Cys Leu Lys Met Tyr Phe Gly His
                535                 540                 545 tcc agt ttt aaa cca gtt cag tgg aaa gtg att cat tca gta tta gaa    1917
Ser Ser Phe Lys Pro Val Gln Trp Lys Val Ile His Ser Val Leu Glu
            550                 555                 560 gaa aga aga gat aat gtt gct gtc atg gca act gga tat gga aag agt    1965
Glu Arg Arg Asp Asn Val Ala Val Met Ala Thr Gly Tyr Gly Lys Ser
        565                 570                 575 ttg tgc ttc cag tat cca cct gtt tat gta ggc aag att ggc ctt gtt    2013
Leu Cys Phe Gln Tyr Pro Pro Val Tyr Val Gly Lys Ile Gly Leu Val
    580                 585                 590 atc tct ccc ctt att tct ctg atg gaa gac caa gtg cta cag ctt aaa    2061
Ile Ser Pro Leu Ile Ser Leu Met Glu Asp Gln Val Leu Gln Leu Lys
595                 600                 605                 610 atg tcc aac atc cca gct tgc ttc ctt gga tca gca cag tca gaa aat    2109
Met Ser Asn Ile Pro Ala Cys Phe Leu Gly Ser Ala Gln Ser Glu Asn
                615                 620                 625
```

-continued

```
gtt cta aca gat att aaa tta ggt aaa tac cgg att gta tac gta act    2157
Val Leu Thr Asp Ile Lys Leu Gly Lys Tyr Arg Ile Val Tyr Val Thr
            630                 635                 640 cca gaa tac tgt tca ggt aac atg ggc ctg ctc cag caa ctt gag gct    2205
Pro Glu Tyr Cys Ser Gly Asn Met Gly Leu Leu Gln Gln Leu Glu Ala
            645                 650                 655 gat att ggt atc acg ctc att gct gtg gat gag gct cac tgt att tct    2253
Asp Ile Gly Ile Thr Leu Ile Ala Val Asp Glu Ala His Cys Ile Ser
            660                 665                 670 gag tgg ggg cat gat ttt agg gat tca ttc agg aag ttg ggc tcc cta    2301
Glu Trp Gly His Asp Phe Arg Asp Ser Phe Arg Lys Leu Gly Ser Leu
675                 680                 685                 690 aag aca gca ctg cca atg gtt cca atc gtt gca ctt act gct act gca    2349
Lys Thr Ala Leu Pro Met Val Pro Ile Val Ala Leu Thr Ala Thr Ala
            695                 700                 705 agt tct tca atc cgg gaa gac att gta cgt tgc tta aat ctg aga aat    2397
Ser Ser Ser Ile Arg Glu Asp Ile Val Arg Cys Leu Asn Leu Arg Asn
            710                 715                 720 cct cag atc acc tgt act ggt ttt gat cga cca aac ctg tat tta gaa    2445
Pro Gln Ile Thr Cys Thr Gly Phe Asp Arg Pro Asn Leu Tyr Leu Glu
            725                 730                 735 gtt agg cga aaa aca ggg aat atc ctt cag gat ctg cag cca ttt ctt    2493
Val Arg Arg Lys Thr Gly Asn Ile Leu Gln Asp Leu Gln Pro Phe Leu
            740                 745                 750 gtc aaa aca agt tcc cac tgg gaa ttt gaa ggt cca aca atc atc tac    2541
Val Lys Thr Ser Ser His Trp Glu Phe Glu Gly Pro Thr Ile Ile Tyr
755                 760                 765                 770 tgt cct tct aga aaa atg aca caa caa gtt aca ggt gaa ctt agg aaa    2589
Cys Pro Ser Arg Lys Met Thr Gln Gln Val Thr Gly Glu Leu Arg Lys
                        775                 780                 785 ctt aat cta tcc tgt gga aca tac cat gcg ggc atg agt ttt agc aca    2637
Leu Asn Leu Ser Cys Gly Thr Tyr His Ala Gly Met Ser Phe Ser Thr
            790                 795                 800 agg aaa gac att cat cat agg ttt gta aga gat gaa att cag tgt gtc    2685
Arg Lys Asp Ile His His Arg Phe Val Arg Asp Glu Ile Gln Cys Val
            805                 810                 815 ata gct acc ata gct ttt gga atg ggc att aat aaa gct gac att cgc    2733
Ile Ala Thr Ile Ala Phe Gly Met Gly Ile Asn Lys Ala Asp Ile Arg
            820                 825                 830 caa gtc att cat tac ggt gct cct aag gac atg gaa tca tat tat cag    2781
Gln Val Ile His Tyr Gly Ala Pro Lys Asp Met Glu Ser Tyr Tyr Gln
835                 840                 845                 850 gag att ggt aga gct ggt cgt gat gga ctt caa agt tct tgt cac gtc    2829
Glu Ile Gly Arg Ala Gly Arg Asp Gly Leu Gln Ser Ser Cys His Val
            855                 860                 865 ctc tgg gct cct gca gac att aac tta aat agg cac ctt ctt act gag    2877
Leu Trp Ala Pro Ala Asp Ile Asn Leu Asn Arg His Leu Leu Thr Glu
            870                 875                 880 ata cgt aat gag aag ttt cga tta tac aaa tta aag atg atg gca aag    2925
Ile Arg Asn Glu Lys Phe Arg Leu Tyr Lys Leu Lys Met Met Ala Lys
            885                 890                 895 atg gaa aaa tat ctt cat tct agc aga tgt agg aga caa atc atc ttg    2973
Met Glu Lys Tyr Leu His Ser Ser Arg Cys Arg Arg Gln Ile Ile Leu
900                 905                 910 tct cat ttt gag gac aaa caa gta caa aaa gcc tcc ttg gga att atg    3021
Ser His Phe Glu Asp Lys Gln Val Gln Lys Ala Ser Leu Gly Ile Met
915                 920                 925                 930 gga act gaa aaa tgc tgt gat aat tgc agg tcc aga ttg gat cat tgc    3069
Gly Thr Glu Lys Cys Cys Asp Asn Cys Arg Ser Arg Leu Asp His Cys
```

-continued

| | | | |
|---|---|---|---|
| | 935 | 940 | 945 |
| tat tcc atg gat gac tca gag gat aca tcc tgg gac ttt ggt cca caa<br>Tyr Ser Met Asp Asp Ser Glu Asp Thr Ser Trp Asp Phe Gly Pro Gln<br>950 955 960 | | | 3117 |
| gca ttt aag ctt ttg tct gct gtg gac atc tta ggc gaa aaa ttt gga<br>Ala Phe Lys Leu Leu Ser Ala Val Asp Ile Leu Gly Glu Lys Phe Gly<br>965 970 975 | | | 3165 |
| att ggg ctt cca att tta ttt ctc cga gga tct aat tct cag cgt ctt<br>Ile Gly Leu Pro Ile Leu Phe Leu Arg Gly Ser Asn Ser Gln Arg Leu<br>980 985 990 | | | 3213 |
| gcc gat caa tat cgc agg cac agt tta ttt ggc act ggc aag gat caa<br>Ala Asp Gln Tyr Arg Arg His Ser Leu Phe Gly Thr Gly Lys Asp Gln<br>995 1000 1005 1010 | | | 3261 |
| aca gag agt tgg tgg aag gct ttt tcc cgt cag ctg atc act gag gga<br>Thr Glu Ser Trp Trp Lys Ala Phe Ser Arg Gln Leu Ile Thr Glu Gly<br>1015 1020 1025 | | | 3309 |
| ttc ttg gta gaa gtt tct cgg tat aac aaa ttt atg aag att tgc gcc<br>Phe Leu Val Glu Val Ser Arg Tyr Asn Lys Phe Met Lys Ile Cys Ala<br>1030 1035 1040 | | | 3357 |
| ctt acg aaa aag ggt aga aat tgg ctt cat aaa gct aat aca gaa tct<br>Leu Thr Lys Lys Gly Arg Asn Trp Leu His Lys Ala Asn Thr Glu Ser<br>1045 1050 1055 | | | 3405 |
| cag agc ctc atc ctt caa gct aat gaa gaa ttg tgt cca aag aag ttt<br>Gln Ser Leu Ile Leu Gln Ala Asn Glu Glu Leu Cys Pro Lys Lys Phe<br>1060 1065 1070 | | | 3453 |
| ctt ctg cct agt tcg aaa act gta tct tcg ggc acc aaa gag cat tgt<br>Leu Leu Pro Ser Ser Lys Thr Val Ser Ser Gly Thr Lys Glu His Cys<br>1075 1080 1085 1090 | | | 3501 |
| tat aat caa gta cca gtt gaa tta agt aca gag aag aag tct aac ttg<br>Tyr Asn Gln Val Pro Val Glu Leu Ser Thr Glu Lys Lys Ser Asn Leu<br>1095 1100 1105 | | | 3549 |
| gag aag tta tat tct tat aaa cca tgt gat aag att tct tct ggg agt<br>Glu Lys Leu Tyr Ser Tyr Lys Pro Cys Asp Lys Ile Ser Ser Gly Ser<br>1110 1115 1120 | | | 3597 |
| aac att tct aaa aaa agt atc atg gta cag tca cca gaa aaa gct tac<br>Asn Ile Ser Lys Lys Ser Ile Met Val Gln Ser Pro Glu Lys Ala Tyr<br>1125 1130 1135 | | | 3645 |
| agt tcc tca cag cct gtt att tcg gca caa gag cag gag act cag att<br>Ser Ser Ser Gln Pro Val Ile Ser Ala Gln Glu Gln Glu Thr Gln Ile<br>1140 1145 1150 | | | 3693 |
| gtg tta tat ggc aaa ttg gta gaa gct agg cag aaa cat gcc aat aaa<br>Val Leu Tyr Gly Lys Leu Val Glu Ala Arg Gln Lys His Ala Asn Lys<br>1155 1160 1165 1170 | | | 3741 |
| atg gat gtt ccc cca gct att ctg gca aca aac aag ata ctg gtg gat<br>Met Asp Val Pro Pro Ala Ile Leu Ala Thr Asn Lys Ile Leu Val Asp<br>1175 1180 1185 | | | 3789 |
| atg gcc aaa atg aga cca act acg gtt gaa aac gta aaa agg att gat<br>Met Ala Lys Met Arg Pro Thr Thr Val Glu Asn Val Lys Arg Ile Asp<br>1190 1195 1200 | | | 3837 |
| ggt gtt tct gaa ggc aaa gct gcc atg ttg gcc cct ctg ttg gaa gtc<br>Gly Val Ser Glu Gly Lys Ala Ala Met Leu Ala Pro Leu Leu Glu Val<br>1205 1210 1215 | | | 3885 |
| atc aaa cat ttc tgc caa aca aat agt gtt cag aca gac ctc ttt tca<br>Ile Lys His Phe Cys Gln Thr Asn Ser Val Gln Thr Asp Leu Phe Ser<br>1220 1225 1230 | | | 3933 |
| agt aca aaa cct caa gaa gaa cag aag acg agt ctg gta gca aaa aat<br>Ser Thr Lys Pro Gln Glu Glu Gln Lys Thr Ser Leu Val Ala Lys Asn<br>1235 1240 1245 1250 | | | 3981 |
| aaa ata tgc aca ctt tca cag tct atg gcc atc aca tac tct tta ttc | | | 4029 |

```
Lys Ile Cys Thr Leu Ser Gln Ser Met Ala Ile Thr Tyr Ser Leu Phe
            1255                1260                1265 caa gaa aag aag atg cct ttg aag agc ata gct gag agc agg att ctg    4077
Gln Glu Lys Lys Met Pro Leu Lys Ser Ile Ala Glu Ser Arg Ile Leu
            1270                1275                1280 cct ctc atg aca att ggc atg cac tta tcc caa gcg gtg aaa gct ggc    4125
Pro Leu Met Thr Ile Gly Met His Leu Ser Gln Ala Val Lys Ala Gly
            1285                1290                1295 tgc ccc ctt gat ttg gag cga gca ggc ctg act cca gag gtt cag aag    4173
Cys Pro Leu Asp Leu Glu Arg Ala Gly Leu Thr Pro Glu Val Gln Lys
            1300                1305                1310 att att gct gat gtt atc cga aac cct ccc gtc aac tca gat atg agt    4221
Ile Ile Ala Asp Val Ile Arg Asn Pro Pro Val Asn Ser Asp Met Ser
1315                1320                1325                1330 aaa att agc cta atc aga atg tta gtt cct gaa aac att gac acg tac    4269
Lys Ile Ser Leu Ile Arg Met Leu Val Pro Glu Asn Ile Asp Thr Tyr
            1335                1340                1345 ctt atc cac atg gca att gag atc ctt aaa cat ggt cct gac agc gga    4317
Leu Ile His Met Ala Ile Glu Ile Leu Lys His Gly Pro Asp Ser Gly
            1350                1355                1360 ctt caa cct tca tgt gat gtc aac aaa agg aga tgt ttt ccc ggt tct    4365
Leu Gln Pro Ser Cys Asp Val Asn Lys Arg Arg Cys Phe Pro Gly Ser
            1365                1370                1375 gaa gag atc tgt tca agt tct aag aga agc aag gaa gaa gta ggc atc    4413
Glu Glu Ile Cys Ser Ser Ser Lys Arg Ser Lys Glu Glu Val Gly Ile
            1380                1385                1390 aat act gag act tca tct gca gag aga aag aga cga tta cct gtg tgg    4461
Asn Thr Glu Thr Ser Ser Ala Glu Arg Lys Arg Arg Leu Pro Val Trp
1395                1400                1405                1410 ttt gcc aaa gga agt gat acc agc aag aaa tta atg gac aaa acg aaa    4509
Phe Ala Lys Gly Ser Asp Thr Ser Lys Lys Leu Met Asp Lys Thr Lys
            1415                1420                1425 agg gga ggt ctt ttt agt taa gctggcaatt accagaacaa ttatgtttct       4560
Arg Gly Gly Leu Phe Ser
            1430 tgctgtatta taagaggata gctatatttt atttctgaag agtaaggagt agtattttgg  4620 cttaaaaatc attctaatta caaagttcac tgtttattga agaactggca tcttaaatca  4680 gccttccgca attcatgtag tttctgggtc ttctgggagc ctacgtgagt acatcaccta  4740 acagaatatt aaattagact tcctgtaaga ttgctttaag aaactgttac tgtcctgttt  4800 tctaatctct ttattaaaac agtgtatttg gaaaatgtta tgtgctctga tttgatatag  4860 ataacagatt agtagttaca tggtaattat gtgatataaa atattcatat attatcaaaa  4920 ttctgttttg taaatgtaag aaagcatagt tattttacaa attgttttta ctgtcttttg  4980 aagaagttct taaatacgtt gttaaatggt attagttgac cagggcagtg aaaatgaaac  5040 cgcattttgg gtgccattaa atagggaaaa aacatgtaaa aaatgtaaaa tggagaccaa  5100 ttgcactagg caagtgtata ttttgtattt tatatacaat ttctattatt tttcaagtaa  5160 taaaacaatg ttttcatac tgaatattaa aaaaaaaaa aaaaaaaa                 5208
```

<210> SEQ ID NO 12
<211> LENGTH: 432
<212> TYPE: DNA
<213> ORGANISM: Homo sapiens
<220> FEATURE:

<400> SEQUENCE: 12

```
ggttgaccag ggcagtgaaa atgaaaccgc attttgggtg ccattaaata gggaaaaaac      60
atgtaaaaaa tgtaaaatgg agaccaattg cactaggcaa gtgtatattt tgtattttat     120
atacaatttc tattattttt caagtaataa aacaatgttt ttcatactga atattatata     180
tatatgcttg cagctttcat ttacttaatt attttaagta cctttatttt tccaggatgt     240
cagaatttga ttctaatctc tcttatgtag cacatgtgac ttaatttaaa acctatactg     300
tgacacagag ttgggtaaac gatgattatt taactttaag cagttcacca tccatttcaa     360
agcctttgat tggctttttt gtaaataaaa ataacttgtt atgagcaaat atatctgtca     420
ttgatgagct tg                                                         432

<210> SEQ ID NO 13
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 13
tctcacggtt tgggactcaa                                                  20

<210> SEQ ID NO 14
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 14
agataatagc tcttctatat                                                  20

<210> SEQ ID NO 15
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 15
tcagtagagc aaagctgctt                                                  20

<210> SEQ ID NO 16
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 16
ggtaattacg tggcaaaacc                                                  20

<210> SEQ ID NO 17
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 17
caaactttag gttttcaatg                                                  20

<210> SEQ ID NO 18
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 18
tcacctaaga tctgtagaaa                                              20

<210> SEQ ID NO 19
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 19
gtcagaaaac actttctata                                              20

<210> SEQ ID NO 20
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 20
cacggtttgc caatgaggca                                              20

<210> SEQ ID NO 21
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 21
taaaggaatc atattccctt                                              20

<210> SEQ ID NO 22
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 22
cagaggttca aagatgttaa                                              20

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 23
atgtgtggct gactgctgag                                              20

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 24
```
tgcttcaaca agtaattaca                                                    20

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
aaactttatt cccgcgctgc                                                    20

<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 26
tcttcatggg taaatacaaa                                                    20

<210> SEQ ID NO 27
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 27
tttcactcat ctttgaaatg                                                    20

<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28
gaacacatgc ctttctttct                                                    20

<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
tagcatcgta actatacaca                                                    20

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30
tagactcatg ctaatatctt                                                    20

<210> SEQ ID NO 31
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 31
atgtcaaatc ccaccacatc                                               20

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32
gaaatttact ccaattgcta                                               20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
agtttctggt cctcagtgag                                               20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
gcatacagtt tctggtcctc                                               20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
gtggctgcat acagtttctg                                               20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
gcatcagtgg ctgcatacag                                               20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
gtttcatctt caacgtgaat                                               20
```

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
tgttgggtcc catgtttcat                                              20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
tgtttagcta aatgatcaag                                              20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
caaaatttgg agttcatgtt                                              20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
gagataaatg ctcagtagat                                              20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
attgggagat aaatgctcag                                              20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
gagataaatg cttaagcatc                                              20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
atcattggga gataaatgct                                           20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
tttctaaaga cttaagcatc                                           20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
tgagttggtt ctaccgtgcc                                           20

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47
gccaaagtac atcttgaggc                                           20

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48
ccactgaact ggtttaaaac                                           20

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 49
catatccagt tgccatgaca                                           20

<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50
gttggacatt ttaagctgta                                           20

<210> SEQ ID NO 51

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51
tgaacagtat tctggagtta                                              20

<210> SEQ ID NO 52
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 52
gcctcatcca cagcaatgag                                              20

<210> SEQ ID NO 53
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 53
cagtgagcct catccacagc                                              20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
ccagtgggaa cttgttttga                                              20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 55
ttggaccttc aaattcccag                                              20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56
acacactgaa tttcatctct                                              20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57
```

```
ctatgacaca ctgaatttca                                                    20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
aatgcccatt ccaaaagcta                                                    20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
tttattaatg cccattccaa                                                    20

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
tgtcagcttt attaatgccc                                                    20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
ggcgaatgtc agctttatta                                                    20

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
caatctcctg ataatatgat                                                    20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
aagaaggtgc ctatttaagt                                                    20

<210> SEQ ID NO 64
<211> LENGTH: 20
<212> TYPE: DNA
```

<213> ORGANISM: Artificial Sequence
<220> FEATURE:
<223> OTHER INFORMATION: Antisense Oligonucleotide

<400> SEQUENCE: 64
caagatgatt tgtctcctac                                           20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65 cattttcag ttcccataat                                            20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 66
tatcacagca tttttcagtt                                           20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
tgcaattatc acagcatttt                                           20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
ttagatcctc ggagaaataa                                           20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
tgagaattag atcctcggag                                           20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
caaataaact gtgcctgcga                                           20

<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
aaagccttcc accaactctc                                              20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
agttttcgaa ctaggcagaa                                              20

<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 73
ccaagttaga cttcttctct                                              20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74
ataacacaat ctgagtctcc                                              20

<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 75
ttcagaaaca ccatcaatcc                                              20

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76
aaatgtttga tgacttccaa                                              20

<210> SEQ ID NO 77
<211> LENGTH: 20
<212> TYPE: DNA
<213> ORGANISM: Artificial Sequence
<220> FEATURE:

```
<223> OTHER INFORMATION: Antisense Oligonucleotide

<400> SEQUENCE: 77
cttgaggttt tgtacttgaa                                           20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
atgtgatggc catagactgt                                           20

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 79
tcaggaacta acattctgat                                           20

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80
atgttttcag gaactaacat                                           20

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81
gatctcaatt gccatgtgga                                           20

<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82
ttgccagctt aactaaaaag                                           20

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83
gaaacataat tgttctggta                                           20
```

```
<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84
tccttactct tcagaaataa                                                    20

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85
taagccaaaa tactactcct                                                    20

<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86
ttcaataaac agtgaacttt                                                    20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87
acgtatttaa gaacttcttc                                                    20

<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 88
aaaaacattg ttttattact                                                    20

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89
gtcacatgtg ctacataaga                                                    20

<210> SEQ ID NO 90
<211> LENGTH: 20
<212> TYPE: DNA
<213> ORGANISM: Artificial Sequence
<220> FEATURE:
<223> OTHER INFORMATION: Antisense Oligonucleotide
```

-continued

```
<400> SEQUENCE: 90
ttacccaact ctgtgtcaca                                                          20
```